United States Patent
Hida et al.

(10) Patent No.: US 6,221,637 B1
(45) Date of Patent: Apr. 24, 2001

(54) XANTHENE DERIVATIVES, THEIR PRODUCTION AND USE

(75) Inventors: Tsuneaki Hida; Masahiko Hattori, both of Ibaraki; Tsutomu Kurokawa, Hyogo; Atsushi Nakanishi, Ibaraki, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 08/812,946

(22) Filed: Mar. 4, 1997

(30) Foreign Application Priority Data

Mar. 5, 1996 (JP) .................................. 8-047795
Oct. 2, 1996 (JP) .................................. 8-262085

(51) Int. Cl.$^7$ ............................ C12P 17/02; C12P 11/00; C12N 1/14; A01N 43/00
(52) U.S. Cl. ..................... 435/123; 435/130; 435/256.1; 514/183; 514/687; 568/308
(58) Field of Search .................... 435/118, 123, 435/130, 256.1; 514/183, 680, 687, 688; 568/308, 338

(56) References Cited

U.S. PATENT DOCUMENTS

| | | | |
|---|---|---|---|
| 3,919,211 | 11/1975 | Santilli et al. | 544/79 |
| 3,951,618 | 4/1976 | Pfister et al. | 514/455 |
| 4,147,798 | 4/1979 | Calton et al. | 514/453 |
| 4,965,284 | * 10/1990 | Nair et al. | 514/443 |
| 5,296,353 | * 3/1994 | Ochoa et al. | 435/7.23 |
| 5,521,315 | * 5/1996 | Underiner et al. | 546/243 |
| 5,670,506 | * 9/1997 | Leigh et al. | 514/258 |

FOREIGN PATENT DOCUMENTS

| | | |
|---|---|---|
| 0 022 478 | 1/1981 | (EP) . |
| 0 093 381 | 11/1983 | (EP) . |
| 0 442 748 | 8/1991 | (EP) . |
| 0 556 699 | 8/1993 | (EP) . |

OTHER PUBLICATIONS

Roitt et al. "Immunology," 3rd ed. (1993) (Mosby: St. Louis) pp. 9.1–9.14, 1993.*

J. Pfister et al., "Synthesis and Antiallergic Activity of Some Mono–and Disubstituted Xanthone–2–carboxylic Acids[1]", Journal of Medicinal Chemistry, vol. 21, No. 7, pp. 669–672, 1978.

J. Pfister et al., "Synthesis and Aldose Reductase Inhibitory Activity of 7–Sulfamoylxanthone–2–carboxylic Acids[1,2]", Journal of Medicinal Chemistry, vol. 23, No. 11, pp. 1264–1267, 1980.

A. Aruffo et al., "Molecular Cloning of a CD28 cDNA by a High–Efficiency COS Cell Expression System", Proc. Natl. Acad. Sci., vol. 84, pp. 8573–8577, 1987.

G. Freeman et al., "B7, A New Member of the Ig Superfamily with Unique Expression on Activated and Neoplastic B Cells[1]", The Journal of Immunology, vol. 143, No. 8, pp. 2714–2722, 1989.

Chemical Abstracts, vol. 98, No. 15, Apr. 11, 1983, Abstract No. 122499p.

* cited by examiner

*Primary Examiner*—Jon P. Weber
*Assistant Examiner*—Susan Hanley
(74) *Attorney, Agent, or Firm*—Wenderoth, Lind & Ponack, L.L.P.

(57) ABSTRACT

Xanthene compounds represented by the formula:

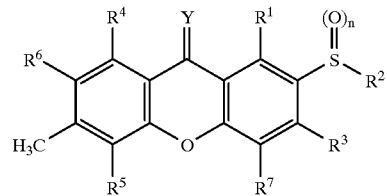

wherein $R^1$ is a carboxyl group which may be esterified or amidated; $R^2$ is a hydrogen atom, a hydroxyl group, or a hydrocarbon group which may be substituted; $R^3$ and $R^4$ are the same or different and are a hydroxyl group which may be substituted; $R^5$ and $R^6$ are a hydrogen atom or a halogen atom; $R^7$ is a hydrogen atom, a nitro group, a halogen atom, a hydrocarbon group which may be substituted, a heterocyclic group which may be substituted, or an acyl group which may be substituted; n is an integer of 0 to 2; and Y is an oxygen atom or two hydrogen atoms; and when n is 0, $R^2$ may be a group represented by the formula:

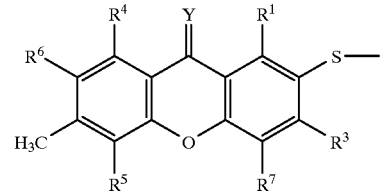

wherein the symbols have the same meanings as defined above, or a salt thereof inhibit a binding of B7-1 to CD28, prevent the B7-1-dependent activation of T cells and inhibit IL-2 production from T cells, thus being used as an immunomodulator such as a graft rejection inhibitor or a pharmaceutical composition for therapeutic treatment of allergy, rheumatoid arthritis, autoimmune disease, nephritis, diabetes mellitus and so on.

20 Claims, 11 Drawing Sheets

FIG. 2

```
1                                                           60
ATGCTCAGGCTGCTCTTGGCTCTCAACTTATTCCCTTCAATTCAAGTAACAGGAAACAAG
 M  L  R  L  L  A  L  N  L  F  P  S  I  Q  V  T  G  N  K
61                                                          120
ATTTTGGTGAAGCAGTCGCCCATGCTTGTAGCGTACGACAATGCGGTCAACCTTAGCTGC
 I  L  V  K  Q  S  P  M  L  V  A  Y  D  N  A  V  N  L  S  C
121                                                         180
AAGTATTCCTACAATCTCTTCTCAAGGGAGTTCCGGGCATCCCTTCACAAAGGACTGGAT
 K  Y  S  Y  N  L  F  S  R  E  F  R  A  S  L  H  K  G  L  D
181                                                         240
AGTGCTGTGGAAGTCTGTGTTGTATATGGGAATTACTCCCAGCAGCTTCAGGTTTACTCA
 S  A  V  E  V  C  V  V  Y  G  N  Y  S  Q  Q  L  Q  V  Y  S
241                                                         300
AAAACGGGGTTCAACTGTGATGGGAAATTGGGCAATGAATCAGTGACATTCTACCTCCAG
 K  T  G  F  N  C  D  G  K  L  G  N  E  S  V  T  F  Y  L  Q
301                                                         360
AATTTGTATGTTAACCAAACAGATATTTACTTCTGCAAAATTGAAGTTATGTATCCTCCT
 N  L  Y  V  N  Q  T  D  I  Y  F  C  K  I  E  V  M  Y  P  P
361                                                         420
CCTTACCTAGACAATGAGAAGAGCAATGGAACCATTATCCATGTGAAAGGGAAACACCTT
 P  Y  L  D  N  E  K  S  N  G  T  I  I  H  V  K  G  K  H  L
421                                                         480
TGTCCAAGTCCCCTATTTCCCGGACCTTCTAAGCCCTTTTGGGTGCTGGTGGTGGTTGGT
 C  P  S  P  L  F  P  G  P  S  K  P  F  W  V  L  V  V  V  G
481                                                         540
GGAGTCCTGGCTTGCTATAGCTTGCTAGTAACAGTGGCCTTTATTATTTTCTGGGTGAGG
 G  V  L  A  C  Y  S  L  L  V  T  V  A  F  I  I  F  W  V  R
541                                                         600
AGTAAGAGGAGCAGGCTCCTGCACAGTGACTACATGAACATGACTCCCCGCCGCCCCGGG
 S  K  R  S  R  L  L  H  S  D  Y  M  N  M  T  P  R  R  P  G
601                                                         660
CCCACCCGCAAGCATTACCAGCCCTATGCCCCACCACGCGACTTCGCAGCCTATCGCTCC
 P  T  R  K  H  Y  Q  P  Y  A  P  P  R  D  F  A  A  Y  R  S
661
TGA
trm
```

FIG. 4

```
1                                                          60
ATGGGCCACACACGGAGGCAGGGAACATCACCATCCAAGTGTCCATACCTCAATTTCTTT
 M  G  H  T  R  R  Q  G  T  S  P  S  K  C  P  Y  L  N  F  F
61                                                         120
CAGCTCTTGGTGCTGGCTGGTCTTTCTCACTTCTGTTCAGGTGTTATCCACGTGACCAAG
 Q  L  L  V  L  A  G  L  S  H  F  C  S  G  V  I  H  V  T  K
121                                                        180
GAAGTCAAAGAAGTGGCAACGCTGTCCTGTGGTCACAATGTTTCTGTTGAAGAGCTGGCA
 E  V  K  E  V  A  T  L  S  C  G  H  N  V  S  V  E  E  L  A
181                                                        240
CAAACTCGCATCTACTGGCAAAAGGAGAAGAAAATGGTGCTGACTATGATGTCTGGGGAC
 Q  T  R  I  Y  W  Q  K  E  K  K  M  V  L  T  M  M  S  G  D
241                                                        300
ATGAATATATGGCCCGAGTACAAGAACCGGACCATCTTTGATATCACTAATAACCTCTCC
 M  N  I  W  P  E  Y  K  N  R  T  I  F  D  I  T  N  N  L  S
301                                                        360
ATTGTGATCCTGGCTCTGCGCCCATCTGACGAGGGCACATACGAGTGTGTTGTTCTGAAG
 I  V  I  L  A  L  R  P  S  D  E  G  T  Y  E  C  V  V  L  K
361                                                        420
TATGAAAAAGACGCTTTCAAGCGGGAACACCTGGCTGAAGTGACGTTATCAGTCAAAGCT
 Y  E  K  D  A  F  K  R  E  H  L  A  E  V  T  L  S  V  K  A
421                                                        480
GACTTCCCTACACCTAGTATATCTGACTTTGAAATTCCAACTTCTAATATTAGAAGGATA
 D  F  P  T  P  S  I  S  D  F  E  I  P  T  S  N  I  R  R  I
481                                                        540
ATTTGCTCAACCTCTGGAGGTTTTCCAGAGCCTCACCTCTCCTGGTTGGAAAATGGAGAA
 I  C  S  T  S  G  G  F  P  E  P  H  L  S  W  L  E  N  G  E
541                                                        600
GAATTAAATGCCATCAACACAACAGTTTCCCAAGATCCTGAAACTGAGCTCTATGCTGTT
 E  L  N  A  I  N  T  T  V  S  Q  D  P  E  T  E  L  Y  A  V
601                                                        660
AGCAGCAAACTGGATTTCAATATGACAACCAACCACAGCTTCATGTGTCTCATCAAGTAT
 S  S  K  L  D  F  N  M  T  T  N  H  S  F  M  C  L  I  K  Y
661                                                        720
GGACATTTAAGAGTGAATCAGACCTTCAACTGGAATACAACCAAGCAAGAGCATTTTCCT
 G  H  L  R  V  N  Q  T  F  N  W  N  T  T  K  Q  E  H  F  P
721                                                        780
GATAACCTGCTCCCATCCTGGGCCATTACCTTAATCTCAGTAAATGGAATTTTTGTGATA
 D  N  L  L  P  S  W  A  I  T  L  I  S  V  N  G  I  F  V  I
781                                                        840
TGCTGCCTGACCTACTGCTTTGCCCCAAGATGCAGAGAGAGAAGGAGGAATGAGAGATTG
 C  C  L  T  Y  C  F  A  P  R  C  R  E  R  R  R  N  E  R  L
841              867
AGAAGGGAAAGTGTACGCCCTGTATAA
 R  R  E  S  V  R  P  V trm
```

FIG. 6

```
1                                                           60
ATGGGCCACACACGGAGGCAGGGAACATCACCATCCAAGTGTCCATACCTCAATTTCTTT
 M  G  H  T  R  R  Q  G  T  S  P  S  K  C  P  Y  L  N  F  F
61                                                         120
CAGCTCTTGGTGCTGGCTGGTCTTTCTCACTTCTGTTCAGGTGTTATCCACGTGACCAAG
 Q  L  L  V  L  A  G  L  S  H  F  C  S  G  V  I  H  V  T  K
121                                                        180
GAAGTCAAAGAAGTGGCAACGCTGTCCTGTGGTCACAATGTTTCTGTTGAAGAGCTGGCA
 E  V  K  E  V  A  T  L  S  C  G  H  N  V  S  V  E  E  L  A
181                                                        240
CAAACTCGCATCTACTGGCAAAAGGAGAAGAAAATGGTGCTGACTATGATGTCTGGGGAC
 Q  T  R  I  Y  W  Q  K  E  K  K  M  V  L  T  M  M  S  G  D
241                                                        300
ATGAATATATGGCCCGAGTACAAGAACCGGACCATCTTTGATATCACTAATAACCTCTCC
 M  N  I  W  P  E  Y  K  N  R  T  I  F  D  I  T  N  N  L  S
301                                                        360
ATTGTGATCCTGGCTCTGCGCCCATCTGACGAGGGCACATACGAGTGTGTTGTTCTGAAG
 I  V  I  L  A  L  R  P  S  D  E  G  T  Y  E  C  V  V  L  K
361                                                        420
TATGAAAAAGACGCTTTCAAGCGGGAACACCTGGCTGAAGTGACGTTATCAGTCAAAGCT
 Y  E  K  D  A  F  K  R  E  H  L  A  E  V  T  L  S  V  K  A
421                                                        480
GACTTCCCTACACCTAGTATATCTGACTTTGAAATTCCAACTTCTAATATTAGAAGGATA
 D  F  P  T  P  S  I  S  D  F  E  I  P  T  S  N  I  R  R  I
481                                                        540
ATTTGCTCAACCTCTGGAGGTTTTCCAGAGCCTCACCTCTCCTGGTTGGAAAATGGAGAA
 I  C  S  T  S  G  G  F  P  E  P  H  L  S  W  L  E  N  G  E
541                                                        600
GAATTAAATGCCATCAACACAACAGTTTCCCAAGATCCTGAAACTGAGCTCTATGCTGTT
 E  L  N  A  I  N  T  T  V  S  Q  D  P  E  T  E  L  Y  A  V
601                                                        660
AGCAGCAAACTGGATTTCAATATGACAACCAACCACAGCTTCATGTGTCTCATCAAGTAT
 S  S  K  L  D  F  N  M  T  T  N  H  S  F  M  C  L  I  K  Y
661                                                        720
GGACATTTAAGAGTGAATCAGACCTTCAACTGGAATACAACCAAGCAAGAGCATTTTCCT
 G  H  L  R  V  N  Q  T  F  N  W  N  T  T  K  Q  E  H  F  P
721 BclI                                                   780
GATCATCAGGAGCCCAAATCTTCTGACAAAACTCACACGTCTCCACCGTCCCCGGCGCCT
 D  H  Q  E  P  K  S  S  D  K  T  H  T  S  P  P  S  P  A  P
781                                                        840
GAACTCCTGGGGGGACCGTCAGTCTTCCTCTTCCCCCCAAAACCCAAGGACACCCTCATG
 E  L  L  G  G  P  S  V  F  L  F  P  P  K  P  K  D  T  L  M
841                                                        900
ATCTCCCGGACCCCTGAGGTCACATGCGTGGTGGTGGACGTGAGCCACGAAGACCCTGAG
 I  S  R  T  P  E  V  T  C  V  V  V  D  V  S  H  E  D  P  E
901                                                        960
GTCAAGTTCAACTGGTACGTGGACGGCGTGGAGGTGCATAATGCCAAGACAAAGCCGCGG
 V  K  F  N  W  Y  V  D  G  V  E  V  H  N  A  K  T  K  P  R
```

FIG. 7

```
961                                                          1020
GAGGAGCAGTACAACAGCACGTACCGTGTGGTCAGCGTCCTCACCGTCCTGCACCAGGAC
 E  E  Q  Y  N  S  T  Y  R  V  V  S  V  L  T  V  L  H  Q  D
1021                                                         1080
TGGCTGAATGGCAAGGAGTACAAGTGCAAGGTCTCCAACAAAGCCCTCCCAGCCCCCATC
 W  L  N  G  K  E  Y  K  C  K  V  S  N  K  A  L  P  A  P  I
1081                                                         1140
GAGAAAACCATCTCCAAAGCCAAAGGGCAGCCCCGAGAACCACAGGTGTACACCCTGCCC
 E  K  T  I  S  K  A  K  G  Q  P  R  E  P  Q  V  Y  T  L  P
1141                                                         1200
CCATCCCGGGAGGAGATGACCAAGAACCAGGTCAGCCTGACCTGCCTGGTCAAAGGCTTC
 P  S  R  E  E  M  T  K  N  Q  V  S  L  T  C  L  V  K  G  F
1201                                                         1260
TATCCCAGCGACATCGCCGTGGAGTGGGAGAGCAATGGGCAGCCGGAGAACAACTACAAG
 Y  P  S  D  I  A  V  E  W  E  S  N  G  Q  P  E  N  N  Y  K
1261                                                         1320
ACCACGCCTCCCGTGCTGGACTCCGACGGCTCCTTCTTCCTCTATAGCAAGCTCACCGTG
 T  T  P  P  V  L  D  S  D  G  S  F  F  L  Y  S  K  L  T  V
1321                                                         1380
GACAAGAGCAGGTGGCAGCAGGGGAACGTCTTCTCATGCTCCGTGATGCATGAGGCTCTG
 D  K  S  R  W  Q  Q  G  N  V  F  S  C  S  V  M  H  E  A  L
1381                                            1428
CACAACCACTACACGCAGAAGAGCCTCTCCCTGTCCCCGGGTAAATGA
 H  N  H  Y  T  Q  K  S  L  S  L  S  P  G  K trm
```

XANTHENE DERIVATIVES, THEIR PRODUCTION AND USE

BACKGROUND OF THE INVENTION

1. Field of the Invention

The present invention relates to xanthene derivatives which are useful as pharmaceutical composition such as immunomodulator and so on.

2. Description of Related Art

An immune reaction is a cellular or humoral reaction in order to eliminate non-self under the basis of self/non-self discrimination. An immune system is a self-defense reaction which is conducted by the body when a foreign antigen invades into the body, including various infectious pathogens, and is an important system for defending oneself against a foreign enemy. The breakdown of this immune system and excess reaction makes it harmful to self, and causes various diseases, including autoimmune diseases and allergic diseases. Various diseases caused by the breakdown of this immune systems and excess reaction can be ameliorated by regulating the immune reaction.

The recent progress of the medical technique made it possible to manage organ transplantation. The immune reaction of the body interferes with this organ transplantation, and the suppression of the immune reaction is required for graft survival. Immunocompetent cells participate in the inflammatory reaction, and the excess immune reaction directly exacerbate the inflammatory reaction. Accordingly, various chronic inflammatory diseases such as rheumatoid arthritis and nephritis, can be ameliorated by suppressing the immune reaction.

When activated through recognition of antigens, T cells start to produce cytokines such as interleukin-2 (hereinafter abbreviated to IL-2) and proliferate. It has recently become clear that full activation of T cells requires second signal, termed costimulatory signal, from antigen presenting cells, in addition to the antigen specific signal delivered by T-cell receptors, hereinafter abbreviated "TCR", engagement. Antigen stimulation through TCR without eostimulatory signal not only results in the suppression of T cell activation but includes an antigen specific unresponsive state (anergy), in which T-cells can not be activated even when they receive both antigenic stimulation through TCR and constimulatory signal again.

It is a B7/CD28 ligand receptor, which is a molecule serving for this costimulatory signal, to which a special attention is paid. B7 is expressed on the surface of the antigen presenting cells or activated B cells, while CD28 is expressed on the surface of T-cells, and the signal is transmitted to T-cells by interaction between them (Annual Review of Immunology, 1993, 11: 191–212). It is known that B7 includes two kinds of molecules, e.g. B7-1 (CD80) and B7-2 (CD86). It is assumed that there is a difference in role between them because timing of their expression on the surface is quite different. A receptor, which binds to B7 ligand includes not only CD28 which transmits an activated signal, but also CTLA-4 which is considered to deliver a negative signal. It is considered that CTLA-4, expressed on the activated T-cells, induces to an apoptosis by binding with B7, thereby terminating the immune response. It is reported that a binding activity of CTLA-4 to B7 is stronger than that of CD28 by one order. These molecules are proteins which belong to the immunoglobulin superfamily.

A trial of inhibiting this costimulatory signal to induce unresponsiveness to a specific antigen has already begun, and antibody against B7 ligand and a solubilized protein of CD28 or CTLA-4 have been tried to use as an inhibitor, thereby obtaining expected results (Annual Review of Immunology, 1993, 11: 191–212).

Heretofore, low-molecular compounds such as antimetabolite inhibiting the proliferation of activated immune cells, and steroids which is considered to have an activity of inhibiting production of various cytokines, have widely been used for immunosuppression. These compounds have a strong side effect, and it is hard to say that they specifically act on the immune cells.

Cyclosporin A and FK506 have recently been found as a drug for inhibiting a signal for activation of T-cells by antigen stimulation, and have generally been used for immunosuppression on organ transplantation. Although these drugs have high specificity to the immune system, toxicity is considerably remarkable.

The drugs for inhibiting the costimulatory signal can be expected not only inhibitory action of the immune cells but also suppressive activity of antigen specific immune response, i.e. action for inducing an unresponsive state to a specific antigen. Such a state makes it possible to ameliorate diseases due to the excess immune reaction against the specific antigen without damaging wide immune reaction of the body. It is particularly advantageous for immunosuppression on organ transplantation and inhibition of an allergic reaction. A trial of inhibiting a signal with an antibody against costimulatory molecules, thereby obtaining expected results. Accordingly, the low-molecular weight compound having such an action is useful as an antigen specific immunosuppressive agents for development of new immunotherapy.

Under these circumstances, the present inventors intensively studied so as to obtain a drug inhibiting binding of B7-1 to CD28 from microorganism metabolites. As a result, the present inventors succeeded in isolating a novel compound referred to as TAN-2421 from a culture, and found that the present compound inhibits not only a binding of B7-1 to CD28 but also an B7-1-dependent activation of T cells. The present inventors made further investigations based on these findings, and accomplished the present invention.

SUMMARY OF THE INVENTION (1) A compound represented by the general formula:

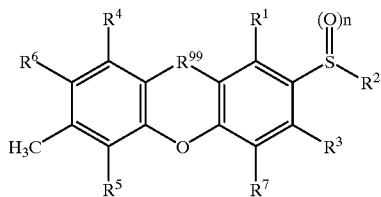

[1]

wherein $R^1$ is a carboxyl group which may be esterified or amidated; $R^2$ is a hydrogen atom, a hydroxyl group, or a hydrocarbon group which may be substituted; $R^3$ and $R^4$ are the same or different and are a hydroxyl group which may be substituted; $R^5$ and $R^6$ are the same or different and are a hydrogen atom or a halogen atom; $R^7$ is a hydrogen atom, a nitro group, a halogen atom, a hydrocarbon group which may be substituted, a heterocyclic group which may be substituted, or an acyl group which may be substituted; n is an integer of 0 to 2; and $R^{99}$ is a carbonyl or —CH$_2$—; and when n is 0, $R^2$ may be a group represented by the formula:

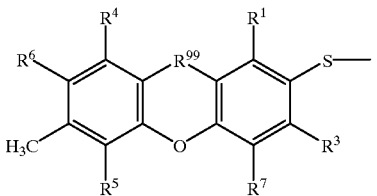

wherein the symbols have the same meanings as defined above, or a salt thereof, (2) The compound according to (1), wherein $R^7$ is a hydrogen atom or a halogen atom, (3) The compound according to (1), wherein $R^2$ is a group represented by —CH$_2$(CHOH)m—$R^{2'}$, wherein m is 0 or 1, and $R^{2'}$ is a carboxyl group which may be esterified or amidated or a hydroxylmethyl group which may be substituted; $R^7$ is a hydrogen atom; and, (4) The compound according to (1), wherein $R^2$ is (i) a hydrogen atom, (ii) a hydroxyl group or (iii) a $C_{1-19}$ hydrocarbon group which may be substituted by a group selected from the group consisting of (a) $C_{1-8}$ alkoxycarbonylcarbonyl, (b) carboxyl which may be esterified or amidated, (c) hydroxyl which may be acylated, (d) amino which may be substituted by $C_{1-10}$ alkyl, $C_{1-6}$ alkanoyl, $C_{1-6}$ alkylsulfonyl or $C_{6-14}$ arylsulfonyl, (e) $C_{1-6}$ alkoxy, (f) cyano, (g) sulfo, (h) a 5- or 6-membered heterocyclic group which may be substituted by $C_{1-6}$ alkyl, $C_{1-6}$ alkoxy, nitro, cyano, amino, halogen, hydroxyl or oxo, (i) nitro, (j) halogen and (k) oxo;

$R^3$ and $R^4$ are the same or different and are a hydroxyl group which may be substituted by (a) a acyl group or (b) a $C_{1-10}$ alkyl group which may be substituted;

$R^7$ is (i) a hydrogen atom, (ii) a nitro group, (iii) a halogen atom, (iv) a $C_{1-19}$ hydrocarbon group which may be substituted by a group selected from the group consisting of (a) carboxyl which may be esterified or amidated, (b) hydroxyl which may be acylated, (c) amino which may be substituted by $C_{1-10}$ alkyl, $C_{1-6}$ alkanoyl, $C_{1-6}$ alkylsulfonyl or $C_{6-14}$ arylsulfonyl, (d) $C_{1-6}$ alkoxy, (e) cyano, (f) sulfo, (g) a 5- or 6-membered heterocyclic group which may be substituted by $C_{1-6}$ alkyl, $C_{1-6}$ alkoxy, nitro, cyano, amino, halogen, hydroxyl or oxo, (h) nitro, (i) halogen and (j) oxo, (v) a 5- or 6-membered heterocyclic group which may be substituted by a group consisting of (a) $C_{1-6}$ alkyl, (b) carboxyl which may be esterified or amidated, (c) hydroxy which may be acylated, (d) amino which may be substituted by $C_{1-10}$ alkyl, $C_{1-6}$ alkanoyl, $C_{1-6}$ alkylsulfonyl or $C_{6-14}$ arylsulfonyl, (e) $C_{1-6}$ alkoxy, (f) cyano, (g) sulfo, (h) nitro, (i) halogen and (j) oxo, or (vi) an acyl group which may be substituted by a group selected from the group consisting of (a) $C_{1-6}$ alkyl, (b) carboxyl which may be esterified or amidated, (c) hydroxyl which may be acylated, (d) amino which may be substituted by $C_{1-10}$ alkyl, $C_{1-6}$ alkanoyl, $C_{1-6}$ alkylsulfonyl or $C_{6-14}$ arylsulfonyl, (e) $C_{1-6}$ alkoxy, (f) cyano, (g) sulfo, (h) a 5- or 6-membered heterocyclic group which may be substituted by $C_{1-6}$ alkyl, $C_{1-6}$ alkoxy, nitro, cyano, amino, halogen, hydroxyl, or oxo, (i) nitro, (j) halogen and (k) oxo or its condensed heterocyclic group, (5) The compound according to (1), wherein $R^1$ is a carboxyl group which may be esterified;

$R^2$ is (i) a hydrogen atom, (ii) a hydroxyl group, (iii) a $C_{1-10}$ alkyl group which may be substituted by a group selected from the group consisting of (a) $C_{1-8}$ alkoxycarbonylcarbonyl, (b) carboxyl which may be esterified or amidated, (c) hydroxyl which may be acylated, (d) amino which may be substituted by $C_{1-4}$ alkylsulfonyl or $C_{6-14}$ arylsulfonyl, (e) $C_{1-6}$ alkoxy, (f) cyano, (g) sulfo and (h) a 5- or 6-membered heterocyclic group which may be substituted by hydroxyl or oxo, (iv) a $C_{2-8}$ alkenyl group which may be substituted by carboxyl, (v) a $C_{7-19}$ aralkyl group which may be substituted by a group selected from the group consisting of (a) cyano, (b) carboxyl which may be esterified or amidated, (c) hydroxyl, (d) nitro, (e) halogen and (f) a 5- or 6-membered nitrogen-containing heterocyclic group;

$R^3$ and $R^4$ are (i) a hydroxyl group which may be substituted by $C_{1-7}$ acyl or (ii) a $C_{1-10}$ alkoxy group which may be substituted by $C_{1-6}$ alkoxy;

$R^7$ is (i) a hydrogen atom, (ii) a nitro group, (iii) a halogen atom, (iv) a $C_{1-10}$ alkyl group, (v) a $C_{6-14}$ aryl group which may be substituted by a group selected from the group consisting of (a) $C_{1-6}$ alkyl, (b) carboxyl, (c) $C_{1-6}$ alkoxy, (d) amino, (e) nitro and (f) halogen, (vi) a $C_{1-6}$ alkanoyl group, or (vii) a 5- or 6-membered heterocyclic group containing 1 to 4 hetero atoms selected from nitrogen, oxygen and sulfur atoms in addition to carbon atom(s) or its condensed heterocyclic group with a benzene ring, (6) The compound according to (1), wherein $R^1$ is a group represented by —COOR$^{28}$, wherein $R^{28}$ is a hydrogen atom or a $C_{1-8}$ alkyl group which may be substituted with a $C_{1-6}$ alkoxy;

$R^2$ is (i) a hydrogen atom, (ii) a hydroxyl group, (iii) a group represented by the formula —CH$_2$(CHOR$^b$)m$^1$COOR$^{29}$, wherein m$^1$ is 0 or 1, R$^b$ is a hydrogen atom or a $C_{1-6}$ alkanoyl group, and $R^{29}$ is a hydrogen atom or a $C_{1-8}$ alkyl group which may be substituted by $C_{1-6}$ alkoxy, $C_{1-6}$ alkanoyloxy or $C_{4-7}$ cycloalkoxycarbonyloxy, (iv) a group represented by the formula —CH$_2$(CHOH)m$^2$CONR$^{30}$R$^{31}$, wherein m$^2$ is 0 or 1, $R^{30}$ and $R^{31}$ are the same or different and are a hydrogen atom or a $C_{1-8}$ alkyl group which may be substituted by carboxyl, $C_{1-6}$ alkoxy or $C_{2-5}$ alkoxycarbonyl, (v) a group represented by the formula —CH$_2$(CHOH)m$^3$CONHS(=O)$_2$R$^{32}$, wherein m$^3$ is 0 or 1, and $R^{32}$ is a $C_{1-4}$ alkyl group which may be substituted by 1 to 3 halogen atoms or a $C_{6-14}$ aryl group which may be substituted by $C_{1-6}$ alkyl, nitro, $C_{1-6}$ alkoxy or halogen, (vi) a group represented by the formula —CH$_2$(CHOH)m$^4$CONHOR$^{33}$, wherein m$^4$ is 0 or 1, and $R^{33}$ is a hydrogen atom or a $C_{1-4}$ alkyl group, (vii) a group represented by the formula —CH$_2$(CHOH)m$^5$R$^{34}$ wherein m$^5$ is 0 or 1, and $R^{34}$ is a 3- to 8-membered heterocyclic group containing 1 to 4 hetero atoms selected from nitrogen, oxygen and sulfur atoms in addition to carbon atoms, which may be substituted by hydroxyl or oxo, (viii) a group represented by the formula —CH$_2$(CHOH)m$^6$—CH$_2$OR$^{35}$, wherein m$^6$ is 0 or 1, and $R^{36}$ is a hydrogen atom, a $C_{1-8}$ alkyl group or a $C_{1-6}$ alkanoyl group, (ix) a group represented by the formula —CH$_2$(CHOH)m$^7$—COCOOR$^{36}$, wherein m$^7$ is 0 or 1, and $R^{36}$ is a hydrogen atom or a $C_{1-8}$ alkyl group, (x) a $C_{2-8}$ alkyl group which may be substituted by carboxyl, or (xi) a $C_{7-19}$ aralkyl group which may be substituted by carboxyl, cyano, halogen, nitro, hydroxyl, carbamoyl, $C_{2-5}$ alkoxycarbonyl or a 3- to 8-membered heterocyclic group containing 1 to 4 hetero atoms selected from nitrogen, oxygen and sulfur atoms in addition to carbon atom(s);

$R^3$ is a group represented by the formula —$OR^{37}$, wherein $R^{37}$ is a hydrogen atom, a $C_{1-8}$ alkyl group which may be substituted by $C_{1-6}$ alkoxy, or a $C_{1-6}$ alkanoyl group;

$R^4$ is (i) a group represented by the formula —$OR^{38}$, wherein $R^{38}$ is (a) a hydrogen atom, (b) a $C_{1-8}$ alkyl group which may be substituted by $C_{1-6}$ alkoxy, (c) a $C_{1-6}$ alkanoyl group or (d) a $C_{7-11}$ aroyl group, or (ii) a group represented by the formula —$OCOOR^{39}$, wherein $R^{39}$ is a $C_{1-6}$ alkyl group or a $C_{6-14}$ aryl group; and $R^7$ is (i) a hydrogen atom, (ii) a nitro group, (iii) a halogen atom, (iv) a $C_{1-8}$ alkyl group, (v) a $C_{6-14}$ aryl group which may be substituted by halogen, carboxyl, $C_{1-6}$ alkyl, $C_{1-6}$ alkoxy, amino or nitro, (vi) a $C_{1-6}$ alkanoyl group or (vii) a 3- to 8-membered heterocyclic group which contains 1 to 4 hetero atoms selected from nitrogen, oxygen and sulfur atoms in addition to carbon atom(s) or its condensed heterocyclic group with a 6- to 8-membered carbon ring or with a 6- to 8-membered heterocyclic group, (7) The compound according to (1), wherein $R^2$ is a group represented by —$CH_2COOR^{40}$, wherein $R^{40}$ is a hydrogen atom or a $C_{1-4}$ alkyl group which may be substituted by $C_{1-6}$ alkoxy, $C_{1-6}$ alkanoyloxy or $C_{4-7}$ cycloalkoxycarbonyloxy; $R^3$ and $R^4$ are a hydroxyl group; $R^5$ and $R^6$ are a chlorine atom; and $R^7$ is a hydrogen atom, a nitro group, a bromine atom or an iodine atom, (8) The compound according to (1), wherein n is 0 or 1, (9) The compound according to (1), wherein $R^{99}$ is a carbonyl,

(10) The compound according to (1), which is represented by the formula:

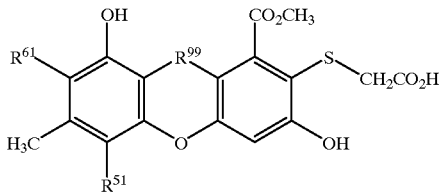

wherein $R^{51}$ and $R^{61}$ are the same or different and are a hydrogen atom or a chlorine atom,

(11) The compound according to (1), which represented by the formula:

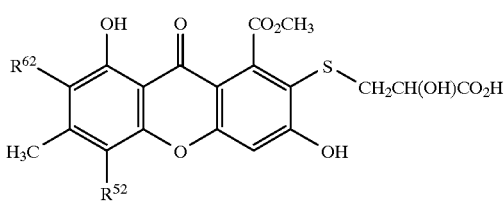

wherein $R^{52}$ and $R^{62}$ are the same or different and are a hydrogen atom or a chlorine atom,

(12) The compound according to (1), wherein the compound is (1) methyl 2-(carboxymethylsulfinyl)-5,7-dichloro-3,8-dihydroxy-6-methyl-9-oxo-9H-xanthene-1-carboxylate, (2) methyl 2-(carboxymethylsulfinyl)-5,7-dichloro-3,8-dihydroxy-4-iodo-6-methyl-9-oxo-9H-xanthene-1-carboxylate, (3) methyl 5,7-dichloro-3,8-dihydroxy-6-methyl-9-oxo-2-(pivaloyloxymethoxycarbonylmethylthio)-9H-xanthene-1-carboxylate, (4) methyl 5,7-dichloro-3,8-dihydroxy-6-methyl-9-oxo-2-(pivaloyloxymethoxycarbonylmethylsulfinyl)-9H-xanthene-1-carboxylate or 5) methyl 5,7-dichloro-2-[1-(cyclohexyloxycarbonyloxy)ethoxycarbonylmethylthio]-3,8-dihydroxy-6-methyl-9-oxo-9H-xanthene-1-carboxylate,

(13) A method for producing the compound according to (10) or (11), or salts thereof, comprising culturing a microorganism, which belongs to the genus Aspergillus and is capable of producing the compound, in a medium; producing the compound to accumulate in a culture; and collecting the compound,

(14) A microorganism, Aspergillus terreus FL-67283 strain, capable of producing the compound according to (10) or (11),

(15) A pharmaceutical composition comprising the compound according to (1), or a salt thereof,

(16) A composition for inhibiting an signal transduction of T-cell, comprising the compound according to (1), or a salt thereof,

(17) The pharmaceutical composition according to (15), which is an immunomodulator,

(18) The pharmaceutical composition according to (17), wherein the immunomodulator is a graft rejection inhibitor, or a composition for therapeutic treatment of allergy, rheumatoid arthritis, autoimmune disease, nephritis or diabetes mellitus,

(19) A method for producing the compound according to (1), which represented by the general formula:

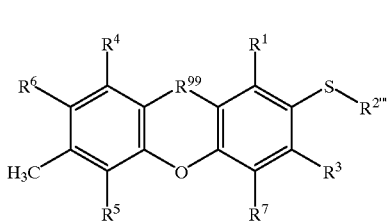

wherein $R^{2'''}$ is a hydrogen atom or a hydrocarbon group which may be substituted, $R^1$ is a carboxyl group which may be esterified or amidated; $R^3$ and $R^4$ are the same or different and are a hydroxyl group which may be substituted; $R^5$ and $R^6$ are the same or different and are a hydrogen atom or a halogen atom; $R^7$ is a hydrogen atom, a nitro group, a halogen atom, a hydrocarbon group which may be substituted, a heterocyclic group which may be substituted, or an acyl group which may be substituted; and $R^{99}$ is a carbonyl or —$CH_2$—; or a salt thereof, which comprises subjecting a compound represented by the general formula:

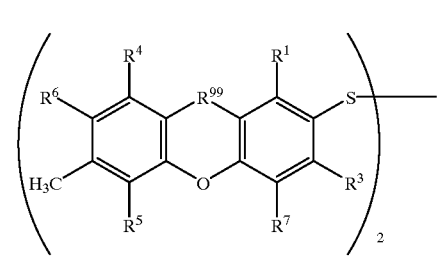

wherein each of symbols is same as above, or a salt thereof to a reduction reaction, followed by an introduction reaction of the hydrocarbon group if necessary,

(20) A method for inhibiting signal transduction of T-cell in a mammal, which comprises administering an effective amount of the compound according to (1), or a salt thereof, to the mammal,

(21) A method for immunomodulation in a mammal, which comprises administering an effective amount of the compound according to (1), or a salt thereof, to the mammal,

(22) A method for treating or preventing graft rejection, allergy, rheumatoid arthritis autoimmune disease, nephritis or diabetes mellitus in a mammal, which comprises administering an effective amount of the compound according to (1), or a salt thereof, to the mammal,

(23) Use of the compound according to (1), or a salt thereof, for production of an inhibitor for signal transduction of T-cell,

(24) Use of the compound according to (1), or a salt thereof, for production of an immunomodulator.

(25) Use of the compound according to (1) or a salt thereof for production of a graft rejection inhibitor, or a pharmaceutical composition for therapeutic treatment of allergy, rheumatoid arthritis, autoimmune disease, nephritis or diabetes mellitus,

(26) A method for screening for a compound having an activity for inhibiting or enhancing a binding of CD28 to B7-1, or a salt thereof, which comprises comparing (1) an amount of binding between CD28 and B7-1-Ig obtained when CHO-cell containing CD28 or its cell membrane fraction is contacted with soluble B7-1-Ig, with (2) an amount of binding between CD28 and B7-1-Ig obtained when CHO-cell containing CD28 or its cell membrane fraction is contacted with soluble B7-1-Ig and a test compound,

(27) A method for screening for a compound having an activity for inhibiting an IL-2 production, or a salt thereof, which comprises comparing (1) an amount of IL-2 produced when CHO-cell containing B7-1 or its cell membrane fraction is contacted with T-cell, with (2) an amount of IL-2 produced when CHO-cell containing B7-1 or its cell membrane fraction is contacted with T-cell and a test compound,

(28) A compound having an activity for inhibiting or enhancing a binding of CD28 to B7-1, or a salt thereof, which is obtained by using the screening method according to (26),

(29) A compound having an activity of inhibiting an IL-2 production, or a salt thereof, which is obtained by using the screening method of (27), and

(30) CHO cell designated by CD28-CHO-11 (FERM BP-5431), CHO cell represented by B7-1-CHO-22 (FERM BP-5430) or CHO cell represented by sB7-1-Ig-CHO-20 (FERM BP-5432).

BRIEF DESCRIPTION OF THE DRAWINGS

FIG. 2 shows the nucleotide sequence of the CD28 gene as cloned, and the amino acid sequence deduced therefrom.

FIG. 4 shows the nucleotide sequence of the B7-1 gene as cloned, and the amino acid sequence deduced therefrom.

FIG. 6 shows the nucleotide sequence of the soluble B7-1-Ig gene as cloned, and the amino acid sequence deduced therefrom.

FIG. 7 shows the nucleotide sequence of the solubilized B7-1 gene as cloned, and the amino acid sequence deduced therefrom. Continued from FIG. 6.

DESCRIPTION OF THE PREFERRED EMBODIMENTS

Figure 1:
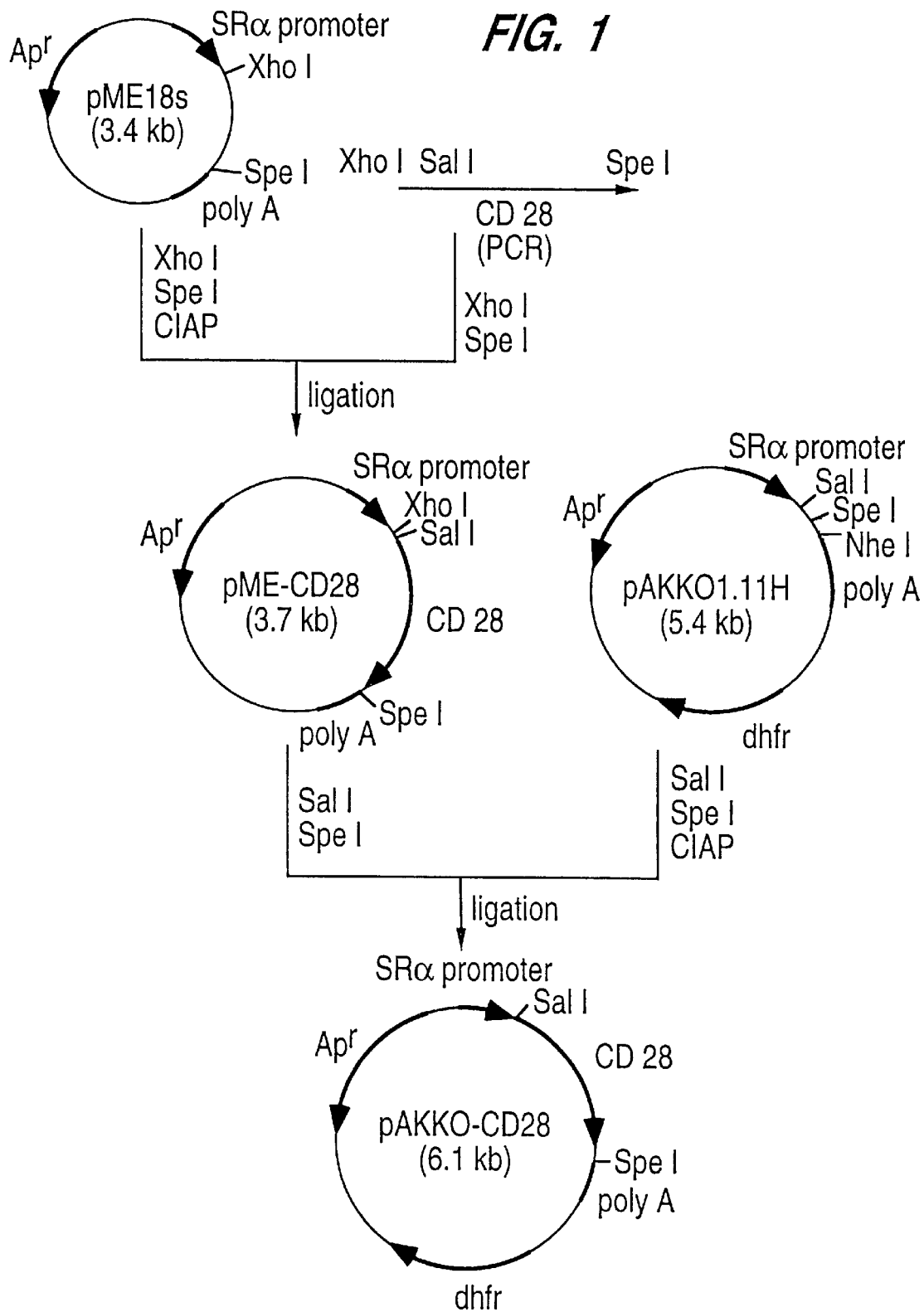
FIG. 1 shows a schematic diagram of construction of a CD28 gene expression plasmid (pAKKO-CD28). CD28 represents the CD28 gene, dhfr represents the dihydrofolate reductase gene; Ap$^r$ represents the ampicillin resistance gene; poly A represents the polyadenylation signal.

With respect to general formula above, the esterified carboxyl group shown by $R^1$ is exemplified by pharmacologically acceptable ones or those which become pharmacologically acceptable in the body.

Examples of the carboxyl group which may be esterified are a group represented by the formula —COOR$^8$, wherein R$^8$ is a hydrogen atom or a hydrocarbon group which may be substituted.

Examples of the hydrocarbon group shown by R$^8$, $C_{1-19}$ hydrocarbon group such as (1) a $C_{1-10}$ alkyl group (e.g. methyl, ethyl, propyl, isopropyl, butyl, isobutyl, sec-butyl, tert-butyl, pentyl, hexyl, heptyl, octyl, etc., preferably a $C_{1-8}$ alkyl group), (2) a $C_{2-8}$ alkenyl group (e.g. vinyl, allyl, isopropenyl, 1-propenyl, 2-butenyl, 3-butenyl, 2-hexenyl, 2-octenyl, etc., preferably a $C_{2-6}$ alkenyl), (3) a $C_{2-8}$ alkynyl group (e.g. ethynyl, 1-propynyl, 2-propynyl, 1-butynyl, 2-butynyl, 3-butynyl, 2-hexynyl, 2-octynyl, etc., preferably a $C_{2-6}$ alkynyl), (4) a $C_{3-6}$ cycloalkyl group (e.g. cyclopropyl, cyclobutyl, cyclopentyl, cyclohexyl, etc.), (5) a $C_{6-14}$ aryl group (e.g. phenyl, naphthyl, etc., optionally having a $C_{1-6}$ alkyl substituent on the aryl ring.) and (6) a $C_{7-19}$ aralkyl group (e.g. benzyl, phenethyl, benzhydryl, trityl, etc.). Of these groups, the $C_{1-8}$ alkyl group, particularly the $C_{1-4}$ alkyl group (e.g. methyl, ethyl, propyl, isopropyl, butyl, isobutyl, sec-butyl, tert-butyl, etc.) are preferred.

Examples of the substituent of the $C_{1-10}$ alkyl group, the $C_{2-8}$ alkenyl group or the $C_{2-8}$ alkynyl group among these hydrocarbon groups, are (1) an amino group which may be substituted by 1 or 2 substituents selected from the group consisting of (a) a $C_{1-10}$ alkyl group (e.g. methyl, ethyl, propyl, isopropyl, butyl, isobutyl, sec-butyl, tert-butyl, etc.), (b) a $C_{1-6}$ alkanoyl group (e.g. formyl, acetyl, propionyl, isopropionyl, butyryl, isobutyryl, valeryl, isovaleryl, pivaloyl, hexanoyl, etc.), (c) a $C_{7-11}$ aroyl group (e.g. benzoyl, p-toluoyl, naphthoyl, etc.), (d) a $C_{2-7}$ alkoxycarbonyl group (e.g. methoxycarbonyl, ethoxycarbonyl, propoxycarbonyl, butoxycarbonyl, tert-butoxycarbonyl, etc.), (e) a $C_{8-14}$ aralkyloxycarbonyl group (e.g. benzyloxycarbonyl, phenethyloxycarbonyl, etc.), (f) a $C_{1-6}$ alkylsulfonyl group (e.g. methylsulfonyl, ethylsulfonyl, propylsulfonyl, etc.) and (g) a $C_{6-14}$ arylsulfonyl group (e.g. benzenesulfonyl, toluenesulfonyl, etc.), (2) a hydroxyl group which may be substituted by a group selected from the group consisting of (a) a $C_{1-6}$ alkyl group, (b) a $C_{7-19}$ aralkyl groups (benzyl, phenethyl, benzhydryl, etc.), (c) a $C_{1-6}$ alkanoyl group, (d) a $C_{7-11}$ aroyl group and (e) a $C_{4-7}$ cycloalkoxycarbonyl group (e.g. cyclohexyloxycarbonyl, etc.), (3) a carboxyl group, (4) a $C_{2-5}$ alkoxycarbonyl group (e.g. methoxycarbonyl, ethoxycarbonyl, etc.), (5) a $C_{8-14}$ aralkyloxycarbonyl group (e.g. benzyloxycarbonyl, etc.), (6) a carbamoyl group, (7) a nitro group, (8) a halogen atom, (9) a cyano group, (10) an oxo group and (11) a sulfo group. The number of the substituents is about 1 to 3. Of these substituents, a hydroxyl group which may be substituted by a $C_{1-6}$ alkyl group is preferred, and more preferable examples are a hydroxyl group substituted by methyl or ethyl.

Examples of the substituent of the $C_{3-6}$ cycloalkyl group, the $C_{6-14}$ aryl group or a $C_{7-19}$ aralkyl group are a $C_{1-6}$ alkyl group which may be substituted by a group selected from the group consisting of (a) halogen, (b) $C_{1-6}$ alkanoyl, (c) $C_{7-11}$ aroyl, (d) $C_{2-7}$ alkoxycarbonyl, (e) $C_{7-15}$ aryloxycarbonyl, (f) $C_{8-14}$ aralkyloxycarbonyl, (g) $C_{1-6}$ alkylsulfonyl, (h) $C_{6-14}$ arylsulfonyl, (i) hydroxyl, (j) carboxyl, (k) nitro and (l) cyano, in addition to the above substituents for the $C_{1-10}$ alkyl group.

The amidated carboxyl group shown by $R^1$ is exemplified by pharmacologically acceptable ones or those which become pharmacologically acceptable in the body. Examples of the amidated carboxyl group are a group represented by the formula —CONR$^9$R$^{10}$, wherein R$^9$ and R$^{10}$ are the same or different and are a hydrogen atom or a hydrocarbon group which may be a substituted or a heterocyclic group which may be substituted, and R$^9$ and R$^{10}$ may be combined with the adjacent nitrogen atom to form a nitrogen-containing heterocyclic group which may be substituted, and so on.

The hydrocarbon group which may be substituted shown by R$^9$ and R$^{10}$ has the same definition as that of the above hydrocarbon group which may be substituted shown by R$^8$. Among them, preferable examples of the hydrocarbon group are the $C_{1-8}$ alkyl group. Preferable examples of the substituent for the hydrocarbon group are a hydroxyl group which may be substituted by an $C_{1-4}$ alkyl group, a carboxyl group and a $C_{2-5}$ alkoxycarbonyl group.

Examples of the heterocyclic group of the heterocyclic group which may be substituted shown by R$^9$ and R$^{10}$ are a 3- to 8-membered, preferably 5- or 6-membered heterocyclic group containing 1 to 4 hetero atoms selected from nitrogen, oxygen and sulfur atoms in addition to carbon atoms, or its condensed heterocyclic group with a 6- to 8-membered carbon ring or with a 6- to 8-membered heterocyclic group (e.g. 2- or 3-thienyl, 2- or 3-furyl, 1-, 2- or 3-pyrrolyl, 3-, 4- or 5-pyrazolyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H- or 2H-tetrazolyl, 2-, 3- or 4-pyridyl, 2-, 4-, or 5-pyrimidinyl, 3- or 4-pyridazinyl, quinolyl, isoquinolyl, indolyl, piperazinyl, morpholinyl, 2H- or 4H-pyranyl, 2-benzo[b]furanyl, etc.).

Examples of the substituent of the heterocyclic group are (1) a $C_{1-6}$ alkyl group which may have 1 to 3 substituents selected from the group consisting of (a) a nitro group, (b) a halogen atom and (c) a $C_{1-6}$ alkoxy group (e.g. methoxy, ethoxy, propoxy, isopropoxy, butoxy, isobutoxy, sec-butoxy, tert-butoxy, etc.), (2) a $C_{6-14}$ aryl group which may have 1 to 4 substituents selected from the group consisting of (a) a nitro group, (b) a halogen atom, (c) a $C_{1-6}$ alkyl group and (d) a $C_{1-6}$ alkoxy group, (3) a $C_{7-13}$ aralkyl group which may have 1 to 4 substituents selected from the group consisting of (a) a nitro group, (b) a halogen atom, (c) a $C_{1-6}$ alkyl group and (d) a $C_{1-6}$ alkoxy group, (4) a hydroxyl group which may be substituted by a group selected from the group consisting of (a) a $C_{1-6}$ alkyl group, (b) $C_{7-13}$ aralkyl group, (c) a $C_{1-6}$ alkanoyl group and (d) a $C_{7-11}$ aroyl group, (5) a carboxyl group, (6) a $C_{2-5}$ alkoxycarbonyl group, (7) a $C_{8-14}$ aralkyloxycarbonyl group, (8) a carbamoyl group, (9) a nitro group, (10) a halogen atom, (11) an amino group which may have 1 to 2 substituents selected from the group consisting of (a) a $C_{1-10}$ alkyl group, (b) a $C_{7-13}$ aralkyl group, (c) a $C_{1-6}$ alkanoyl group, (d) a $C_{7-11}$ aroyl group, (e) a $C_{2-7}$ alkoxycarbonyl group, (f) a $C_{8-14}$ aralkyloxycarbonyl group, (g) a $C_{1-6}$ alkylsulfonyl group and (h) a $C_{6-14}$ arylsulfonyl group, (12) a cyano group, (13) an oxo group, and (14) a sulfo group. The number of the substituents is about 1 to 5.

Examples of the nitrogen-containing heterocyclic group of the nitrogen-containing heterocyclic group which may be substituted, formed by R$^9$ and R$^{10}$ in combination with the adjacent nitrogen atom, are a 5- to 8-membered, preferably 5- or 6-membered heterocyclic group which may contain 1 to 4 hetero atoms selected from oxygen, sulfur and nitrogen atoms in addition to the nitrogen atom, or its condensed heterocyclic group with a 6- to 8-membered carbon ring or with a 6- to 8-membered heterocyclic group.

Specifically, preferable examples of the nitrogen-containing heterocyclic group are (1) a 5-membered heterocyclic group which may contain 1 to 3 hetero atoms selected from oxygen, sulfur and nitrogen atoms in addition to the nitrogen atom (e.g. pyrrolidin-1-yl, 2-pyrrolin-1-yl, 1,3-diazabicyclopentan-1-yl, 1-aza-3-oxacyclopentan-1-yl, 1-aza-3-thiacyclopentan-1-yl, pyrazol-1-yl, pyrazolidin-1-yl, 3-pyrazolin-2-yl, 2-imidazolidin-1-yl, 1,2,3-triazol-1-yl, 1,2,3-triazol-2-yl, 1,2,4-triazol-1-yl, tetrazol-1-yl, tetrazol-2-yl, etc.), (2) a 6-membered heterocyclic group which may contain 1 or 2 hetero atoms selected from oxygen, sulfur and nitrogen atoms in addition to the nitrogen atom (e.g. piperidino, thiomorpholino, morpholino, piperazinyl, 1,4-oxazin-4-yl, 1,4-thiazine-4-yl, etc.), (3) a dicyclic or tricyclic condensed heterocyclic group which may contain 1 or 2 hetero atoms selected from oxygen, sulfur and nitrogen atoms in addition to the nitrogen atom (e.g. 1H-indazol-1-yl, purin-7-yl, phenothiazin-10-yl, phenoxazin-10-yl, indol-1-yl, etc.).

Of these heterocyclic groups, the 6-membered heterocyclic group which may contain 1 or 2 hetero atoms selected from oxygen, sulfur and nitrogen atoms in addition to the nitrogen atom (e.g. piperidino, thiomorpholino, morpholino, piperazinyl, 1,4-oxazin-4-yl, 1,4-thiazin-4-yl, etc.) are preferably used.

Examples of the substituent of these heterocyclic group are the same substituent as that of the heterocyclic group which may be substituted shown by R$^9$ and R$^{10}$. The number of the substituents is about 1 to 5.

Examples of the hydrocarbon group shown by R$^2$ are the same one as the hydrocarbon group shown by R$^8$. Among them, a $C_{1-19}$ hydrocarbon group is preferred, and a $C_{1-10}$ alkyl group, a $C_{2-8}$ alkenyl group and a $C_{7-19}$ aralkyl group are more preferred. More preferable examples are a $C_{1-8}$ alkyl group and a $C_{7-19}$ aralkyl group, and particularly, a $C_{1-3}$ alkyl group (e.g. methyl, ethyl, propyl, etc.) and a benzyl group are preferred.

Examples of the substituent of the hydrocarbon group are the same substituent as that of the hydrocarbon group shown by R$^8$. In addition, examples of the substituent of the hydrocarbon group are (1) a group represented by the formula —COOR$^{11}$, wherein R$^{11}$ is a hydrocarbon group which may be substituted, in place of the $C_{2-5}$ alkoxycarbonyl group and the $C_{8-14}$ aralkyloxycarbonyl group, (2) a group represented by the formula —$CONR^{12}R^{13}$, wherein $R^{12}$ and $R^{13}$ are the same or different and represent a hydrogen atom, a hydrocarbon group which may be substituted or a heterocyclic group which may be substituted, and $R^{12}$ and $R^{13}$ may be combined with the adjacent nitrogen atom to form a nitrogen-containing heterocyclic group, (3) a group represented by the formula —$CONHS(=O)_2R^{14}$, wherein $R^{14}$ is a hydrocarbon group which may be substituted, (4) a group represented by the formula —$CONHOR^{15}$, wherein $R^{15}$ is a hydrogen atom or a hydrocarbon group which may be substituted, (5) a heterocyclic group which may be substituted, (6) a group represented by the formula —$OR^{16}$, wherein $R^{16}$ is a hydrogen atom, a hydrocarbon group which may be substituted or an acyl group which may be substituted, in place of a hydroxyl group which may have a substituent and (7) a group represented by the formula —$COCOOR^{17}$, wherein $R^{17}$ represents a hydrogen atom or a hydrocarbon group which may be substituted.

The hydrocarbon group which may be substituted shown by $R^{11}$, $R^{12}$, $R^{13}$, $R^{14}$, $R^{15}$, $R^{16}$ or $R^{17}$ has the same meaning as that of the hydrocarbon group which may be substituted shown by $R^8$.

The heterocyclic group which may be substituted shown by $R^{12}$ or $R^{13}$ has the same meaning as that of the heterocyclic group which may be substituted shown by $R^9$ or $R^{10}$. When $R^{12}$ and $R^{13}$ are combined with the adjacent nitrogen atom to form a nitrogen-containing heterocyclic group, the nitrogen-containing heterocyclic group has the same meaning as that of the nitrogen-containing heterocyclic group when $R^9$ and $R^{10}$ are combined with the adjacent nitrogen atom to form a nitrogen-containing heterocyclic group.

Examples of the acyl group which may be substituted shown by $R^{16}$ are a $C_{1-16}$ acyl group. Preferable examples of the acyl group are (1) a $C_{1-16}$ alkanoyl group (e.g. formyl, acetyl, propionyl, isopropionyl, butyryl, isobutyryl, valeryl, isovaleryl, pivaloyl, hexanoyl, myristoyl, palmitoyl, etc.), (2) a $C_{3-6}$ alkenoyl group (e.g. acryloyl, methacryloyl, crotonoyl, isocrotonoyl, etc.), (3) a $C_{4-7}$ cycloalkanecarbonyl group (e.g. cyclopropanecarbonyl, cyclobutanecarbonyl, cyclopentanecarbonyl, cyclohexanecarbonyl, etc.), (4) a $C_{7-11}$ aroyl group (e.g. benzoyl, naphthoyl, etc.), (5) a $C_{8-13}$ arylalkanoyl group (e.g. phenylacetyl, phenylpropionyl, phenylbutyryl, etc.), (6) a $C_{9-13}$ arylalkenoyl group (e.g. cinnamoyl, atropoyl, etc.), (7) a $C_{1-6}$ alkylsulfonyl group (e.g. methylsulfonyl, ethylsulfonyl, propylsulfonyl, etc.), (8) a $C_{6-14}$ arylsulfonyl group (e.g. benzenesulfonyl, etc.), (9) a $C_{1-6}$ alkoxy-carbonyl group (e.g. methoxycarbonyl, ethoxycarbonyl, etc.), (10) a $C_{6-12}$ aryloxy-carbonyl group (e.g. phenyloxycarbonyl, naphthyloxycarbony, etc.), (11) a $C_{7-12}$ aralkyloxy-carbonyl group (e.g. benzyloxycarbonyl, etc.) and so on. More preferable examples of the acyl group are a $C_{1-13}$ acyl group, etc. such as (1) a $C_{1-6}$ alkanoyl group (e.g. formyl, acetyl, propionyl, isopropionyl, butyryl, isobutyryl, valeryl, isovaleryl, pivaloyl, hexanoyl, etc.), (2) a $C_{3-6}$ alkenoyl group, (3) a $C_{4-7}$ cycloalkanecarbonyl group, (4) a $C_{7-11}$ aroyl group, (5) a $C_{8-13}$ arylalkanoyl group, (6) a $C_{9-13}$ arylalkenoyl group, (7) a $C_{1-6}$ alkylsulfonyl group, (8) a $C_{6-14}$ arylsulfonyl group and so on. Among them, a $C_{1-7}$ acyl group, etc. such as a $C_{1-6}$ alkanoyl group (e.g. $C_{1-3}$ alkanoyl such as formyl, acetyl, propionyl, isopropionyl) and a benzoyl group are preferably used.

As the substituent of the acyl group, the same substituents as those of the hydrocarbon group which may be substituted shown by $R^8$ are used. The number of substituents is about 1 to 3.

The heterocyclic group which may be substituted used as the substituent of the hydrocarbon group which may be substituted shown by $R^2$ has the same meaning as that of the heterocyclic group which may be substituted shown by $R^9$ or $R^{10}$. As the substituent of the heterocyclic group, the same substituents as those of the heterocyclic group which may be substituted shown by $R^9$ and $R^{10}$ are used. The number of the substituents is about 1 to 5.

Of these substituents of the hydrocarbon group shown by $R^2$, preferable examples are (1) a $C_{1-8}$ alkoxycarbonylcarbonyl group, (2) a carboxyl group which may be esterified, (3) a carboxyl group which may be amidated (ex. a carbamoyl group which may be substituted by a group selected from the group consisting of (i) a hydroxyl, (ii) a $C_{1-6}$ alkoxy, (iii) a halogeno-$C_{1-6}$ arylsulfonyl, (iv) a $C_{1-6}$ alkylsulfonyl, (v) a $C_{6-14}$ arylsulfonyl which may be substituted by halogen, nitro, $C_{1-6}$ alkyl or $C_{1-6}$ alkoxy, (vi) a $C_{1-6}$ alkyl which may be substituted by a carboxyl group which may be esterified and (vii) a $C_{1-6}$ alkoxy-$C_{1-8}$ alkyl, etc.), (4) a hydroxyl group which may be acylated, (5) an amino group which may be substituted by $C_{1-10}$ alkyl, $C_{1-6}$ alkanoyl, $C_{1-6}$ alkylsulfonyl or $C_{6-14}$ arylsulfonyl, (6) a $C_{1-6}$ alkoxy group, (7) a cyano group, (8) a sulfo group, (9) a 5- or 6-membered heterocyclic group (ex. 5- or 6-membered heterocyclic group containing 1 to 4 hetero atoms selected from nitrogen, oxygen and sulfur atoms) which may be substituted by $C_{1-6}$ alkyl, $C_{1-6}$ alkoxy, nitro, cyano, amino, halogen, hydroxyl or oxo, (10) a nitro group, (11) a halogen atom, (12) a $C_{1-6}$ alkyl group, (13) an oxo group and so on.

Other preferable examples are (1) a group represented by the formula —$COOR^{11'}$, wherein $R^{11'}$ is a hydrogen atom or a $C_{1-8}$ alkyl group which may be substituted with $C_{1-6}$ alkoxy, $C_{1-6}$ alkanoyloxy or $C_{4-7}$ cycloalkyloxycarbonyloxy, (2) a group represented by the formula —$CONR^{12'}R^{13'}$, wherein $R^{12'}$ and $R^{13'}$ are the same or different and are a hydrogen atom, or a $C_{1-8}$ alkyl group which may be substituted by carboxyl, $C_{1-6}$ alkoxy or $C_{2-5}$ alkyloxycarbonyl, (3) a group represented by the formula —$CONHS(=O)_2R^{14'}$, wherein $R^{14'}$ is a $C_{1-4}$ alkyl group which may optionally be substituted by 1 to 3 halogen atoms, or a $C_{6-14}$ aryl group which may be substituted by $C_{1-6}$ alkyl, nitro, $C_{1-6}$ alkoxy or halogen, (4) a group represented by the formula —$CONHOR^{15'}$, wherein $R^{15'}$ is a hydrogen atom or a $C_{1-4}$ alkyl group, (5) a group represented by the formula —$OR^{16'}$, wherein $R^{16'}$ is a hydrogen atom, a $C_{1-8}$ alkyl group or a $C_{1-6}$ alkanoyl group, (6) a group represented by the formula —$COCOOR^{17'}$, wherein $R^{17'}$ is a hydrogen atom or a $C_{1-8}$ alkyl group, (7) a 3- to 8-membered heterocyclic group containing 1 to 4 hetero atoms selected from oxygen, sulfur and nitrogen atoms in addition to carbon atom(s), which may be substituted by $C_{1-6}$ alkyl, $C_{1-6}$ alkoxy, nitro, cyano, amino, halogen, hydroxyl or oxo (e.g. 1H- or 2H-tetrazolyl group, 5-hydroxy-4H-pyran-4-on-2-yl, etc.), (8) an amino group which may be substituted by $C_{1-10}$ alkyl, $C_{1-6}$ alkanoyl, $C_{1-6}$ alkylsulfonyl or $C_{6-14}$ arylsulfonyl, (9) a $C_{8-14}$ aralkyloxycarbonyl group, (10) a nitro group, (11) a halogen atom, (12) a cyano group, (13) an oxo group and (14) a sulfo group.

Of the hydrocarbon group which may be substituted shown by $R^2$, for example, a group represented by the formula —$CH_2(CHOH)mR^{2''}$, wherein m is 0 or 1, and $R^{2''}$ is a carboxyl group which may be esterified or amidated, a heterocyclic group which may be substituted or a hydroxymethyl group which may be substituted is preferred, and a group represented by the formula —$CH_2(CHOH)mR^{2'}$, wherein m is 0 or 1, and $R^{2'}$ is a carboxyl group which may be esterified or amidated or a hydroxymethyl group which may be substituted is more preferred.

Examples of the carboxyl group which may be esterified or amidated shown by $R^{2'}$ or $R^{2''}$ are the same those as the carboxyl group which may be esterified or amidated shown by $R^1$.

Examples of the heterocyclic group which may be substituted shown by $R^{2''}$ are the same those as the heterocyclic group which may be substituted shown by $R^9$ or $R^{10}$.

Examples of the hydroxymethyl group which may be substituted shown by $R^{2''}$ are a group represented by the formula:

wherein $R^a$ is a hydrogen atom, a hydrocarbon group which may be substituted or an acyl group which may be substituted and so on.

Examples of the hydrocarbon group which may be substituted shown by $R^a$ are the same those as the hydrocarbon group which may be substituted shown by $R^8$. As the hydrocarbon group, for example, a $C_{1-8}$ alkyl group etc. are preferred.

Examples of the acyl group which may be substituted shown by $R^a$ are the same those as the acyl group which may be substituted shown by $R^{16}$. Among them, the $C_{1-6}$ alkanoyl group is preferably used.

As the hydrocarbon group which may be substituted shown by $R^2$, for example, (1) a group represented by the formula —$CH_2(CHOR^b)$ $m^1COOR^{18}$, wherein $m^1$ is 0 or 1, $R^b$ is a hydrogen atom or a $C_{1-6}$ alkanoyl group, and $R^{18}$ is a hydrogen atom or a hydrocarbon group which may be substituted, (2) a group represented by the formula —$CH_2(CHOH)$ $m^2CONR^{19}R^{20}$, wherein $m^2$ is 0 or 1, $R^{19}$ and $R^{20}$ are the same or different and are a hydrogen atom, a hydrocarbon group which may be substituted or a heterocyclic group which may be substituted, and $R^{19}$ and $R^{20}$ may be combined with the adjacent nitrogen atom to form a nitrogen-containing heterocyclic group, (3) a group represented by the formula —$CH_2(CHOH)$ $m^3CONHS(=O)_2R^{21}$, wherein $m^3$ is 0 or 1, and $R^{21}$ is a hydrocarbon group which may be substituted, (4) a group represented by the formula —$CH_2(CHOH)$ $m^4CONHOR^{22}$, wherein $m^4$ is 0 or 1, and $R^{22}$ is a hydrogen atom or a hydrocarbon group which may be substituted, (5) a group represented by the formula —$CH_2(CHOH)$ $m^5R^{23}$ wherein $m^5$ is 0 or 1, and $R^{23}$ is a heterocyclic group which optionally be substituted, (6) a group represented by the formula —$CH_2(CHOH)$ $m^6CH_2OR^{24}$, wherein $m^6$ is 0 or 1, and $R^{24}$ is a hydrogen atom, a hydrocarbon group which may be substituted or an acyl group which may be substituted, (7) a group represented by the formula —$CH_2(CHOH)$ $m^7COCOOR^{25}$, wherein $m^7$ is 0 or 1, and $R^{25}$ is a hydrogen atom or a hydrocarbon group which may be substituted, etc. are preferred. In addition, (8) a $C_{2-8}$ alkyl groups which may substituted by a group represented by the formula —$COOR^{18'}$, wherein $R^{18'}$ is a hydrogen atom or a $C_{1-8}$ alkyl group, and (9) a $C_{7-19}$ aralkyl group (particularly, a benzyl group) which may be substituted by a carboxyl, a cyano, a hydroxyl, a carbamoyl, a $C_{2-5}$ alkoxycarbonyl or a heterocyclic group which may be substituted are also preferred.

Examples of the hydrocarbon group which may be substituted shown by $R^{18}$, $R^{19}$, $R^{20}$, $R^{21}$, $R^{22}$, $R^{24}$ or $R^{25}$ are the same those as the hydrocarbon group which may be substituted shown by $R^8$.

Examples of the heterocyclic group which may be substituted shown by $R^{19}$, $R^{20}$ or $R^{23}$ are the same those as the heterocyclic group which may be substituted shown by $R^9$ or $R^{10}$.

Examples of the nitrogen-containing heterocyclic group formed by combining $R^{19}$ and $R^{20}$ with the adjacent nitrogen atom are the same those as the nitrogen-containing heterocyclic group formed by combining $R^9$ and $R^{10}$ with the adjacent nitrogen atom.

Examples of the heterocyclic group which may be substituted used as the substituent of the $C_{7-19}$ aralkyl group are the same those as the heterocyclic group which may be substituted shown by $R^9$ or $R^{10}$.

Examples of the acyl group which may be substituted shown by $R^{24}$ are the same those as the acyl group shown by $R^{16}$. Among them, a $C_{1-6}$ alkanoyl group, particularly a $C_{1-4}$ alkanoyl group (e.g. formyl, acetyl, propionyl, isopropionyl, etc.) is preferred. As the substituent of these acyl group, the same substituent as those of the hydrocarbon shown by $R^8$ are used.

Examples of the hydroxyl group which may be substituted shown by $R^3$ or $R^4$ are a group represented by the formula —$OR^{26}$, wherein $R^{26}$ is a hydrogen atom, a hydrocarbon group which may be substituted or an acyl group which may be substituted, a group represented by the formula —$OCOOR^{27}$, wherein $R^{27}$ is a hydrocarbon group which may be substituted, and so on.

Examples of the hydrocarbon group which may optionally be substituted, shown by $R^{26}$ or $R^{27}$ are the same those as the hydrocarbon group which may be substituted shown by $R^8$. As the hydrocarbon group, for example, a $C_{1-8}$ alkyl group and a $C_{6-14}$ aryl group are preferred. As the substituent of the hydrocarbon group, for example, a $C_{1-6}$ alkoxy group, etc. are preferred.

Examples of the acyl group which may be substituted shown by $R^{26}$ are the same those as the acyl group which may optionally be substituted shown by $R^{16}$. As the acyl group, for example, a $C_{1-6}$ alkanoyl group, a $C_{7-11}$ aroyl group (e.g. benzoyl group, etc.), etc. are preferred. More preferable examples are a $C_{1-7}$ acyl group such as a $C_{1-6}$ alkanoyl group and a benzoyl group, etc.

As the hydrocarbon group represented by $R^{26}$ in —$OR^{26}$ for $R^3$, for example, a $C_{1-8}$ alkyl group, particularly a $C_{1-3}$ alkyl group, etc. are preferred. As its substituent, for example, a $C_{1-6}$ alkoxy group (e.g. methoxy, etc.) etc. are preferred.

As the acyl group represented by $R^{26}$ in —$OR^{26}$ for $R^3$, for example, a $C_{1-6}$ alkanoyl group, etc. are preferred.

As the hydrocarbon group represented by $R^{26}$ in —$OR^{26}$ for $R^4$, for example, a $C_{1-8}$ alkyl group or a $C_{6-14}$ aryl group is preferred. Particularly, a $C_{1-3}$ alkyl group or a phenyl group is preferred.

As the acyl group represented by $R^{26}$ in —$OR^{26}$ for $R^4$, for example, a $C_{1-6}$ alkanoyl group, a $C_{7-11}$ aroyl group, particularly a $C_{1-4}$ alkanoyl group, a benzoyl group, etc. are preferred. As its substituent, for example, a $C_{1-3}$ alkyl group (e.g. methyl group, etc.), etc. are preferred.

As the hydrocarbon group represented by $R^{27}$ in —$OCOOR^{27}$ for $R^3$ or $R^4$, for example, a $C_{1-8}$ alkyl group or a $C_{6-14}$ aryl group is preferred. Particularly, a $C_{1-3}$ alkyl group or a phenyl group is preferred.

Examples of the halogen atom shown by $R^5$, $R^6$ or $R^7$ are a fluorine atom, a chlorine atom, a bromine atom, an iodine atom, and so on. Among them, a chlorine atom or a bromine atom is preferable for $R^5$ and $R^6$, and a bromine atom or an iodine atom is preferable for $R^7$.

Examples of the hydrocarbon group which may be substituted shown by $R^7$ are the same those as the hydrocarbon group which may be substituted shown by $R^8$. As the hydrocarbon group, a $C_{1-19}$ hydrocarbon group is preferred. More preferable examples are a $C_{1-8}$ alkyl group, a $C_{6-14}$ aryl group, etc. Particularly, a $C_{6-14}$ aryl group is preferred. As the substituent of the hydrocarbon group, for example, a halogen atom, a carboxyl group, a $C_{1-6}$ alkyl group, a $C_{1-6}$ alkoxy group, an amino group and a nitro group are preferred.

Examples of the heterocyclic group which may be substituted shown by $R^7$ are the same those as the heterocyclic group which may be substituted shown by $R^9$ or $R^{10}$. For example, 2- or 3-thienyl and 2-benzo[b]furanyl are preferred.

Examples of the acyl group which may be substituted shown by $R^7$ are the same those as the acyl group which may be substituted shown by $R^{16}$. As the acyl group, for example, a $C_{1-6}$ alkanoyl group, etc. are preferred.

Of the above-described groups, preferable examples of $R^1$ are a group represented by the formula —$COOR^{28}$, wherein $R^{28}$ is a hydrogen atom or a $C_{1-8}$ alkyl group which may be substituted by $C_{1-6}$ alkoxy, and so on. Among them, a carboxyl group which may be esterified by a $C_{1-3}$ alkyl group (particularly, methyl group, etc.) are preferably used.

Preferable examples of $R^2$ are (i) a hydrogen atom, (ii) a hydroxyl group, (iii) a $C_{1-19}$ hydrocarbon group which may be substituted by a group selected from the group consisting of (a) $C_{1-8}$ alkoxy-carbonylcarbonyl, (b) carboxyl which may be esterified or amidated, (c) hydroxyl which may be acylated, (d) amino group which may be substituted by $C_{1-10}$ alkyl, $C_{1-6}$ alkanoyl, $C_{1-6}$ alkylsulfonyl or $C_{6-14}$ arylsulfonyl, (e) $C_{1-6}$ alkoxy, (f) cyano, (g) sulfo, (h) a 5- or 6-membered heterocyclic group which may be substituted by $C_{1-6}$ alkyl, $C_{1-6}$ alkoxy, nitro, cyano, amino, halogen, hydroxyl or oxo, (i) nitro, (j) halogen, (k) oxo, and so on.

More preferable examples of $R^2$ are (i) a hydrogen atom, (ii) a hydroxyl group, (iii) a $C_{1-10}$ alkyl group which may be substituted by a group selected from the group consisting of (a) $C_{1-8}$ alkoxy-carbonylcarbonyl, (b) carboxyl which may be esterified or amidated, (c) hydroxyl which may be acylated, (d) amino which may be substituted by $C_{1-6}$ alkylsulfonyl or $C_{6-14}$ arysulfonyl, (e) $C_{1-6}$ alkoxy, (f) cyano, (g) sulfo and (h) a 5- or 6-membered heterocyclic (ex. a 5- or 6-membered heterocyclic group containing 1 to 4 hetero atoms selected from nitrogen, oxygen and sulfur atoms, etc.) which may be substituted by hydroxyl or oxo, (iv) a $C_{2-8}$ alkenyl group which may be substituted by carboxyl, (v) a $C_{7-19}$ aralkyl group which may be substituted by a group selected from the group consisting of (a) cyano, (b) carboxyl which may be esterified or amidated, (c) hydroxyl, (d) nitro, (e) halogen and (f) a 5- or 6-membered nitrogen-containing heterocyclic group, and so on.

And, other preferable examples of $R^2$ are (1) a hydrogen atom, (2) a hydroxyl group; (3) a group represented by the formula —$CH_2(CHOR^b)m^1COOR^{29}$, wherein $m^1$ is 0 or 1, $R^b$ is a hydrogen atom or a $C_{1-6}$ alkanoyl group, and $R^{29}$ is a hydrogen atom or a $C_{1-8}$ alkyl group which may be substituted by $C_{1-6}$ alkoxy, $C_{1-6}$ alkanoyloxy or $C_{4-7}$ cycloalkyloxycarbonyloxy, (4) a group represented by the formula —$CH_2(CHOH)m^2CONR^{30}R^{31}$, wherein $m^2$ is 0 or 1, $R^{30}$ and $R^{31}$ are the same or different and are a hydrogen atom or a $C_{1-8}$ alkyl group which may be substituted by carboxyl, $C_{1-6}$ alkoxy or $C_{2-5}$ alkoxycarbonyl, (5) a group represented by the formula —$CH_2(CHOH)m^3CONHS(=O)_2R^{32}$, wherein $m^3$ is 0 or 1, and $R^{32}$ is a $C_{1-4}$ alkyl group which may be substituted by 1 to 3 halogen atoms or a $C_{6-14}$ aryl group which may be substituted by $C_{1-6}$ alkyl, nitro, $C_{1-6}$ alkoxy or halogen, (6) a group represented by the formula —$CH_2(CHOH)m^4CONHOR^{33}$, wherein $m^4$ is 0 or 1, and $R^{33}$ is a hydrogen atom or a $C_{1-4}$ alkyl group, (7) a group represented by the formula —$CH_2(CHOH)m^5R^{34}$, wherein $m^5$ is 0 or 1, and $R^{34}$ is a 3- to 8-membered heterocyclic group containing 1 to 4 hetero atoms selected from nitrogen, oxygen and sulfur atoms in addition to carbon atom(s), which may be substituted by hydroxyl or oxo, (e.g. 1H- or 2H-tetrazolyl group, 5-hydroxy-4H-pyran-4-on-2-yl group, etc.), (8) a group represented by the formula —$CH_2(CHOH)m^6—CH_2OR^{35}$, wherein $m^6$ is 0 or 1, and $R^{35}$ is a hydrogen atom, a $C_{1-8}$ alkyl group or a $C_{1-6}$ alkanoyl group, (9) a group represented by the formula —$CH_2(CHOH)m^7—COCOOR^{36}$, wherein $m^7$ is 0 or 1, and $R^{36}$ represents a hydrogen atom or a $C_{1-8}$ alkyl group, (10) a $C_{2-8}$ alkyl group which may be substituted by carboxyl, etc. and (11) a $C_{7-19}$ aralkyl group (particularly, benzyl group) which may be substituted by carboxyl, cyano, hydroxyl, carbamoyl, $C_{2-5}$ alkoxycarbonyl or a 3- to 8-membered heterocyclic group containing 1 to 4 hetero atoms selected from nitrogen, oxygen and sulfur atoms in addition to carbon atoms (e.g. 2-tetrazolyl group, etc.), and so on.

Preferable examples of $R^3$ and $R^4$ are a hydroxyl group which may be substituted by (i) an acyl group or (ii) a $C_{1-10}$ alkyl group which may be substituted, and more preferable examples are (i) a hydroxyl group which may be substituted by $C_{1-7}$ acyl or (ii) a $C_{1-10}$ alkoxy group which may be substituted by $C_{1-6}$ alkoxy.

More preferable examples of $R^3$ and $R^4$ are (i) a group represented by the formula —$OR^{26'}$, wherein $R^{26'}$ is a hydrogen atom, a $C_{1-8}$ alkyl group which may be substituted by $C_{1-6}$ alkoxy, $C_{1-6}$ alkanoyl group or $C_{7-11}$ aroyl group, (ii) a group represented by the formula —$OCOOR^{27'}$, wherein $R^{27'}$ is a $C_{1-8}$ alkyl group or a $C_{6-14}$ aryl group, and so on.

More preferable examples of $R^3$ are a group represented by the formula —$OR^{37}$, wherein $R^{37}$ is a hydrogen atom, a $C_{1-8}$ alkyl group which may be substituted by $C_{1-6}$ alkoxy, or a $C_{1-6}$ alkanoyl group, and so on.

More preferable examples of $R^4$ are (i) a group represented by the formula —$OR^{38}$, wherein $R^{31}$ is a hydrogen atom, a $C_{1-8}$ alkyl group which may be substituted by $C_{1-6}$ alkoxy, a $C_{1-6}$ alkanoyl group or a $C_{7-11}$ aroyl group, (ii) a group represented by the formula —$OCOOR^{39}$, wherein $R^{39}$ is a $C_{1-6}$ alkyl group or a $C_{6-14}$ aryl group, and so on.

As $R^3$ and $R^4$, a hydroxyl group, a methoxy group, an acetoxy group, a propionyloxy group, an isopropionyloxy group and a butyryloxy group are preferred, and a hydroxyl group is particularly preferred.

Preferable examples of $R^5$ and $R^6$ are a hydrogen atom, a chlorine atom and a bromine atom are preferred, and a chlorine atom and a bromine atom are particularly preferred. Above all, the case where $R^5$ and $R^6$ simultaneously represent chlorine atom is especially preferred.

Preferable examples of $R^7$ is (i) a hydrogen atom, (ii) a nitro group, (iii) a halogen group, (iv) a $C_{1-19}$ hydrocarbon group which may be substituted by a group selected from the group consisting of (a) carboxyl which may be esterified or amidated, (b) hydroxyl which may be acylated, (c) amino which may be substituted by $C_{1-10}$ alkyl, $C_{1-6}$ alkanoyl, $C_{1-6}$ alkylsulfonyl or $C_{6-14}$ arylsulfonyl, (d) $C_{1-6}$ alkoxy, (e) cyano, (f) sulfo, (g) a 5- or 6-membered heterocyclic group which may be substituted by $C_{1-6}$ alkyl, $C_{1-6}$ alkoxy, nitro, cyano, amino, halogen, hydroxyl or oxo, (h) nitro, (i) halogen and (j) oxo, (v) a 5- or 6-membered heterocyclic group which may be substituted by a group selected from the group consisting of (a) $C_{1-6}$ alkyl, (b) carboxyl which may be esterified or amidated, (c) hydroxyl which may be acylated, (d) amino which may be substituted by $C_{1-10}$ alkyl, $C_{1-6}$ alkanoyl, $C_{1-6}$ alkylsulfonyl or $C_{6-14}$ arylsulfonyl, (e) $C_{1-6}$ alkoxy, (f) cyano, (g) sulfo, (h) nitro, (i) halogen and (j) oxo, or (vi) an acyl group which may be substituted by a group selected from the group consisting of (a) $C_{1-6}$ alkyl, (b) carboxyl which may be esterified or amidated, (c) hydroxyl which may be acylated, (d) amino which may be substituted by $C_{1-10}$ alkyl, $C_{1-6}$ alkanoyl, $C_{1-6}$ alkylsulfonyl or $C_{6-14}$ arylsulfonyl, (e) $C_{1-6}$ alkoxy, (f) cyano, (g) sulfo, (h) a 5- or 6-membered heterocyclic group which may be substituted by $C_{1-6}$ alkyl, $C_{1-6}$ alkoxy, nitro, cyano, amino, halogen, hydroxyl or oxo, (i) nitro, (j) halogen and (k) oxo or its condensed heterocyclic group, and so on.

More preferable examples of $R^7$ are (i) a hydrogen atom, (ii) a nitro group, (iii) a halogen atom, (iv) a $C_{1-8}$ alkyl group, (v) a $C_{6-14}$ aryl group which may be substituted by halogen, carboxyl, $C_{1-6}$ alkyl, $C_{1-6}$ alkoxy, amino or nitro, (vi) a $C_{1-6}$ alkanoyl group or (vii) a 3- to 8-membered heterocyclic group which contains 1 to 4 hetero atoms selected from nitrogen, oxygen and sulfur atoms in addition to carbon atom(s) or its condensed heterocyclic group with a 6- to 8-membered carbon ring (e.g. benzene ring, etc.) or with a 6- to 8-membered heterocyclic group, and so on.

Among them, hydrogen atom, nitro group, bromine atom and iodine atom are preferred, and particularly, nitro group, bromine atom, iodine atom are preferred as $R^7$.

As n, 0 or 1is particularly preferred.

As $R^{99}$, carbonyl is particularly preferred.

When n is 0, $R^2$ may be a group represented by the formula:

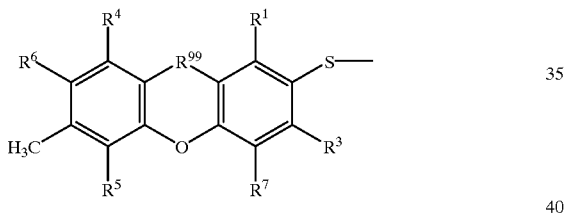

wherein the symbols have the same meanings as defined above.

Preferable examples of $R^1$, $R^3$, $R^4$, $R^5$, $R^6$, $R^7$ and $R^{99}$ are the same those as mentioned above.

More preferable examples of $R^1$ are a carboxyl group which may be esterified by $C_{1-8}$ alkyl, etc. More preferable examples of $R^3$ and $R^4$ are a hydroxyl group, etc. More preferable examples of $R^5$ and $R^6$ are a hydrogen atom or a halogen atom such as a chlorine atom. More preferable examples of $R^7$ are a hydrogen atom, etc. More preferable examples of $R^{99}$ is a carbonyl.

Preferable examples of the compound (I) of the present invention include all compounds having a combination of the groups exemplified as the preferable example of these respective symbols.

More preferable examples of the compound (I) of the present invention are a compound (Ia), a compound (Ib), a compound (Ic), a compound (Id), a compound (Ie) and so on.

[Compound (Ia)]

$R^1$ is a carboxyl group which may be esterified or amidated;

$R^2$ is (i) a hydrogen atom, (ii) a hydroxyl group or (iii) a $C_{1-19}$ hydrocarbon group which may be substituted by a group selected from the group consisting of (a) $C_{1-8}$ alkoxy-carbonylcarbonyl, (b) carboxyl which may be esterified or amidated, (c) hydroxyl which may be acylated, (d) amino group which may be substituted by $C_{1-10}$ alkyl, $C_{1-6}$ alkanoyl, $C_{1-6}$ alkylsulfonyl or $C_{6-14}$ arylsulfonyl, (e) $C_{1-6}$ alkoxy, (f) cyano, (g) sulfo, (h) a 5- or 6-membered heterocyclic group which may be substituted by $C_{1-6}$ alkyl, $C_{1-6}$ alkoxy, nitro, cyano, amino, halogen, hydroxyl or oxo, (i) nitro, (j) halogen and (k) oxo;

$R^3$ and $R^4$ are the same or different and are a hydroxyl group which may be substituted by (a) an acyl group or (b) a $C_{1-10}$ alkyl group which may be substituted;

$R^5$ and $R^6$ are the same or different and are a hydrogen atom or a halogen atom;

$R^7$ is (i) a hydrogen atom, (ii) a nitro group, (iii) a halogen atom, (iv) a $C_{1-19}$ hydrocarbon group which may be substituted by a group selected from the group consisting of (a) carboxyl which may be esterified or amidated, (b) hydroxyl which may be acylated, (c) amino which may be substituted by $C_{1-10}$ alkyl, $C_{1-6}$ alkanoyl, $C_{1-6}$ alkylsulfonyl or $C_{6-14}$ arylsulfonyl, (d) $C_{1-6}$ alkoxy, (e) cyano, (f) sulfo, (g) a 5- or 6-membered heterocyclic group which may be substituted by $C_{1-6}$ alkyl, $C_{1-6}$ alkoxy, nitro, cyano, amino, halogen, hydroxyl or oxo, (h) nitro, (i) halogen and (j) oxo, (v) a 5- or 6-membered heterocyclic group which may be substituted by a group selected from the group consisting of (a) $C_{1-6}$ alkyl, (b) carboxyl which may be esterified or amidated, (c) hydroxy which may be acylated, (d) amino which may be substituted by $C_{1-10}$ alkyl, $C_{1-6}$ alkanoyl, $C_{-6}$ alkylsulfonyl or $C_{6-14}$ arylsulfonyl, (e) $C_{1-6}$ alkoxy, (f) cyano, (g) sulfo, (h) nitro, (i) halogen and (j) oxo or its condensed heterocyclic ring, or (vi) an acyl group which may be substituted by a group selected from the group consisting of (a) $C_{1-6}$ alkyl, (b) carboxyl which may be esterified or amidated, (c) hydroxyl which may be acylated, (d) amino which may be substituted by $C_{1-10}$ alkyl, $C_{1-6}$ alkanoyl, $C_{1-6}$ alkylsulfonyl or $C_{6-14}$ arylsulfonyl, (e) $C_{1-6}$ alkoxy, (f) cyano, (g) sulfo, (h) a 5- or 6-membered heterocyclic group which may be substituted by $C_{1-6}$ alkyl, $C_{1-6}$ alkoxy, nitro, cyano, amino, halogen, hydroxyl or oxo, (i) nitro and (j) halogen and (k) oxo;

when n is 0, $R^2$ may be a group represented by the formula:

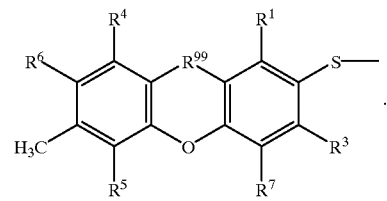

[Compound (Ib)]

$R^1$ is a carboxyl group which may be esterified;

$R^2$ is (i) a hydrogen atom, (ii) a hydroxyl group, (iii) a $C_{1-10}$ alkyl group which may be substituted by a group selected from the group consisting of (a) $C_{1-8}$ alkoxy-carbonylcarbonyl, (b) carboxyl which may be esterified or amidated, (c) hydroxyl which may be acylated, (d) amino which may be substituted by $C_{1-6}$ alkylsulfonyl or $C_{6-14}$ arylsulfonyl, (e) $C_{1-6}$ alkoxy, (f) cyano, (g) sulfo and (h) a 5- or 6-membered heterocyclic group (e.g. a 5- or 6-membered heterocyclic group containing 1 to 4 hetero atoms selected from nitrogen, oxygen and sulfur atoms) which may be substituted by hydroxy group or oxo group, (iv) a $C_{2-8}$ alkenyl group which may be substituted by carboxyl, (v) a $C_{7-19}$ aralkyl group which may be substituted by a group selected from the group consisting of (a) cyano, (b) carboxyl which may be esterified or amidated, (c) hydroxyl, (d) nitro, (e) halogen and (f) a 5- or 6-membered nitrogen-containing heterocyclic group, $R^3$ and $R^4$ are the same or different and are (i) a hydroxyl group which may be substituted by $C_{1-7}$ acyl group or (ii) a $C_{1-10}$ alkoxy group which may be substituted by $C_{1-6}$ alkoxy group, $R^5$ and $R^6$ are the same or different and are a hydrogen atom or a halogen atom, $R^7$ is (i) a hydrogen atom, (ii) a nitro group, (iii) a halogen atom, (iv) a $C_{1-10}$ alkyl group, (v) a $C_{6-14}$ aryl group which may be substituted by a group selected from the group consisting of (a) $C_{1-6}$ alkyl, (b) carboxyl, (c) $C_{1-6}$ alkoxy, (d) amino, (e) nitro and (f) halogen, (vi) $C_{1-6}$ alkanoyl, or (vii) a 5- or 6-membered heterocyclic group containing 1 to 4 hetero atoms selected from nitrogen, oxygen and sulfur atoms in addition to carbon atoms or its condensed heterocyclic group with a benzene ring; when n is 0, $R^2$ may be a group represented by the formula:

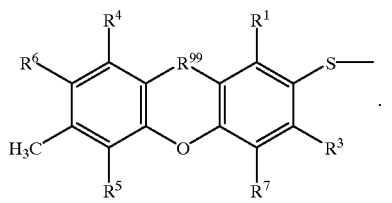

[Compound (Ic)]

$R^1$ is a group represented by —COOR$^{28}$ wherein $R^{28}$ is a hydrogen atom, or a $C_{1-8}$ alkyl group which may be substituted by $C_{1-6}$ alkoxy;

$R^2$ is (1) a hydrogen atom, (2) a hydroxyl group, (3) a group represented by the formula —CH$_2$(CHOR$^b$)m$^1$COOR$^{29}$, wherein m$^1$ is 0 or 1, R$^b$ is a hydrogen atom or a $C_{1-6}$ alkanoyl group, and R$^{29}$ is a hydrogen atom or a $C_{1-8}$ alkyl group which may be substituted by $C_{1-6}$ alkoxy, $C_{1-6}$ alkanoyloxy or $C_{4-7}$ cycloalkyloxycarbonyloxy, (4) a group represented by the formula —CH$_2$(CHOH)m$^2$CONR$^{30}$R$^{31}$, wherein m is 0 or 1, R$^{30}$ and R$^{31}$ are the same or different and are a hydrogen atom or a $C_{1-8}$ alkyl group which may be substituted by carboxyl, $C_{1-6}$ alkoxy or $C_{2-5}$ alkoxycarbonyl, (5) a group represented by the formula —CH$_2$(CHOH)m$^3$CONHS(=O)$_2$R$^{32}$, wherein m$^3$ is 0 or 1, and R$^{32}$ is a $C_{1-4}$ alkyl group which may be substituted by 1 to 3 halogen atoms or a $C_{6-14}$ aryl group which may be substituted by $C_{1-6}$ alkyl, nitro, $C_{1-6}$ alkoxy or halogen, (6) a group represented by the formula —CH$_2$(CHOH)m$^4$CONHOR$^{33}$, wherein m$^4$ is 0 or 1, and R$^{33}$ is a hydrogen atom or a $C_{1-4}$ alkyl group, (7) a group represented by the formula —CH$_2$(CHOH)m$^5$R$^{34}$, wherein m$^5$ is 0 or 1, and R$^{34}$ is a 3- to 8-membered heterocyclic group containing 1 to 4 hetero atoms selected from nitrogen, oxygen and sulfur atoms in addition to carbon atom(s) (e.g. 2-pyridyl group, 1H or 2H-tetrazolyl group, 5-hydroxy-4H-pyran-4-on-2-yl group, etc.), which may be substituted by hydroxyl or oxo, (8) a group represented by the formula —CH$_2$(CHOH)m$^6$CH$_2$OR$^{35}$, wherein m$^6$ is 0 or 1, and R$^{35}$ is a hydrogen atom, a $C_{1-8}$ alkyl group or a $C_{1-6}$ alkanoyl group, (9) a group represented by the formula —CH$_2$(CHOH)m$^7$COCOOR$^{36}$, wherein m$^7$ is 0 or 1, and R$^{36}$ is a hydrogen atom or a $C_{1-8}$ alkyl group, (10) a $C_{2-8}$ alkyl groups which may be substituted with a carboxyl group, or (11) a $C_{7-19}$ aralkyl group which may be substituted by carboxyl, cyano, halogen, nitro, hydroxyl, carbamoyl, $C_{2-5}$ alkoxycarbonyl or a 3- to 8-membered heterocyclic group containing 1 to 4 hetero atoms selected from nitrogen, oxygen and sulfur atoms in addition to carbon atom(s) (e.g. 1H- or 2H-tetrazolyl group, etc.);

$R^3$ is a group represented by the formula —OR$^{37}$ wherein R$^{37}$ is (i) a hydrogen atom, (ii) a $C_{1-8}$ alkyl group which may be substituted by $C_{1-6}$ alkoxy, or (iii) a $C_{1-6}$ alkanoyl group;

$R^4$ is (1) a group represented by the formula —OR$^{38}$ wherein R$^{38}$ is (i) a hydrogen atom, (ii) a $C_{1-8}$ alkyl group which may be substituted by $C_{1-6}$ alkoxy, (iii) a $C_{1-6}$ alkanoyl group or (iv) a $C_{7-11}$ aroyl group, or (2) a group represented by the formula —OCOOR$^{39}$, wherein R$^{39}$ is a $C_{1-6}$ alkyl group or a $C_{6-14}$ aryl group;

$R^5$ and $R^6$ are the same or different and are a hydrogen atom or a halogen atom; and $R^7$ is (1) a hydrogen atom, (2) a nitro group, (3) a halogen atom, (4) a $C_{1-8}$ alkyl group, (5) a $C_{6-14}$ aryl group which may be substituted by halogen, carboxyl, $C_{1-6}$ alkyl, $C_{1-6}$ alkoxy, amino or nitro, (6) a $C_{1-6}$ alkanoyl group or (7) a 3- to 8-membered heterocyclic group which contains 1 to 4 hetero atoms selected from nitrogen, oxygen and sulfur atoms in addition to carbon atoms (e.g. 2- or 3-thienyl, etc.) or its condensed heterocyclic group with a 6- to 8-membered carbon ring such as benzene ring or with a heterocyclic group (e.g. 2-benzo[b]furanyl, etc.); when n is 0, $R^2$ may be a group represented by the formula:

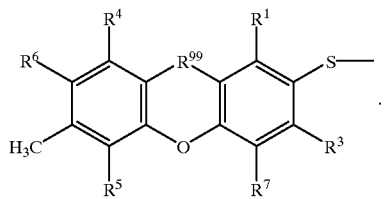

[Compound (Id)]

$R^1$ is a carboxyl group which may be esterified with a methyl group, etc.;

$R^2$ is a group represented by the formula —CH$_2$COOR$^{40}$, wherein R$^{40}$ is a hydrogen atom, or a $C_{1-4}$ alkyl group (e.g. methyl, ethyl, etc.) which may be substituted by $C_{1-6}$ alkoxy, $C_{1-6}$ alkanoyloxy or $C_{4-7}$ cycloalkyloxy-carbonyloxy;

$R^3$ and $R^4$ are a hydroxyl group;

$R^5$ and $R^6$ are a chlorine atom; and $R^7$ is a hydrogen atom, a nitro group, a bromine atom or an iodine atom; when n is 0, $R^2$ may be a group represented by the formula:

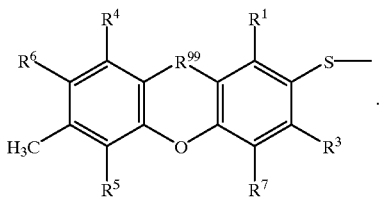

[Compound (Ie)]

(1) methyl 2-(carboxymethylsulfinyl)-5,7-dichloro-3,8-dihydroxy-6-methyl-9-oxo-9H-xanthene-1-carboxylate, (2) methyl 2-(carboxymethylsulfinyl)-5,7-dichloro-3,8-dihydroxy-4-iodo-6-methyl-9-oxo-9H-xanthene-1-carboxylate, (3) methyl 5,7-dichloro-3,8-dihydroxy-6-methyl-9-oxo-2-(pivaloyloxymethoxycarbonylmethythio-9H-xanthene-1-carboxylate, (4) methyl 5,7-dichloro-3,8-dihydroxy-6-methyl-9-oxo-2-(pivaloyloxymethoxycarbonylmethylsulfinyl)-9H-xanthene-1-carboxylate or (5) methyl 5,7-dichloro-2-[1-(cyclohexyloxycarbonyloxy)ethoxycarbonylmethylthio]3,8-dihydroxy-6-methyl-9-oxo-9H-xanthene-1-carboxylate.

The screening method of the present invention includes:

(1) a method for screening for a compound having an activity for inhibiting or enhancing a binding of CD28 to B7-1, or a salt thereof, which comprises comparing (i) an amount of binding between CD28 and B7-1-Ig obtained when CHO-cell containing CD28, or a cell membrane fraction is contacted with soluble B7-1-Ig, with (ii) an amount of binding between CD28 and B7-1-Ig obtained when CHO-cell containing CD28 or its cell membrane fraction is contacted with soluble B7-1-Ig and a test compound, and (2) a method for screening for a compound having an activity for inhibiting an interleukin-2 production, or a salt thereof, which comprises comparing (i) an amount of interleukin-2 produced when CHO-cell containing B7-1 or its cell membrane fraction is contacted with T-cell (specifically, T-cell to which a first signal was given by an anti-CD3 antibody), with (ii) an amount of interluekin 2 produced when CHO-cell containing B7-1 or its cell membrane fraction is contacted with T-cell (Specifically, T-cell to which a first signal was given by an anti-CD3 antibody) and a test compound.

As the microorganism of producing TAN-2421A1, A2, A3, A4, B1, B2 and/or B3 used for the production of the present invention, for example, any microorganism can be used, so long as it belongs to the genus Aspergillus and is capable of producing TAN-2421A1, A2, A3, A4, B1, B2 and/or B3. Such microorganisms include FL-67283 strain, a mold strain newly isolated from soil of India. This strain has the following properties.

(I) Cultural properties (1) Malt extract agar medium

Growth at 24° C. is moderate; colony diameter reaches 25 mm 2 weeks later. Surface is flat, comprising a slightly arisen velvet-like mycelia in the center, with a regular outer margin. Development of aerial mycelia is good but formation of conidum is poor. Red-brown to pale red-brown from the center to the intermediate portion, the periphery being ivory. From the center to the intermediate portion of the back face, dark yellow-brown to pale yellow-brown. No soluble pigments are formed.

(2) Potato-glucose agar medium

Growth at 24° C. is good; colony diameter reaches 46–50 mm 2 weeks later. Surface is flat, comprising a slightly arisen velvet-like mycelia in the center, with a central hollow and radially expands from the center to the periphery. Outer margin is slightly irregular. Development of aerial mycelia is good but formation of conidum is slightly late. Red-brown from the center to the intermediate portion, the periphery being ivory. The center of the back face is dark red-brown to red-brown, the central portion is pale red-brown, and the periphery is pale yellow-brown. No soluble pigments are formed. The strain grows over the pH range 3–12. The growth temperature range is 11–44° C., the optimum temperature being 24–30° C. The strain grows even at 37° C.

(3) Czapek agar medium Growth at 24° C. is moderate; colony diameter reaches 35–40 mm 2 weeks later. Surface comprising a slightly arisen velvet-like, rarely wool-like mycelia in the center, with a slightly irregular outer margin. Development of aerial mycelia is moderate but formation of conidum is poor. Pale yellow-brown from the center to the intermediate portion, the periphery being ivory. From the center to the intermediate portion of the back face, reddish yellow-brown to pale reddish yellow-brown. No soluble pigments are formed.

(4) Oatmeal agar medium

Growth at 24° C. is good; colony diameter reaches 60–65 mm 2 weeks later. Surface is flat, comprising velvet-like mycelia, with a central hollow and radially thinly expands from the center to the periphery portion. Outer margin is slightly irregular. Development of aerial mycelia and formation of conidum are good. Red-brown to pale red-brown from the center to the intermediate portion, the periphery being pale yellow-brown. The central portion of the back face is yellow-brown, the center to the periphery being pale yellow-brown to ivory. No soluble pigments are formed.

(II) Morphological characteristics

| | |
|---|---|
| Conidia: | cylindrical and 100–180 $\mu$m × 40–60 $\mu$m in size |
| Conidiophore: | formed on aerial mycelia and 60–100 $\mu$m × 6.0–8.0 $\mu$m in size, septal wall being recognized. It is slightly curved, with a smooth surface. Its top end thickens to form a vesicle. |
| Vesicle: | semi-spherical and 15–20 $\mu$m in diameter, with metulae in the upper half |
| Metula: | cylindrical and 4.5–5.0 $\mu$m × 1.5–2.0 $\mu$m in size |
| Phialide: | bottle-shaped and 5–6 $\mu$m × 1.2–1.8 $\mu$m in size, with a smooth surface thereon, 2 to 4 phialides being fascicled on metula |
| Conidia: | spherical to semi-spherical and 1.6–2.0 $\mu$m × 1.3–1.7 $\mu$m in size, linked together, with a smooth surface |

On the basis of the above various properties and with reference to the identification key table described on page 51 in "Separation, Cultivation and Identification of Fungi" (by D. Malloch, translated into Japanese by S. Udagawa, 1983, Ishiyaku Publishers), it is apparent that this strain belongs to the genus Aspergillus because the spore comprises one cell, the conidia, conidium and conidiophore being colorless or light-colored, and the condiophore having a vesicle to form a bottle-shaped phialide.

With reference to various properties of the fungi of the genus Aspergillus described in "THE GENUS Aspergillus"

by K. B. Raper et al., (1965, THE Williams & Wilkins Company), it is considered that this strain belongs to the Aspergillus terreus group because metulae are formed on the vesicle and a bottle-shaped phialide is formed thereon, the conidia being cylindrical with yellow-brown color, and conidiophore being colorless.

Accordingly, this strain can be identified as Aspergillus terreus FL-67283 strain.

This strain has been deposited under accession number FERM BP-5433 at the National Institute of Bioscience and Human-Technology (NIBH), Agency of Industrial Science and Technology, Ministry of International Trade and Industry, under the treaty BUDAPEST since Feb. 28, 1996.

The compounds TAN-2421A1, A2, A3, A4, B1 B2 and/or B3 of the present invention can be produced by culturing not only this strain but also mutant capable of producing the present compound, which is derived from the strain by a per se known method including a gene manipulation technique, and microorganism capable of producing the relevant compound in a medium, producing the present compound to accumulate in a culture; and collecting the compound.

The medium used to culture the producer fungi of the compounds TAN-2421A1, A2, A3, A4, B1 B2 and/or B3 of the present invention may be liquid or solid, so long as it contains the nutrient sources available thereby. In the case of large-scale cultivation, it is preferable to use a liquid medium.

The medium is supplemented with carbon sources, nitrogen sources, inorganic substances and trace nutrients assimilable by the producer fungus as appropriate. Carbon sources include glucose, lactose, sucrose, maltose, dextrin, starch, glycerine, mannitol, sorbitol, oils and fats (e.g. cottonseed oil, soybean oil, lard oil, chicken oil, etc.), n-paraffin and so on. Nitrogen sources include meat extract, yeast extract, dry yeast, soybean flour, corn steep liquor, peptone, green soybean flour, cottonseed flour, tomato paste, peanut meal, blackstrap molasses, urea and ammonia salts (e.g. ammonium sulfate, ammonium chloride, ammonium nitrate, ammonium acetate, etc.) and so on.

Salts containing sodium, potassium, calcium, magnesium, salts of metals such as iron, manganese, zinc, cobalt and nickel, salts of phosphoric acid or boric acid, and salts of organic acids such as acetic acid and propionic acid are used as appropriate. The medium may also incorporate amino acids (e.g. glycine, glutamic acid, aspartic acid, alanine, lysine, methionine, proline, etc.), peptides (e.g. dipeptide, tripeptide, etc.), vitamins (e.g. B1, B2, nicotinic acid, B12, C, etc.) and nucleic acids (e.g. purine, pyrimidine, derivative thereof, etc.). Inorganic acids, organic acids, alkalis, buffers and other additives may be added to regulate the pH of the medium. Appropriate amounts of oils and fats, detergents and other additives may be added for the purpose of defoaming.

As means for cultivation, for example, means such as stationary cultivation, shake cultivation, aeration cultivation, etc. may be used. In the case of large-scale cultivation, it is preferable to use a so-called depth aeration cultivation. The conditions for cultivation vary depending on the state and composition of the medium, kind of the strain, means of cultivation, etc. It is preferable to select the conditions of the temperature of about 12–44° C. and initial pH of about 5–9. In case of the intermediate stage of cultivation, the conditions of the temperature of about 14–30° C. and initial pH of about 6–8 are particularly preferable. Although the culturing time also vary depending on the above various conditions, it is preferred to culture until the concentration of various bioactive substances become maximum. In case of the shake cultivation or aeration cultivation, the time required to this case is normally about 1–14 days.

The method of collecting the desired compounds TAN-2421A1, A2, A3, A4, B1, B2 and/or B3 from the culture is described hereinafter. Since the compounds are acidic fat-soluble, general means utilizing this property may be used. After adjusting the pH of the culture or culture filtrate to acidic, organic solvents which is not miscible with water, for example, halogenated hydrocarbons (e.g. dichloromethane, etc.), esters (e.g. ethyl acetate, etc.), ketones (e.g. methyl isobutyl ketone, etc.) or alcohols (e.g. isobutanol, etc.) are added to extract TAN-2421A1, A2, A3, A4, B1, B2 and/or B3. When the resulting organic solvent layer is extracted with an aqueous alkaline solution, the desired product is dissolved to the aqueous layer. A crude substance containing TAN-2421A1, A2, A3, A4, B1, B2 and/or B3 is obtained by adjusting the pH of the resulting aqueous layer to acidic, extracting again with the above-described organic solvents, washed the resulting organic solvent layer with water, followed by concentration.

In order to obtain pure TAN-2421A1, A2, A3, A4, B1, B2 or B3 by purifying the crude substance, various known chromatography techniques are advantageously used. Useful carriers include carriers utilizing absorptivity differences among compounds such as activated charcoal, silica gel, microcrystalline cellulose, adsorptive resin, etc. or those for gel-filtration, etc. To elute the desired compound from these carriers, there may be used each or mixed solvents in an appropriate ratio, e.g. organic solvents (e.g. halogenated hydrocarbons such as dichloromethane, chloroform, etc.; aromatic hydrocarbons such as toluene, etc.; esters such as ethyl acetate, etc.; ketones such as acetone, etc.; alcohols such as methanol, ethanol, isobutanol, etc.; and nitrites such as acetonitrile, etc.), organic acids (e.g. acetic acid, formic acid, etc.), and aqueous solutions [e.g. water, aqueous dilute alkalis (e.g. sodium hydroxide, potassium hydroxide, sodium hydrogen carbonate, ammonia, etc.), aqueous dilute acids (e.g. hydrochloric acid, acetic acid, formic acid, phosphoric acid, trifluoroacetic acid, etc.) and aqueous dilute salts (e.g. saline, acetate buffers, phosphate buffers, etc.)], the combination depending on the kind and nature of the carrier.

More specifically, there may be advantageously used carriers such as activated carbon for chromatography (produced by Takeda Chemical Industries), Kiesel gel 60 (produced by Merck, German), microcrystalline cellulose [e.g. Avicel (produced by Asahi Chemical), Funacel (produced by Funakoshi Pharmaceutical), etc.], absorptive resin [e.g. Diaion HP-20 or SP-207 (produced by Mitsubishi Chemical Industries) and Amberlite XAD-I or II (produced by Rohm & Haas, USA), etc.], and carriers for gel-filtration [e.g. Sephadex LH-20 (produced by Pharmacia, Sweden), etc.]. In some cases, preparative high performance liquid chromatography (HPLC.) can be advantageously used to purify the compounds. When this method is used, octadecylsilane (ODS) carriers, polymer carriers and silica gel carriers are advantageously used. In case of ODS carriers, YMC gel (produced by YMC.) or TSK gel (produced by Toyo Soda Manufacturing) or the like is used. In case of polymer carriers, ODP (produced by Asahi Chemical) prepared by introducing an octadecyl group into a polymer or NH2P (produced by Asahi Chemical) prepared by introducing polyamine into a polymer or the like is used. A mixed solution of methanol or acetonitrile and water or an aqueous dilute salts or acids (e.g. hydrochloric acid, trifluoroacetic acid, acetic acid, formic acid, etc.) is advantageously used as a mobile phase.

Since TAN-2421A1, A2, A3, A4, B1, B2 and/or B3 are acidic substances, they can also be obtained as a base-addition salt, such a salt of an alkali metal as sodium, potassium, etc. and a salt of an alkali earth metal as calcium, magnesium, etc.

The structures of TAN-2421A1(compound 1), A2(compound 2), A3(compound 3), A4(compound 4), B1 (compound 5), B2 (compound 6) and B3 (compound 7) obtained in Examples 2 and 3 described hereinafter were determined based on the detailed study of physicochemical data and NMR spectra, as shown in Table 1 and Table 2.

TABLE 1

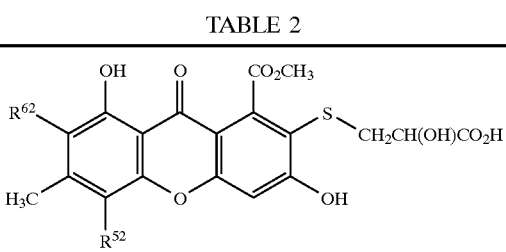

| Compound | Comp. No. | $R^{51}$ | $R^{61}$ |
|---|---|---|---|
| TAN-2421A1 | 1 | Cl | Cl |
| TAN-2421A2 | 2 | H | Cl |
| TAN-2421A3 | 3 | Cl | H |
| TAN-2421A4 | 4 | H | H |

TABLE 2

| Compound | Comp. No. | $R^{52}$ | $R^{62}$ |
|---|---|---|---|
| TAN-2421B1 | 5 | Cl | Cl |
| TAN-2421B2 | 6 | H | Cl |
| TAN-2421B3 | 7 | Cl | H |

A method of producing the above compound [I] or a salt thereof is described hereinafter.

In the reactions as described hereafter, with respect to the protection of functional groups not to be involved in the reaction, the protecting groups used, elimination of the protecting groups, etc., per se known protecting groups or per se known means can be chosen as appropriate.

Reagents often mentioned herein are abbreviated as follows:

| | |
|---|---|
| DCC: | dicyclohexylcarbodiimide |
| WSC: | 1-ethyl-3-(3-dimethylaminopropyl)carbodiimide hydrochloride (water-soluble carbodiimide hydrochloride) |
| DIC: | N,N'-diisopropylcarbodiimide |
| HOBT: | 1-hydroxybenzotriazole |
| THF: | Tetrahydrofuran |
| DMF: | N,N-dimethylformamide |
| TEA: | triethylamine |
| TFA: | trifluoroacetic acid |

A compound represented by the general formula [I] wherein $R^1$ is an esterified carboxyl group, or a salt thereof, can be produced by subjecting a compound represented by the general formula [I] wherein $R^1$ is a carboxyl group, or a salt thereof, to an esterification reaction. The esterification reaction can be conducted, for example, by a per se known method described hereinafter.

1) A starting material compound is reacted with a diazoalkane (e.g. diazomethane, phenyldiazomethane, diphenyldiazomethane, etc.).

2) A starting material compound is reacted with an activated alkyl halide (e.g. methyl iodide, benzyl bromide, chloromethyl methyl ether, etc.).

3) A starting material compound is reacted with an alcohol (e.g. methanol, ethanol, benzyl alcohol, etc.) in the presence of an acid catalyst or a condensing agent. As the acid catalyst, for example, there may be used hydrochloric acid, sulfuric acid, camphorsulfonic acid and the like. As the condensing agent, for example, there may be used DCC, WSC, DIC and the like.

4) An active ester is derived from a starting material compound, and then reacted with an alcohol (e.g. methanol, ethanol, benzyl alcohol, etc.). As the active ester, for example, there may be used an ester with 1-hydroxy-1-H-2-pyridone, N-hydroxysuccinimide, N-hydroxyphthalimide, HOBT and the like.

5) A starting material compound is reacted with an acid halide (e.g. ethyl chloroformate, benzyl chloroformate, etc.) to give an acid anhydride which is then reacted with an alcohol (e.g. methanol, ethanol, benzyl alcohol, etc.).

6) An acid halide (e.g. acid chloride, acid bromide, etc.) is derived from a starting material compound, and then reacted with an alcohol (e.g. methanol, ethanol, benzyl alcohol, etc.).

This reaction may be conducted in the presence of a base. Useful bases include tertiary amines (e.g. trimethylamine, triethylamine, tripropylamine, N-methylpiperidine, N-methylpyrrolidine, cyclohexyldimethylamine, N-methylmorpholine, etc.), secondary amines (e.g. di-n-butylamine, diisobutylamine, dicyclohexylamine, etc.), aromatic tertiary amines (e.g. pyridine, lutidine, collidine, 4-dimethylaminopyridine, etc.), hydroxides of alkali metals (e.g. sodium hydroxide, potassium hydroxide, etc.), carbonates of alkali metals (e.g. sodium carbonate, potassium carbonate, etc.), hydrogen carbonates of alkali metals (e.g. sodium hydrogen carbonate, etc.), and hydroxides of alkali earth metals (e.g. calcium hydroxide, etc.).

This reaction is normally conducted in a solvent which does not affect the reaction. Examples of the solvent include amides (e.g. formamide, DMF, N,N-dimethylacetamide, N-methylpyrrolidone, etc.), sulfoxides (e.g. dimethyl sulfoxide, etc.), aromatic bases (e.g. pyridine, etc.), halogenated hydrocarbons (e.g. chloroform, dichloromethane, etc.), ethers (e.g. diethyl ether, tetrahydrofuran, dioxane, etc.), nitrites (e.g. acetonitrile, etc.), esters (e.g. ethyl acetate, ethyl formate, etc.), aliphatic or aromatic hydrocarbons (e.g. hexane, benzene, toluene, etc.) ketones (e.g. acetone, methylethylketone, methylisobutylketone, etc.) and so on.

The alcohols used as the reaction agent may be used as solvents in excess.

The solvents may be mixed at appropriate ratio.

The reaction temperature is normally about −50 to 150° C., preferably about −30 to 80° C., although it does not subject to limitation, so long as the reaction proceeds. The reaction time is normally several scores of minutes to several scores of hours, depending on the starting material, base, reaction temperature and kind of solvent used.

A compound of the general formula [I] wherein $R^1$ is an amidated carboxyl group, or a salt thereof, can be produced by subjecting a compound of the general formula [I] wherein $R^1$ is a carboxyl group, or a salt thereof, to an amidation reaction.

The amidation reaction can be conducted, for example, by reacting a compound wherein $R^1$ is a carboxyl group (hereinafter abbreviated to "carboxylic acid") or a reactive derivative thereof, with a compound represented by the general formula:

$$HN-(R^9)R^{10} \qquad [III]$$

wherein $R^9$ and $R^{10}$ are the same meanings as defined above, or a salt thereof.

As the reactive derivative of carboxylic acid, for example, acid halides and active esters are used. Such a reactive derivative is specifically described as follows.

1) Acid halide

Examples of the acid halide are an acid chloride, an acid bromide and so on.

2) Active ester

Examples of the active ester are esters such as methyl ester, ethyl ester, methoxymethyl ester, propargyl ester, 4-nitrophenyl ester, 2,4-dinitrophenyl ester, trichlorophenyl ester, pentachlorophenyl ester, mecylphenyl ester, etc, and esters with such as 1-hydroxy-1H-2-pyridone, N-hydroxysuccinimide, N-hydroxyphthalimide, HOBT, etc.

When carboxylic acid is reacted directly with the compound [III] or a salt thereof, for example, a condensing agent such as DCC, WSC, DIC, etc. may be used. These condensing agents may be used for synthesis of an active ester such as 1-hydroxy-1H-2-pyridone, N-hydroxysuccinimide, N-hydroxyphthalimide, HOBT and so on.

This reaction may be conducted in the presence of a base. Examples of the base are the same as mentioned above.

In this method, the compound. [III] or a salt thereof is normally used at 1 mol per mol of carboxylic acid or a reactive derivative thereof, but may be used in excess, so long as the reaction is not interfered with. When a base is used, its amount is normally 1 to 5 mol, preferably about 1 to 3 mol per mol of carboxylic acid or a reactive derivative thereof, varying depending on the starting material compound used, kind of carboxylic acid and reactive derivative thereof and other reaction conditions.

This reaction is normally conducted in a solvent which does not affect the reaction. Examples of the solvent include amides (e.g. formamide, DMF, N,N-dimethylacetamide, N-methylpyrrolidone, etc.), sulfoxides (e.g. dimethyl sulfoxide, etc.), aromatic amines (e.g. pyridine, etc.), halogenated hydrocarbons (e.g. chloroform, dichloromethane, etc.), ethers (e.g. tetrahydrofuran, dioxane, etc.), nitriles (e.g. acetonitrile, etc.), esters (e.g. ethyl acetate, ethyl formate, etc.), aliphatic or aromatic hydrocarbons (e.g. hexane, benzene, toluene, etc.), ketones (e.g. acetone, methylethylketone, methylisobutylketone, etc.), water and so on. These solvents may be mixed at appropriate ratio.

The reaction temperature is normally about −50 to 150° C., preferably about −30 to 80° C., although it does not subject to limitation, so long as the reaction proceeds. The reaction time is normally several scores of minutes to several scores of hours, depending on the starting material, base, reaction temperature and kind of solvent used.

A compound of the general formula [I] wherein $R^2$ is represented by the formula $-CH_2(CHOH)m^1COOR^{18}$ wherein $m^1$ and $R^{18}$ are the same meanings as defined above, or a salt thereof, can be produced by subjecting a compound of the general formula [I] wherein $R^2$ is represented by the formula $-CH_2(CHOH)m^1COOH$ wherein m is the same meanings as defined above, or a salt thereof, to the above-described esterification reaction.

A compound of the general formula [I] wherein $R^2$ is represented by the formula $-CH_2(CHOH)m^2CONR^{19}R^{20}$ wherein $m^2$, $R^{19}$ and $R^{20}$ are the same meanings as defined above, or a salt thereof, can be produced by subjecting a compound of the general formula [I] wherein $R^2$ is represented by the formula $-CH_2(CHOH)m^2COOH$ wherein $m^2$ is the same meanings as defined above, or a salt thereof, to the above-described amidation reaction.

The amidation reaction can be conducted by reacting a compound wherein $R^2$ is represented by the formula $-CH_2(CHOH)m^2COOH$, or a reactive derivative thereof, with a compound represented by the general formula:

$$HN-(R^{19})R^{20} \qquad [IV]$$

wherein $R^{19}$ and $R^{20}$ are the same meanings as defined above, or a salt thereof according to the above-described method.

A compound of the general formula [I] wherein $R^2$ is represented by the formula $-CH_2(CHOH)m^3CONHS(=O)_2R^{21}$ wherein $m^3$ and $R^{21}$ are the same meaning as defined above, or a salt thereof, can be produced, for example, by subjecting a compound of the general formula [I] wherein $R^2$ is represented by the formula $-CH_2(CHOH)m^3COOH$ wherein m is the same meaning as defined above, or a salt thereof, to the above-described amidation reaction. This reaction can be conducted by reacting a compound wherein $R^2$ is represented by the formula $-CH_2(CHOH)m^3COOH$, or a reactive derivative thereof, with a compound represented by the general formula:

$$H_2NS(=O)_2R^{21} \qquad [V]$$

wherein $R^{21}$ is the same meaning as defined above, or a salt thereof according to the above-described method.

A compound of the general formula [I] wherein $R^2$ is represented by the formula $-CH_2(CHOH)m^4CONHOR^{22}$ wherein $m^4$ and $R^{22}$ are the same meaning as defined above, or a salt thereof, can be produced, for example, by subjecting a compound of the general formula [I] wherein $R^2$ is represented by the formula $-CH_2(CHOH)m^4COOH$ wherein $m^4$ is the same meaning as defined above, or a salt thereof, to the above-described amidation reaction. This reaction can be conducted by reacting a compound wherein $R^2$ is represented by the formula $-CH_2(CHOH)m^4COOH$, or a reactive derivative thereof, with a compound represented by the general formula:

$$H_2NOR^{22} \qquad [VI]$$

wherein $R^{22}$ is the same meaning as defined above, or a salt thereof according to the above-described method.

A compound of the general formula [I] wherein $R^2$ is represented by the formula $-CH_2(CHOH)m^5R^{23}$ wherein $m^5$ and $R^{23}$ are the same meaning as defined above, or a salt thereof, can be produced, for example, by reacting a compound of the general formula [I] wherein $R^2$ is a hydrogen and n is 0, or a salt thereof, with a compound having a leaving group in the presence of a base. This reaction can be conducted by the same reaction used in the method of producing compound of the general formula [I] wherein $R^2$ is a hydrocarbon group which may be substituted, or a salt thereof, described hereinafter.

A compound of the general formula [I] wherein $R^2$ is represented by the formula $-CH_2(CHOH)m^6CH_2OH$ wherein $m^6$ is the same meaning as defined above, or a salt thereof, can be produced, for example, by subjecting a compound of the general formula [I] wherein $R^2$ is represented by the formula —$CH_2(CHOH)m^6COOR^{18}$ wherein $m^6$ and $R^{18}$ are the same meaning as defined above, or a salt thereof, to a reduction reaction.

This reduction reaction is preferably conducted using a reducing agent. As the reducing agent, for example, there may be used metal hydride compounds (e.g. lithium aluminum hydride, diisobutylaluminum hydride, lithium tri-t-butoxyaluminum hydride, lithium borohydride, sodium borohydride, sodium borocyanohydride, diborane, etc.) metals or metal salts (e.g. zinc, etc.), thiols (e.g. thiophenol, dithioerythrytol, dithiothreitol, etc.) and so on.

This reaction may be conducted in the presence of an acid. Examples of the acid used include mineral acids (e.g. hydrochloric acid, sulfuric acid, etc.), organic acids (e.g. acetic acid, propionic acid, TFA, methansulfonic acid, toluenesulfonic acid, camphorsulfonic acid, etc.) and Lewis acid (e.g. aluminum chloride, boron trifluoride, titanium tetrachloride, etc.).

This reaction is normally conducted in a solvent which does not affect the reaction. Examples of the solvent include ethers (e.g. diethyl ether, tetrahydrofuran (hereinafter abbreviated to "THF"), dioxane, etc.), amides (e.g. formamide, DMF, N,N-dimethylacetamide, N-methylpyrrolidone, etc.), sulfoxides (e.g. dimethyl sulfoxide, etc.), aromatic amines (e.g. pyridine, etc.), halogenated hydrocarbons (e.g. chloroform, dichloromethane, etc.), ethers (e.g. diethyl ether, THF, dioxane, etc.), nitriles (e.g. acetonitrile, etc.), aliphatic or aromatic hydrocarbons (e.g. hexane, benzene, toluene, etc.), water and so on. These solvents may be mixed at appropriate ratio.

The reaction temperature is normally about –70 to 150° C., preferably about –40 to 100° C., although it does not subject to limitation, so long as the reaction proceeds. The reaction time is normally several scores of minutes to several scores of hours, depending on the starting material, reaction temperature and kind of solvent used.

A compound of the general formula [I] wherein $R^2$ is represented by the formula —$CH_2(CHOH)m^6CH_2OR^{24'}$ wherein $m^6$ is the same meaning as defined above, and $R^{24'}$ is a hydrocarbon group which may be substituted, or a salt thereof, can be produced by reacting a compound of the general formula [I] wherein $R^2$ is represented by the formula —$CH_2(CHOH)m^6 CH_2OH$ wherein $m^6$ is the same meaning as defined above, or a salt thereof, with a compound (hereinafter abbreviated to a "compound having a leaving group") represented by the general formula:

$$R^{24'}—X'$$

wherein $R^{24'}$ is a hydrocarbon group which may be substituted, and X' is a leaving group. Examples of the leaving group shown by X' are a halogen atom, a sulfonyloxy group and so on.

With respect to the compound having a leaving group, base, solvent, reaction temperature and reaction time used in this reaction, the same conditions as those of a method of producing a compound of the general formula [I] wherein $R^3$ or $R^4$ is a hydroxyl group substituted with a hydrocarbon group which may be substituted, or a salt thereof, described hereinafter.

A compound of the general formula [I] wherein $R^2$ is represented by the formula —$CH_2(CHOH)m^6CH_2OR^{24''}$ wherein $m^6$ is the same meaning as defined above, and $R^{24''}$ is an acyl group which may be substituted, or a salt thereof, can be produced, for example, by subjecting a compound of the general formula [I] wherein $R^2$ is represented by the formula —$CH_2(CHOH)m^6CH_2OH$ wherein $m^6$ is the same meaning as defined above, or a salt thereof, to an acylation reaction.

With respect to the acylating agent, base, solvent, reaction temperature and reaction time used in this reaction, the same conditions as those of a method of producing a compound of the general formula [I] wherein $R^3$ or $R^4$ is a hydroxyl group substituted with an acyl group which may be substituted, or a salt thereof, described hereinafter.

A compound of the general formula [I] wherein $R^2$ is a hydroxyl group and n is 1 or 2, or a salt thereof, can be produced, for example, by subjecting a compound of the general formula [I] wherein $R^2$ is a hydrogen atom or a hydrocarbon group which may be substituted and n is 0, or a salt thereof, or a compound represented by the general formula [II], or a salt thereof, to an oxidation reaction.

This oxidation reaction is preferably conducted using an oxidizing agent. Examples of the oxidizing agent are peracids (e.g. peracetic acid, performic acid, perbenzoic acid, m-chloroperbenzoic acid, etc.), peracid esters (e.g. tert-butyl perbenzoate, tert-butyl m-chloroperbenzoate, etc.), chromic acids (e.g. chromic anhydride, sulfuric acid chromate, acetic acid chromate, etc.), chromates (e.g. potassium chromate, sodium chromate, pyridinium chromate, pyridinum chlorochromate, etc.), bicromates (e.g. potassium bichromate, sodium bichromate, pyridinium bichromate, etc.), permanganates (e.g. potassium permanganate, sodium permanganate, etc.), perhalo acids (e.g. periodic acid, perbromic acid, perchloric acid, etc.), perhalo acid salts (e.g. sodium periodide, potassium perbromate, sodium perchloride, etc.), halogen (e.g. iodine, bromine, chlorine, etc.), peroxides (e.g. hydrogen peroxide, butyl hydroperoxide, etc.), lead tetraacetate, nitric acid, oxygen, sulfuryl chloride, dimethyl-sulfoxide and so on.

This reaction can normally be conducted in a solvent which does not affect the reaction. Examples of the solvent include amides (e.g. formamide, DMF, N,N-dimethylacetamide, N-methylpyrrolidone, etc.), sulfoxides (e.g. dimethyl sulfoxide, etc.), aromatic amines (e.g. pyridine, etc.), halogenated hydrocarbons (e.g. chloroform, dichloromethane, etc.), ethers (e.g. diethyl ether, THF, dioxane, etc.), nitriles (e.g. acetonitrile, etc.), esters (e.g. ethyl acetate, ethyl formate, etc.), ketones (e.g. acetone, methyl ethyl ketone, methyl isobutyl ketone, etc.), alcohols (e.g. methanol, ethanol, tert-butanol, etc.), aliphatic carboxylic acids (e.g. formic acid, acetic acid, propionic acid, etc.), aliphatic or aromatic hydrocarbons (e.g. hexane, benzene, toluene, etc.), water and so on. These solvents may be mixed at appropriate ratio.

This reaction may be conducted in the presence of an acid. Examples of the acid used include mineral acids (e.g. hydrochloric acid, sulfuric acid, phosphoric acid, etc.), organic acids (e.g. formic acid, acetic acid, propionic acid, TFA, methansulfonic acid, toluenesulfonic acid, camphorsulfonic acid, etc.) and Lewis acid (e.g. aluminum chloride, boron trifluoride, titanium tetrachloride, etc.).

This reaction may be conducted in the presence of a base. Examples of the base include alkali metal hydrides (e.g. sodium hydride, potassium hydride, etc.), alkali earth metal hydrides (e.g. calcium hydride, etc,.), alkoxides of alkali metals (e.g. sodium methoxide, sodium ethoxide, etc.), hydroxides of alkali metals (e.g. sodium hydroxide, potassium hydroxide, etc.), carbonates of alkali metals (e.g. sodium carbonate, potassium carbonate, etc.), hydrogen carbonates of alkali metals (e.g. sodium hydrogen carbonate, etc.), hydroxides of alkali earth metals (e.g. calcium hydroxide, etc.), phosphates of alkali metals (e.g. tripotassium phosphate, etc.), tertiary amines (e.g. trimethylamine, triethylamine, tripropylamine, N-methylpiperidine, N-methylpyrrolidine, cyclohexyldimethylamine, N-methylmorpholine, etc.), secondary amines (e.g. di-n-butylamine, diisobutylamine, dicyclohexylamine, etc.) and aromatic tertiary amines (e.g. pyridine, lutidine, collidine, 4-dimethylaminopyridine, etc.).

The reaction temperature is normally about −70 to 150° C., preferably about −30 to 100° C., although it does not subject to limitation, so long as the reaction proceeds. The reaction time is normally several scores of minutes to several scores of hours, depending on the starting material, reaction temperature and kind of solvent used.

A compound of the general formula [I] wherein $R^2$ is a hydrogen atom and n is 0, or a salt thereof, can be produced, for example, by subjecting a compound of the general formula [I] wherein $R^2$ is the formula —$CH_2COOH$ and n is 1, or a salt thereof, to a reaction according to the method described in the literature (Journal of Organic Chemistry, 31, 835, (1966)). In this method, a compound represented by the general formula:

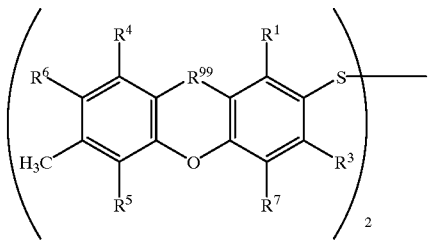

[II]

wherein $R^1$, $R^3$, $R^4$, $R^5$, $R^6$, $R^7$ and $R^{99}$ are the same meanings as defined, or a salt thereof may be formed.

In that case, it is possible to convert a compound represented by the general formula [II], or a salt thereof into a compound represented by the general formula:

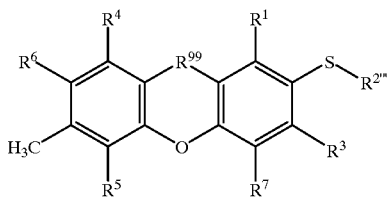

wherein $R^{2'''}$ is a hydrogen atom or a hydrocarbon group which may be substituted, and other symbols are the same meanings as defined, or a salt thereof, for example, by reduction reaction, followed by an introduction reaction of the hydrocarbon group if necessary. Examples of the hydrocarbon group which may be substituted shown by $R^{2'''}$ are the same hydrocarbon group which may be substituted shown by $R^2$.

This reduction reaction is conducted by the same reduction reaction as mentioned above. The introduction reaction of hydrocarbon groups can be conducted as follows.

A compound of the general formula [I] wherein $R^2$ is a hydrocarbon group which may be substituted, or a salt thereof, can also be produced by reacting a compound of the general formula [I] wherein $R^2$ is a hydrogen atom and n is 0, or a salt thereof, with a compound having a leaving group in the presence of a base.

The above compound having a leaving group is a compound having a functional group which is easily leaved by a substitution, etc. by a chemical reaction. Specifically, a compound represented by the general formula:

$$R^2\text{—X} \quad [VII]$$

wherein $R^2$ is a hydrocarbon group which may be substituted, and X is a chorine atom, a bromine atom or an iodine atom, or a salt thereof, a compound represented by the general formula:

$$R^2\text{—OSO}_2R^{41} \quad [VIII]$$

wherein $R^2$ is a hydrocarbon group which may be substituted, and $R^{41}$ is a hydrocarbon atom which may be substituted, or a salt thereof, or a compound represented by the general formula:

$$(R^2\text{—OSO}_2)O \quad [IX]$$

wherein $R^2$ is a hydrocarbon group which may be substituted, or a salt thereof is preferred.

Examples of the hydrocarbon group which may be substituted shown by $R^{41}$ are a methyl group, an ethyl group, a phenyl group optionally substituted by methyl or bromine atom, a trifluoromethyl group and so on.

As the compound having a leaving group, epoxides can also be used. Examples of the epoxides are propylene oxide, glycidol, ethyl 2,3-epoxypropionate and so on.

This reaction may be conducted in the presence of a base. Examples of the base are the same those mentioned in the above oxidation reaction.

This reaction can normally be conducted in a solvent which does not affect the reaction. Examples of the solvent are the same those as mentioned in the above oxidation reaction.

The reaction temperature is normally about −70 to 150° C., preferably about −30 to 80° C., although it does not subject to limitation, so long as the reaction proceeds. The reaction time is normally several scores of minutes to several scores of hours, depending on the starting material, base, reaction temperature and kind of solvent used.

The reduction reaction of a disulfide group into thiol and the introduction reaction of the hydrocarbon group into the resulting thiol group can also be conducted continuously in the same reaction vessel.

A compound of the general formula [I] wherein $R^3$ or $R^4$ is a hydroxyl group substituted with a thereof can be produced, for example, by reacting a compound of the general formula [I] wherein $R^3$ or $R^4$ is compound of the general formula [I] wherein $R^3$ or $R^4$ is having a leaving group in the presence of a base, or reacting a starting material compound with a diazoalkane (e.g. diazomethane, phenyldiazomethane, diphenyldiazomethane, etc.).

The above compound having a leaving group is a compound having a functional group which is easily substituted by a chemical reaction. Examples of the leaving group are halides (e.g. methyl iodide, ethyl iodide, propyl iodide, isopropyl iodide, butyl iodide, pentyl iodide, allyl bromide, benzyl bromide, chloromethyl methyl ether, etc.), sulfonates (e.g. methyl methanesulfonate, methyl p-toluenesulfonate, ethyl p-toluenesulfonate, methyl benzenesulfonate, methyl trifluoromethanesulfonate, ethyl trifluoromethanesulfonate, etc.) and sulfates (e.g. dimethyl sulfate, diethyl sulfate, etc.).

This reaction may be conducted in the presence of a base. Examples of the base are the same those mentioned in the above oxidation reaction.

This reaction can normally be conducted in a solvent which does not affect the reaction. Examples of the solvent are the same those as mentioned in the above oxidation reaction.

The reaction temperature is normally about −70 to 150° C., preferably about −30 to 80° C., although it does proceeds. The reaction time is normally several scores of minutes to several scores of hours, depending on the starting material, base, reaction temperature and kind of solvent used.

A compound of the general formula [I] wherein $R^3$ or $R^4$ is a hydroxyl group substituted with an acyl group which may be substituted, or a salt thereof, can be produced, for example, by subjecting a compound of the general formula [I] wherein $R^3$ and/or $R^4$ is a hydroxyl group, or a salt thereof, to an acylation reaction.

The acylation reaction can be conducted, for example, by reacting a starting material compound with an acylating agent, for example, organic acid (e.g. organic carboxylic acid, organic sulfonic acid, etc.) or a reactive derivative thereof in a solvent. Examples of the reactive derivative of the organic acid are the acid halides, the acid anhydrides, the mixed acid anhydride, the active esters and so on as mentioned above.

When a compound of the general formula [I] wherein $R^3$ and/or $R^4$ is a hydroxyl group, or a salt thereof is reacted directly with the an organic acid, a condensing agent such as DCC, WSC, DIC, etc. may be used. These condensing agents may be used for synthesis of an active ester with 1-hydroxy-1H-2-pyridone, N-hydroxysuccinimide, N-hydroxyphthalimide, HOBT and so on.

This reaction may be conducted in the presence of a base. Examples of the base are the same those mentioned in the above esterification reaction.

This reaction can normally be conducted in a mentioned in the above esterification reaction. of the solvent are the same those as mentioned in the above esterification reaction.

The reaction temperature is normally about −50 to 150° C., preferably about −30 to 80° C., although it does not subject to limitation, so long as the reaction proceeds. The reaction time is normally several scores of minutes to several scores of hours, depending on the starting material, base, reaction temperature and kind of solvent used.

A compound of the general formula [I] wherein $R^3$ and/or $R^4$ is represented by the formula $OCOR^{27}$ wherein $R^{27}$ is the same meaning as defined above, or a salt thereof, can be produced, for example, by subjecting a compound of the general formula [I] wherein $R^3$ and/or $R^4$ is a hydroxyl group, or a salt thereof, to a reaction between a compound represented by the general formula:

$$X\text{—}COOR^{27} \qquad [X]$$

wherein $R^{27}$ is the same meaning as defined above, and X is a chlorine atom or a bromine atom, or a salt thereof and a compound represented by the general formula:

$$(R^{27}OCO)_2O \qquad [XI]$$

wherein $R^{27}$ is the same meaning as defined above, or a salt therof.

This reaction may be conducted in the presence of a base. Examples of the base are the same those mentioned in the above esterification reaction.

This reaction can normally be conducted in a solvent which does not affect the reaction. Examples of the solvent are the same those as mentioned in the above esterification reaction.

The reaction temperature is normally about −50 to 150° C., preferably about −30 to 80° C., although it does not subject to limitation, so long as the reaction proceeds. The reaction time is normally several scores of minutes to several scores of hours, depending on the starting material, base, reaction temperature and kind of solvent used.

A compound of the general formula [I] wherein $R^5$, $R^6$ and/or $R^7$ is a halogen atom, or a salt thereof, can be produced, for example, by subjecting a compound of the general formula [I] wherein $R^5$, $R^6$ and/or $R^7$ is a hydrogen atom, or a salt therof, to a halogenation reaction.

Examples of a halogenating agent used for this reaction include chlorine, bromine, iodine, N-bromosuccinimide, N-chlorosuccinimide, N-bromoacetamide, pyridinium tribromide, t-butyl hypochlorite, sulfuryl chloride and the like.

This reaction may be conducted in the presence of a radical initiator such as 2,2'-azobis(isobutyronitrile) and the like.

This reaction may be conducted in the presence of an acid. Examples of the acid are the same those mentioned in the above oxidation reaction.

This reaction may be conducted in the presence of a base. Examples of the base are the same those mentioned in the above oxidation reaction.

The reaction temperature is normally about −70 to 150° C., preferably about −30 to 100° C., although it does not subject to limitation, so long as the reaction proceeds. The reaction time is normally several scores of minutes to several scores of hours, depending on the starting material, reaction temperature and kind of solvent used.

A compound of the general formula [I] wherein $R^7$ is a nitro group, or a salt thereof, can be produced, for example, by the method of synthesizing a nitro compound described in literatures [edited by the Chemical Society of Japan, Shinjikken Kagaku Koza, Vol. 14, pages 1261–1300, Maruzen (1978); and edited by the Chemical Society of Japan, the fourth edition of Jikken Kagaku Koza, Vol. 20, pages 394–405, Maruzen (1992)], or modifications thereof.

Examples of the starting material compound of this reaction include a compound of the general formula [I] wherein $R^7$ is a hydrogen atom or a halogen atom, or a salt thereof. Examples of the reagent used for the reaction include nitric acid, nitrates (e.g. sodium nitrate, potassium nitrate, etc.), nitrobenzene, benzoylnitric acid, acetylnitric acid, diacetylorthonitric acid, dinitrogen tetraoxide, dinitrogen pentaoxide, nitrous acid and nitrites (e.g. sodium nitrite, potassium nitrite, etc.).

This reaction may be conducted in the presence of an acid. Examples of the acid are the same those as mentioned in the above oxidation reaction.

This reaction can normally be conducted in a solvent which does not affect the reaction. Examples of the solvent are the same those as mentioned in the above oxidation reaction.

The reaction temperature is normally about −70 to 150° C., preferably about −40 to 100° C., although it does not subject to limitation, so long as the reaction proceeeds. The reactiontime is normally several scores of minutes to several scores of hours, depending on the starting material, reaction temperature and kind of solvent used.

A compound of the general formula [I] wherein $R^7$ is an acyl group which may be substituted, or a salt thereof, can be produced, for example, by the Friedel-Crafts reaction described in literatures [edited by the Chemical Society of Japan, Shinjikken Kagaku Koza, Vol. 14, pages 751–875, Maruzen (1977); and edited by the Chemical Society of Japan, the fourth edition of Jikken Kagaku Koza, Vol. 21, pages 394–405, Maruzen (1991)].

Examples of the starting material compound of this reaction include a compound of the general formula [I] wherein $R^7$ is a hydrogen atom, or a salt thereof. Examples of the acylating agent used for the reaction include carboxylic acid, carboxylic acid halide and carboxylic acid anhydride.

This reaction may be conducted in the presence of an acid. Examples of the acid are the same those as mentioned in the above oxidation reaction.

This reaction can normally be conducted in a solvent which does not affect the reaction. Examples of the solvent are the same those as mentioned in the above oxidation reaction.

The reaction temperature is normally about −70 to 150° C., preferably about −40 to 100° C., although it does not subject to limitation, so long as the reaction proceeds. The reaction time is normally several scores of minutes to several scores of hours, depending on the starting material, reaction temperature and kind of solvent used.

A compound of the general formula [I] wherein $R^7$ is a formyl group, or a salt thereof, can be produced, for example, by the formylation reaction described in literatures [edited by the Chemical Society of Japan, Shinjikken Kagaku Koza, Vol. 14, pages 636–751, Maruzen (1977); and edited by the Chemical Society of Japan, the fourth edition of Jikken Kagaku Koza, Vol. 21, pages 106–124, Maruzen (1991)], or modifications thereof.

Examples of the starting material compound of this reaction include a compound of the general formula [I] wherein $R^7$ is a hydrogen atom, or a salt thereof. Examples of the formylation reaction include Vilsmeier reaction.

This reaction can be conducted, for example, by using a halogenating agent (e.g. phosphoryl chloride, phosgene, oxalyl chloride, thionyl chloride, triphenylphosphine bromide, hexachlorotriphosphazatriene, etc.) and a formyl group donating reagent (e.g. DMF, N-methylformanilide, N-formylmorpholine, N,N-diisopropylformamide, ethyl orthoformate, etc.) in combination.

This reaction can normally be conducted in a solvent which does not affect the reaction. Examples of the solvent are the same those as mentioned in the above oxidation reaction.

The reaction temperature is normally about −70 to 150° C., preferably about −40 to 100° C., although it does not subject to limitation, so long as the reaction proceeds. The reaction time is normally several scores of minutes to several scores of hours, depending on the starting material, reaction temperature and kind of solvent used.

A compound of the general formula [I] wherein $R^7$ is a hydrocarbon group which may be substituted or a heterocyclic group which may be substituted, or a salt thereof, can be produced, for example, by the coupling reaction between a compound of the general formula [I] wherein $R^7$ is a halogen atom, or a salt thereof, and an organoboron compound. This reaction can be conducted, for example, by the method described in the literature [Synthetic Communication, 11, 513 (1981); Journal of American Chemical Society, 111, 314 (1989); Tetrahedron Letters, 33, 2773 (1992); Synlett, 207 (1992); and Journal of American Chemical Society, 116, 10847 (1994)], or modifications thereof.

In this reaction, a catalytic amount of palladium reagents (e.g. tetrakis(triphenylphosphine)palladium, palladium (II) acetate, palladium (II) chloride, etc.) are normally used. One or more equivalents of them are used sometimes.

This reaction may be conducted in the presence of a phosphorus compound. Examples of the phosphorus compound include triphenylphosphine, tris(2-methylphenyl) phosphine and the like.

This reaction may be conducted in the presence of a base. Examples of the base are the same those mentioned in the above oxidation reaction.

This reaction can normally be conducted in a solvent which does not affect the reaction. Examples of the solvent are the same those as mentioned in the above oxidation reaction.

The reaction temperature is normally about −70 to 200° C., preferably about −20 to 150° C., although it does not subject to limitation, so long as the reaction proceeds. The reaction time is normally several scores of minutes to several scores of hours, depending on the starting material, reaction temperature and kind of solvent used.

A compound of the general formula [I] wherein $R_7$ is a hydrocarbon group which may be substituted, or a salt thereof, can also be produced, for example, by subjecting a compound of the general formula [I] wherein $R^7$ is an acyl group which may be substituted, or a salt thereof, to the reduction reaction.

This reaction can be conducted, for example, by the same method as that for producing a compound of the general formula [I] wherein $R^2$ is represented by the formula —$CH_2$(CHOH)$m^6$$CH_2OH$, or a salt thereof.

A compound of the general formula [I] wherein n is 1 or 2, or a salt thereof can be produced, for example, by oxidizing a compound a compound of the general formula [I] wherein n is 0, or a salt thereof.

This oxidation reaction is preferably conducted using an oxidizing agent. Examples of the oxidizing agent are the same those as mentioned in the above oxidation reaction.

This reaction can normally be conducted in a solvent which does not affect the reaction. Examples of the solvent are the same those as mentioned in the above oxidation reaction.

A compound of the general formula [I] wherein $R^{99}$, is —$CH_2$ or a salt thereof, can be produced, for example, by subjecting a compound of the general formula [I] wherein $R^{99}$ is carbonyl, or a salt thereof, to a reduction reaction.

This reduction reaction is preferably conducted using a reducing agent. Examples of the reducing agent are the same those as mentioned in the above reduction reaction.

This reaction may be conducted in the presence of an acid. Examples of the acid are the same those as mentioned in the above reduction reaction.

This reaction can normally be conducted in a solvent which does not affect the reaction. Examples of the solvent are the same those as mentioned in the above reduction reaction.

The reaction tmeperature is normally about −70 to 150° C., preferably about −40 to 100° C., although it does not subject to limitaiton, so long as the reaciton proceeds. The reaction time is normally several scores of minutes to several scores of hours, depending on the starting material, reaction temperature and kind of solvent used.

Examples of the compounds obtained by the above-described production method are shown in Table 3 to Table 11.

TABLE 3

| Comp. No. | Example No. | $R^1$ | $R^2$ | $R^3$ | $R^4$ | $R^5$ | $R^6$ | $R^7$ | n | $R^{99}$ |
|---|---|---|---|---|---|---|---|---|---|---|
| 1 | 2 | $CO_2CH_3$ | $CH_2CO_2H$ | OH | OH | Cl | Cl | H | 0 | C=O |
| 2 | 3 | $CO_2CH_3$ | $CH_2CO_2H$ | OH | OH | H | Cl | H | 0 | C=O |
| 3 | 3 | $CO_2CH_3$ | $CH_2CO_2H$ | OH | OH | Cl | H | H | 0 | C=O |
| 4 | 3 | $CO_2CH_3$ | $CH_2CO_2H$ | OH | OH | H | H | H | 0 | C=O |
| 5 | 3 | $CO_2CH_3$ | $CH_2CH(OH)CO_2H$ | OH | OH | Cl | Cl | H | 0 | C=O |
| 6 | 3 | $CO_2CH_3$ | $CH_2CH(OH)CO_2H$ | OH | OH | H | Cl | H | 0 | C=O |
| 7 | 3 | $CO_2CH_3$ | $CH_2CH(OH)CO_2H$ | OH | OH | Cl | H | H | 0 | C=O |
| 8 | 4 | $CO_2CH_3$ | $CH_2CO_2CH_3$ | $OCH_3$ | OH | Cl | Cl | H | 0 | C=O |
| 9 | 5 | $CO_2CH_3$ | $CH_2CO_2H$ | $OCH_3$ | OH | Cl | Cl | H | 0 | C=O |
| 10 | 6 | $CO_2CH_3$ | $CH_2CO_2CH_3$ | OH | OH | Cl | Cl | H | 0 | C=O |
| 11 | 7 | $CO_2CH_3$ | $CH_2CO_2CH_2OCH_3$ | $OCH_2OCH_3$ | OH | Cl | Cl | H | 0 | C=O |
| 12 | 8 | $CO_2CH_3$ | $CH_2CO_2H$ | OH | $OCH_3$ | Cl | Cl | H | 0 | C=O |
| 13 | 9 | $CO_2CH_3$ | $CH_2CONH_2$ | OH | OH | Cl | Cl | H | 0 | C=O |
| 14 | 10 | $CO_2CH_3$ | $CH_2CONH(CH_2)_2OCH_3$ | OH | OH | Cl | Cl | H | 0 | C=O |
| 15 | 11 | $CO_2CH_3$ | $CH_2CO$—Gly—$OCH_2CH_3$ | OH | OH | Cl | Cl | H | 0 | C=O |
| 16 | 12 | $CO_2CH_3$ | $CH_2CO$—Gly—OH | OH | OH | Cl | Cl | H | 0 | C=O |
| 17 | 13 | $CO_2CH_3$ | $CH_2CO_2H$ | OH | OH | Cl | Cl | H | 1 | C=O |
| 18 | 14 | $CO_2CH_3$ | $CH_2CO_2H$ | OH | $OCOCH_3$ | Cl | Cl | H | 0 | C=O |

TABLE 4

| Comp. No. | Example No. | $R^1$ | $R^2$ | $R^3$ | $R^4$ | $R^5$ | $R^6$ | $R^7$ | n | $R^{99}$ |
|---|---|---|---|---|---|---|---|---|---|---|
| 19 |  | $CO_2CH_3$ | $CH_2CO_2CH_3$ | $OCOCH_3$ | $OCOCH_3$ | Cl | Cl | H | 0 | C=O |
| 20 | 15 | $CO_2CH_3$ | $CH_2CH_2OH$ | OH | $OCOCH_3$ | Cl | Cl | H | 0 | C=O |
| 21 | 16 | $CO_2CH_3$ | $CH_2CH_2OH$ | OH | OH | Cl | Cl | H | 0 | C=O |
| 22 |  | $CO_2CH_3$ | $CH_2CH_2OH$ | OH | OH | Cl | Cl | H | 1 | C=O |
| 23 |  | $CO_2CH_3$ | $CH_2CH_2OCOCH_3$ | OH | OH | Cl | Cl | H | 0 | C=O |
| 24 |  | $CO_2CH_3$ | $CH_2CH_2OCH_3$ | OH | OH | Cl | Cl | H | 0 | C=O |
| 25 |  | $CO_2CH_3$ | $CH_2CO_2H$ | OH | OH | Br | Br | H | 0 | C=O |
| 26 | 17 | $CO_2CH_3$ | $CH_2CO_2CH_3$ | OH | $OCOCH_3$ | Cl | Cl | H | 0 | C=O |
| 27 | 18 | $CO_2CH_3$ | $CH_2CO_2H$ | OH | $OCOCH_2CH_3$ | Cl | Cl | H | 0 | C=O |
| 28 | 19 | $CO_2CH_3$ | $CH_2CO_2H$ | OH | $OCOCH(CH_3)_2$ | Cl | Cl | H | 0 | C=O |
| 29 | 20 | $CO_2CH_3$ | $CH_2CO_2H$ | OH | OCOPh | Cl | Cl | H | 0 | C=O |
| 30 | 21 | $CO_2CH_3$ | $CH_2CO_2CH_3$ | OH | OH | Cl | Cl | H | 0 | $CH_2$ |
| 31 | 22 | $CO_2CH_3$ | $CH_2CH_2OH$ | OH | OH | Cl | Cl | H | 0 | $CH_2$ |
| 32 | 23 | $CO_2CH_3$ | $CH_2CO_2H$ | OH | OH | Cl | Cl | H | 0 | $CH_2$ |
| 33 | 24 | $CO_2H$ | $CH_2CO_2H$ | OH | OH | Cl | Cl | H | 0 | C=O |
| 34 | 25 | $CO_2CH_3$ | $CH_2CO_2CH_2OCH_3$ | $OCH_2OCH_3$ | $OCH_2OCH_3$ | Cl | Cl | H | 0 | C=O |
| 35 | 26 | $CO_2CH_3$ | $CH_2CO_2CH_2OCH_3$ | OH | OH | Cl | Cl | H | 0 | C=O |
| 36 | 27 | $CO_2CH_3$ | $CH_2CO_2CH_2OCH_3$ | $OCOCH_3$ | $OCOCH_3$ | Cl | Cl | H | 0 | C=O |

TABLE 5

| Comp. No. | Example No. | $R^1$ | $R^2$ | $R^3$ | $R^4$ | $R^5$ | $R^6$ | $R^7$ | n | $R^{99}$ |
|---|---|---|---|---|---|---|---|---|---|---|
| 37 | 28 | $CO_2CH_3$ | $CH_2CO_2H$ | $OCOCH_3$ | $OCOCH_3$ | Cl | Cl | H | 0 | C=O |
| 38 | 29 | $CO_2CH_3$ | $CH_2CO_2H$ | $OCOCH_3$ | OH | Cl | Cl | H | 0 | C=O |
| 39 | 30 | $CO_2CH_3$ | $CH_2CO_2H$ | OH | OH | Cl | Cl | Br | 0 | C=O |
| 40 | 31 | $CO_2CH_3$ | $CH_2CO_2H$ | OH | OH | Cl | Cl | I | 0 | C=O |
| 41 | 32 | $CO_2CH_3$ | $CH_2CO_2H$ | OH | OH | Cl | Cl | H | 2 | C=O |
| 42 | 33 | $CO_2CH_2OCH_3$ | $CH_2CO_2CH_2OCH_3$ | OH | OH | Cl | Cl | H | 0 | C=O |
| 43 | 34 | $CO_2CH_2OCH_3$ | $CH_2CO_2H$ | OH | OH | Cl | Cl | H | 0 | C=O |
| 44 | 35 | $CO_2H$ | $CH_2CO_2CH_3$ | OH | OH | Cl | Cl | H | 0 | C=O |
| 45 | 36 | $CO_2H$ | $CH_2CO_2CH_2OCH_3$ | OH | OH | Cl | Cl | H | 0 | C=O |
| 46 | 37 | $CO_2CH_2CH_3$ | $CH_2CO_2CH_2CH_3$ | OH | OH | Cl | Cl | H | 0 | C=O |
| 47 | 37 | $CO_2CH_2CH_3$ | $CH_2CO_2H$ | OH | OH | CL | Cl | H | 0 | C=O |
| 48 | 38 | $CO_2CH_3$ | $CH_2CO_2CH_2Ph$ | OH | OH | Cl | Cl | H | 0 | C=O |
| 49 | 39 | $CO_2CH_3$ | $CH_2CO_2CH_2Ph$ | $OCH_2OCH_3$ | $OCH_2OCH_3$ | Cl | Cl | H | 0 | C=O |
| 50 | 40 | $CO_2CH_3$ | $CH_2CO_2H$ | $OCH_2OCH_3$ | $OCH_2OCH_3$ | Cl | Cl | H | 0 | C=O |
| 51 | 40 | $CO_2CH_3$ | $CH_2CO_2H$ | $OCH_2OCH_3$ | OH | Cl | Cl | H | 0 | C=O |
| 52 | 41 | $CO_2CH_3$ | $CH_2CO_2H$ | OH | $OCOCH_3$ | Cl | Cl | H | 1 | C=O |
| 53 | 42 | $CO_2CH_3$ | $CH_2CO_2H$ | OH | $OCOCH_2CH_3$ | Cl | Cl | H | 1 | C=O |
| 54 | 43 | $CO_2CH_3$ | $CH_2CO_2H$ | OH | OH | Cl | Cl | I | 1 | C=O |

TABLE 6

| Comp. No. | Example No. | R¹ | R² | R³ | R⁴ | R⁵ | R⁶ | R⁷ | n | R⁹⁹ |
|---|---|---|---|---|---|---|---|---|---|---|
| 55 | 44 | CO₂CH₃ | CH₂CO₂H | OH | OCOCH₂CH₃ | Cl | Cl | I | 0 | C=O |
| 56 | 45 | CO₂CH₃ | CH₂CO₂H | OH | OCOCH₂CH₃ | Cl | Cl | I | 1 | C=O |
| 57 | 46 | CO₂CH₃ | CH₂CO₂H | OH | OCO₂Ph | Cl | Cl | H | 0 | C=O |
| 58 | 47 | CO₂CH₃ | CH₂CO₂H | OH | OCO₂CH₃ | Cl | Cl | H | 0 | C=O |
| 59 | 48 | | | | | | | | | |

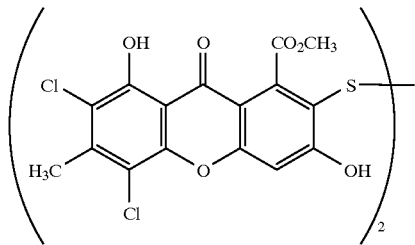

TABLE 7

| Comp. No. | Example No. | R¹ | R² | R³ | R⁴ | R⁵ | R⁶ | R⁷ | n | R⁹⁹ |
|---|---|---|---|---|---|---|---|---|---|---|
| 60 | 49 | CO₂CH₃ | H | OH | OH | Cl | Cl | H | 0 | C=O |
| 61 | 50 | CO₂CH₃ | CH₂Ph-4-CO₂H | OH | OH | Cl | Cl | H | 0 | C=O |
| 62 | 51 | CO₂CH₃ | (CH₂)₇CO₂H | OH | OH | Cl | Cl | H | 0 | C=O |
| 63 | 52 | CO₂CH₃ | CH(CO₂H)(CH₂)₅CH₃ | OH | OH | Cl | Cl | H | 0 | C=O |
| 64 | 53 | CO₂CH₃ | CH₂CH₂NH₂·HCl | OH | OH | Cl | Cl | H | 0 | C=O |
| 65 | 54 | CO₂CH₃ | (CH₂)₂CO₂H | OH | OH | Cl | Cl | H | 0 | C=O |
| 66 | 55 | CO₂CH₃ | CH₂CH₃ | OH | OH | Cl | Cl | H | 0 | C=O |
| 67 | 56 | CO₂CH₃ | (CH₂)₂CH₃ | OH | OH | Cl | Cl | H | 0 | C=O |
| 68 | 57 | CO₂CH₃ | CH₂CN | OH | OH | Cl | Cl | H | 0 | C=O |
| 69 | 58 | CO₂CH₃ | (CH₂)₂SO3Na | OH | OH | Cl | Cl | H | 0 | C=O |
| 70 | 59 | CO₂CH₃ | CH(CO₂H)Ph | OH | OH | Cl | Cl | H | 0 | C=O |
| 71 | 60 | CO₂CH₃ | CH(CO₂H)CH₃ | OH | OH | Cl | Cl | H | 0 | C=O |
| 72 | 61 | CO₂CH₃ | CH₂-Tetrazole | OH | OH | Cl | Cl | H | 0 | C=O |
| 73 | 62 | CO₂CH₃ | CH₂Ph-2-CN | OH | OH | Cl | Cl | H | 0 | C=O |
| 74 | 63 | CO₂CH₃ | CH₂Ph-3-CO₂CH₃ | OH | OH | Cl | Cl | H | 0 | C=O |
| 75 | 64 | CO₂CH₃ | CH(CO₂H)CH₂CO₂H | OH | OH | Cl | Cl | H | 0 | C=O |
| 76 | 65 | CO₂CH₃ | (CH₂)₂NHSO₂Ph | OH | OH | Cl | Cl | H | 0 | C=O |
| 77 | 66 | CO₂CH₃ | (CH₂)₂NHSO₂CH₃ | OH | OH | Cl | Cl | H | 0 | C=O |

TABLE 8

| Comp. No. | Example No. | R¹ | R² | R³ | R⁴ | R⁵ | R⁶ | R⁷ | n | R⁹⁹ |
|---|---|---|---|---|---|---|---|---|---|---|
| 78 | 67 | CO₂CH₃ | CH₂Ph-5-NO₂-2-OH | OH | OH | Cl | Cl | H | 0 | C=O |
| 79 | 68 | CO₂CH₃ | CH₂Ph-3.5-diBr-2-OH | OH | OH | Cl | Cl | H | 0 | C=O |
| 80 | 69 | CO₂CH₃ | Kojic acid | OH | OH | Cl | Cl | H | 0 | C=O |
| 81 | 70 | CO₂H | CH₂Ph-2-CONH₂ | OH | OH | Cl | Cl | H | 0 | C=O |
| 82 | 71 | CO₂CH₃ | CH₂Ph-2-CONH₂ | OCH₃ | OH | Cl | Cl | H | 0 | C=O |
| 83 | 72 | CO₂CH₃ | CH₂Ph-2-tetrazol | OH | OH | Cl | Cl | H | 0 | C=O |
| 84 | 73 | CO₂CH₃ | CH₂Ph-3-CO₂R | OH | OH | Cl | Cl | H | 0 | C=O |
| 85 | 74 | CO₂CH₃ | CH₂Ph-2-CO₂H | OH | OR | Cl | Cl | H | 0 | C=O |
| 86 | 75 | CO₂CH₃ | CH₂-2-Pyridyl | OH | OH | Cl | Cl | H | 0 | C=O |
| 87 | 76 | CO₂CH₃ | CH₂CONHSO₂Ph | OH | OH | Cl | Cl | H | 0 | C=O |
| 88 | 77 | CO₂CH₃ | CH₂CONHSO₂CH₃ | OH | OH | Cl | Cl | H | 0 | C=O |
| 89 | 78 | CO₂CH₃ | CH₂CONHSO₂Ph-4-CH₃ | OH | OH | Cl | Cl | H | 0 | C=O |
| 90 | 79 | CO₂CH₃ | CH₂CONHSO₂-2-Naphthyl | 0H | OH | Cl | Cl | H | 0 | C=O |
| 91 | 80 | CO₂CH₃ | CH₂CONHSO₂Ph-4-Cl | OH | OH | Cl | Cl | H | 0 | C=O |
| 92 | 81 | CO₂CI(3 | CH₂CONHSO₂Ph-4-NO₂ | OH | OH | Cl | Cl | H | 0 | C=O |
| 93 | 82 | CO₂CH₃ | CH₂CONHSO₂CF₃ | OH | OH | Cl | Cl | H | 0 | C=O |
| 94 | 83 | CO₂CH₃ | CH₂CONHOH | OH | OH | Cl | Cl | H | 0 | C=O |
| 95 | 84 | CO₂CH₃ | CH₂CONHOH₃ | OH | OH | Cl | Cl | H | 0 | C=O |

TABLE 9

| Comp. No. | Example No. | $R^1$ | $R^2$ | $R^3$ | $R^4$ | $R^5$ | $R^6$ | $R^7$ | n | $R^{99}$ |
|---|---|---|---|---|---|---|---|---|---|---|
| 96 | 85 | $CO_2CH_3$ | $CH_2CH(OH)CO_2H$ | OH | OH | Cl | Cl | H | 1 | C=O |
| 97 | 86 | $CO_2CH_3$ | $CH_2CH(OH)CO_2H$ | OH | OH | Cl | Cl | H | 2 | C=O |
| 98 | 87 | $CO_2CH_3$ | $CH_2CH(OH)CO_2CH_3$ | $OCH_3$ | $OCH_3$ | Cl | Cl | H | 0 | C=O |
| 99 | 88 | $CO_2CH_3$ | $CH_2CH(6H)CO_2CH_3$ | $OCH_3$ | $OCH_3$ | Cl | Cl | H | 2 | C=O |
| 100 | 89 | $CO_2CH_3$ | $CH_2CH(OH)CO_2CH_2CH_3$ | OH | OH | Cl | Cl | H | 0 | C=O |
| 101 | 90 | $CO_2CH_3$ | $CH_2CH(OAC)CO_2CH_3$ | $OCH_3$ | $OCH_3$ | Cl | Ci | H | 0 | C=O |
| 102 | 91 | $CO_2CH_3$ | $CH_2CH(OH)CO_2CH_2CH_3$ | $OCH_2OCH_3$ | OH | Cl | Cl | H | 0 | C=O |
| 103 | 92 | $CO_2CH_3$ | $CH_2CH(OH)CO_2CH_2OCH_3$ | $OCH_2CCH_3$ | OH | Cl | Cl | H | 0 | C=O |
| 104 | 93 | $CO_2CH_3$ | OH | OH | OH | Cl | Cl | $NO_2$ | 2 | C=O |
| 105 | 94 | $CO_2CH_3$ | $CH_2CH(OAc)CO_2H$ | OH | OH | Cl | Cl | H | 0 | C=O |
| 106 | 95 | $CO_2CH_3$ | $CH_3$ | OH | OH | Cl | Cl | H | 0 | C=O |
| 107 | 96 | $CO_2CH_3$ | $CH_3$ | OH | OH | Cl | Cl | H | 1 | C=O |
| 108 | 97 | $CO_2CH_3$ | $CH_3$ | OH | OH | Cl | Cl | H | 2 | C=O |
| 109 | 98 | $CO_2CH_3$ | $CH_3$ | $OCH_3$ | $OCH_3$ | Cl | Cl | H | 2 | C=O |
| 110 | 99 | $CO_2CH_3$ | $CH_2CO_2CH_2CH_3$ | OH | OH | Cl | Cl | H | 0 | C=O |
| 111 | 100 | $CO_2CH_3$ | $CH_2CO_2CH_2OC(=O)C(CH_3)_3$ | OH | OH | Cl | Cl | H | 0 | C=O |
| 112 | 101 | $CO_2CH_3$ | $CH_2C(=O)CO_2CH_2CH_3$ | OH | OH | Cl | Cl | H | 0 | C=O |
| 113 | 102 | $CO_2CH_3$ | $CH_2CH(NH_2)CO_2CH_2CH_3$ | OH | OH | Cl | Cl | H | 0 | C=O |

TABLE 10

| Comp. No. | Example No. | $R^1$ | $R^2$ | $R^3$ | $R^4$ | $R^5$ | $R^6$ | $R^7$ | n | $R^{99}$ |
|---|---|---|---|---|---|---|---|---|---|---|
| 114 | 103 | $CO_2CH_3$ | $CH_2CH(NH_2)CO_2H$ | OH | OH | Cl | Cl | H | 0 | C=O |
| 115 | 104 | $CO_2CH_3$ | $CH_2CONHSO_2Ph-4-OCH_3$ | OH | OH | Cl | Cl | H | 0 | C=O |
| 116 | 105 | $CO_2CH_3$ | $CH_2CO_2H$ | OH | OH | Cl | Cl | Ph | 0 | C=O |
| 117 | 106 | $CO_2CH_3$ | $CH_2CO_2H$ | OH | OH | Cl | Cl | $Ph-4-CH_3$ | 0 | C=O |
| 118 | 107 | $CO_2CH_3$ | $CH_2CO_2H$ | OH | OH | Cl | Cl | $Ph-4-CO_2H$ | 0 | C=O |
| 119 | 108 | $CO_2CH_3$ | $CH_2CO_2H$ | OH | OH | Cl | Cl | 2-Naphthyl | 0 | C=O |
| 120 | 109 | $CO_2CH_3$ | $CH_2CO_2H$ | OH | OH | Cl | Cl | Ph-4-Cl | 0 | C=O |
| 121 | 110 | $CO_2CH_3$ | $CH_2CO_2H$ | OH | OH | Cl | Cl | $Ph-4-OCH_3$ | 0 | C=O |
| 122 | 112 | $CO_2CH_3$ | ONa | OH | OH | Cl | Cl | H | 2 | C=O |
| 123 | 113 | $CO_2CH_3$ | $CH_2C(=CH_2)CO_2H$ | OH | OH | Cl | Cl | H | 0 | C=O |
| 124 | 111 | $CO_2CH_3$ | $CH_2CO_2H$ | OH | OH | Cl | Cl | $Ph-3-NH_2$ | 0 | C=O |
| 125 | | $CO_2CH_3$ | $CH_2CO_2H$ | OH | OH | Cl | Cl | $Ph-3-NO_2$ | 0 | C=O |
| 126 | 121 | $CO_2CH_3$ | $CH_2CO_2H$ | OH | OH | Cl | Cl | 2-thienyl | 0 | C=O |
| 127 | | $CO_2CH_3$ | $CH_2CO_2H$ | OH | OH | Cl | Cl | 3-thienyl | 0 | C=O |
| 128 | | $CO_2CH_3$ | $CH_2CO_2H$ | OH | OH | Cl | Cl | 2-benzo[b]-furanyl | 0 | C=O |
| 129 | | $CO_2CH_3$ | $CH_2CO_2H$ | OH | OH | Cl | Cl | $(CH_2)_3CH_3$ | 0 | C=O |
| 130 | | $CO_2CH_3$ | $CH_2CO_2H$ | OH | OH | Cl | Cl | $(CH_2)_7CH_3$ | 0 | C=O |

TABLE 11

| Comp. No. | Example No. | $R^1$ | $R^2$ | $R^3$ | $R^4$ | $R^5$ | $R^6$ | $R^7$ | n | $R^{99}$ |
|---|---|---|---|---|---|---|---|---|---|---|
| 131 | | $CO_2CH_3$ | $CH_2CO_2H$ | OH | OH | Cl | Cl | CHO | 0 | C=O |
| 132 | 115 | $CO_2CH_3$ | $CH_2CO_2H$ | OH | OH | Cl | Cl | $NO_2$ | 0 | C=O |
| 133 | 114 | $CO_2CH_3$ | $CH_2CO_2CH_2OC(=O)C(CH_3)_3$ | OH | OH | Cl | Cl | H | 1 | C=O |
| 134 | 116 | $CO_2CH_3$ | $CH_2CO_2CH(CH3)$-—$OC(=O)O$-Cyc-hexyl | OH | OH | Cl | Cl | H | 0 | C=O |
| 135 | 117 | $CO_2CH_3$ | $CH_2CO_2H$ | OH | OH | Cl | Cl | $NO_2$ | 1 | C=O |
| 136 | 118 | $CO_2CH_3$ | $CH_2$-Tetrazole | OH | OH | Cl | Cl | $NO_2$ | 1 | C=O |
| 137 | 119 | $CO_2CH_3$ | $CH_2CONHSO_2CH_3$ | OH | OH | Cl | Cl | H | 1 | C=O |
| 138 | 120 | $CO_2CH_3$ | $CH_2CO_2CH(CH3)$-—$OC(=O))O$-Cyc-hexyl | OH | OH | Cl | Cl | H | 1 | C=O |

Abbreviations in the above tables are as followings.

TABLE 12

| | | | |
|---|---|---|---|
| CH₂Ph-4-CO₂H | 4-ethylbenzoic acid | CH₂-Tetrazole | 5-ethyl-1H-tetrazole |
| CH₂Ph-4-CN | 2-ethylbenzonitrile | CH₂Ph-3-CO₂CH₃ | methyl 3-ethylbenzoate |
| CH₂Ph-5-NO₂-2-OH | 2-ethyl-4-nitrophenol | CH₂Ph-3,5-diBr-2-OH | 2,6-dibromo-4-ethylphenol |
| kojic acid | 2-ethyl-5-hydroxy-4H-pyran-4-one | CH₂Ph-2-Tetrazole | 5-(2-ethylphenyl)-1H-tetrazole |
| CH₂Ph-2-CONH₂ | 2-ethylbenzamide | CH₂Ph-2-CO₂H | 2-ethylbenzoic acid |
| CH₂Ph-3-CO₂H | 3-ethylbenzoic acid | CH₂-2-Pyridyl | 2-ethylpyridine |
| CH₂CONHSO₂Ph-4-CH₃ | N-(4-methylphenylsulfonyl)propanamide | | |
| CH₂CONHSO₂-2-Naphthyl | N-(naphthalen-2-ylsulfonyl)propanamide | | |
| CH₂CONHSO₂Ph-4-Cl | N-(4-chlorophenylsulfonyl)propanamide | | |

TABLE 12-continued

| | |
|---|---|
| CH$_2$CONHSO$_2$Ph-4-NO$_2$ | 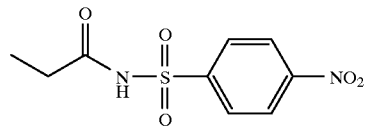 |
| CH$_2$CONHSO$_2$Ph-4-OCH$_3$ | 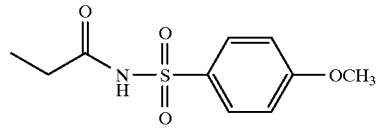 |

Gly: —NHCH$_2$CO—
Ph: Phenyl
Ac: Acetyl
cyc-hexyl: Cyclohexyl

When the compound [I] of the present invention has an asymmetric carbon atom or an asymmetric sulfur atom, a stereoisomer can be present. Such stereoisomers and mixtures thereof are also included in the scope of the present invention. When an asymmetric carbon atom or an asymmetric sulfur atom is present on a substituent of compound [I], a stereoisomer can also be present. Such stereoisomers and mixtures thereof are also included in the scope of the present invention.

The compound [I] obtained by the above-described production method may be used as a salt, preferably a pharmacologically acceptable salt. Examples of the salts are base salts such as salts with alkali metals (e.g., sodium, potassium) and salts with alkaline earth metals (e.g., calcium, magnesium) when compound [I] has an acidic group, and acid adduct salts such as salts with inorganic acids (e.g., hydrochloric acid, sulfuric acid, phosphoric acid) and salts with organic acids (e.g., acetic acid, propionic acid, citric acid, tartaric acid, malic acid, oxalic acid, methanesulfonic acid) when compound [I] has a basic group.

The compound [I] of the present invention or a salt thereof is capable of inhibiting a binding of the ligand B7-1 to the receptor protein CD28, and also inhibits IL-2 production from T cells. The compound [I] or a salt thereof of the present invention can therefore be used as a safe pharmaceutical, such as an immunomodulator, with low toxicity, in humans and mammals (e.g. mice, guinea pigs, rats, cats, dogs, sheep, horses, bovines, monkeys etc.). Specifically, it can be used as a graft rejection inhibitor, a pharmaceutical composition for therapeutic treatment of allergy, rheumatoid arthritis, autoimmune disease, nephritis, diabetes mellitus, and so on.

For administration to a human, for instance, the compound [I] or a salt thereof of the present invention can be safely administered orally or non-orally as such or in a pharmaceutical composition along with an appropriate pharmacologically acceptable carrier, excipient or diluent.

Such pharmaceutical compositions include oral preparations, e.g., powders, granules, capsules and tablets, and non-oral preparations, e.g., injectable preparations, drip infusions, external preparations (e.g., transnasal preparations, percutaneous preparations) and suppositories (e.g., rectal suppositories, vaginal suppositories).

These preparations can be produced by commonly known methods in common use for pharmaceutical making processes.

An oral preparation can be produced by subjecting compound [I] or a salt thereof to compressive shaping in the presence of an excipient (e.g., lactose, sucrose, starch, mannitol), a disintegrant (e.g., calcium carbonate, carboxymethyl cellulose calcium), a binder (e.g., gelatinized starch, gum arabic, carboxymethyl cellulose, polyvinylpyrrolidone, hydroxypropyl cellulose), a lubricant (e.g., talc, magnesium stearate, polyethylene glycol 6000) and other additives, followed by coating as necessary for the purpose of taste masking, enteric release or sustained release by a commonly known method. Examples of useful coating agents include ethyl cellulose, hydroxymethyl cellulose, polyoxyethylene glycol, cellulose acetate phthalate, hydroxypropylmethyl cellulose phthalate and Eudragit (produced by Rohm, Germany, methacrylic acid-acrylic acid copolymer).

An injectable preparation can be produced by shaping the compound [I] or a salt thereof into an aqueous injectable preparation along with a dispersing agent [e.g., Tween 80 (produced by Atlas Powder, USA), HCO 60 (produced by Nikko Chemicals), polyethylene glycol, carboxymethyl cellulose, sodium alginate], a preservative (e.g., methyl paraben, propyl paraben, benzyl alcohol, chlorobutanol), an isotonizing agent (e.g., sodium chloride, glycerol, sorbitol, glucose) and other additives, or as an oily injectable preparation in solution, suspension or emulsion in a vegetable oil such as olive oil, sesame oil, cottonseed oil or corn oil, propylene glycol or the like.

An external preparation can be produced by compounding the compound [I] or a salt thereof as a solid, semi-solid or liquid composition. Such a solid composition is produced by, for example, powdering the compound of the present invention as such or in mixture with an excipient (e.g., lactose, mannitol, starch, microcrystalline cellulose, sucrose), a thickening agent (e.g., natural rubber, cellulose derivative, acrylic acid polymer) and other additives. Such a liquid composition is produced by preparing the compound of the present invention as an oily or aqueous suspension in almost the same manner as with the injectable preparation. The semi-solid composition is preferably an aqueous or oily gel, or an ointment. All carbonic acid, phosphoric acid, citric acid, hydrochloric acid, sodium hydroxide), preservatives (e.g., paraoxybenzoates, chlorobutanol, benzalkonium chloride) and other additives.

A suppository is produced by preparing the compound [I] or a salt thereof as an oily or aqueous solid, semi-solid or liquid composition. Useful oily bases for said composition include glycerides of higher fatty acids [e.g., cacao fat, uitepsol series (produced by Dynamite Nobel Company)], moderate fatty acids [e.g., MIGLYOL series (produced by Dynamite Nobel Company)] and vegetable oils (e.g., sesame oil, soybean oil, cottonseed oil). Aqueous bases include polyethylene glycols and propylene glycol. Aqueous gel bases include natural rubbers, cellulose derivatives, vinyl polymers and acrylic acid polymers.

Varying depending on kind and severity of target disease, age of patient and other factors, it is preferable that the compound of the present invention or a salt thereof be used to treat the disease at about 1 mg to 1 g, more preferably about 4 mg to 200 mg, for an adult (50 kg body weight) per day, based on active ingredient content in oral administration. Such a preparation can be administered in 1 to 3 portions daily.

When the compound [I] or a salt thereof of the present invention is non-orally administered by subcutaneous, intravenous or intramuscular injection as an injectable preparation, its dose is normally about 0.5 mg to 200 mg, preferably about 1 mg to 50 mg for an adult per day.

The present invention provides a method for screening for a compound having an activity for inhibiting or enhancing a binding of CD28 to B7-1, or a salt thereof, which comprises comparing (1) an amount of binding between CD28 and B7-1-Ig obtained when CHO-cell containing CD28 or its cell membrane fraction is contacted with soluble B7-1-Ig, with (2) an amount of binding between CD28 and B7-1-Ig obtained when CHO-cell containing CD28 or its cell membrane fraction is contacted with soluble B7-1-Ig and a test compound.

In the method of the present invention for screening for a compound that inhibits or enhancing a binding of the B7-1 ligand to the receptor protein CD28, or a salt thereof, CD28-containing CHO cells can be produced by introducing an expression vector harboring the gene for CD28 into CHO cells, and culturing the cells under conditions enabling the expression of that gene.

Examples of the gene encoding CD28 include, but are not limited to, CD28-encoding cDNA and genomic DNA, as long as a CD28-encoding nucleotide sequence is contained. Examples of the gene are a CD28-encoding DNA having the nucleotide sequence represented by SEQ ID NO:1 (FIG. 2). These DNAs can also be produced using commonly known gene engineering techniques.

Examples of the expression vectors include pAKKO-1.11H, pXT1, pRC/CMV, pRC/RSV and pcDNA I Neo, and preferable examples is pAKKO-1.11H.

Any promoter can be used, as long as it functions efficiently in host cells; preferable promoters include SV40 promoter, CMV promoter, HSV-TK promoter, SRα promoter and RSV promoter, with greater preference given to the SRα promoter.

It is preferable to use the expression vector having an enhancer, a splicing signal, a polyadenylation signal, a selection marker etc., in addition to the above components.

Selection markers include the dihydrofolate reductase gene (hereinafter also referred to as dhfr), the ampicillin resistance gene (hereinafter also referred to as Ap$^r$) and the neomycin resistance gene (G418 resistance), the dhfr gene is preferable.

Examples of the expression vectors harboring the gene encoding CD28 include one prepared by inserting one of the above-mentioned promoters (especially SRα promoter, CMV promoter, RSV promoter etc.) upstream the gene encoding CD28, inserting a polyadenylation signal downstream the gene encoding CD28, inserting a selection marker such as the dhfr gene or the neomycin resistance gene further downstream, and inserting the ampicillin resistance gene further downstream.

More specifically, the expression vector called pAKKO-CD28 (FIG. 1, Reference Example 1), which can be prepared by the method schematized in FIG. 1, by inserting the SRα promoter upstream the gene encoding CD28, inserting a poly A adduct signal downstream the gene encoding CD28, inserting the dhfr gene further downstream, and inserting the ampicillin resistance gene further downstream, for instance, is preferred.

By introducing the thus-prepared expression vector harboring the gene encoding CD28 into CHO cells, CHO cells expressing high amount of CD28 can be established.

Preferable examples of the CHO cells [Journal of Experimental Medicine, 108: 945 (1995)] are those lacking the dhfr gene [Proceedings of the National Academy of Sciences of the United State of America, 77: 4216–4220 (1980)] (hereinafter also referred to as CHO(dhfr$^-$) cells), CHO K-1 cells [Proceedings of the National Academy of Sciences of the United State of America, 60: 1275 (1968)] etc. and so on. When the dhfr gene is inserted as a selection marker into the expression vector, CHO(dhfr$^-$) cells are preferred. In this case, transformants can very easily be selected by culturing the cells in a medium containing no nucleic acids. CHO cells are capable of expressing the gene encoding CD28 not only at high levels but also with marked stability.

Any preferable combination of an expression vector and host cells can be chosen as appropriate. For example, a combination of the expression vector called pAKKO-CD28 (Reference Example 1) and CHO(dhfr$^-$) cells is preferred.

An expression vector can be introduced into host cells using known methods such as the calcium phosphate method [Virology, 52: 456–467 (1973)] and the electropolation method [EMBO Journal, 1: 841–845 (1982)].

CHO cells showing high expression of CD28 can be obtained by first selecting transformant CHO cells incorporating the above-described expression vector using a selection marker as an indicator, and subsequently by cloning the cells. When the dhfr gene is used, cells strain showing higher expression can be obtained by selecting resistant cells to methotrexate (MTX) in culture at gradually increased MTX concentrations and amplifying the introduced gene in the cells. Examples of CHO cells capable of expressing high level of CD28 include the CHO cell called CD28-CHO-11 (FERM BP-5431), which contains the above-mentioned expression vector called pAKKO-CD28.

CD28-containing CHO cells can be produced by culturing CHO cells containing an expression vector harboring the gene encoding CD28 of the present invention under conditions enabling the expression of that gene.

Media for cultivating CHO cells containing an expression vector harboring the gene encoding CD28 include EMEM, DMEM, RPMI 1640 and MEM-α all of which contain about 0.5 to 20% fetal bovine serum. When an expression vector harboring the dhfr gene is used as a selection marker, it is preferable to use DMEM medium containing dialyzed fetal bovine serum containing no nucleic acid or α-MEM medium containing dialyzed fetal bovine serum containing no nucleic acid. The pH is preferably about 6 to 8.

Cultivation is normally carried out at about 30 to 40° C. for about 15 to 200 hours, with medium exchange, aeration, stirring etc. as necessary.

The cell membrane fraction of CD28-containing CHO cells is a fraction which is rich in cell membrane obtained by homogenizing such CHO cells by a commonly known method.

Cell homogenizing methods include cell squashing using a Potter-Elvehjem homogenizer, disruption using a Waring blender or Polytron (produced by Kinematica), ultrasonic disruption, disruption by cell spraying via a thin nozzle under increased pressure using a French press or the like, and freeze-thawing.

Cell membrane fractionation is achieved mainly by such methods as fractional centrifugation and density gradient centrifugation. For example, homogenized cells are centrifuged at low rate (500–3,000 rpm) for a short period of time (normally about 1–10 minutes), after which the resulting supernatant is centrifuged at higher rate (15,000–30,000 rpm) normally for about 30 minutes to 2 hours to yield a precipitate as a membrane fraction. Said membrane fraction is rich in CD28 expressed and membrane components such as cell-derived phospholipids and membrane proteins.

The amount of CD28 in CHO cells containing the CD28 of the present invention or its membrane fraction is preferably $10^3$ to $10^7$ molecules per cell, more preferably $10^4$ to $10^6$ molecules.

When CD28-containing CHO cells are used for the screening method of the present invention, said CHO cells may be used as viable cells. Said CHO cells can also be used after immobilization using glutaraldehyde, paraformaldehyde etc. by a commonly known method.

Soluble B7-1-Ig used for the screening method of the present invention is a protein resulting from fusion of B7-1 and the Fc region of IgG.

B7-1, a cell surface protein, has a secretory signal and a trans-membrane site. Soluble B7-1-Ig acts as an extracellularly secreted protein because it is prepared by removing the trans-membrane site of B7-1 and fused the Fc region of immunoglobulin instead.

Soluble B7-1-Ig can be produced by a commonly known method or a modification thereof. For example, the method described in Journal of Experimental Medicine, 1991, 173: 721–730 etc. can be used for its production.

Also, CHO cells containing and extracellularly secreting soluble B7-1-Ig can be produced by constructing an expression vector (FIG. 5) harboring the gene encoding B7-1 having the nucleotide sequence represented by SEQ ID NO:2 (FIG. 4) and the gene containing the gene encoding the Fc region of IgG having the nucleotide sequence shown by SEQ ID NO:3 (FIGS. 6 and 7), introducing said expression vector into CHO cells, then culturing the cells under conditions enabling the expression of said gene encoding B7-1-Ig.

Figure 5:
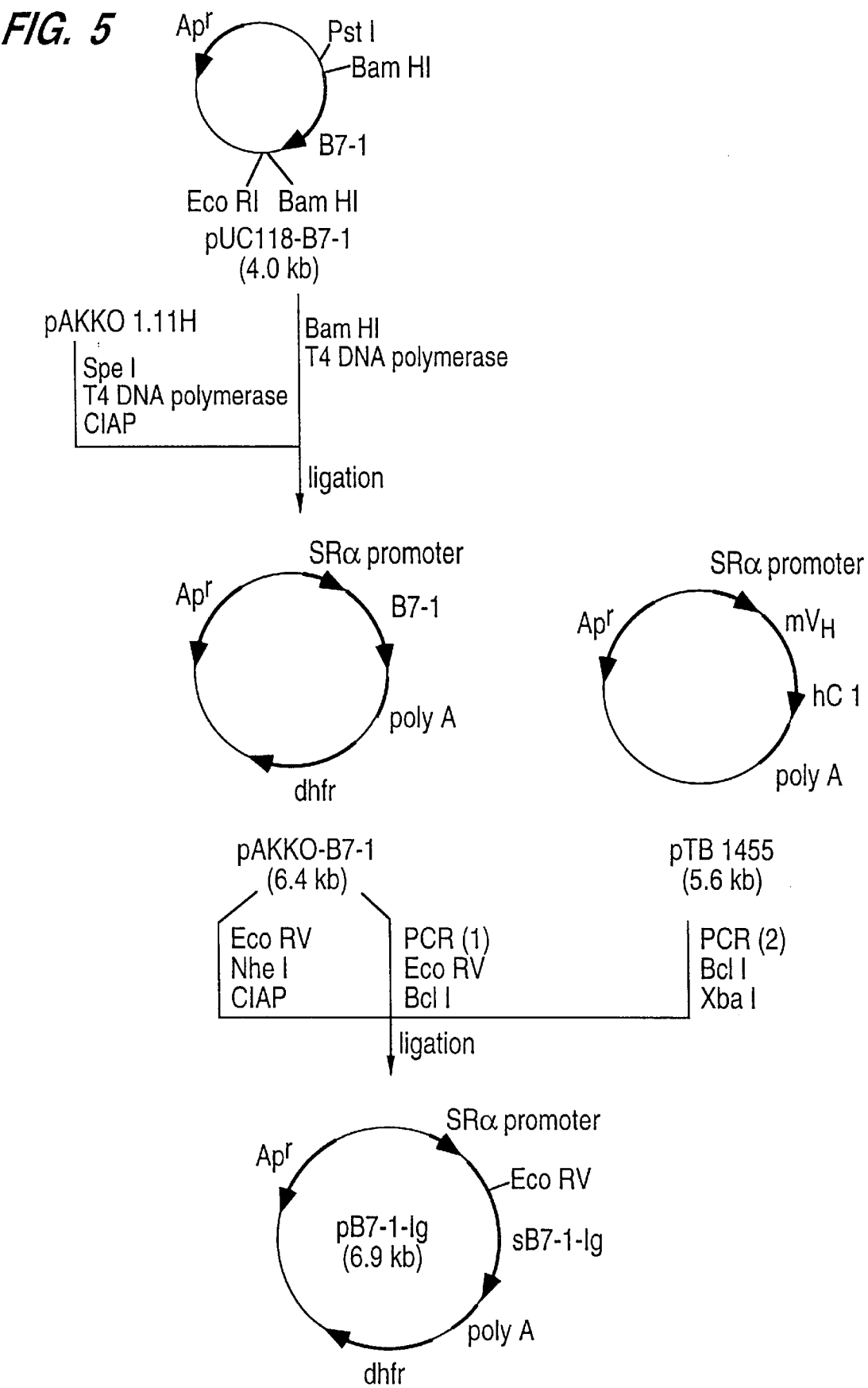
FIG. 5 shows a schematic diagram of construction of a soluble B7-1-Ig-encoding gene expression plasmid (pB7-1-Ig). sB7-1-Ig represents the soluble B7-1-Ig gene; dhfr represents the dihydrofolate reductase gene; Ap$^r$ represents the ampicillin resistance gene; poly A represents the polyadenylation signal.
Figure 8:
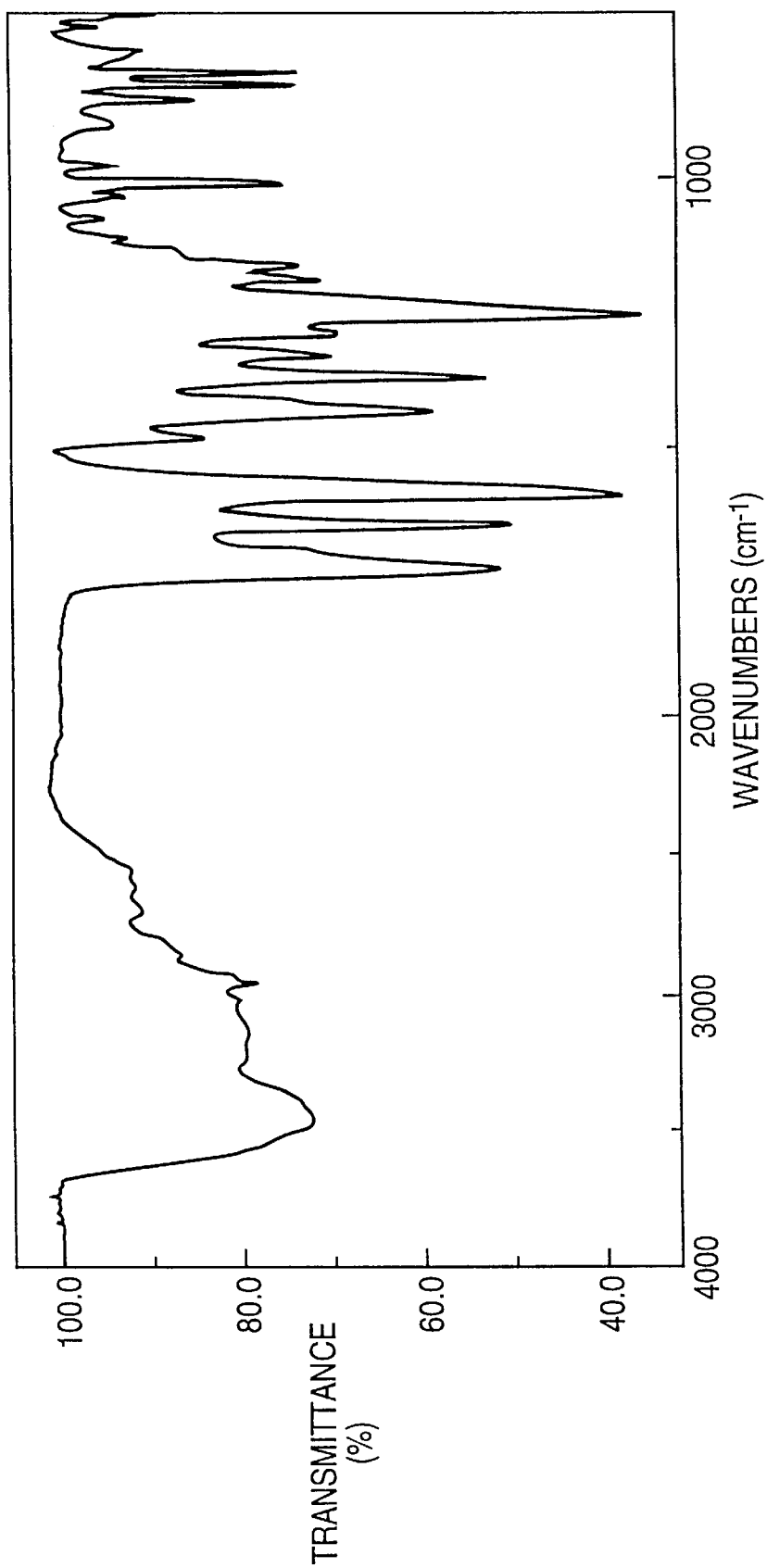
FIG. 8 shows an IR spectrum (in KBr tablet) of TAN-2421 A1.
Figure 9:
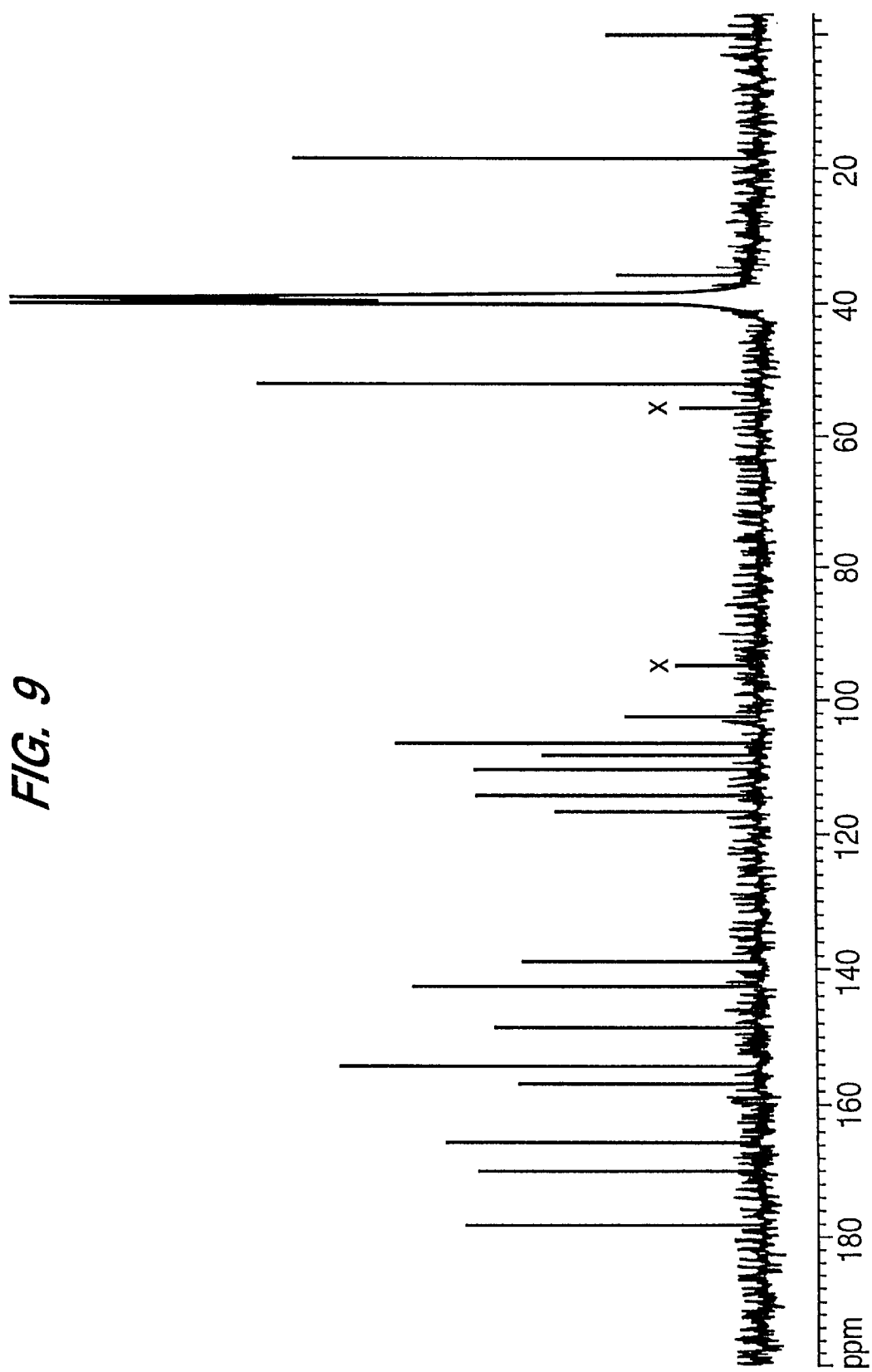
FIG. 9 shows a $^{13}$C NMR spectrum (75 MHz, in DMSO-$d_6$, 27° C.) of TAN-2421 A1.
Figure 10:
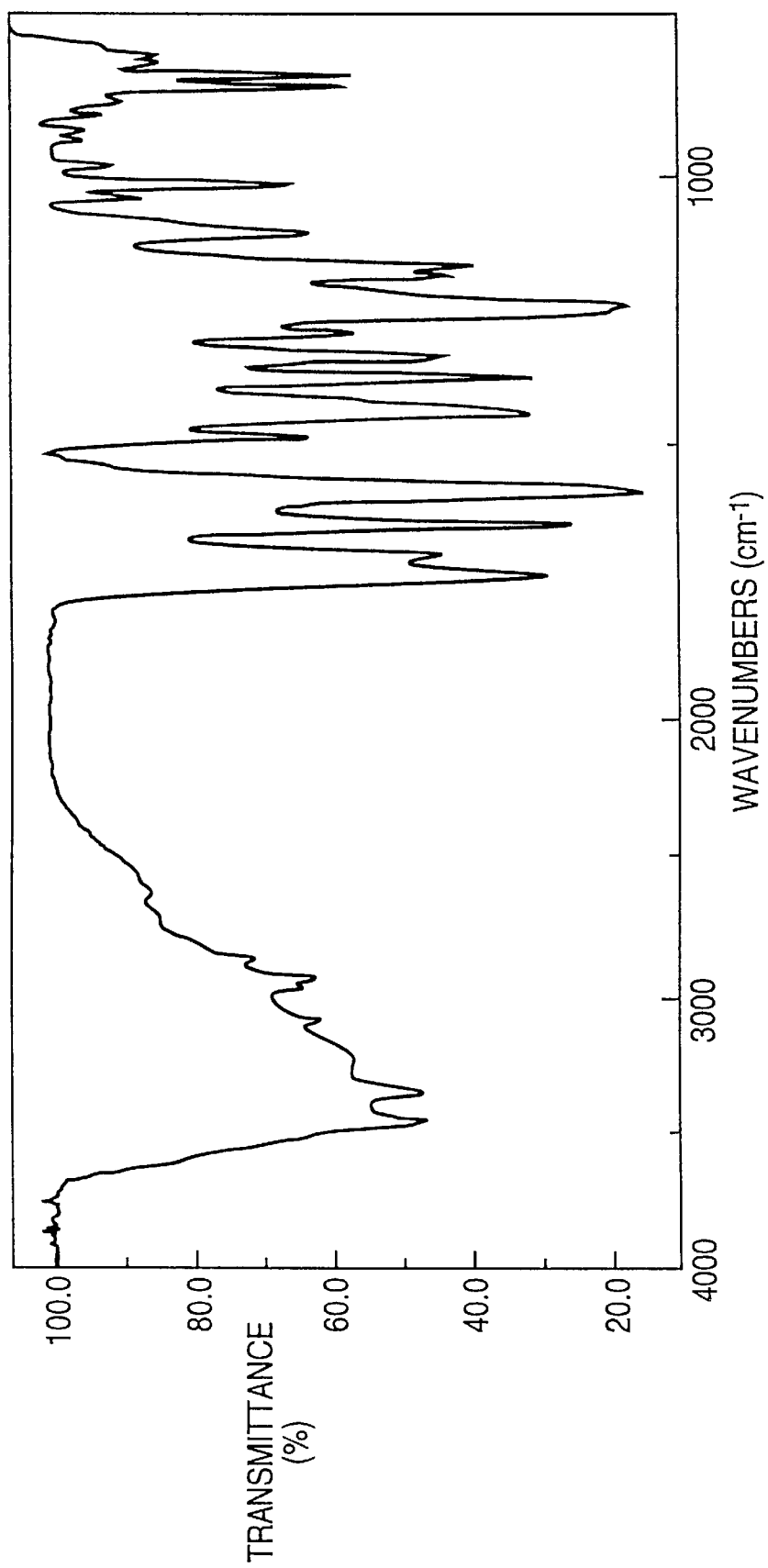
FIG. 10 shows an IR spectrum (in KBr tablet) of TAN-2421 B1.
Figure 11:
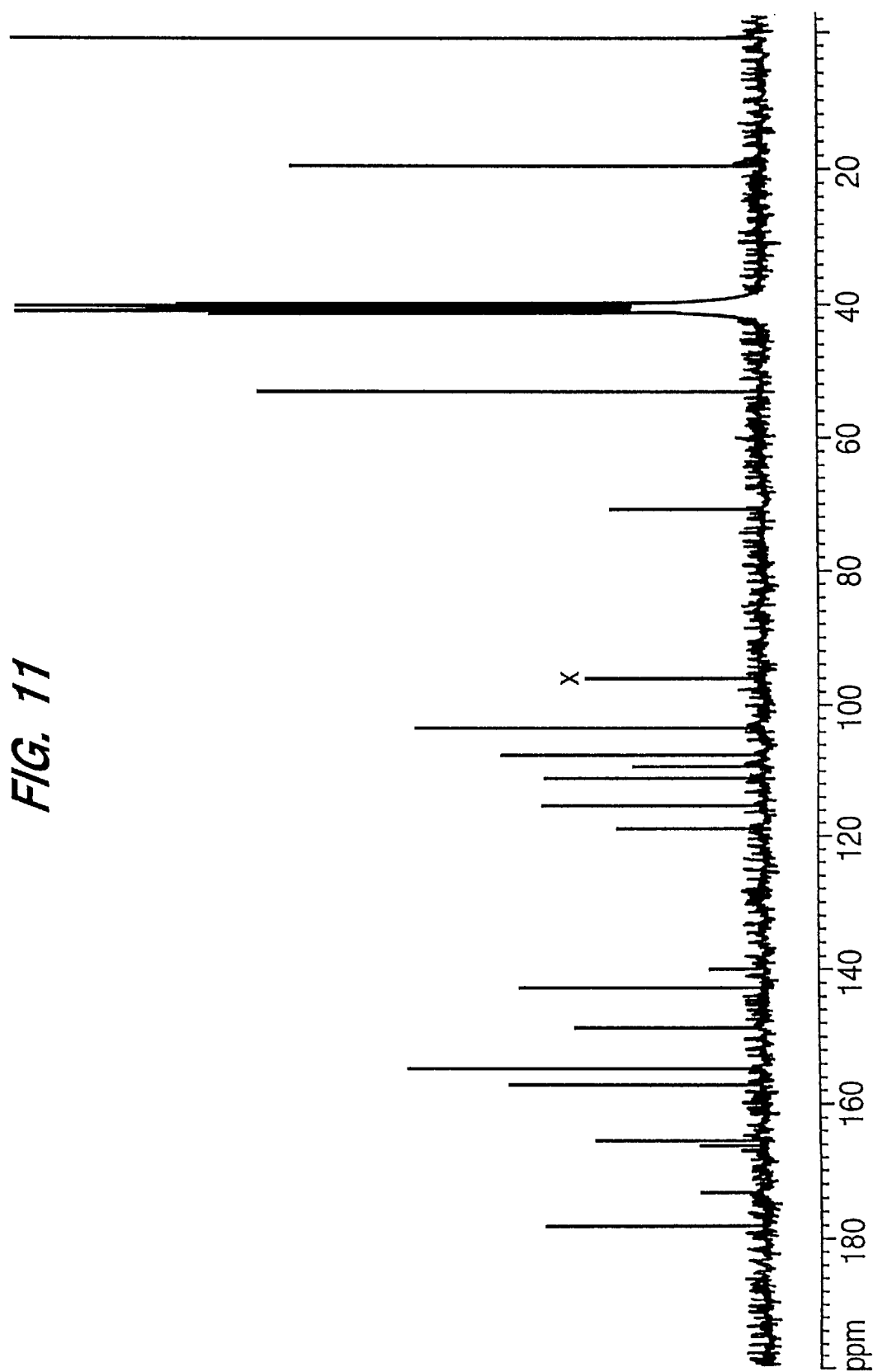
FIG. 11 shows a $^{13}$C NMR spectrum (75 MHz, in DMSO-$d_6$, 6° C.) of TAN-2421 B1.

Preferable example of the expression vectors is an expression vector called pB7-1-Ig (FIG. 5, Reference Example 2), which can be prepared by the method schematized in FIG. 5 and which incorporate SRα promoter upstream the gene encoding soluble B7-1-Ig, a polyadenylation signal downstream the gene encoding soluble B7-1-Ig, the dhfr gene further downstream, and the ampicillin resistance gene further downstream.

By introducing the thus-prepared expression vector harboring the gene for B7-1-Ig into CHO cells, CHO cells expressing high amount of B7-1-Ig can be prepared.

Preferable examples of the CHO cells are the CHO(dhfr⁻) cells the CHO K-1 cells and so on. When the dhfr gene is inserted as a selection marker into the expression vector, CHO(dhfr⁻) cells are preferred. In this case, transformants can very easily be selected by culturing the cells in a medium containing no nucleic acid.

Any preferable combination of an expression vector and host cells can be chosen as appropriate. For example, a combination of the expression vector called pB7-1-Ig (Reference Example 2) and CHO(dhfr⁻) cells is preferred.

An expression vector can be introduced into host cells using known methods such as the calcium phosphate method [Virology, 52: 456–467 (1973)] and the electropolation method [EMBO Journal, 1: 841–845 (1982)).

CHO cells showing high expression of B7-1-Ig can be obtained by first selecting transformant CHO cells incorporating the above-described expression vector using a selection marker as an indicator, and subsequently by cloning the cells. When the dhfr gene is used, cells showing higher expression can be obtained by selecting resistant cells to methotrexate (MTX) in culture at gradually increased MTX concentrations and amplifying the introduced gene in the cells.

Examples of CHO cells capable of expressing high amount of B7-1-Ig include the CHO cells called sB7-1-Ig-CHO-20 (FERM BP-5432), which contain the above-mentioned expression vector called pB7-1-Ig.

Soluble B7-1-Ig can be produced by culturing CHO cells containing an expression vector harboring the gene encoding B7-1-Ig of the present invention under conditions enabling the expression of that gene.

Media for cultivating CHO cells containing an expression vector harboring the gene for B7-1-Ig include EMEM, DMEM, RPMI 1640 and MEM-α all of which contain about 0.5 to 20% fetal bovine serum. When an expression vector harboring the dhfr gene is used as a selection marker, it is preferable to use DMEM medium containing dialyzed fetal bovine serum containing no nucleic acid or α-MEM medium containing dialyzed fetal bovine serum containing no nucleic acid. The pH is preferably about 6 to 8. Cultivation is normally carried out at about 30° to 40° C. for about 24 to 200 hours, preferably about 48 to 96 hours, with medium exchange, aeration, stirring etc. as necessary.

Soluble B7-1-Ig can be obtained and purified from such CHO cells that produce soluble B7-1-Ig or a culture supernatant thereof, preferably from a culture supernatant.

This purification can be achieved by a commonly known method for immunoglobulin purification using the immunoglobulin Fc region of B7-1-Ig. When soluble B7-1-Ig is obtained and purified from a culture supernatant, contamination of serum immunoglobulin into the standard preparation of soluble B7-1-Ig can be prevented by replacing the medium with a fresh one of lower serum concentration, preferably one containing 0–1% serum after the B7-1-Ig-producing CHO cells have adhered to the cultivation device to almost form a monolayer, continuing the cultivation, and collecting the medium and purifying.

Useful methods of purification from the medium include ultrafiltration, ammonium sulfate fractionation, ion exchange chromatography, affinity chromatography and gel filtration, with preference given to affinity chromatography because of procedural simplicity. A column packed with protein A or protein G as a carrier, in particular, is preferred. Contaminating serum immunoglobulin can be removed by gel filtration etc.

Examples of test compounds for this screening method include peptides, proteins, non-peptide compounds, synthetic compounds, microbial fermentation products, marine organism extract, plant extract, cell extract and animal tissue extract. These test compounds may be new compounds or known compounds.

In this screening method, the amount of binding of soluble B7-1-Ig to CD28 is compared between case (1), in which CD28-containing CHO cells or their cell membrane fraction and soluble B7-1-Ig are contacted with each other, and case (2) in which CD28-containing CHO cells or their cell membrane fraction, soluble B7-1-Ig and a test compound are contacted with each other.

When the amount of binding is lower in case (2) than in case (1), the compound obtained can be determined as a compound that inhibits the binding of B7 to CD28; in the reverse case, the compound obtained can be determined as a compound that enhances the binding of B7 to CD28.

The amount of binding of CD28 to B7 can be determined using a known method such as the radioimmunoassay (RIA) using B7-1-Ig labeled with a radioisotope, or the enzyme immunoassay (Zoku Seikagaku Jikken Koza, 5th edition, Meneki Kagaku Kenkyuho, 1986, pp. 62–65, Tokyo Kagaku Dojin) using a labeled secondary antibody binding to the Ig portion of B7-1-Ig.

In the EIA method, for instance, the amount of soluble B7-1-Ig bound to CHO cells expressing CD28 can be determined by incubating CD28-expressing CHO cells grown on a microplate in the presence of soluble B7-1-Ig and a test compound, then thoroughly washing the mixture, adding an anti-human immunoglobulin antibody, protein A, or the like, labeled with horseradish peroxidase (HRP), for instance, washing the mixture, then developing a coloring reaction. Specifically, the amount can be determined in accordance with Test Example 1 below.

The present invention provides a method for screening for a compound having an activity for inhibiting an IL-2 production, or a salt thereof, which comprises comparing (1) an amount of IL-2 produced when CHO-cell containing B7-1 or its cell membrane fraction is contacted with T-cell, with (2) an amount of IL-2 produced when CHO-cell containing B7-1 or its cell membrane fraction is contacted with T-cell and a test compound.

In the method of the present invention for screening for a compound possessing an activity of inhibiting IL-2 production or a salt thereof, B7-1-containing CHO cells can be produced in the same manner as the above-described production method for CD28-containing CHO cells or their cell membrane fraction.

For example, B7-1-containing CHO cells can be produced by constructing an expression vector (FIG. 3) harboring the gene encoding B7-1 having the nucleotide sequence represented by SEQ ID NO:2 (FIG. 4), introducing said expression vector into CHO cells, then culturing the cells under conditions enabling the expression of said gene encoding B7-1.

Figure 3:
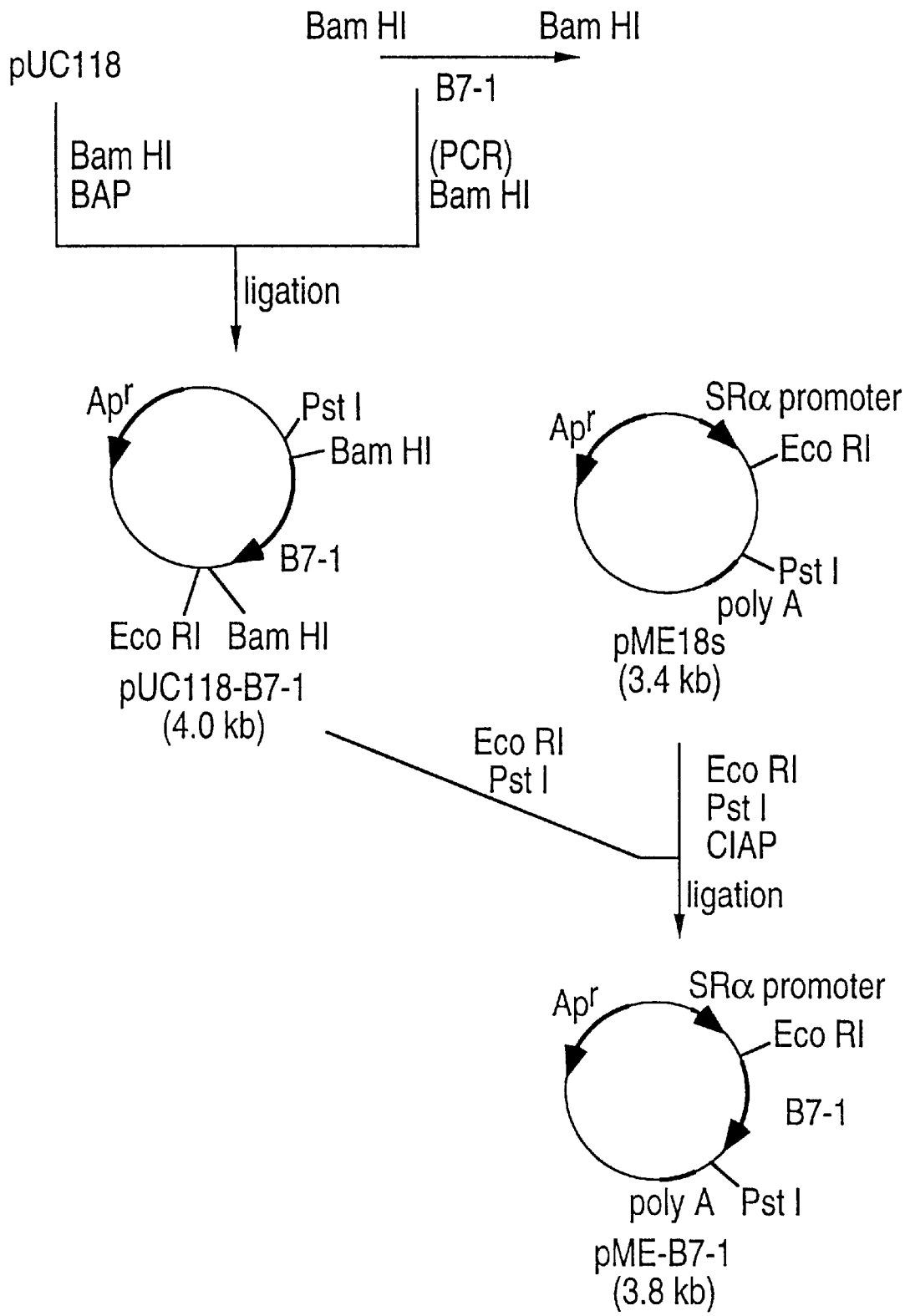
FIG. 3 shows a schematic diagram of construction of a B7-1 gene expression plasmid (pME-B7-1). B7-1 represents the B7-1 gene; Ap$^r$ represents the ampicillin resistance gene; poly A represents the polyadenylation signal.

Preferable examples of the expression vectors include the expression vector called pME-B7-1 (FIG. 3, Reference Example 1), which can be prepared by the method schematized in FIG. 3 and which incorporates the SRα promoter upstream the gene encoding B7-1, and the ampicillin resistance gene downstream the gene encoding B7-1.

Examples of useful CHO cells capable of expressing high amount of B7-1 include the CHO cell called B7-1-CHO-22 (FERM BP-5430), which contains the above-described expression vector called pME-B7-1.

The human T cells used to produce IL-2 with the addition of a constimulatory signal may be collected from a healthy human. A human T cell line capable of producing IL-2 can also be used.

For T cell collection from a healthy human, peripheral blood may be overlaid on Lymphocyte Separation Medium (Organon Teknika Co.) or the like and centrifuged to yield a mononuclear cell fraction. T cells can be separated from the mononuclear cell fraction using some methods, including the use of a commonly known nylon wool column, the use of an antibody and the use of flow cytometry, the use of a nylon wool column being convenient and preferable. By applying the mononuclear cell fraction to the nylon wool column and harvesting non-adsorbed cells, T cells can be enriched. By repeating this procedure, T cell purity can be increased.

When T cells are stimulated with a stimulation mimicking antigen stimulation, e.g., with an anti-CD3 antibody, followed by constimulatory signal stimulation from B7-1 to CD28 on the T cells, the T cells are activated to efficiently produce IL-2.

Examples of useful human T cell lines capable of producing IL-2 include Jurkat cells. In the case of Jurkat cells, not only an anti-CD3 antibody but also PHA etc. can be used to confer the first signal involving antigen stimulation.

The same test compounds as those mentioned above can be used.

In this screening method, the amount of IL-2 produced is compared between case (1), in which B7-1-containing CHO cells or their cell membrane fraction and T cells (specifically T cells conferred with a first signal by means of an anti-CD3 antibody or the like) are contacted with each other, and case (2) in which CHO cells containing B7-1 or their cell membrane fraction, T cells (specifically T cells conferred with a first signal by means of an anti-CD3 antibody or the like), and a test compound are contacted with each other.

When the amount of IL-2 produced is lower in case (2) than in case (1), the compound obtained can be determined as a compound that suppresses IL-2 production.

The amount of IL-2 produced can be determined by the EIA using an anti-IL-2 antibody, the bioassay for growth of IL-2-dependent cells, and other known methods. When various test compounds are present within a single sample, quantitation by the EIA is preferred, since they can act on cells. IL-2 quantitation by the EIA can be achieved using the known method described in "Meneki Jikken Sousa II," p. 819, Nankodo, or using a commercially available IL-2 EIA kit. Specifically, the amount can be determined in accordance with Test Example 2 below.

The compound or a salt thereof, obtained using the screening method of the present invention, is a compound or a salt thereof selected using said screening method from various test compounds (e.g., peptides, proteins, nonpeptide compounds, synthetic compounds, microbial fermentation products, marine organism extract, plant extract, cell extract, animal tissue extract; these test compounds may be new compounds or known compounds). For example, compounds wherein the structural formula of said compound obtained using the screening method of the present invention, is partially changed by addition, deletion, substitution, or the like, are also included in the compound or a salt thereof obtained using the screening method of the present invention.

The compound or a salt thereof, obtained using the screening method of the present invention, is a compound that inhibits or enhances the binding of CD28 to B7 or that possesses an activity of inhibiting IL-2 production, and can be used as a safe pharmaceutical, such as an immunomodulator, with low toxicity. Specifically, it is useful as a graft rejection inhibitor, a pharmaceutical composition for therapeutic treatment of allergy, rheumatoid arthritis, autoimmune disease, nephritis, diabetes mellitus, and so on.

When the compound or a salt thereof, obtained using the screening method of the present invention, is used as a pharmaceutical, it can be used as an appropriate pharmaceutical composition, as with compound [I] of the present invention or a salt thereof. Specifically, it can be used as a safe pharmaceutical, such as an immunomodulator, with low toxicity, more specifically as a graft rejection inhibitor, or a pharmaceutical composition for therapeutic treatment of allergy, rheumatoid arthritis, autoimmune disease, nephritis or diabetes mellitus.

Abbreviations for nucleotides, amino acids and others used in the present specification and attached figures are based on abbreviations specified by the IUPAC-IUB Commission on Biochemical Nomenclature or abbreviations in common use in relevant fields. Some examples are given below. When an optical isomer may be present in amino acid, it is of the L-configuration, unless otherwise stated.

DNA: Deoxyribonucleic acid
A: Adenine
T: Thymine
G: Guanine
C: Cytosine
G: Glycine
A: Alanine
V: Valine
L: Leucine
I: Isoleucine
S: Serine
T: Threonine
C: Cysteine
M: Methionine
E: Glutamic acid
D: Aspartic acid
K: Lysine
R: Arginine
H: Histidine
F: Phenylalanine
Y: Tyrosine
W: Tryptophan
P: Proline
N: Asparagine
Q: Glutamine
BAS: Bovine serum albumin
FBS: Fetal bovine serum
SDS: Sodium dodecyl sulfate
CHO: Chinese hamster ovary cell
DMEM: Dulbeccols modified Eagle medium
PBS: Phosphate-buffered saline The sequence numbers shown in the SEQUENCE LISTING of the specification are described below.

SEQ ID NO:1 shows the nucleotide sequence of the gene encoding CD28 obtained in Reference Example 1.

SEQ ID NO:2 shows the nucleotide sequence of the B7-1 encoding obtained in Reference Example 1.

SEQ ID NO:3 shows the nucleotide sequence of the gene encoding soluble B7-1-Ig obtained in Reference Example 2.

SEQ ID NO:4 shows the nucleotide sequence of the synthetic primer 77 used for cloning of the B7-1 gene.

SEQ ID NO:5 shows the nucleotide sequence of the synthetic primer 78 used for cloning of the B7-1 gene.

SEQ ID NO:6 shows the nucleotide sequence of the synthetic primer 28-A used for cloning of the gene for CD28.

SEQ ID NO:7 shows the nucleotide sequence of the synthetic primer 28-B used for cloning of the gene for CD28.

SEQ ID NO:8 shows the nucleotide sequence of the synthetic primer IG-3 used for cloning of the gene for soluble B7-1-Ig.

SEQ ID NO:9 shows the nucleotide sequence of the synthetic primer IG-4 used for cloning of the gene for soluble B7-1-Ig.

SEQ ID NO:10 shows the nucleotide sequence of the synthetic primer IG-1 used for cloning of the gene for soluble B7-1-Ig.

SEQ ID NO:11 shows the nucleotide sequence of the synthetic primer IG-2 used for cloning of the gene for soluble B7-1-Ig.

B7-1-CHO-22 as obtained in Example 122 has been deposited under accession number FERM BP-5430 at the National Institute of Bioscience and Human-Technology (NIBH), Agency of Industrial Science and Technology, Ministry of International Trade and Industry, under the Budapest Treaty since Feb. 28, 1996.

CD28-CHO-11 as obtained in Example 122 has been deposited under accession number FERM BP-5431 at the National Institute of Bioscience and Human-Technology (NIBH), Agency of Industrial Science and Technology, Ministry of International Trade and Industry, under the Budapest Treaty since Feb. 28, 1996.

sB7-1-Ig-CHO-20 as obtained in Example 122 has been deposited under accession number FERM BP-5432 at the National Institute of Bioscience and Human-Technology (NIBH), Agency of Industrial Science and Technology, Ministry of International Trade and Industry, under the Budapest Treaty since Feb. 28, 1996.

EXAMPLES

The present invention is hereinafter described in more detail by means of, but not limited to, the following reference examples, examples, test examples and preparation examples.

The compound of the present invention has a xanthene frame. The frame and its numbering are as follows.

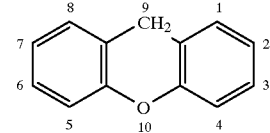

Percent (%) ratios are weight/volume percent ratios, unless otherwise stated. Solvent mixing ratios are ratios by volume, unless otherwise stated.

NMR spectra were taken using the Bruker DPX-300 spectrometer ($^1$H NMR; 300 MHz, $^{13}$C NMR; 75 MHz). The internal substance used was tetramethylsilane; all δ values are shown in ppm.

The symbols used in the present specification have the following meanings: s, singlet; d, doublet; t, triplet; q, quartet; dd, double doublet; dt, double triplet; m, multiplet; br, broad peak; J, binding constant (Hz); Q, quaternary carbon; CH, methine; $CH_2$, methylene; $CH_3$, methyl.

Reference Example 1

Cloning of constimulatory molecules and construction of various expression vectors a) Cloning of B7-1 gene On the basis of the report regarding the DNA nucleotide sequence of B7-1 by Freeman et al. [Journal of Immunology, 143, 2714 (1989)], two cloning primers 77 and 78 were prepared for the N- and C-terminal sides of B7-1, respectively.

The sequence of primer 77 is 5'-T G G AT C C AT G G G C C A C A C A C G

GAGGCAGGGAAC-3' (SEQ ID NO:4), having a Bam HI site on the 5'-side adjacent to the N-terminal initiation codon of B7-1.

The sequence of primer 78 is 5'-TGGATCCTTATACAGGGCGTA CACTTTCCCTTCTC-3' (SEQ ID NO:5), having a Bam HI site on the 5'-side adjacent to the C-terminal termination codon of B7-1.

The B7-1-encoding DNA was amplified from a human lymphocyte B-cell cDNA library (Clontech Laboratories Inc., Palo Alto, Calif., USA) by the PCR method using primers 77 and 78, and cloned into the Bam HI site of the plasmid vector pUC118 to yield pUC118-B7-1 (FIG. 3). The entire nucleotide sequence of the translation region was then determined (FIG. 4).

b) Construction of plasmid for B7-1 expression in cells pUC188-B7-1 was digested with PstI and EcoRI; the B7-1 DNA fragment obtained was introduced into the PstI-EcoRI site of pME18S to yield pMEB7-1, a plasmid for B7-1 expression in animal cells (FIG. 3).

c) Cloning of CD28 gene

On the basis of the report regarding the DNA nucleotide sequence of CD28 by Aruffo et al. [Proceedings of the National Academy of Sciences of the Unites States of America, 84, 8573 (1987)], two cloning primers 28-A and 28-B were prepared for the N- and C-terminal sides of CD28, respectively.

The sequence of primer 28-A is 5'-TCTCGAGGTCGACATGCTCA GGCTGCTCTTGGCTC-3' (SEQ ID NO:6), having an Xho I site and an Sal I site on the 5'-side adjacent to the N-terminal initiation codon of CD28.

The sequence of primer 28-B is 5'-AACTAGTTCAGGAGCGAT AGGCTGCGAAG-3' (SEQ ID NO:7), having an Spe I site on the 5'-side adjacent to the C-terminal termination codon of CD28. The CD28-encoding DNA was amplified from a human lymphoma (Raji) quick-clone cDNA library (Clontech Laboratories Inc., Palo Alto, Calif., USA) by the PCR method using 28-A and 28-B, and cloned between the Xho I and Sal I sites of the plasmid vector pME18S to yield pME-CD28 (FIG. 1). The entire nucleotide sequence of the translation region was then determined (FIG. 2).

d) Construction of plasmid for CD28expression in CHO cells

A DNA fragment obtained by digesting pME-CD28 with Sal I and Spe I was introduced between the Sal I and Spe I sites of pAKKO1.11H to yield pAKKO-CD28 (FIG. 1).

Reference Example 2

Construction of plasmid encoding solubilized B7-1

A plasmid encoding solubilized B7-1 was constructed by ligating the Fc region of human IgG to the C-terminal side of the extracellular region of B7-1. To amplify the portion beyond the Eco RV site in the DNA encoding the extracellular region of B7-1 by the PCR method, primers IG-3 and IG-4 were prepared.

The sequence of primer IG-3 is 5'-CTTTGATATCACTAATAACC TC-3' (SEQ ID NO:8), having an Eco RV site on the 5'-side.

The sequence of primer IG-4 is 5'-GGTGATCAGGAAAATGCTCT TGCTTGGTTG-3' (SEQ ID NO:9), having a Bcl I site on the 5'side.

To introduce the Fc region of human IgG into the C-terminal side of solubilized B7-1, the plasmid pTB1455, prepared by Tada et al. [Journal of Biotechnology, 33, 157 (1994)], encoding the Fc region of human IgG, was used. To amplify the Fc region of human IgG by the PCR method, primers IG-1 and IG-2 were prepared. To prevent dimerization of solubilized B7-1, these primers were designed to replace the three cysteine residues in the hinge region of IgG with serine residues, as in the method of Linsley et al. [Journal of Experimental Medicine, 173, 721 (1991)].

The sequence of primer IG-1 is 5'-GGTGATCAGGAGCCCAAAT CTTCTGACAAAACT-CACACGTCTCCACCGTCCCCGGC GCCTGAACTCCTG-3' (SEQ ID NO:10), having a Bcl I site on the 5'-side.

The sequence of IG-2 is 5'-CCCTGCAGTCTAGATCATTTACCCGGG GACAGGGAG-3' (SEQ ID NO:11), having a Pst I site and an Xba I site on the 5'-side.

(1) A DNA fragment obtained by digesting with Eco RV and Nhe I the plasmid pAKKO-B7-1, which harbors both the B7-1 gene and the dhfr gene, and treating the digestion product with CIAP (2) A DNA fragment obtained by amplifying the DNA portion encoding the extracellular region of B7-1 by the PCR method using IG-3 and IG-4 with pAKKO-B7-1 as a template, and digesting the amplification product with Eco RV and Bcl I (3) A DNA fragment obtained by-amplifying the DNA portion encoding the Fc region of IgG by the PCR method using IG-1 and IG-2 with pTB1455 as a template, and digesting the amplification product with Xba I and Bcl I The three DNA fragments obtained from (1), (2) and (3) were ligated together to construct the desired plasmid pB7-1-Ig (FIG. 5). During construction of pB7-1-Ig, the sequence of the portion amplified by the PCR method was examined to determine the entire nucleotide sequence (FIG. 6).

Reference Example 3

Preparation of N-Boc-2-bromoethylamine 2-bromoethylammonium bromide (produced by Wako Pure Chemical Industries) (500 mg) was dissolved in THF-water (10:1, 11.0 ml); triethylamine (711 µl) and di-t-butyl dicarbonate (produced by Wako Pure Chemical Industries) (617 µl) were added under ice cooling conditions, followed by stirring at room temperature for 1 hour. The reaction mixture was concentrated under reduced pressure; the residue obtained was dissolved in ethyl acetate (30 ml) and washed with water (2×10 ml) and brine (5 ml). Next, the organic layer was dried over anhydrous sodium sulfate, after which it was concentrated under reduced pressure; the residue obtained was purified by silica gel column chromatography (eluted with 90:10–85:15 n-hexane/ethyl acetate) to yield N-Boc-2-bromoethylamine (350 mg) as a colorless oily substance.

$^1$H NMR, CDCl$_3$, δ ppm; 4.94 (1H, br s), 3.59–3.41 (4H, m), 1.45 (9H, s)

Reference Example 4

Preparation of 2-bromoethylamine-N-benzenesulfonamide 2-bromoethylammonium bromide (500 mg) was dissolved in dichloromethane (10.0 ml); benzenesulfonyl chloride (produced by Wako Pure Chemical Industries) (350 µl) and triethylamine (710 µl) were added under ice cooling conditions, followed by stirring at room temperature for 2 hours. The reaction mixture was concentrated under reduced pressure; the residue obtained was disolved in ethyl acetate (40 ml) and washed with water (3×10 ml) and brine (5 ml). Next, the organic layer was dried over anhydrous sodium sulfate, after which it was concentrated under reduced pressure; the residue obtained was purified by silica gel column chromatography (eluted with 80:20 n-hexane/ethyl acetate) to yield 2-bromoethylamine-N-benzenesulfonamide (640 mg) as colorless crystals.

$^1$H NMR, CDCl$_3$, δ ppm; 7.9—7.85 (2H, m), 7.65–7.50 (3H, m), 5.00 (1H, br s), 3.43–3.37 (4H, m)

Reference Example 5

Preparation of 2-bromoethylamine-N-methanesulfonamide 2-bromoethylammonium bromide (500 mg) was dissolved in dichloromethane (10.0 ml); methanesulfonyl chloride (produced by Wako Pure Chemical Industries) (210 μl) and triethylamine (710 μl) were added under ice cooling conditions, followed by stirring at room temperature for 2 hours. The reaction mixture was concentrated under reduced pressure; the residue obtained was dissolved in ethyl acetate (40 ml) and washed with water (3×10 ml) and brine (3 ml). Next, the organic layer was dried over anhydrous sodium sulfate, after which it was concentrated under reduced pressure; the residue obtained was purified by silica gel column chromatography (eluted with 70:30–60:40 n-hexane/ethyl acetate) to yield 2-bromoethylamine-N-methanesulfonamide (320 mg) as a colorless oily substance.

$^1$H NMR, CDCl$_3$, δ ppm; 4.81 (1H, br s), 3.61–3.48 (4H, m), silica gel column chromatography (eluted with 80:20 hexane/ethyl Reference Example 6

Preparation of α-chloro-α-deoxykojic acid

Kojic acid (150 mg, produced by Sigma Corporation) was dissolved in chloroform (5.0 ml); thionyl chloride (308 μl, produced by Wako Pure Chemical Industries) was added, followed by refluxing for 5 hours. After chloroform (50 ml) was added, the reaction mixture was washed with water (2×10 ml); the organic layer was then dried over anhydrous sodium sulfate, after which it was concentrated under reduced pressure. The residue obtained was subjected to silica gel column chromatography and eluted with chloroform. The eluate was concentrated under reduced pressure to yield α-chloro-α-deoxykojic acid (64 mg) as a brown powder.

Reference Example 7

Preparation of 5-(2-bromomethyl)phenyltetrazole o-tolunitrile (500 mg, produced by Wako Pure Chemical Industries) was dissolved in DMF (10 ml); sodium azide (555 mg, produced by Wako Pure Chemical Industries) and ammonium chloride (453 mg) were added, followed by stirring at 127° C. for 14 hours. After ethyl acetate (50 ml) was added, the reaction mixture was washed with 0.01M hydrochloric acid (2×30 ml); the organic layer was then extracted with 2% aqueous sodium hydrogen carbonate (2×20 ml). After pH correction to 2.0, the water layer obtained was extracted with ethyl acetate (40 ml). After washing with water (3×20 ml), the organic layer was dried over anhydrous sodium sulfate, after which it was concentrated under reduced pressure to yield 5-(2-methyl) phenyltetrazole (111 mg) as a white powder. This powder (60 mg) was dissolved in carbon tetrachloride (10 ml); N-bromosuccinimide (67 mg, produced by Wako Pure Chemical Industries) and 2,2'-azobisisobutyronitrile (1.0 mg, Wako Pure Chemical Industries) were added, followed by stirring at 90° C. for 2 hours. After the reaction mixture was concentrated, the residue was subjected to silica gel column chromatography, washed with chloroform, then eluted and fractionated with chloroform/methanol (80:20). The eluate was concentrated under reduced pressure to yield 5-(2-bromomethyl)phenyltetrazole (25 mg) as a brown oily substance.

Reference Example 8

Preparation of 3-(bromomethyl)benzoic acid methoxymethyl ester

After m-toluic acid (500 mg, produced by Wako Pure Chemical Industries) was dissolved in dichloromethane (10 ml), chloromethylmethyl ether (360 μl) and triethylamine (665 μl) were added, followed by stirring at room temperature for 2 hours. After ethyl acetate (50 ml) was added, the reaction mixture was washed with 0.01M hydrochloric acid, 2% aqueous sodium hydrogen carbonate and water, each in an amount of (2×30 ml). The organic layer obtained was dried over anhydrous sodium sulfate, after which it was concentrated under reduced pressure to yield a brown oily substance (588 mg). This oily substance (300 mg) was dissolved in carbon tetrachloride (20 ml); N-bromosuccinimide (296 mg) and 2,2'-azobisisobutyronitrile (3.0 mg) were added, followed by stirring at 90° C. for 4 hours. After filtration to remove the succinimide, the reaction mixture was concentrated. To the oily residue, hexane was added, followed by stirring; the supernatant obtained was concentrated under reduced pressure to yield 3-(bromomethyl) benzoic acid methoxymethyl ester (374 mg) as a colorless oily substance.

Reference Example 9

Preparation of 2-(bromomethyl)benzoic acid methoxymethyl ester

After o-toluic acid (500 mg, produced by Wako Pure Chemical Industries) was dissolved in dichloromethane (10 ml), chloromethylmethyl ether (360 μl) and triethylamine (665 μl) were added, followed by stirring at room temperature for 2 hours. After ethyl acetate (50 ml) was added, the reaction mixture was washed with 0.01M hydrochloric acid, 2% aqueous sodium hydrogen carbonate and water, each in an amount of (2×30 ml). The organic layer obtained was dried over anhydrous sodium sulfate, after which it was concentrated under reduced pressure to yield a colorless oily substance (600 mg). This oily substance (200 mg) was dissolved in carbon tetrachloride (10 ml); N-bromosuccinimide (198 mg) and 2,2'-azobisisobutyronitrile (1.8 mg) were added, followed by stirring at 90° C. for 3 hours. After filtration to remove the succinimide, the reaction mixture was concentrated. The residue obtained was subjected to silica gel column chromatography, washed with hexane and hexane/ethyl acetate (50:1), then eluted and fractionated with hexane/ethyl acetate (20:1). The eluate was concentrated under reduced pressure to yield 2-(bromomethyl)benzoic acid methoxymethyl ester (65 mg) as a colorless oily substance.

$^1$H NMR, CDCl$_3$, δ ppm; 8.03 (1H, d, J=7.8 Hz), 7.50 (2H, m), 7.40 (1H, m), 5.52 (2H, s), 4.98 (2H, s), 3.59 (3H, s)

Reference Example 10

Preparation of 2-thiophene boronic acid trimethylene glycol ester 2-thiophene boronic acid (produced by Aldrich Chemical Company, Inc.) (200 mg) was suspended in toluene (2.0 ml);

1,3-propanediol (produced by Wako Pure Chemical Industries) (230 μl) was added, followed by stirring at room temperature for 1 hour. The reaction mixture was dried over anhydrous sodium sulfate, after which it was concentrated under reduced pressure; the residue obtained was purified by silica gel chromatography (eluted with 90:10–70:30 n-hexane/ethyl acetate) to yield 2-thiophene boronic acid trimethylene glycol ester (221 mg) as a white powder.

$^1$H NMR, CDCl$_3$, δ ppm; 7.59–7.52 (2H, m), 7.15 (1H, dd, J=4.3, 3.8 Hz), 4.16 (4H, t, J=5.5 Hz), 2.06 (2H,m).

Example 1

Production of TAN-2421 A1, A2, A3, A4, B1, B2 and B3

FL-67283, a strain of a microbial species of the genus Aspergillus, cultured at 28° C. for 7 days on a slant medium consisting of 24 g of potato dextrose broth (produced by Difco, USA), 20 g of agar and 1 l of water, was inoculated to 40 ml of a seed medium (pH 6.0) containing 2% glucose, 3% maltose, 1.5% raw soybean flour, 1% corn steep liquor, 0.5% polypeptone, 0.3% yeast extract and 0.3% sodium chloride, and cultured in a 200 ml conical flask at 28° C. for 48 hours to yield a seed culture liquid. One liter of the seed culture liquid obtained was transplanted to a 200 l cultivation tank containing 120 l of a principal medium (pH 6.5) containing 3% dextrin, 0.5% glucose, 1% SBF, 0.3% malt extract, 0.05% ammonium tartrate, 0.05% monopotassium phosphate, 0.015% magnesium sulfate, 0.007% calcium chloride, 0.05% actcol and 0.02% silicone, and cultured at 28° C. and a stirring rate of 120 rpm for 5 days.

Example 2

Isolation of TAN-2421 A1

The culture liquid (120 l) obtained in Example 1 was combined with a culture liquid (120 l) obtained using the same conditions (240 l in total); after the mixture was adjusted to pH 3.0, ethyl acetate (200 l) was added, followed by stirring and mixing at room temperature for 30 minutes. This mixture was filtered using a filter aid (Radiolite 600, produced by Showa Kagaku Kogyo); the cells were washed with ethyl acetate (60 l). The organic layer obtained (215 l) was extracted with 2% aqueous sodium bicarbonate (140 l). After adjustment to pH 3.0, the water layer was extracted with ethyl acetate (100 l). The organic layer was washed with water (40 l), after which it was concentrated to 200 ml under reduced pressure. This concentrate was subjected to column chromatography with silica gel (Kiesel Gel 60, 500 g), washed with hexane/ethyl acetate (4:1, 4 l, 2:1, 4 l), and eluted with hexane/ethyl acetate (1:1, 4 l) and ethyl acetate (4 l). The eluate was concentrated to 500 ml under reduced pressure to yield a concentrate, which was then twice extracted with 2% aqueous sodium bicarbonate (500 ml), combined with the water layer, and again concentrated to 500 ml under reduced pressure. After adjustment to pH 7.5, the solution obtained was applied to Diaion HP-20 (200 ml) and washed with water (1 l) and aqueous methanol (20%, 1 l, 50%, 1 l, 80%, 1 l), after which it was eluted with 80% methanol/0.02N aqueous ammonia (1 l).

The eluate was concentrated to 100 ml; after water (100 ml) was added, the concentrate was adjusted to pH 3.0 and twice extracted with ethyl acetate (400 ml). The organic layers were combined (400 ml) together and washed with water (300 ml), then dried over anhydrous sodium sulfate and concentrated under reduced pressure to yield a crude powder (2.36 g). The crude powder obtained was subjected to column chromatography with Sephadex LH-20 (3.0 l), then eluted and fractionated with methanol (each 300 ml). Fractions 14 through 17 were combined and concentrated to dryness to yield a powder (635 mg). This powder was dissolved in dimethylsulfoxide-methanol (1:1, 4.0 ml); 2 ml portions of this solution were subjected to preparative high performance liquid chromatography [column; YMC-Pack ODS SH-363-15 (produced by YMC.), mobile phase; 55% (v/v) acetonitrile/0.02M phosphate buffer (pH 3.0), flow rate; 15 ml/min] to obtain 20 ml fractions. Fraction 14 from the two runs was combined; after the acetonitrile was distilled off under reduced pressure, the residue was extracted 1) and aqueous methanol (20%, 1 l, 50%, 1 l, 80%, 1 l), after which it was eluted with 80% methanol/0.02N aqueous under reduced pressure to yield a powder (34 mg) containing TAN-2421 A4. Fractions 15 and 16 from the two runs were combined and treated in the same manner as above to yield a powder (54 mg) containing TAN-2421 B2 and B3. Fractions 18 and 19 from the two runs were combined and treated in the same manner as above to yield a powder (38 mg) containing TAN-2421 A2and A3. Fractions 22 through 24 from the two runs were combined and treated in the same manner as above to yield a powder (30 mg) containing TAN-2421 B1. Fractions 26 through 31 from the two runs were combined and treated in the same manner as above to yield TAN-2421 A1 (182 mg) as a light-yellow powder.

[TAN-2421 A1]

1) Appearance: Light-yellow powder
2) Molecular formula: $C_{18}H_{12}Cl_2O_8S$
3) Elemental analysis data: (%) Calcd; C, 47.08; H, 2.63; Cl, 15.44; S, 6.98 Found; C, 47.10; H, 2.84; Cl, 15.43; S, 7.11
4) High resolution FAB-MS spectrum: m/z 458.9753 Calculated value for $(C_{18}H_{12}Cl_2O_8S+H)^+$; m/z 458.9709
5) UV spectrum: In methanol Maximum nm ($E_{1cm}$ 1%); 243 (765), 267 (shoulder, 630), 275 (645), 315 (290), 368 (200)
6) IR spectrum: In KBr tablet, major absorption peaks shown (wave number, cm$^{-1}$) 3700-2300 (br), 1725, 1645, 1585, 1480, 1435, 1370, 1330, 1290, 1250, 1190, 1170, 1015
7) $^{13}$C NMR spectrum: 75 MHz, in DMSO-d$_6$, 27° C., δ ppm 178.1 (Q), 170.1 (Q), 166.2 (Q), 165.7 (Q), 157.1 (Q), 154.5 (Q), 148.7 (Q), 142.8 (Q), 139.3 (Q), 117.0 (Q), 114.6 (Q), 110.6 (Q), 108.6 (Q), 106.8 (Q), 102.9 (CH), 52.4 (CH$_3$), 35.8 (CH$_2$), 18.4 (CH$_3$)

Example 3

Isolation of TAN-2421 A2, A3, A4, B1, B2 and B3

The powder obtained in Example 2 (36 mg), which contained TAN-2421 A2and A3, was subjected to preparative high performance liquid chromatography in two runs [column; YMC-Pack ODS SH-343-5 (produced by YMC.), mobile phase; 30% (v/v) acetonitrile/0.01M phosphate buffer (pH 7.0), flow rate; 10 ml/min] to obtain 10 ml fractions. Fraction 18 through 20 from the two runs were combined; the acetonitrile was distilled off under reduced pressure. After adjustment to pH 2.5, the residue was extracted with ethyl acetate. The organic layer was dried over anhydrous sodium sulfate, after which it was concentrated under reduced pressure to yield TAN-2421 A3(12 mg) as a light-yellow powder. Fractions 22 through 25 from the two runs were 3700-2300 (br), 1725, 1645, 1585, 1480, 1435, 1370, TAN-2421 A2(6 mg) as a light-yellow powder.

The powder obtained in Example 2 (32 mg), which contained TAN-2421 A4, was subjected to preparative high performance liquid chromatography [column; YMC-Pack ODS SH-343-5, mobile phase; 32% (v/v) acetonitrile/0.01M phosphate buffer (pH 6.3), flow rate; 10 ml/min] to obtain 10 ml fractions. Fraction 15 through 17 from the two runs were combined; the acetonitrile was distilled off under reduced pressure. After adjustment to pH 2.5, the residue was extracted with ethyl acetate. The organic layer was dried over anhydrous sodium sulfate, after which it was concentrated under reduced pressure to yield TAN-2421 A4(15 mg) as a light-yellow powder.

The powder obtained in Example 2 (28mg), which contained TAN-2421 B1, was subjected to preparative high performance liquid chromatography [column; YMC-Pack ODS SH-343-5, mobile phase; 32% (v/v) acetonitrile/0.01M phosphate buffer (pH 6.3), flow rate; 10 ml/min] to obtain 10 ml fractions. Fraction 18 through 24 from the two runs were combined; the acetonitrile was distilled off under reduced pressure. After adjustment to pH 2.5, the residue was extracted with ethyl acetate. The organic layer was dried over anhydrous sodium sulfate, after which it was concentrated under reduced pressure to yield TAN-2421 B1 (14 mg) as a light-yellow powder.

The powder obtained in Example 2 (52 mg), which contained TAN-2421 B2 and B3, was subjected to preparative high performance liquid chromatography in two runs [column; YMC-Pack ODS SH-343-5, mobile phase; 27% (v/v) acetonitrile/0.01M phosphate buffer (pH 7.0), flow rate; 10 ml/min] to obtain 10 ml fractions. Fraction 16 through 20 from the two runs were combined; the acetonitrile was distilled off under reduced pressure. After adjustment to pH 2.5, the residue was extracted with ethyl acetate. The organic layer was dried over anhydrous sodium sulfate, after which it was concentrated under reduced pressure to yield TAN-2421 B2 (8 mg) as a light-yellow powder. Fractions 12 and 13 from the first run and fractions 11 and 12 from the second run were combined and treated in the same manner as above to yield a powder (17 mg) containing TAN-2421 B3. This powder was subjected to preparative high performance liquid chromatography [column; YMC-Pack ODS SH-343-5, mobile phase; 50% (v/v) aqueous acetonitrile (containing 0.05% TFA), flow rate; 10 ml/min] to obtain 10 ml fractions. Fraction 17 and 18 were combined; the acetonitrile was distilled off under reduced pressure. After adjustment to pH 2.5, the residue was extracted with ethyl acetate. The organic layer was dried over anhydrous sodium sulfate, after which it was concentrated under reduced pressure to yield TAN-2421 B3 (13 mg) as a light-yellow powder.

[TAN-2421 A2]

1) Appearance: Light-yellow powder
2) Molecular formula: $C_{18}H_{13}ClO_8S$
3) High resolution FAB-MS spectrum: m/z 425.0114 Calculated value for $(C_{18}H_{13}ClO_8S+H)^+$; m/z 425.0098
4) UV spectrum: In methanol Maximum nm ($E_{1cm}$ 1%); 244 (760), 270 (690), 315 (320), 361 (195)
5) IR spectrum: In KBr tablet, major absorption peaks shown (wave number, $cm^{-1}$) 3700-2300 (br), 1720, 1700, 1650, 1590, 1570, 1480, 1435, 1410, 1370, 1310, 1265, 1200, 1015
6) $^{13}$C NMR spectrum: 75 MHz, in DMSO-$d_6$, 27° C., δ ppm; 178.4 (Q), 170.1 (Q), 166.4 (Q), 165.3 (Q), 157.4 (Q), 155.7 (Q), 152.9 (Q), 145.7 (Q), 139.4 (Q), 116.2 (Q), 113.9 (Q), 108.9 (Q), 108.6 (CH), 106.4 (Q), 102.8 (CH), 52.3 ($CH_3$), 35.8 ($CH_2$), 20.7 ($CH_3$)

[TAN-2421 A3]

1) Appearance: Light-yellow powder
2) Molecular formula: $C_{18}H_{13}ClO_8S$
3) High resolution FAB-MS spectrum: m/z 425.0108 Calculated value for $(C_{18}H_{13}ClO_8S+H)^+$; m/z 425.0098
4) UV spectrum: In methanol Maximum nm ($E_{1cm}$ 1%); 242 (740), 266 (shoulder, 610), 274 (625), 305 (290), 365 (205)
5) IR spectrum: In KBr tablet, major absorption peaks shown (wave number, $cm^{-1}$) 3700–2800 (br), 1730, 1650, 1590, 1485, 1435, 1365, 1255, 1880, 1160, 1010
6) $^{13}$C NMR spectrum: 75 MHz, in DMSO-$d_6$, 27° C., δ ppm; 178.4 (Q), 170.1 (Q), 166.3 (Q), 165.3 (Q), 158.6 (Q), 157.1 (Q), 150.2 (Q), 145.8 (Q), 139.3 (Q), 116.5 (Q), 112.4 (CH), 109.7 (Q), 109.0 (Q), 106.8 (Q), 102.9 (CH), 52.3 ($CH_3$), 35.8 ($CH_2$), 20.5 ($CH_3$)

[TAN-2421 A4]

1) Appearance: Light-yellow powder
2) Molecular formula: $C_{18}H_{14}O_8S$
3) High resolution FAB-MS spectrum: m/z 391.0472 Calculated value for $(C_{18}H_{14}O_8S+H)^+$; m/z 391.0488
4) UV spectrum: In methanol Maximum nm ($E_{1cm}$ 1%); 242 (855), 263 (shoulder, 750), 269 (765), 307 (365), 358 (240)
5) IR spectrum: In KBr tablet, major absorption peaks shown (wave number, $cm^{-1}$) 3700–2200 (br), 1725, 1650, 1615, 1590, 1575, 1480, 1435, 1370, 1255, 1210, 1015
6) $^{13}$C NMR spectrum: 75 MHz, in DMSO-$d_6$, 27° C., δ ppm 178.6 (Q), 170.1 (Q), 166.5 (Q), 164.8 (Q), 160.5 (Q), 157.3 (Q), 155.0 (Q), 148.8 (Q), 139.5 (Q), 115.7 (Q), (CH), 52.3 ($CH_3$), 35.8 ($CH_2$), 21.9 ($CH_3$)

[TAN-2421 B1]

1) Appearance: Light-yellow powder
2) Molecular formula: $C_{19}H_{14}Cl_2O_9S$
3) High resolution FAB-MS spectrum: m/z 488.9808 Calculated value for $(C_{19}H_{14}Cl_2O_9S+H)^+$; m/z 488.9814
4) UV spectrum: In methanol Maximum nm ($E_{1cm}$ 1%); 245 (555), 270 (460), 275 (shoulder, 460), 308 (200), 370 (165)
5) IR spectrum: In KBr tablet, major absorption peaks shown (wave number, $cm^{-1}$) 3700–2300 (br), 1740, 1700, 1645, 1590, 1485, 1440, 1370, 1335, 1290, 1240, 1885, 1170, 1105, 1010
6) $^{13}$C NMR spectrum: 75 MHz, in DMSO-$d_6$, 6° C., δ ppm 178.3 (Q), 173.5 (br, Q), 166.3 (br, Q), 165.6 (Q), 157.2 (Q), 154.7 (Q), 148.9 (Q), 142.9 (Q), 139.8 (br, Q), 118.4 (Q), 114.8 (Q), 110.8 (Q), 109.0 (Q), 107.1 (Q), 103.1 (CH), 69.8 (CH), 52.4 ($CH_3$), 38.8 (br, $CH_2$), 18.4 ($CH_3$)
7) Specific rotation: $[\alpha]_D^{24}$ -22.9° (c 0.49, DMF)

[TAN-2421 B2]

1) Appearance: Light-yellow powder
2) Molecular formula: $C_{19}H_{15}ClO_9S$
3) High resolution FAB-MS spectrum: m/z 455.0197 Calculated value for $(C_{19}H_{15}ClO_9S+H)^+$; m/z 455.0204
4) UV spectrum: In methanol Maximum nm ($E_{1cm}$ 1%); 245 (560), 266 (510), 314 (220), 362 (155)
5) IR spectrum: In KBr tablet, major absorption peaks shown (wave number, $cm^{-1}$) 3700–2300 (br), 1715, 1650, 1590, 1570, 1480, 1435, 1410, 1370, 1335, 1255, 1200, 1100, 1070, 1010

6) $^{13}$C NMR spectrum: 75 MHz, in DMSO-d$_6$, 6° C., δ ppm 178.6 (Q), 173.3–173.5 (br, Q), 166.5 (br, Q), 165.1 (Q), 157.5 (Q), 156.0 (Q), 153.1 (Q), 145.8 (Q), 139.9 (br, Q), 117.7 (Q), 114.1 (Q), 109.3 (br, Q), 108.6 (CH), 106.6 (Q), 103.1 (CH), 69.8 (CH), 52.3 (CH$_3$), 38.8–39.0 (br, CH$_2$), 20.7 (CH$_3$)

[TAN-2421 B3]

1) Appearance: Light-yellow powder
2) Molecular formula: C$_{19}$H$_{15}$ClO$_9$S
3) High resolution FAB-MS spectrum: m/z 455.0200 Calculated value for (C$_{19}$H$_{15}$ClO$_9$S+H)$^+$; m/z 455.0204
4) UV spectrum: In methanol Maximum nm (E$_{1cm}$ 1%); 240 (665), 266 (shoulder, 570), 272 (585), 303 (265), 364 (195)
5) IR spectrum: In KBr tablet, major absorption peaks shown (wave number, cm$^{-1}$) 3700-2300 (br), 1725, 1650, 1590, 1485, 1435, 1365, 1330, 1305, 1255, 1880, 1160, 1100, 1010
6) $^{13}$C NMR spectrum: 75 MHz, in DMSO-d$_6$, 6° C., δ ppm 178.5 (Q), 173.3 (br, Q), 166.5 (br, Q), 165.2 (Q), 158.8 (Q), 157.2 (Q), 150.4 (Q), 145.8 (Q), 139.8 (br, Q), 117.9 (Q), 112.4 (CH), 109.8 (Q), 109.3 (Q), 107.0 (Q), 103.1 (CH), 69.8 (CH), 52.3 (CH$_3$), 38.8–38.9 (br, CH$_2$), 20.5 (CH$_3$)

For the components obtained in Examples 2 and 3, the following retention times in high performance liquid chromatography, Rf values in silica gel thin-layer chromatography, and results in coloring reaction were obtained.

1) Retention times in high performance liquid chromatography

Conditions

Column: YMC-Pack A312, ODS, 6.0×150 mm (produced by YMC)

Flow rate: 2.0 ml/min

Detection: UV 214 nm

Mobile phase 1: 55% (v/v) aqueous acetonitrile (containing 0.05% TFA)

Mobile phase 2: 35% (v/v) aqueous acetonitrile/0.01M phosphate buffer (pH 6.3)

|  | Retention time (min) | |
| --- | --- | --- |
|  | Mobile phase 1 | Mobile phase 2 |
| TAN-2421 A1 | 7.7 | 16.8 |
| TAN-2421 A2 | 5.0 | 10.2 |
| TAN-2421 A3 | 5.0 | 9.6 |
| TAN-2421 A4 | 3.6 | 6.1 |
| TAN-2421 B1 | 5.8 | 4.8 |
| TAN-2421 B2 | 3.8 | 3.3 |
| TAN-2421 B3 | 3.8 | 3.0 |

2) Rf values in silica gel thin-layer chromatography

Conditions

Carrier: Kiesel Gel 60F254, 0.25 mm thickness (produced by Merck, Germany)

Developing solvent: Chloroform/methanol/formic acid (9:1:0.5)

|  | Rf value |
| --- | --- |
| TAN-2421 A1 | 0.63 |
| TAN-2421 A2 | 0.63 |
| TAN-2421 A3 | 0.64 |
| TAN-2421 A4 | 0.62 |
| TAN-2421 B1 | 0.41 |
| TAN-2421 B2 | 0.39 |
| TAN-2421 B3 | 0.41 |

3) Results in coloring reaction (common to all components)

Positive; Barton reagent, iodine, potassium permanganate, phosphomolybdic acid

Negative; ninhydrin, Sakaguchi reagent

Example 4

Compound 1 (40 mg) was suspended in ethyl acetate (9.4 ml); methanol (40 µl) and a 2.0M hexane solution of (trimethylsilyl)diazomethane (produced by Tokyo Kasei) (500 µl) were added, followed by stirring at room temperature for 25 minutes. The reaction mixture was concentrated under reduced pressure; the residue obtained was purified by silica gel column chromatography (eluted with chloroform), after which it was again purified by silica gel column chromatography (eluted with ethyl acetate/hexane and chloroform/methanol) to yield compound 8 (32 mg) as a light-yellow powder.

$^1$H NMR, CDCl$_3$, δ ppm; 12.90 (1H, s), 7.05 (1H, s), 4.10 (3H, s), 4.05 (3H, s), 3.67 (3H, s), 3.56 (1H, d, J=13.7 Hz), 3.49 (1H, d, J=13.7 Hz), 2.65 (3H, s)

FAB-MS spectrum (M+H)$^+$: m/z 487

Example 5

Compound 8 (11 mg) was suspended in methanol/acetonitrile/water (3:2:1, 6 ml); an aqueous solution of 1M sodium hydroxide (100 µl) was added, followed by stirring at room temperature for 2 hours and then at 6° C. for 2 hours. After water was added, the reaction mixture was neutralized with dilute hydrochloric acid, then concentrated. The residue obtained was acidified by the addition of a 10% aqueous solution of citric acid and extracted with chloroform (3×10 ml). Next, the organic layer was dried over anhydrous sodium sulfate, after which it was concentrated under reduced pressure. The residue obtained was subjected to silica gel column chromatography and eluted with chloroform/methanol/formic acid (90:10:0 and 80:20:1). After the eluate was concentrated under reduced pressure, chloroform (9 ml) was added; the concentrate was washed with a 10% aqueous solution of citric acid (2×3 ml) and brine (3 ml). The organic layer obtained was dried over anhydrous sodium sulfate, after which it was concentrated under reduced pressure to yield compound 9 (2.7 mg) as a light-yellow powder.

$^1$H NMR, CDCl$_3$CD$_3$OD, δ ppm; 7.07 (1H, s), 4.09 (3H, s), 4.06 (3H, s), 3.51 (2H, s), 2.65 (3H, s)

FAB-MS spectrum (M+H)$^+$: m/z 473

Example 6

Compound 1 (50 mg) was suspended in 10% hydrochloric acid-methanol (produced by Tokyo Kasei) (10 ml), followed by stirring at room temperature for 1 hour. The reaction mixture was concentrated under reduced pressure; the residue obtained was purified by silica gel column chromatography (eluted with chloroform) to yield compound 10 (46 mg) as a light-yellow powder.

¹H NMR, CDCl₃, δ ppm; 12.87 (1H, s), 9.12 (1H, br s), 7.18 (1H, s), 4.07 (3H, s), 3.77 (3H, s), 3.74 (1H, d, J=17.5 Hz), 3.60 (1H, d, J=17.5 Hz), 2.64 (3H, s)

Example 7

Compound 1 (40 mg) was disolved in DMF (1.0 ml); sodium hydrogen carbonate (36 mg) and chloromethylmethyl ether (produced by Tokyo Kasei) (33 μl) were added, followed by stirring at room temperature for 2 hours. After ethyl acetate (20 ml) was added, the reaction mixture was washed with 0.1M hydrochloric acid (10 ml) and water (3×10 ml). Next, the organic layer was dried over anhydrous sodium sulfate, after which it was concentrated under reduced pressure; the residue obtained was purified by silica gel column chromatography (eluted with chloroform) to yield compound 11 (40 mg) as a light-yellow powder.;

¹H NMR, CDCl₃, δ ppm; 12.87 (1H, s), 7.36 (1H, s), 5.45 (2H, s), 5.24 (1H, d, J=5.9 Hz), 5.18 (1H, d, J=5.9 Hz), 4.05 (3H, s), 3.58 (3H, s), 3.42 (3H, s), 2.65 (3H, s)

Example 8

Compound 11 (20 mg) was dissolved in DMF (1.0 ml); potassium carbonate (10 mg) and methyl iodide (produced by Wako Pure Chemical Industries) (11.4 μl) were added, followed by stirring at room temperature for 16 hours. After ethyl acetate (30 ml) was added, the reaction mixture was washed with water (3×15 ml). Next, the organic layer was dried over anhydrous sodium sulfate, after which it was concentrated under reduced pressure to yield a light-yellow powder (20 mg). This powder was dissolved in THF (0.8 ml); 1M hydrochloric acid (0.2 ml) was added, followed by stirring at 6° C. for 24 hours. After the reaction mixture was concentrated under reduced pressure to remove the THF, the residue was suspended in ethyl acetate (10 ml) and washed with water (2×5 ml). Next, the organic layer was dried over anhydrous sodium sulfate, after which it was concentrated under reduced pressure; the residue obtained was subjected to preparative high performance liquid chromatography [column; YMC-Pack ODS SH-343-5, mobile phase; 55% aqueous acetonitrile (containing 0.05% TFA), flow rate; 10 ml/min] to obtain 10 ml fractions. Fractions 19 and 20 were combined and concentrated under reduced pressure to remove the acetonitrile, after which the concentrate was extracted with ethyl acetate (10 ml). Next, the organic layer was washed with water (3×5 ml), after which it was dried over anhydrous sodium sulfate and concentrated under reduced pressure to yield compound 12 as a white powder (11 mg).

¹H NMR, DMSO-d₆, δ ppm; 12.34 (1H, br), 7.00 (1H, s), 3.89 (3H, s), 3.82 (3H, s), 3.54 (2H, s), 2.60 (3H, s)

Example 9

Compound 10 (15 mg) was dissolved in 7.2M ammonia/methanol (3.0 ml), followed by stirring at room temperature for 21 hours. After the reaction mixture was concentrated under reduced pressure, the residue was suspended in 0.1M hydrochloric acid (5 ml) and extracted with ethyl acetate (30 ml). The organic layer was washed with water (2×15 ml), after which it was dried over anhydrous sodium sulfate and concentrated under reduced pressure. The residue obtained was suspended in methanol (3 ml); insoluble substances were centrifugally collected to yield compound 13 (13 mg) as a light-yellow powder.

¹H NMR, DMSO-d₆, δ ppm; 13.00 (1H, s), 12.52 (1H, br), 7.55 (1H, br s), 7.32 (1H, br s), 7.08 (1H, s), 3.93 (3H, s), 3.55 (2H, s), 2.58 (3H, s)

Example 10

Compound 10 (13 mg) was dissolved in dichloromethane (0.5 ml); 2-methoxyethylamine (produced by Aldrich, USA) (0.1 ml) was added, followed by stirring at room temperature for 19 hours. After ethyl acetate (20 ml) was added, the reaction mixture was washed with 1M hydrochloric acid (10 ml) and water (2×15 ml), after which the organic layer was dried over anhydrous sodium sulfate and concentrated under reduced pressure. The residue obtained was purified by silica gel column chromatography (eluted with 10:1 chloroform/methanol) to yield compound 14 (14 mg) as a lightyellow powder.

¹H NMR, DMSO-d₆, δ ppm; 13.08 (1H, s), 8.17 (1H, br t, J=5.3 Hz), 7.02 (1H, s), 3.91 (3H, s), 3.54 (2H, s), 3.33 (4H, m), 3.22 (3H, s), 2.57 (3H, s)

Example 11

Compound 1 (25 mg) was dissolved in DMF (0.5 ml); WSC (produced by Dojin Kagaku Kenkyujo) (14 mg), HOBT (produced by Dojin Kagaku Kenkyujo) (9.5 mg), glycine ethyl ester hydrochloride (produced by Wako Pure Chemical Industries) (9.8 mg) and triethylamine (15 μl) were added, followed by stirring at room temperature for 2 hours. After ethyl acetate (30 ml) was added, the reaction mixture was washed with 0.1M hydrochloric acid (10 ml), 2% aqueous sodium hydrogen carbonate (10 ml) and water (2×10 ml), after which it was dried over anhydrous sodium sulfate and concentrated under reduced pressure. The residue obtained was purified by silica gel column chromatography (eluted with 10:1 chloroform/methanol) to yield compound 15 (24 mg) as a light-yellow powder.

¹H NMR, DMSO-d₆, δ ppm; 13.24 (1H, s), 8.66 (1H, br), 6.91 (1H, s), 4.07 (2H, q, J=7.1 Hz), 3.89 (3H, s), 3.82 (2H, m), 3.57 (2H, s), 2.57 (3H, s), 1.17 (3H, t, J=7.1 Hz)

Example 12

Compound 15 (14 mg) was suspended in methanol (1.4 ml); an aqueous solution of 1M sodium hydroxide (100 μl) was added, followed by stirring at room temperature for 20 hours. The reaction mixture was concentrated under reduced pressure; the residue was suspended in ethyl acetate (15 ml) and washed with 0.1M hydrochloric acid (5 ml) and water (2×5 ml). Next, the organic layer was dried over anhydrous sodium sulfate, after which it was concentrated under reduced pressure. The residue obtained was subjected to preparative high performance liquid chromatography [column; YMC-Pack ODS SH-343-5, mobile phase; 50% (v/v) aqueous acetonitrile (containing 0.05% TFA), flow rate; 10 ml/min] to obtain 10 ml fractions. Fractions 19 through 25 were combined and concentrated under reduced pressure to remove the acetonitrile, after which the concentrate was extracted with ethyl acetate (20 ml). The organic layer was washed with water (2×10 ml), after which it was dried over anhydrous sodium sulfate and concentrated under reduced pressure to yield compound 16 (12 mg) as a light-yellow powder.

¹H NMR, DMSO-d₆, δ ppm; 13.02 (1H, s), 12.50 (1H, br), 8.34 (1H, br t, J=5.7 Hz), 7.08 (1H, s), 3.91 (3H, s), 3.75 (2H, m), 3.60 (2H, s), 2.59 (3H, s)

Example 13

Compound 1 (15 mg) was suspended in chloroform (3 ml); m-chloroperbenzoic acid (produced by Wako Pure Chemical Industries, purity 70%) (8.1 mg) was added, followed by stirring at room temperature for 1 hour. The reaction mixture was concentrated under reduced pressure; the residue obtained was purified by silica gel column chromatography (eluted with 20:1:0.5 chloroform/methanol/formic acid) to yield compound 17 (13 mg) as a light-yellow powder.

$^1$H NMR, CD$_3$OD, δ ppm; 7.04 (1H, s), 4.30 (1H, d, J=14.7 Hz), 4.15 (1H, d, J=14.7 Hz), 3.98 (3H, s), 2.61 (3H, s)

Example 14

Compound 1 (10 mg) was dissolved in pyridine (0.4 ml); acetic anhydride (0.1 ml) was added, followed by stirring at room temperature for 1.5 hours. After the reaction mixture was concentrated to dryness under reduced pressure, the residue was dissolved in 70% (v/v) aqueous acetonitrile (10 ml), followed by stirring at room temperature for 18 hours. The reaction mixture was concentrated; the residue obtained was subjected to preparative high performance liquid chromatography [column; YMC-Pack ODS SH-343-5, mobile phase; 60% (v/v) aqueous acetonitrile (containing 0.05% TFA), flow rate; 10 ml/min] to obtain 10 ml fractions. Fractions 12 and 13 were combined and concentrated under reduced pressure to yield compound 18 (9.1 mg) as a white powder.

$^1$H NMR, DMSO-d$_6$, δ ppm; 12.45 (1H, br), 7.02 (1H, s), 3.86 (3H, s), 3.54 (2H, m), 2.64 (3H, s), 2.41 (3H, s)

Example 15

Compound 1 (30 mg) was dissolved in pyridine (2.4 ml); acetic anhydride (0.6 ml) was added, followed by stirring at room temperature for 2 hours. After the reaction mixture was concentrated to dryness under reduced pressure, the residue was dissolved in anhydrous THF (2.5 ml); a 1.0M THF solution of borane-THF complex salt (produced by Aldrich) (1.0 ml) was added, followed by stirring at room temperature in an argon atmosphere for 3 hours. After the reaction mixture was concentrated to dryness under reduced pressure, the residue was suspended in ethyl acetate (30 ml) and washed with 0.1M hydrochloric acid (5 ml) and brine (2×5 ml). Next, the organic layer was dried over anhydrous sodium sulfate, after which it was concentrated under reduced pressure; the residue obtained was purified by silica gel column chromatography (eluted with 98:2–97:3 chloroform/methanol) to yield compound 20 (26 mg) as a white powder.

$^1$H NMR, CDCl$_3$, δ ppm; 8.13 (1H, br), 7.16 (1H, s), 4.05 (3H, s), 3.69 (2H, t, J=5.0 Hz), 2.92 (2H, m), 2.67 (3H, s), 2.47 (3H, s)

Example 16

Compound 20 (13 mg) was dissolved in methanol (4.4 ml); 0.1M aqueous potassium carbonate (1.4 ml) was added under ice cooling conditions, followed by stirring at room temperature for 5 hours. After 0.1M hydrochloric acid (2.7 ml) was added, the reaction mixture was concentrated under reduced pressure. The residue was suspended in ethyl acetate (25 ml) and washed with 0.1M hydrochloric acid (5 ml) and brine (2×5 ml). Next, the organic layer was dried over anhydrous sodium sulfate, after which it was concentrated under reduced pressure. The residue obtained was subjected to preparative high performance liquid chromatography [column; YMC-Pack ODS SH-343-5, mobile phase; 60% (v/v) aqueous acetonitrile (containing 0.05% TFA), flow rate; 10 ml/min] to obtain 10 ml fractions. Fractions 31 through 35 were combined and concentrated under reduced pressure to yield compound 21 (10 mg) as a light-yellow powder.

$^1$H NMR, DMSO-d$_6$, δ ppm; 13.11 (1H, s), 7.04 (1H, s), 3.91 (3H, s), 3.44 (2H, t, J=7.0 Hz), 2.88 (2H, t, J=7.0 Hz), 2.58 (3H, s)

Example 17

Compound 1 (10 mg) was dissolved in pyridine (0.4 ml); acetic anhydride (0.1 ml) was added, followed by stirring at room temperature for 1.5 hours. After the reaction mixture was concentrated to dryness under reduced pressure, the residue was dissolved in methanol (10 ml), followed by stirring at room temperature for 18 hours. The reaction mixture was concentrated under reduced pressure; the residue obtained was subjected to preparative high performance liquid chromatography [column; YMC-Pack ODS SH-343-5, mobile phase; 60% (v/v) aqueous acetonitrile (containing 0.05% TFA), flow rate; 10 ml/min] to obtain 10 ml fractions. Fractions 18 and 19 were combined and concentrated under reduced pressure to yield compound 26 (8.2 mg) as a white powder.

$^1$H NMR, CDCl$_3$, δ ppm; 8.96 (1H, br), 7.15 (1H, s), 4.04 (3H, s), 3.76 (3H, s), 3.67 (2H, m), 2.67 (3H, s), 2.47 (3H, s)

Example 18

Compound 1 (15 mg) was dissolved in pyridine (1.5 ml); propionic anhydride (12.7 µl, produced by Wako Pure Chemical Industries) was added, followed by stirring at room temperature for 2 hours. After the reaction mixture was concentrated to dryness under reduced pressure, the residue was suspended in 70% (v/v) aqueous acetonitrile (15 ml), followed by stirring at room temperature for 18 hours. The reaction mixture was concentrated under reduced pressure; the residue obtained was subjected to preparative high performance liquid chromatography [column; YMC-Pack ODS SH-343-5, mobile phase; 60% (v/v) aqueous acetonitrile (containing 0.05% TFA), flow rate; 10 ml/min] to obtain 10 ml fractions. Fractions 19 and 20 were combined and concentrated under reduced pressure to yield compound 27 (15 mg) as a white powder.

$^1$H NMR, DMSO-d$_6$, δ ppm; 12.40 (1H, br), 7.03 (1H, s), 3.85 (3H, s), 3.54 (2H, m), 2.74 (2H, q, J=7.5 Hz), 2.64 (3H, s), 1.23 (3H, t, J=7.5 Hz)

Example 19

Compound 1 (15 mg) was dissolved in pyridine (1.5 ml); isobutyryl chloride (10.4 µl, produced by Wako Pure Chemical Industries) was added, followed by stirring at room temperature for 2 hours. After the reaction mixture was concentrated to dryness under reduced pressure, the residue was suspended in 70% (v/v) aqueous acetonitrile (15 ml), followed by stirring at room temperature for 18 hours and then at 60° C. for 2 hours. The reaction mixture was concentrated under reduced pressure; the residue obtained was subjected to preparative high performance liquid chromatography [column; YMC-Pack ODS SH-343-5, mobile phase; 60% (v/v) aqueous acetonitrile (containing 0.05% TFA), flow rate; 10 ml/min] to obtain 10 ml fractions. Fractions 27 through 29 were combined and concentrated under reduced pressure to yield compound 28 (16 mg) as a white powder.

$^1$H NMR, DMSO-d$_6$, δ ppm; 12.24 (1H, br), 7.04 (1H, s), 3.83 (3H, s), 3.54 (2H, m), 2.97 (1H, m), 2.63 (3H, s), 1.33 (6H, d, J=6.9 Hz)

Example 20

Compound 1 (12 mg) was dissolved in DMF (1.2 ml); WSC (15 mg) was added, followed by stirring at room temperature for 30 minutes. To the reaction mixture, benzoic acid (6.4 mg, produced by Wako Pure Chemical Industries) and 4-dimethylaminopyridine (3.2 mg, produced by Wako Pure Chemical Industries) were added, followed by stirring at room temperature for 3 hours. The reaction mixture was diluted with 70% (v/v) aqueous acetonitrile (3.5 ml), followed by stirring at room temperature for 18 hours. The reaction mixture was concentrated under reduced pressure; the concentrate (2.5 ml) was diluted with ethyl acetate (15 ml). The dilution was washed with 0.1M hydrochloric acid (10 ml) and water (3×10 ml). Next, the organic layer was dried over anhydrous sodium sulfate, after which it was concentrated under reduced pressure. The residue obtained was subjected to preparative high performance liquid chromatography [column; YMC-Pack ODS SH-343-5, mobile phase; 65% (v/v) aqueous acetonitrile (containing 0.05% TFA), flow rate; 10 ml/min] to obtain 10 ml fractions. Fractions 22 and 23 were combined and concentrated under reduced pressure to yield compound 29 (11 mg) as a white powder.

$^1$H NMR, DMSO-$d_6$, δ ppm; 12.22 (1H, br), 8.15 (2H, br d, J=7.5 Hz), 7.80 (1H, br t, J=7.5 Hz), 7.66 (2H, t, J=7.5 Hz), 7.06 (1H, s), 3.68–3.50 (5H, m), 2.67 (3H, s)

Example 21

Compound 10 (40 mg) was dissolved in anhydrous THF (4.0 ml); a 1.0M THF solution of borane-THF complex salt (1.0 ml) was added under ice cooling conditions, followed by stirring at 0° C. in an argon atmosphere for 2 hours. After saturated aqueous ammonium chloride (2.0 ml) was added under ice cooling conditions, the reaction mixture was concentrated under reduced pressure. The residue was suspended in ethyl acetate (30 ml) and washed with 0.1M hydrochloric acid (5 ml) and brine (2×5 ml). Next, the organic layer was dried over anhydrous sodium sulfate, after which it was concentrated under reduced pressure. The residue obtained was subjected to preparative high performance liquid chromatography [column; YMC-Pack ODS SH-343-5, mobile phase; 60% (v/v) aqueous acetonitrile (containing 0.05% TFA), flow rate; 10 ml/min] to obtain 10 ml fractions. Fractions 34 through 38 were combined and concentrated under reduced pressure to yield compound 30 (19 mg) as a yellow powder.

$^1$H NMR, CDCl$_3$, δ ppm; 8.05 (1H, br), 6.86 (1H, s), 5.74 (1H, br), 4.00 (3H, s), 3.82 (2H, s), 3.75 (3H, s), 3.56 (2H, s), 2.46 (3H, s)

Example 22

Compound 1 (15 mg) was dissolved in anhydrous THF (2.5 ml); a 1.0M THF solution of borane-THF complex salt (0.5 ml) was added at room temperature, followed by stirring at room temperature in an argon atmosphere for 3 hours. The reaction mixture was concentrated under reduced pressure; the residue obtained was suspended in ethyl acetate (30 ml) and washed with 0.1M hydrochloric acid (5 ml) and brine (2×5 ml). Next, the organic layer was dried over anhydrous sodium sulfate, after which it was concentrated under reduced pressure; the residue obtained was subjected to preparative high performance liquid chromatography [column; YMC-Pack ODS SH-343-5, mobile phase; 60% (v/v) aqueous acetonitrile (containing 0.05% TFA), flow rate; 10 ml/min] to obtain 10 ml fractions. Fractions 22 through 25 were combined and concentrated under reduced pressure to yield compound 31 (12 mg) as a light-brown powder.

$^1$H NMR, DMSO-$d_6$, δ ppm; 10.40 (1H, s), 9.78 (1H, s), 6.69 (1H, s), 3.90 (3H, s), 3.68 (2H, s), 3.43 (2H, t, J=7.2 Hz), 2.80 (2H, t, J=7.2 Hz), 2.41 (3H, s)

Example 23

Compound 11 (19 mg) was dissolved in anhydrous THF (3.0 ml); a 1.0M THF solution of borane-THF complex salt (0.5 ml) was added under ice cooling conditions, followed by stirring at 0° C. in an argon atmosphere for 3 hours. After saturated aqueous ammonium chloride (2.0 ml) was added under ice cooling conditions, the reaction mixture was concentrated under reduced pressure. The residue obtained was suspended in ethyl acetate (30 ml) and washed with 0.1M hydrochloric acid (5 ml) and brine (2×5 ml). Next, the organic layer was dried over anhydrous sodium sulfate, after which it was concentrated under reduced pressure. To the residue obtained, trifluoroacetic acid (0.5 ml) was added, and allowed to stand at room temperature for 20 minutes. The reaction mixture was concentrated under reduced pressure; the residue obtained was subjected to preparative high performance liquid chromatography [column; YMC-Pack ODS SH-343-5, mobile phase; 55% (v/v) aqueous acetonitrile (containing 0.05% TFA), flow rate; 10 ml/min] to obtain 10 ml fractions. Fractions 28 and 29 were combined and concentrated under reduced pressure to yield compound 32 (7.8 mg) as a brown powder.

$^1$H NMR, DMSO-$d_6$, δ ppm; 10.56 (1H, br s), 9.77 (1H, br s), 6.69 (1H, s), 3.88 (3H, s), 3.68 (2H, s), 3.50 (2H, s), 2.40 (3H, s)

Example 24

Compound 1 (15 mg) was dissolved in a 25% solution of hydrogen bromide in acetic acid (3.0 ml, produced by Wako Pure Chemical Industries), followed by stirring at 100° C. for 15 hours. After the reaction mixture was concentrated to dryness under reduced pressure, the residue obtained was subjected to preparative high performance liquid chromatography [column; YMC-Pack ODS SH-343-5, mobile phase; 55% (v/v) aqueous acetonitrile (containing 0.05% TFA), flow rate; 10 ml/min] to obtain 10 ml fractions. Fractions 10 through 12 were combined and concentrated under reduced pressure to yield compound 33 (12 mg) as a light-yellow powder.

$^1$H NMR, DMSO-$d_6$, δ ppm; 13.20 (1H, s), 7.00 (1H, s), 3.58 (2H, s), 2.58 (3H, s)

Example 25

Compound 1 (50 mg) was dissolved in DMF (5.0 ml); potassium carbonate (150 mg) and chloromethylmethyl ether (83 μl) were added, followed by stirring at room temperature for 30 minutes. After ethyl acetate (30 ml) was added, the reaction mixture was washed with 10% aqueous citric acid, 2% aqueous sodium hydrogen carbonate and water (each 2×10 ml). Next, the organic layer was dried over anhydrous sodium sulfate, after which it was concentrated under reduced pressure; the residue obtained was subjected to silica gel column chromatography (5.0 ml) and washed with hexane/ethyl acetate (90:10 and 80:20), after which it was eluted with hexane/ethyl acetate (70:30 and 65:35); the eluate were collected and concentrated to dryness to yield compound 34 (55 mg) as a light-yellow powder.

$^1$H NMR, CDCl$_3$, δ ppm; 7.32 (1H, s), 5.45 (2H, s), 5.22 (4H, m), 4.05 (3H, s), 3.69 (3H, s), 3.58 (2H, m), 3.57 (3H, s), 3.41 (3H, s), 2.67 (3H, s)

Example 26

Compound 1 (50 mg) was suspended in dichloromethane (5.0 ml); TEA (15 μl), produced by Wako Pure Chemical Industries) and chloromethylmethyl ether (13 μl) were added, followed by stirring at room temperature for 2 hours. After ethyl acetate (30 ml) was added, the reaction mixture was washed with 10% aqueous citric acid, 2% aqueous sodium hydrogen carbonate and water (each 2×10 ml). Next, the organic layer was dried over anhydrous sodium sulfate, after which it was concentrated under reduced pressure; the residue obtained was subjected to silica gel column chromatography (5.0 ml) and eluted with hexane/acetone (70:30, 60:40 and 50:50); the eluate were collected and concentrated to dryness to yield compound 35 (33 mg) as a yellow powder.

$^1$H NMR, CDCl$_3$, δ ppm; 12.86 (1H, s), 7.18 (1H, s), 5.32 (1H, d, J=5.8 Hz), 5.26 (1H, d, J=5.8 Hz), 4.08 (3H, s), 3.79 (1H, d, J=17.7 Hz), 3.65 (1H, d, J=17.7 Hz), 3.46 (3H, s), 2.64 (3H, s)

Example 27

Compound 35 (25 mg) was dissolved in pyridine (1.0 ml); acetic anhydride (1.0 ml) was added; the solution was kept standing at room temperature for 1 hour. After the reaction mixture was concentrated, ethyl acetate (30 ml) was added; the mixture was washed with 0.01M hydrochloric acid (5×20 ml) and water (2×20 ml). Next, the organic layer was dried over anhydrous sodium sulfate, after which it was concentrated to dryness to yield compound 36 (30 mg) as a light-yellow powder.

$^1$H NMR, CDCl$_3$, δ ppm; 7.49 (1H, s), 5.22 (2H, d, J=10.7 Hz), 4.03 (3H, s), 3.56 (2H, s), 3.41 (3H, s), 2.68 (3H, s), 2.47 (3H, s), 2.42 (3H, s)

Example 28

Compound 36 (20 mg) was dissolved in a 5% TFA solution in dichloromethane (2.0 ml); the solution was kept standing at room temperature for 1 hour. After ethyl acetate (30 ml) was added, the reaction mixture was washed with water (5×20 ml). Next, the organic layer was dried over anhydrous sodium sulfate, after which it was concentrated under reduced pressure. The residue obtained was subjected to preparative high performance liquid chromatography [column; YMC-Pack ODS SH-343-5, mobile phase; 70% (v/v) acetonitrile-10 mM phosphate buffer (pH 3.0), flow rate; 10 ml/min] to obtain 60–80 ml fractions, which were collected and concentrated under reduced pressure to remove the acetonitrile, after which the concentrate was adjusted to pH 3.0 and extracted with ethyl acetate (30 ml). The organic layer was washed with water (2×10 ml), after which it was dried over anhydrous sodium sulfate and concentrated under reduced pressure to yield compound 37 (18 mg) as a white powder.

$^1$H NMR, CDCl$_3$, δ ppm; 7.90 (1H, s), 3.92 (3H, s), 3.49 (2H, m), 2.67 (3H, s), 2.43 (3H, s), 2.39 (3H, s)

Example 29

Compound 36 (5.5 mg) was dissolved in TFA (100 μl); the solution was kept standing at room temperature for 30 minutes. After ethyl acetate (30 ml) was added, the reaction mixture was washed with water (3×10 ml). Next, the organic layer was dried over anhydrous sodium sulfate, after which it was concentrated under reduced pressure. The residue obtained was subjected to preparative high performance liquid chromatography [column; YMC-Pack ODS AM-324, mobile phase; 70% (v/v) aqueous acetonitrile (containing 0.05% TFA), flow rate; 3.0 ml/min] to obtain 42–48 ml fractions, which were collected and concentrated under reduced pressure to remove the acetonitrile, after which the concentrate was extracted with ethyl acetate (20 ml). The organic layer was washed with water (3×10 ml), after which it was dried over anhydrous sodium sulfate and concentrated under reduced pressure to yield compound 38 (3.1 mg) as a yellow powder.

$^1$H NMR, DMSO-d$_6$, δ ppm; 12.62 (1H, s), 7.95 (1H, s), 3.95 (3H, s), 3.51 (2H, m), 2.62 (3H, s), 2.40 (3H, s)

Example 30

Compound 1 (15 mg) was dissolved in DMF (1.0 ml); N-bromosuccinimide (5.8 mg, produced by Wako Pure Chemical Industries) was added under ice cooling conditions, followed by stirring at 0° C. for 20 minutes. The reaction mixture was diluted with ethyl acetate (20 ml) and washed with 0.1M hydrochloric acid (10 ml) and water (3×10 ml). Next, the organic layer was dried over anhydrous sodium sulfate, after which it was concentrated under reduced pressure. The residue obtained was subjected to preparative high performance liquid chromatography [column; YMC-Pack ODS SH-343-5, mobile phase; 65% (v/v) aqueous acetonitrile (containing 0.05% TFA), flow rate; 10 ml/min] to obtain 10 ml fractions. Fractions 33 through 37 were combined and concentrated under reduced pressure to yield compound 39 (14 mg) as a light-yellow powder.

$^1$H NMR, DMSO-d$_6$, δ ppm; 12.99 (1H, s), 3.91 (3H, s), 3.56 (2H, br s), 2.59 (3H, s)

Example 31

Compound 1 (12 mg) was dissolved in DMF (1.5 ml); iodine (7.3 mg, produced by Wako Pure Chemical Industries) was added, followed by stirring at room temperature for 2 hours, after which iodine (10 mg) was again added, followed by further stirring at room temperature for 1 hour. The reaction mixture was diluted with ethyl acetate (15 ml) and washed with a 2% aqueous solution of sodium thiosulfate (10 ml), water (2×10 ml) and brine (10 ml). Next, the organic layer was dried over anhydrous sodium sulfate, after which it was concentrated under reduced pressure. The residue obtained was subjected to preparative high performance liquid chromatography [column; YMC-Pack ODS SH-343-5, mobile phase; 75% (v/v) aqueous acetonitrile (containing 0.05% TFA), flow rate; 10 ml/min] to obtain 10 ml fractions. Fractions 21 and 22 were combined and concentrated under reduced pressure to yield compound 40 (11 mg) as a light-yellow powder.

$^1$H NMR, DMSO-d$_6$, δ ppm; 13.10 (1H, br s), 3.90 (3H, s), 3.52 (2H, br s), 2.60 (3H, s)

Example 32

Compound 1 (12 mg) was dissolved in formic acid (2.9 ml); 30% aqueous hydrogen peroxide (0.15 ml, produced by Wako Pure Chemical Industries) was added, followed by stirring at 60° C. for 2 hours. The reaction mixture was concentrated under reduced pressure; the residue obtained was subjected to preparative high performance liquid chromatography [column; YMC-Pack ODS SH-343-5, mobile phase; 50% (v/v) aqueous acetonitrile (containing 0.05% TFA), flow rate; 10 ml/min] to obtain 10 ml fractions. Fractions 17 through 19 were combined and concentrated under reduced pressure to yield compound 41 (11 mg) as a light-yellow powder.

¹H NMR, DMSO-d$_6$, δ ppm; 13.05 (1H, s), 6.99 (1H, s), 4.55 (2H, s), 3.85 (3H, s), 2.58 (3H, s)

Example 33

Compound 33 (27 mg) was dissolved in dichloromethane (2.7 ml); triethylamine (17 μl) and chloromethylmethyl ether (15 μl) were added, followed by stirring at room temperature for 1.5 hours. After 0.1M phosphate buffer (pH 3.0) (10 ml) was added, the reaction mixture was extracted with ethyl acetate (30 ml); the organic layer was washed with water (2×10 ml) and brine (5 ml). Next, the organic layer was dried over anhydrous sodium sulfate, after which it was concentrated under reduced pressure; the residue obtained was subjected to preparative high performance liquid chromatography [column; YMC-Pack ODS SH-343-5, mobile phase; 68% (v/v) acetonitrile-0.01M phosphate buffer (pH 3.0), flow rate; 10 ml/min] to obtain 10 ml fractions. Fractions 27 through 32 were combined and concentrated under reduced pressure to remove the acetonitrile, after which the concentrate was extracted with ethyl acetate (30 ml). The organic layer was washed with water (10 ml) and brine (5 ml), then dried over anhydrous sodium sulfate, after which it was concentrated under reduced pressure to yield compound 42 (22 mg) as a light-yellow powder.

¹H NMR, CDCl$_3$, δ ppm; 12.87 (1H, s), 9.06 (1H, br), 7.19 (1H, s), 5.72 (1H, d, J=5.8 Hz), 5.56 (1H, d, J=5.8 Hz), 5.32 (1H, d, J=5.8 Hz), 5.27 (1H, d, J=5.8 Hz), 3.80 (1H, d, J=17.8 Hz), 3.67 (1H, d, J=17.8 Hz), 3.63 (3H, s), 3.46 (3H, s), 2.65 (3H, s)

Example 34

Compound 42 (16 mg) was dissolved in THF (1.5 ml); 1.0M aqueous sodium hydroxide (89 μl) was added under ice cooling conditions, followed by stirring at 0° C. for 30 minutes. After 0.1M phosphate buffer (pH 3.0) (10 ml) was added, the reaction mixture was extracted with ethyl acetate (30 ml); the organic layer was washed with water (10 ml) and brine (5 ml). Next, the organic layer was dried over anhydrous sodium sulfate, after which it was concentrated under reduced pressure; the residue obtained was subjected to preparative high performance liquid chromatography [column; YMC-Pack ODS SH-343-5, mobile phase; 65% (v/v) acetonitrile-0.02M phosphate buffer (pH 3.0), flow rate; 10 ml/min] to obtain 10 ml fractions. Fractions 15 through 18 were combined and concentrated under reduced pressure to remove the acetonitrile, after which the concentrate was extracted with ethyl acetate (30 ml). The organic layer was washed with water (10 ml) and brine (5 ml), then dried over anhydrous sodium sulfate, after which it was concentrated under reduced pressure to yield compound 43 (13 mg) as a light-yellow powder.

¹H NMR, DMSO-d$_6$, δ ppm; 13.07 (1H, s), 7.03 (1H, s), 5.55 (1H, d, J=5.8 Hz), 5.44 (1H, d, J=5.8 Hz), 3.59 (2H, s), 3.51 (3H, s), 2.57 (3H, s)

Example 35

Compound 33 (15 mg) was dissolved in 10% hydrochloric acid-methanol (3.0 ml), followed by stirring at room temperature for 1 hour. The reaction mixture was concentrated under reduced pressure; the residue obtained was subjected to preparative high performance liquid chromatography [column; YMC-Pack ODS SH-343-5, mobile phase; 55% (v/v) aqueous acetonitrile (containing 0.05% TFA), flow rate; 10 ml/min] to obtain 10 ml fractions. Fractions 22 through 24 were combined and concentrated under reduced pressure to remove the acetonitrile, after which the concentrate was extracted with ethyl acetate (30 ml). The organic layer was washed with water (2×10 ml) and brine (5 ml), then dried over anhydrous sodium sulfate, after which it was concentrated under reduced pressure to yield compound 44 (13 mg) as a light-yellow powder.

¹H NMR, DMSO-d$_6$, δ ppm; 13.17 (1H, s), 7.00 (1H, s), 3.60 (2H, s), 3.55 (3H, s), 2.57 (3H, s)

Example 36

Compound 33 (15 mg) was suspended in ethanol (1.0 ml); 10% (v/v) concentrated sulfuric acid-ethanol (10 μl) was added, followed by refluxing for 1 hour. The reaction mixture was concentrated under reduced pressure, after which it was dissolved in ethyl acetate (15 ml) and washed with brine (2×5 ml). The organic layer was dried over anhydrous sodium sulfate, after which it was concentrated under reduced pressure; the residue obtained was subjected to preparative high performance liquid chromatography [column; YMC-Pack ODS SH-343-5, mobile phase; 60% (v/v) aqueous acetonitrile (containing 0.05% TFA), flow rate; 10 ml/min] to obtain 10 ml fractions. Fractions 21 through 23 were combined and concentrated under reduced pressure to remove the acetonitrile, after which the concentrate was extracted with ethyl acetate (30 ml). The organic layer was washed with water (2×10 ml) and brine (5 ml), then dried over anhydrous sodium sulfate, after which it was concentrated under reduced pressure to yield compound 45 (14 mg) as a light-yellow powder.

¹H NMR, DMSO-d$_6$, δ ppm; 13.18 (1H, s), 7.01 (1H, s), 3.99 (2H, q, J=7.1 Hz), 3.59 (2H, s), 2.58 (3H, s), 1.08 (3H, t, J=7.1 Hz)

Example 37

Compound 33 (40 mg) was dissolved in DMF (2.0 ml); triethylamine (25 μl) and ethyl iodide (produced by Wako Pure Chemical Industries) (145 μl) were added, followed by stirring at room temperature for 13 hours. The reaction mixture was dissolved in ethyl acetate (30 ml) and washed with 10% aqueous citric acid (2×5 ml), water (3×5 ml) and brine (5 ml). The organic layer was dried over anhydrous sodium sulfate, after which it was concentrated under reduced pressure; the residue obtained was subjected to preparative high performance liquid chromatography [column; YMC-Pack ODS SH-343-5, mobile phase; 65% (v/v) aqueous acetonitrile (containing 0.05% TFA), flow rate; 10 ml/min] to obtain 10 ml fractions. Fractions 26 through 29 were combined and concentrated under reduced pressure to remove the acetonitrile, after which the concentrate was extracted with ethyl acetate (30 ml). The organic layer was washed with water (2×10 ml) and brine (5 ml), then dried over anhydrous sodium sulfate, after which it was concentrated under reduced pressure to yield compound 47 (10 mg) as a light-yellow powder.

¹H NMR, DMSO-d$_6$, δ ppm; 13.09 (1H, s), 7.02 (1H, s), 4.40 (2H, m), 3.60 (1H, d, J=14.5 Hz), 3.53 (1H, d, J=14.5 Hz), 2.57 (3H, s), 1.35 (3H, t, J=7.1 Hz)

Fractions 55 through 65 were combined and concentrated under reduced pressure to remove the acetonitrile, after which the concentrate was extracted with ethyl acetate (30 ml); the organic layer was washed with water (2×10 ml) and brine (5 ml), then dried over anhydrous sodium sulfate, after which it was concentrated under reduced pressure to yield compound 46 (13 mg) as a light-yellow powder.

¹H NMR, CDCl$_3$, δ ppm; 12.94 (1H, s), 9.23 (1H, br s), 7.17 (1H, s), 4.58 (2H, m), 4.22 (2H, q, J=7.2 Hz), 3.72 (1H, d, J=17.6 Hz), 3.59 (1H, d, J=17.6 Hz), 2.64 (3H, s), 1.45 (3H, t, J=7.2 Hz), 1.27 (3H, t, J=7.2 Hz)

Example 38

Compound 1 (50 mg) was dissolved in DMF (5.0 ml); potassium carbonate (15 mg) and benzyl bromide (17 μl, produced by Wako Pure Chemical Industries) were added, followed by stirring at room temperature for 11 hours. After ethyl acetate (30 ml) was added, the reaction mixture was washed with 10% aqueous citric acid, 2% aqueous sodium hydrogen carbonate and water (each 2×10 ml). Next, the organic layer was dried over anhydrous sodium sulfate, after which it was concentrated under reduced pressure. The residue obtained was subjected to preparative high performance liquid chromatography [column; YMC-Pack ODS SH-343, mobile phase; 75% (v/v) aqueous acetonitrile (containing 0.05% TFA), flow rate; 10 ml/min] to obtain 250–320 ml fractions, which were collected and concentrated under reduced pressure to remove the acetonitrile, after which the concentrate was extracted with ethyl acetate (30 ml). The organic layer was washed with water (3×10 ml), after which it was dried over anhydrous sodium sulfate and concentrated under reduced pressure to yield compound 48 (22 mg) as a yellow powder.

$^1$H NMR, CDCl$_3$, δ ppm; 12.87 (1H, s), 9.05 (1H, br s), 7.32 (5H, m), 7.15 (1H, s), 5.20 (1H, d, J=12.1 Hz), 5.14 (1H, d, J=12.1 Hz), 4.06 (3H, s), 3.77 (1H, d, J=17.4 Hz), 3.62 (1H, d, J=17.4 Hz), 2.65 (3H, s)

Example 39

Compound 48 (15 mg) was dissolved in DMF (2.0 ml); potassium carbonate (11 mg) and chloromethylmethyl ether (6.2 μl) were added, followed by stirring at room temperature for 4 hours. After ethyl acetate (30 ml) was added, the reaction mixture was washed with 10% aqueous citric acid, 2% aqueous sodium hydrogen carbonate and water (each 2×10 ml). Next, the organic layer was dried over anhydrous sodium sulfate, after which it was concentrated to dryness to yield compound 49 (17 mg) as a light-yellow powder.

$^1$H NMR, CDCl$_3$, δ ppm; 7.17 (5H, m), 7.16 (1H, s), 5.34 (2H, s), 5.19 (2H, d, J=14.4 Hz), 5.02 (2H, s), 4.02 (3H, s), 3.69 (3H, s), 3.52 (5H, s), 2.69 (3H, s)

Example 40

Compound 49 (15 mg) was dissolved in methanol (20 ml); 10% palladium-activated carbon (5.0 mg, produced by Wako Pure Chemical Industries) was added, followed by stirring in a 1 atm hydrogen atmosphere at room temperature for 1 hour. After the catalyst was filtered off from the reaction mixture, the filtrate was concentrated. The residue was again dissolved in methanol (20 ml); 10% palladium-activated carbon (5.0 mg) was added, followed by stirring in a 1 atm hydrogen atmosphere at room temperature for 2 hours. After the catalyst was filtered off from the reaction mixture, the filtrate was concentrated under reduced. pressure. The residue obtained was subjected to preparative high performance liquid chromatography [column; D-ODS-5 YMC, mobile phase; 73% (v/v) acetonitrile-20 mM phosphate buffer (pH 3.0), flow rate; 10 ml/min] to obtain 115–145 ml and 145–170 ml fractions, which were separately collected and concentrated under reduced pressure to remove the acetonitrile. These concentrates were extracted with ethyl acetate (30 ml). Each organic layer was washed with water (2×10 ml), after which it was dried over anhydrous sodium sulfate and concentrated under reduced pressure to yield compound 50 (4.4 mg) and compound 51 (2.6 mg) each as a yellow powder.

Compound 50
$^1$H NMR, CDCl$_3$, δ ppm; 7.31 (1H, s), 5.42 (2H, s), 5.20 (2H, br s), 4.04 (3H, s), 3.69 (3H, s), 3.59 (2H, s), 3.55 (3H, s), 2.67 (3H, s)

Compound 51
$^1$H NMR, CDCl$_3$, δ ppm; 12.84 (1H, br s), 7.36 (1H, s), 5.44 (2H, s), 4.06 (3H, s), 3.59 (2H, s), 3.56 (3H, s), 2.65 (3H, s)

Example 41

Compound 1 (15 mg) was dissolved in pyridine (0.5 ml); acetic anhydride (0.1 ml) was added, followed by stirring at room temperature for 1 hour. The reaction mixture was concentrated under reduced pressure; the residue was dissolved in chloroform (1.5 ml); m-chloroperbenzoic acid (8.1 mg) was added, followed by stirring at room temperature for 1 hour. After the reaction mixture was concentrated to dryness under reduced pressure, the residue was suspended in 70% (v/v) aqueous acetonitrile (15 ml), followed by stirring at room temperature for 15 hours. The reaction mixture was concentrated under reduced pressure; the residue obtained was subjected to preparative high performance liquid chromatography [column; YMC-Pack ODS SH-343-5, mobile phase; 50% (v/v) aqueous acetonitrile (containing 0.05% TFA), flow rate; 10 ml/min] to obtain 10 ml fractions. Fractions 14 through 16 were combined and concentrated under reduced pressure to yield compound 52 (13 mg) as a white powder.

$^1$H NMR, DMSO-d$_6$, δ ppm; 12.67 (1H, br), 7.04 (1H, s), 4.10 (2H, s), 3.81 (3H, s), 2.64 (3H, s), 2.41 (3H, s)

Example 42

Compound 27 (19 mg) was dissolved in acetic acid (3.61 ml); 30% aqueous hydrogen peroxide (0.19 ml) was added, followed by stirring at 60° C. for 45 minutes. The reaction mixture was concentrated under reduced pressure; the residue obtained was subjected to preparative high performance liquid chromatography [column; YMC-Pack ODS SH-343-5, mobile phase; 55% (v/v) aqueous acetonitrile (containing 0.05% TFA), flow rate; 10 ml/min] to obtain 10 ml fractions. Fractions 22 and 23 were combined and concentrated under reduced pressure to yield compound 53 (10 mg) as a brown powder.

$^1$H NMR, DMSO-d$_6$, δ ppm; 6.99 (1H, s), 4.09 (2H, s), 3.79 (3H, s), 2.74 (2H, m), 2.64 (3H, s), 1.23 (3H, t, J=7.3 Hz)

Example 43

Compound 40 (15 mg) was suspended in acetic acid (2.85 ml); 30% aqueous hydrogen peroxide (0.15 ml) was added, followed by stirring at 60° C. for 1 hour. The reaction mixture was concentrated under reduced pressure; the residue obtained was subjected to preparative high performance liquid chromatography (column; YMC-Pack ODS SH-343-5, mobile phase; 75% (v/v) aqueous acetonitrile (containing 0.05% TFA), flow rate; 10 ml/min] to obtain 10 ml fractions. Fractions 20 through 23 were combined and concentrated under reduced pressure to yield compound 54 (13 mg) as a light-yellow powder.

$^1$H NMR, DMSO-d$_6$, δ ppm; 13.38 (1H, s), 4.12 (1H, d, J=14.4 Hz), 3.96 (1H, d, J=14.4 Hz), 3.80 (3H, s), 2.58 (3H, s)

Example 44

Compound 40 (40 mg) was dissolved in pyridine (4.0 ml); propionic anhydride (26 μl) was added, followed by stirring at room temperature for 1 hour. After the reaction mixture was concentrated to dryness under reduced pressure, the residue was dissolved in 80% (v/v) aqueous acetonitrile (40 ml), followed by stirring at room temperature for 15 hours. The reaction mixture was concentrated; the residue obtained was subjected to preparative high performance liquid chromatography [column; YMC-Pack ODS SH-343-5, mobile phase; 75% (v/v) aqueous acetonitrile (containing 0.05% TFA), flow rate; 10 ml/min] to obtain 10 ml fractions. Fractions 25 through 27 were combined and concentrated under reduced pressure to yield compound 55 (33 mg) as a white powder.

$^1$H NMR, DMSO-$d_6$, δ ppm; 3.87 (3H, s), 3.55 (2H, s), 2.74 (2H, q, J=7.5 Hz), 2.65 (3H, s), 1.23 (3H, t, J=7.5 Hz)

Example 45

Compound 55 (16 mg) was suspended in acetic acid (3.04 ml); 30% aqueous hydrogen peroxide (0.16 ml) was added, followed by stirring at 50° C. for 2 hours. The reaction mixture was concentrated under reduced pressure; the residue obtained was subjected to preparative high performance liquid chromatography [column; YMC-Pack ODS SH-343-5, mobile phase; 75% (v/v) aqueous acetonitrile (containing 0.05% TFA), flow rate; 10 ml/min] to obtain 10 ml fractions. Fractions 20 through 24 were combined and concentrated under reduced pressure to yield compound 56 (15 mg) as a white powder.

$^1$H NMR, DMSO-$d_6$, δ ppm; 4.11 (2H, s), 3.79 (3H, s), 2.74 (2H, m), 2.65 (3H, s), 1.23 (3H, t, J=7.3 Hz)

Example 46

Compound 11 (15 mg) was dissolved in dichloromethane (1.5 ml); triethylamine (7.7 μl) and phenyl chlorocarbonate (4.1 μl, produced by Wako Pure Chemical Industries) were added, followed by stirring at room temperature for 30 minutes. The reaction mixture was diluted with ethyl acetate (10 ml) and washed with 0.1M hydrochloric acid (3 ml) and water (2×3 ml). Next, the organic layer was dried over anhydrous sodium sulfate, after which it was concentrated under reduced pressure. The residue was dissolved in TFA (1.5 ml) and kept standing at room temperature for 20 minutes, after which it was concentrated under reduced pressure. The residue obtained was subjected to preparative high performance liquid chromatography [column; YMC-Pack ODS SH-343-5, mobile phase; 65% (v/v) aqueous acetonitrile (containing 0.05% TFA), flow rate; 10 ml/min] to obtain 10 ml fractions. Fractions 21 through 24 were combined and concentrated under reduced pressure; the suspension obtained (10 ml) was extracted with ethyl acetate (10 ml). The organic layer was washed with water (2×5 ml) and dried over anhydrous sodium sulfate, after which it was concentrated under reduced pressure to yield compound 57 (16 mg) as a white powder.

$^1$H NMR, DMSO-$d_6$, δ ppm; 7.52 (2H, t, J=7.9 Hz), 7.39 (3H, m), 7.01 (1H, s), 3.91 (3H, s), 3.54 (2H, s), 2.67 (3H, s)

Example 47

Compound 11 (15 mg) was dissolved in dichloromethane (1.5 ml); triethylamine (7.7 μl) and methyl chlorocarbonate (4.2 μl, produced by Wako Pure Chemical Industries) were added, followed by stirring at room temperature for 30 minutes. The reaction mixture was diluted with ethyl acetate (10 ml) and washed with 0.1M hydrochloric acid (3 ml) and water (2×3 ml). Next, the organic layer was dried over anhydrous sodium sulfate, after which it was concentrated under reduced pressure. The residue was dissolved in TFA (1.5 ml) and kept standing at room temperature for 20 minutes, after which it was concentrated under reduced pressure. The residue obtained was subjected to preparative high performance liquid chromatography [column; YMC-Pack ODS SH-343-5, mobile phase; 60% (v/v) aqueous acetonitrile (containing 0.05% TFA), flow rate; 10 ml/min] to obtain 10 ml fractions. Fractions 14 through 16 were combined and concentrated under reduced pressure; the suspension obtained (10 ml) was extracted with ethyl acetate (10 ml). The organic layer was washed with water (2×5 ml) and dried over anhydrous sodium sulfate, after which it was concentrated under reduced pressure to yield compound 58 (13 mg) as a white powder.

$^1$H NMR, DMSO-$d_6$, δ ppm; 7.02 (1H, s), 3.89 (3H, s), 3.86 (3H, s), 3.53 (2H, m), 2.65 (3H, s)

Example 48

Compound 17 (265 mg) was suspended in dioxane (50 ml); 1M sulfuric acid (50 ml) was added, followed by stirring at 100° C. for 8 hours. After the reaction mixture was concentrated to remove the dioxane, ethyl acetate (100 ml) was added; the mixture was washed with water (4×50 ml). The organic layer was concentrated under reduced pressure; the residue obtained was subjected to silica gel column chromatography (25 ml) and washed with chloroform/TEA (100:2, 80 ml), after which it was eluted and fractionated with chloroform/methanol/TEA (100:2:2, 10×10 ml, fractions 1–10; 100:5:2, 10×10 ml, fractions 11–20 ; 50:50:5, 5×20 ml, fractions 21–25). Fractions 2–8 and 22–24 were separately combined and concentrated. Fractions 2–8 were concentrated to dryness, after which the concentrate was dissolved in pyridine (30 ml) and kept standing for 12 hours. Next, this solution was concentrated, combined with the concentration residue of fractions 22–24, and dissolved in ethyl acetate (80 ml). The ethyl acetate solution obtained was washed with 0.02M hydrochloric acid and water (each 2×40 ml) and dried over anhydrous sodium sulfate, after which it was concentrated to dryness to yield compound 59 (175 mg) as a light-yellow powder.

$^1$H NMR, Pyridine-$d_5$, δ ppm; 7.31 (2H, s), 4.06 (6H, s), 2.46 (6H, s)

Example 49

Compound 59 (10 mg) was suspended in DMF (2.0 ml); sodium borohydride (10 mg, produced by Wako Pure Chemical Industries) was added, followed by stirring at room temperature for 30 minutes. After ethyl acetate (30 ml) was added, the reaction mixture was washed with 0.02M hydrochloric acid and water (each 2×10 ml), after which the organic layer was dried over anhydrous sodium sulfate and concentrated under reduced pressure. The residue obtained was subjected to preparative high performance liquid chromatography [column; D-ODS-5 YMC, mobile phase; 70% (v/v) aqueous acetonitrile (containing 0.05% TFA), flow rate; 10 ml/min] to obtain 170–250 ml fractions, which were collected and concentrated under reduced pressure to remove the acetonitrile, after which the concentrate was extracted with ethyl acetate (30 ml). The organic layer was washed with water (3×10 ml), after which it was dried over anhydrous sodium sulfate and concentrated under reduced pressure to yield compound 60 (6.9 mg) as a yellow powder.

$^1$H NMR, CDCl$_3$, δ ppm; 12.84 (1H, s), 7.18 (1H, s), 4.09 (3H, s), 2.64 (3H, s)

Example 50

Compound 59 (10 mg) was suspended in pyridine (2.0 ml); sodium borohydride (5.0 mg) was added, followed by stirring at room temperature for 30 minutes. After α-bromo-p-toluic acid (8.1 mg, produced by Aldrich Chemical Company, Inc.) was added, the reaction mixture was stirred at room temperature for 2 hours. After the reaction mixture was concentrated, ethyl acetate (30 ml) was added; the mixture was washed with 0.02M hydrochloric acid (3×10 ml) and brine (2×10 ml), after which the organic layer was dried over anhydrous sodium sulfate and concentrated under reduced pressure. The residue obtained was subjected to preparative high performance liquid chromatography [column; YMC-Pack ODS SH-343-5, mobile phase; 65% (v/v) aqueous acetonitrile (containing 0.05% TFA), flow rate; 10 ml/min] to obtain 210–255 ml fractions, which were collected and concentrated under reduced pressure to remove the acetonitrile, after which the concentrate was extracted with ethyl acetate (30 ml). The organic layer was washed with water (3×10 ml), after which it was dried over anhydrous sodium sulfate and concentrated under reduced pressure to yield compound 61 (6.5 mg) as a yellow powder.

$^1$H NMR, Pyridine-$d_5$, δ ppm; 8.37 (2H, d, J=8.1 Hz), 7.59 (2H, d, J=8.1 Hz), 7.25 (1H, s), 4.58 (1H, d, J=12.5 Hz), 4.42 (1H, d, J=12.5 Hz), 4.13 (3H, s), 2.47 (3H, s)

Example 51

Compound 59 (10 mg) was suspended in pyridine (2.0 ml); sodium borohydride (10 mg) was added, followed by stirring at room temperature for 30 minutes. After 8-bromooctanoic acid (11 mg, produced by Aldrich Chemical Company, Inc.) was added, the reaction mixture was stirred at room temperature for 1 hour. After the reaction mixture was concentrated, ethyl acetate (30 ml) was added; the mixture was washed with 0.02M hydrochloric acid (3×10 ml) and brine (2×10 ml), after which the organic layer was dried over anhydrous sodium sulfate and concentrated under reduced pressure. The residue obtained was subjected to preparative high performance liquid chromatography [column; YMC-Pack ODS SH-343-5, mobile phase; 70% (v/v) aqueous acetonitrile (containing 0.05% TFA), flow rate; 10 ml/min] to obtain 280–330 ml fractions, which were collected and concentrated under reduced pressure to remove the acetonitrile, after which the concentrate was extracted with ethyl acetate (30 ml). The organic layer was washed with water (3×10 ml), after which it was dried over anhydrous sodium sulfate and concentrated under reduced pressure to yield compound 62 (7.0 mg) as a yellow powder.

$^1$H NMR, CDCl$_3$, δ ppm; 12.89 (1H, s), 7.20 (1H, s), 4.07 (3H, s), 2.77 (2H, t, J=7.5 Hz), 2.64 (3H, s), 2.34 (2H, t, J=7.4 Hz), 1.60 (4H, m), 1.33 (6H, m)

Example 52

Compound 59 (10 mg) was suspended in pyridine (2.0 ml); sodium borohydride (10 mg) was added, followed by stirring at room temperature for 30 minutes. After 2-bromooctanoic acid (8.7 μl, produced by Wako Pure Chemical Industries) was added, the reaction mixture was stirred at room temperature for 1 hour. After the reaction mixture was concentrated under reduced pressure, ethyl acetate (30 ml) was added; the mixture was washed with 0.02M hydrochloric acid (3×10 ml) and brine (2×10 ml). The organic layer obtained was dried over anhydrous sodium to obtain 280–330 ml fractions, which were collected and which the residue obtained was subjected to preparative high performance liquid chromatography [column; YMC-Pack ODS SH-343-5, mobile phase; 80% (v/v) aqueous acetonitrile (containing 0.05% TFA), flow rate; 10 ml/min] to obtain 220–250 ml fractions, which were collected and concentrated under reduced pressure to remove the acetonitrile, after which the concentrate was extracted with ethyl acetate (30 ml). The organic layer was washed with water (3×10 ml), after which it was dried over anhydrous sodium sulfate and concentrated under reduced pressure to yield compound 63 (7.5 mg) as a yellow powder.

$^1$H NMR, Pyridine-$d_5$, δ ppm; 7.25 (0.5H, s), 7.24 (0.5H, s), 4.57 (1H, m), 4.22 (1.5H, s), 4.19 (1.5H, s), 2.47 (3H, s), 2.32 (1H, m), 2.19 (1H, m), 1.72 (2H, m), 1.33 (2H, m), 1.20 (4H, m), 0.77 (3H, t, J=6.6 Hz)

Example 53

Compound 59 (15 mg) was suspended in pyridine (3.0 ml); sodium borohydride (15 mg) was added, followed by stirring at room temperature for 30 minutes. To this suspension, N-Boc-2-bromoethylamine (21 mg) as obtained in Reference Example 3 was added, followed by stirring at room temperature for 1 hour. The reaction mixture was concentrated under reduced pressure; the residue obtained was suspended in ethyl acetate (30 ml) and washed with 0.1M phosphate buffer (pH 3.0) (2×10 ml), water (2×10 ml) and brine (5 ml). Next, the organic layer obtained was dried over anhydrous sodium sulfate, after which it was concentrated under reduced pressure. The residue obtained was subjected to preparative high performance liquid chromatography [column; YMC-Pack ODS SH-343-5, mobile phase; 82% (v/v) acetonitrile-0.02M phosphate buffer (pH 3.0), flow rate; 10 ml/min] to obtain 10 ml fractions. Fractions 17 through 22 were combined and concentrated under reduced pressure to remove the acetonitrile, after which the concentrate was extracted with ethyl acetate (15 ml). The organic layer was washed with water (2×5 ml) and brine (3 ml), after which it was dried over anhydrous sodium sulfate and concentrated under reduced pressure. The residue obtained was dissolved in a 4N hydrochloric acid-ethyl acetate solution (produced by Kokusan Kagaku) (3.0 ml), followed by stirring at room temperature for 30 minutes. The reaction mixture was concentrated under reduced pressure to yield compound 64 (13 mg) as a light-yellow powder.

$^1$H NMR, DMSO-$d_6$, δ ppm; 12.99 (1H, s), 7.90 (3H, br s), 7.25 (1H, s), 3.95 (3H, s), 3.02 (2H, m), 2.85 (2H, m), 2.58 (3H, s)

Example 54

Compound 59 (10 mg) was suspended in pyridine (2.0 ml); sodium borohydride (10 mg) was added, followed by stirring at room temperature for 30 minutes. To this suspension, 3-bromopropionic acid (produced by Wako Pure Chemical Industries) (10 mg) was added, followed by stirring at room temperature for 1 hour. The reaction mixture was concentrated under reduced suspended in the residue obtained was suspended in ethyl acetate (30 ml) and washed with 0.02M hydrochloric acid (2×10 ml), water (2×10 ml) and brine (5 ml). The organic layer was dried over anhydrous sodium sulfate, after which it was concentrated under reduced pressure; the residue obtained was subjected to preparative high performance liquid chromatography [column; YMC-Pack ODS SH-343-5, mobile phase; 60% (v/v) aqueous acetonitrile (containing 0.05% TFA), flow rate; 10 ml/min] to obtain 10 ml fractions. Fractions 26 through 29 were combined and concentrated under reduced pressure to remove the acetonitrile, after which the concentrate was extracted with ethyl acetate (15 ml). The organic layer was washed with water (2×5 ml) and brine (5 ml), then dried over anhydrous sodium sulfate, after which it was concentrated under reduced pressure to yield compound 65 (7.6 mg) as a light-yellow powder.

¹H NMR, DMSO-d₆, δ ppm; 13.03 (1H, s), 7.07 (1H, s), 3.90 (3H, s), 2.99 (2H, m), 2.57 (3H, s), 2.41 (2H, m)

Example 55

Compound 59 (10 mg) was suspended in pyridine (2.0 ml); sodium borohydride (10 mg) was added, followed by stirring at room temperature for 30 minutes. To this suspension, ethyl iodide (5 μl) was added, followed by stirring at room temperature for 45 minutes. The reaction mixture was concentrated under reduced pressure; the residue obtained was suspended in ethyl acetate (30 ml) and washed with 0.02M hydrochloric acid (2×10 ml), water (2×10 ml) and brine (5 ml). The organic layer was dried over anhydrous sodium sulfate, after which it was concentrated under reduced pressure; the residue obtained was subjected to preparative high performance liquid chromatography [column; YMC-Pack ODS SH-343-5, mobile phase; 75% (v/v) aqueous acetonitrile (containing 0.05% TFA), flow rate; 10 ml/min] to obtain 10 ml fractions. Fractions 26 through 29 were combined and concentrated under reduced pressure to remove the acetonitrile, after which the concentrate was extracted with ethyl acetate (15 ml). The organic layer was washed with water (3×5 ml) and brine (5 ml), then dried over anhydrous sodium sulfate, after which it was concentrated under reduced pressure to yield compound 66 (8.1 mg) as a light-yellow powder.

¹H NMR, CDCl₃, δ ppm; 12.90 (1H, s), 7.80 (1H, br), 7.21 (1H, s), 4.08 (3H, s), 2.83 (2H, m), 2.64 (3H, s), 1.24 (3H, t, J=7.4 Hz)

Example 56

Compound 59 (10 mg) was suspended in pyridine (2.0 ml); sodium borohydride (10 mg) was added, followed by stirring at room temperature for 30 minutes. To this suspension, 1-bromopropane (produced by Wako Pure Chemical Industries) (12 μl) was added, followed by stirring at room temperature for 6 hours. The reaction mixture was concentrated under reduced pressure; the residue obtained was suspended in ethyl acetate (30 ml) and washed with 0.02M hydrochloric acid (2×10 ml), water (2×10 ml) and brine (5 ml). The organic layer was dried over anhydrous sodium sulfate, after which it was concentrated under reduced pressure; the residue obtained was subjected to preparative high performance liquid chromatography [column; YMC-Pack ODS SH-343-5, mobile phase; 85% (v/v) aqueous acetonitrile (containing 0.05% TFA), flow rate; 10 ml/min] to obtain 10 ml fractions. Fractions 19 and 20 were combined and concentrated under reduced pressure to remove the acetonitrile, after which the concentrate was extracted with ethyl acetate (15 ml). The organic layer was washed with water (3×5 ml) and brine (5 ml), then dried over anhydrous sodium sulfate, after which it was concentrated under reduced pressure to yield compound 67 (5.7 mg) as a light-yellow powder.

¹H NMR, CDCl₃, δ ppm; 12.90 (1H, s), 7.79 (1H, br), 7.20 (1H, s), 4.08 (3H, s), 2.77 (2H, m), 2.64 (3H, s), 1.61 (2H, m), 1.00 (3H, t, J=7.3 Hz)

Example 57

Compound 59 (20 mg) was suspended in pyridine (4.0 ml); sodium borohydride (20 mg) was added, followed by stirring at room temperature for 30 minutes. To the reaction mixture, bromoacetonitrile (3.5 μl), produced by Tokyo Kasei) was added, followed by stirring at room temperature for 1 hour. After the reaction mixture was concentrated, ethyl acetate (30 ml) was added; the mixture was washed with 0.02M hydrochloric acid (3×10 ml) and brine (2×10 ml), after which the organic layer was dried over anhydrous sodium sulfate and concentrated under reduced pressure. The residue obtained was subjected to preparative high performance liquid chromatography (column; YMC-Pack ODS SH-343-5, mobile phase; 65% (v/v) aqueous acetonitrile (containing 0.05% TFA), flow rate; 10 ml/min] to obtain 170–230 ml fractions, which were collected and concentrated under reduced pressure to remove the acetonitrile, after which the concentrate was extracted with ethyl acetate (30 ml). The organic layer was washed with water (3×10 ml), after which it was dried over anhydrous sodium sulfate and concentrated under reduced pressure to yield compound 68 (13 mg) as a yellow powder.

¹H NMR, Pyridine-d₅, δ ppm; 7.21 (1H, s), 4.45 (1H, d, J=16.8 Hz), 4.32 (1H, d, J=16.8 Hz), 4.20 (3H, s), 2.48 (3H, s)

Example 58

Compound 59 (10 mg) was suspended in pyridine (2.0 ml); sodium borohydride (10 mg) was added, followed by stirring at room temperature for 30 minutes. After sodium 2-bromoethanesulfonate (11 mg, produced by Wako Pure Chemical Industries) was added, the reaction mixture was stirred at room temperature for 2 hours. After the reaction mixture was concentrated to distill off the pyridine, 0.02M hydrochloric acid (30 ml) was added; the concentrate was extracted with ethyl acetate (3×30 ml). The organic layer was concentrated under reduced pressure; the residue obtained was subjected to preparative high performance liquid chromatography [column; YMC-Pack ODS SH-343-5, mobile phase; 45% (v/v) aqueous acetonitrile (containing 0.05% TFA), flow rate; 10 ml/min] to obtain 120–180 ml fractions, which were collected and concentrated under reduced pressure to remove the acetonitrile, after which the concentrate was extracted with ethyl acetate (3×30 ml). The organic layer was extracted with 2% aqueous sodium hydrogen carbonate (3×20 ml), after which the water layer obtained was concentrated and corrected to pH 8.0. This water layer was subjected to column chromatography with Diaion HP-20 (3.0 ml) and washed with water (9.0 ml), after which it was eluted with 80% aqueous methanol (9.0 ml). The eluate was concentrated, after which it was freeze-dried to yield compound 69 (7.8 mg) as a yellow powder.

¹H NMR, D₂O, δ ppm; 6.52 (1H, s), 4.07 (3H, s), 3.10 (4H, br s), 2.22 (3H, s)

Example 59

Compound 59 (10 mg) was suspended in pyridine (2.0 ml); sodium borohydride (10 mg) was added, followed by stirring at room temperature for 30 minutes. After α-bromophenylacetic acid (11 mg, produced by Aldrich Chemical Company, Inc.) was added, the reaction mixture was stirred at room temperature for 1 hour. After the reaction mixture was concentrated, ethyl acetate (30 ml) was added; the mixture was washed with 0.02 M hydrochloric acid (3×10 ml) and brine (2×10 ml), after which the organic layer obtained was dried over anhydrous sodium sulfate and concentrated under reduced pressure. The residue obtained was subjected to preparative high performance liquid chromatography [column; YMC-Pack ODS SH-343-5, mobile phase; 67% (v/v) aqueous acetonitrile (containing 0.05% TFA), flow rate; 10 ml/min] to obtain 190–230 ml fractions, which were collected and concentrated under reduced pressure to remove the acetonitrile, after which the concentrate was extracted with ethyl acetate (30 ml). The organic layer was washed with water (2×10 ml), after which it was dried over anhydrous sodium sulfate and concentrated under reduced pressure to yield compound 70 (7.1 mg) as a yellow powder.

$^1$H NMR, CDCl$_3$, δ ppm; 12.88 (0.7H, s), 12.84 (0.3H, s), 7.40 (5H, m), 7.14 (0.7H, s), 7.04 (0.3H, s), 5.20 (0.7H, s), 4.99 (0.3H, s), 4.06 (0.9H, s), 4.02 (2.1H, s), 2.65 (3H, s)

Example 60

Compound 59 (10 mg) was suspended in pyridine (2.0 ml); sodium borohydride (10 mg) was added, followed by stirring at room temperature for 30 minutes. After 2-bromopropionic acid (produced by Wako Pure Chemical Industries) (6 µl) was added, the reaction mixture was stirred at room temperature for 30 minutes. The reaction mixture was concentrated under reduced pressure; the residue obtained was suspended in ethyl acetate (30 ml) and washed with 0.02M hydrochloric acid (2×10 ml), water (2×10 ml) and brine (5 ml). The organic layer was dried over anhydrous sodium sulfate, after which it was concentrated under reduced pressure; the residue obtained was subjected to preparative high performance liquid chromatography [column; YMC-Pack ODS SH-343-5, mobile phase; 65% (v/v) aqueous acetonitrile (containing 0.05% TFA), flow rate; 10 ml/min] to obtain 10 ml fractions. Fractions 21 and 22 were combined and concentrated under reduced pressure to remove the acetonitrile, after which the concentrate was extracted with ethyl acetate (15 ml). The organic layer was washed with water (2×5 ml) and brine (3 ml), after which it was dried over anhydrous sodium sulfate and concentrated under reduced pressure to yield compound 71 (3.9 mg) as a light-yellow powder.

$^1$H NMR, DMSO-d$_6$, δ ppm; 13.06 (0.5H, s), 13.05 (0.5H, s), 7.05 (0.5H, s), 7.03 (0.5H, s), 4.02–3.85 (4H, m), 2.58 (3H, s), 1.34–1.22 (3H, m)

Example 61

Compound 68 (13 mg) was dissolved in DMF (2.0 ml); sodium azide (3.8 mg, produced by Wako Pure Chemical Industries) and ammonium chloride (3.1 mg) were added, followed by stirring at 127° C. for 13 hours. After ethyl acetate (30 ml) was added, the reaction mixture was washed with 0.01M hydrochloric acid and brine (each 2×10 ml). The organic layer was dried over anhydrous sodium sulfate and concentrated under reduced pressure. The residue obtained was subjected to preparative high performance liquid chromatography [column; D-ODS-5 YMC (produced by YMC.), mobile phase; 52% (v/v) aqueous acetonitrile (containing 0.05% TFA), flow rate; 10 ml/min] to obtain 220–320 ml fractions, which were collected and concentrated under reduced pressure to remove the acetonitrile, after which the concentrate was extracted with ethyl acetate (30 ml). The organic layer was washed with water (2×10 ml), after which it was dried over anhydrous sodium sulfate and concentrated under reduced pressure to yield compound 72 (10 mg) as a yellow powder.

$^1$H NMR, Pyridine-d$_5$, δ ppm; 7.12 (1H, s), 4.93 (1H, d, J=14.9 Hz), 4.79 (1H, d, J=14.9 Hz), 4.07 (3H, s), 2.47 (3H, s)

Example 62

Compound 59 (20 mg) was suspended in pyridine (1.0 ml); sodium borohydride (20 mg) was added, followed by stirring at room temperature for 30 minutes. After α-bromo-o-tolunitrile (20 mg, produced by Aldrich Chemical Company, Inc.) was added, the reaction mixture was stirred at room temperature for 1 hour. After the reaction mixture was concentrated, ethyl acetate (30 ml) was added; the mixture was washed with 0.02M hydrochloric acid (3×10 ml) and brine (2×10 ml), after which the organic layer was dried over anhydrous sodium sulfate and concentrated under reduced pressure. The residue obtained was subjected to preparative high performance liquid chromatography [column; D-ODS-5 YMC, mobile phase; 72% (v/v) aqueous acetonitrile (containing 0.05% TFA), flow rate; 10 ml/min] to obtain 180–260 ml fractions, which were collected and concentrated under reduced pressure to remove the acetonitrile, after which the concentrate was extracted with ethyl acetate (30 ml). The organic layer was washed with water (3×10 ml), after which it was dried over anhydrous sodium sulfate and concentrated under reduced pressure to yield compound 73 (20 mg) as a yellow powder.

$^1$H NMR, CDCl$_3$, δ ppm; 12.87 (1H, s), 7.70 (1H, dd, J=8.8, 2.1 Hz), 7.40 (2H, m), 7.14 (1H, dd, J=8.6, 1.7 Hz), 7.06 (1H, s), 4.19 (2H, m), 4.09 (3H, s), 2.65 (3H, s)

Example 63

Compound 59 (20 mg) was suspended in pyridine (2.0 ml); sodium borohydride (20 mg) was added, followed by stirring at room temperature for 30 minutes. After 3-(bromomethyl)benzoic acid methyl ester (23 mg, produced by Lancaster Synthesis, Ltd.) was added, the reaction mixture was stirred at room temperature for 1 hour. After the reaction mixture was concentrated, ethyl acetate (30 ml) was added; the mixture was washed with 0.02M hydrochloric acid (3×10 ml) and brine (2×10 ml), after which the organic layer was dried over anhydrous sodium sulfate and concentrated under reduced pressure. The residue obtained was subjected to preparative high performance liquid chromatography [column; D-ODS-5 YMC, mobile phase; 72% (v/v) aqueous acetonitrile (containing 0.05% TFA), flow rate; 10 ml/min] to obtain 290–370 ml fractions, which were collected and concentrated under reduced pressure to remove the acetonitrile, after which the concentrate was extracted with ethyl acetate (50 ml). The organic layer was washed with water (3×20 ml), after which it was dried over anhydrous sodium sulfate and concentrated under reduced pressure to yield compound 74 (19 mg) as a yellow powder.

$^1$H NMR, CDCl$_3$, δ ppm; 12.90 (1H, s), 7.94 (1H, dt, J=7.5, 1.5 Hz), 7.84 (1H, br t, J=1.5 Hz), 7.28 (2H, m), 7.01 (1H, s), 4.11 (3H, s), 4.05 (1H, d, J=12.5 Hz), 3.99 (1H, d, J=12.5 Hz), 3.88 (3H, s), 2.66 (3H, s)

Example 64

Compound 59 (10 mg) was suspended in pyridine (2.0 ml); sodium borohydride (10 mg) was added, followed by stirring at room temperature for 30 minutes. After (±)-bromosuccinic acid (9.8 mg, produced by Aldrich Chemical Company, Inc.) was added, the reaction mixture was stirred at room temperature for 16 hours. Sodium borohydride (10 mg) was further added to the reaction mixture, followed by stirring at room temperature for 20 minutes, after which (±)-bromosuccinic acid (5.0 mg) was added, followed by stirring at room temperature for 2 hours. After the reaction mixture was concentrated, ethyl acetate (30 ml) was added; the mixture was washed with 0.02M hydrochloric acid (3×10 ml) and brine (2×10 ml), after which the organic layer was dried over anhydrous sodium sulfate and concentrated under reduced pressure. The residue obtained was subjected to preparative high performance liquid chromatography [column; D-ODS-5 YMC, mobile phase; 52% (v/v) aqueous acetonitrile (containing 0.05% TFA), flow rate; 10 ml/min] to obtain 220–240 ml fractions, which were collected and concentrated under reduced pressure to remove the acetonitrile, after which the concentrate was extracted with ethyl acetate (30 ml). The organic layer was washed with water (2×10 ml), after which it was dried over anhydrous sodium sulfate and concentrated under reduced pressure to yield compound 75 (2.3 mg) as a yellow powder.

$^1$H NMR, Pyridine-$d_5$, δ ppm; 7.23 (1H, s), 5.10 (1H, m), 4.20 (1.5H, s), 4.15 (1.5H, s), 3.72 (1H, m), 3.48 (1H, m), 2.48 (3H, s)

Example 65

Compound 59 (10 mg) was suspended in pyridine (2.0 ml); sodium borohydride (10 mg) was added, followed by stirring at room temperature for 30 minutes. To the reaction mixture, 2-bromoethylamine-N-benzenesulfonamide as obtained in Reference Example 4 (17 mg) was added, followed by stirring at room temperature for 1 hour. The reaction mixture was concentrated under reduced pressure; the residue obtained was suspended in ethyl acetate (30 ml); the mixture was washed with 0.02M hydrochloric acid (2×10 ml), water (2×10 ml) and brine (5 ml). The organic layer was dried over anhydrous sodium sulfate, after which it was concentrated under reduced pressure; the residue obtained was subjected to preparative high performance liquid chromatography (column; YMC-Pack ODS SH-343-5, mobile phase; 75% (v/v) aqueous acetonitrile (containing 0.05% TFA), flow rate; 10 ml/min] to obtain 10 ml fractions. Fractions 20 and 21 were combined and concentrated under reduced pressure to remove the acetonitrile, after which the concentrate was extracted with ethyl acetate (15 ml). The organic layer was washed with water (3×5 ml) and brine (3 ml), then dried over anhydrous sodium sulfate, after which it was concentrated under reduced pressure to yield compound 76 (13 mg) as a light-yellow powder.

$^1$H NMR, CDCl$_3$, δ ppm; 12.80 (1H, s), 7.88–7.81 (2H, m), 7.57–7.43 (3H, m), 7.17 (1H, s), 5.53 (1H, m), 4.08 (3H, s), 3.24–2.83 (4H, m), 2.64 (3H, S)

Example 66

Compound 59 (10 mg) was suspended in pyridine (2.0 ml); sodium borohydride (10 mg) was added, followed by stirring at room temperature for 30 minutes. To the reaction mixture, 2-bromoethylamine-N-methanesulfonamide as obtained in Reference Example 5 (14 mg) was added, followed by stirring at room temperature for 30 minutes. The reaction mixture was concentrated under reduced pressure; the residue obtained was suspended in ethyl acetate (30 ml); the mixture was washed with 0.02M hydrochloric acid (2×10 ml), water (2×10 ml) and brine (5 ml). The organic layer was dried over anhydrous sodium sulfate, after which it was concentrated under reduced pressure; the residue obtained was subjected to preparative high performance liquid chromatography [column; YMC-Pack ODS SH-343-5, mobile phase; 55% (v/v) aqueous acetonitrile (containing 0.05% TFA), flow rate; 10 ml/min] to obtain 10 ml fractions. Fractions 43 through 49 were combined and concentrated under reduced pressure to remove the acetonitrile, after which the concentrate was extracted with ethyl acetate (15 ml). The organic layer was washed with water (3×5 ml) and brine (3 ml), then dried over anhydrous sodium sulfate, after which it was concentrated under reduced pressure to yield compound 77 (10 mg) as a light-yellow powder.

$^1$H NMR, DMSO-$d_6$, δ ppm; 13.00 (1H, s), 7.08 (1H, s), 7.05 (1H, m), 3.93 (3H, s), 3.08–2.90 (4H, m), 2.86 (3H, s), 2.57 (3H, s)

Example 67

Compound 59 (10 mg) was suspended in DMF (1.0 ml); sodium borohydride (4.0 mg) was added, followed by stirring at room temperature for 15 minutes. After 2-hydroxy-5-nitrobenzylbromide (4.6 mg, produced by Tokyo Kasei) was added, the reaction mixture was stirred at room temperature for 30 minutes. Sodium borohydride (2.0 mg) was further added to the reaction mixture, followed by stirring at room temperature for 30 minutes, after which 2-hydroxy-5-nitrobenzylbromide (46 mg) was added, followed by stirring at room temperature for 30 minutes. After ethyl acetate (30 ml) was added, the reaction mixture was washed with 0.02M hydrochloric acid (3×10 ml), after which the organic layer was extracted with 2% aqueous sodium hydrogen carbonate (2×15 ml). The water layer obtained was corrected to pH 2.0, after which it was again extracted with ethyl acetate (30 ml); the organic layer was dried over anhydrous sodium sulfate and concentrated under reduced pressure. The residue obtained was subjected to preparative high performance liquid chromatography [column; D-ODS-5 YMC, mobile phase; 62% (v/v) aqueous acetonitrile (containing 0.05% TFA), flow rate; 10 ml/min] to obtain 295–325 ml fractions, which were collected and concentrated under reduced pressure to remove the acetonitrile, after which the concentrate was extracted with ethyl acetate (30 ml). The organic layer was washed with water (2×10 ml), after which it was dried over anhydrous sodium sulfate and concentrated under reduced pressure to yield compound 78 (3.0 mg) as a yellow powder.

$^1$H NMR, Pyridine-$d_5$, δ ppm; 8.36 (1H, d, J=2.8 Hz), 8.12 (1H, dd, J=8.9, 2.8 Hz), 7.26 (1H, s), 7.07 (1H, d, J=8.9 Hz), 4.69 (1H, d, J=12.7 Hz), 4.56 (1H, d, J=12.7 Hz), 4.11 (3H, s), 2.46 (3H, s)

Example 68

Compound 59 (10 mg) was suspended in DMF (2.0 ml); sodium borohydride (10 mg) was added, followed by stirring at room temperature for 15 minutes. After α,3,5-tribromo-2-hydroxytoluene (20 mg, produced by Tokyo Kasei) was added, the reaction mixture was stirred at room temperature for 30 minutes. α,3,5-tribromo-2-hydroxytoluene (100 mg) was further added to the reaction mixture, followed by stirring at room temperature for 15 minutes. After ethyl acetate (30 ml) was added, the reaction mixture was washed with 0.02M hydrochloric acid (3×10 ml) and brine (2×10 ml), after which the organic layer was dried over anhydrous sodium sulfate and concentrated under reduced pressure. The residue obtained was subjected to preparative high performance liquid chromatography [column; D-ODS-5 YMC, mobile phase; 77% (v/v) aqueous acetonitrile (containing 0.05% TFA), flow rate; 10 ml/min] to obtain 250–290 ml fractions, which were collected and concentrated under reduced pressure to remove the acetonitrile, after which the concentrate was extracted with ethyl acetate (20 ml). The organic layer was washed with water (3×10 ml), after which it was dried over anhydrous sodium sulfate and concentrated under reduced pressure to yield compound 79 (3.7 mg) as a yellow powder.

$^1$H NMR, Pyridine-$d_5$, δ ppm; 7.70 (1H, d, J=2.4 Hz), 7.40 (1H, d, J=2.4 Hz), 7.20 (1H, s), 4.62 (1H, d, J=12.6 Hz), 4.46 (1H, d, J=12.6 Hz), 4.13 (3H, s), 2.47 (3H, s)

Example 69

Compound 59 (10 mg) was suspended in pyridine (2.0 ml); sodium borohydride (10 mg) was added, followed by stirring at room temperature for 15 minutes. After α-chloro-α-deoxykojic acid as obtained in Reference Example 6 (12 mg) was added, the reaction mixture was stirred at room temperature for 1.5 hours. After the reaction mixture was concentrated, ethyl acetate (30 ml) was added; the mixture was washed with 0.02M hydrochloric acid (3×10 ml) and brine (2×10 ml), after which the organic layer was dried over anhydrous sodium sulfate and concentrated under reduced pressure. The residue obtained was subjected to preparative high performance liquid chromatography [column; D-ODS-5 YMC, mobile phase; 52% (v/v) aqueous acetonitrile (containing 0.05% TFA), flow rate; 10 ml/min] to obtain 250–300 ml fractions, which were collected and concentrated under reduced pressure to remove the acetonitrile, after which the concentrate was extracted with ethyl acetate (30 ml). The organic layer was washed with water (3×10 ml), after which it was dried over anhydrous sodium sulfate and concentrated under reduced pressure to yield compound 80 (6.0 mg) as a yellow powder.

$^1$H NMR, Pyridine-$d_5$, δ ppm; 8.20 (1H, s), 7.20 (1H, s), 6.53 (1H, s), 4.35 (1H, d, J=14.0 Hz), 4.14 (1H, d, J=14.0 Hz), 4.13 (3H, s), 2.48 (3H, s)

Example 70

Compound 73 (5.0 mg) was suspended in 75% sulfuric acid (2.5 ml), followed by stirring at 110° C. for 1 hour. After ethyl acetate (30 ml) was added, the reaction mixture was washed with water (3×10 ml), after which the organic layer was dried over anhydrous sodium sulfate and concentrated under reduced pressure to yield compound 81 (5.0 mg) as a light-yellow powder.

$^1$H NMR, DMSO-$d_6$, δ ppm; 13.22 (1H, s), 7.66 (1H, br s), 7.44 (1H, br s), 7.41 (1H, m), 7.28 (3H, m), 7.00 (1H, s), 4.28(2H, s), 2.59 (3H, s)

Example 71

Compound 81 (2.0 mg) was suspended in ethyl acetate (2.5 ml); methanol (200 μl) and a 2.0M hexane solution of (trimethylsilyl)diazomethane (produced by Tokyo Kasei) (300 μl) were added, followed by stirring at room temperature for 1 hour. The reaction mixture was concentrated under reduced pressure; the residue obtained was subjected to silica gel column chromatography (4.0 ml) and washed with chloroform, after which it was eluted with chloroform/methanol (100:1); the fractions eluted were collected and concentrated to dryness to yield compound 82 (2.0 mg) as a light-yellow powder.

$^1$H NMR, Pyridine-$d_5$+$D_2O$, δ ppm; 7.72 (1H, d, J=7.7 Hz), 7.43 (1H, d, J=7.7 Hz), 7.36 (1H, t, J=7.7 Hz), 7.29 (1H, s), 7.22 (1H, t, J=7.7 Hz), 4.97 (1H, d, J=12.9 Hz), 4.67 (1H, d, J=12.9 Hz), 4.11 (3H, s), 4.07 (3H, s), 2.57 (3H, s)

Example 72

Compound 59 (15 mg) was suspended in pyridine (2.0 ml); sodium borohydride (15 mg) was added, followed by stirring at room temperature for 30 minutes. After 5-(2-bromomethyl)phenyltetrazole as obtained in Reference Example 7 (20 mg) was added, the reaction mixture was stirred at room temperature for 1 hour. After the reaction mixture was concentrated, ethyl acetate (30 ml) was added to the residue obtained; the reaction mixture was washed with 0.02M hydrochloric acid (2×10 ml), after which the organic layer was extracted with 2% aqueous sodium hydrogen carbonate (2×15 ml). The water layer obtained was corrected to pH 2.0, after which it was again extracted with ethyl acetate (30 ml); the organic layer was dried over anhydrous sodium sulfate and concentrated under reduced pressure. The residue obtained was subjected to preparative high performance liquid chromatography [column; D-ODS-5 YMC, mobile phase; 67% (v/v) aqueous acetonitrile (containing 0.05% TFA), flow rate; 10 ml/min] to obtain 220–270 ml fractions, which were collected and concentrated under reduced pressure to remove the acetonitrile, after which the concentrate was extracted with ethyl acetate (30 ml). The organic layer was washed with water (3×10 ml), after which it was dried over anhydrous sodium sulfate and concentrated under reduced pressure to yield compound 83 (3.0 mg) as a yellow powder.

$^1$H NMR, Pyridine-$d_5$+$D_2O$, δ ppm; 8.26 (1H, d, J=7.2 Hz), 7.59 (1H, d, J=7.2 Hz), 7.41 (2H, m), 7.26 (1H, s), 5.12 (1H, d, J=12.0 Hz), 4.84 (1H, d, J=12.0 Hz), 4.01 (3H, s), 2.48 (3H, s)

Example 73

Compound 59 (10 mg) was suspended in pyridine (2.0 ml); sodium borohydride (10 mg) was added, followed by stirring at room temperature for 15 minutes. After 3-(bromomethyl)benzoic acid methoxymethyl ester as obtained in Reference Example 8 (13 mg) was added, the reaction mixture was stirred at room temperature for 1 hour. After the reaction mixture was concentrated, ethyl acetate (30 ml) was added; the mixture was washed with 0.02M hydrochloric acid (2×10 ml), after which the organic layer was extracted with 2% aqueous sodium hydrogen carbonate (2×10 ml). The water layer obtained was corrected to pH 2.0, after which it was again extracted with ethyl acetate (20 ml); the organic layer was dried over anhydrous sodium sulfate and concentrated under reduced pressure. The residue obtained was subjected to preparative high performance liquid chromatography [column; D-ODS-5 YMC, mobile phase; 65% (v/v) aqueous acetonitrile (containing 0.05% TFA), flow rate; 10 ml/min] to obtain 190–240 ml fractions, which were collected and concentrated under reduced pressure to remove the acetonitrile, after which the concentrate was extracted with ethyl acetate (30 ml). The organic layer was washed with water (2×10 ml), after which it was dried over anhydrous sodium sulfate and concentrated under reduced pressure to yield compound 84 (2.3 mg) as a yellow powder.

$^1$H NMR, Pyridine-$d_5$, δ ppm; 8.51 (1H, s), 8.28(1H, d, J=7.6 Hz), 7.67 (1H, d, J=7.6 Hz), 7.43 (1H, t, J=7.6 Hz), 7.24 (1H, s), 4.62 (1H, d, J=12.5 Hz), 4.43 (1H, d, J=12.5 Hz), 4.16 (3H, s), 2.46 (3H, s)

Example 74

Compound 59 (15 mg) was suspended in pyridine (2.0 ml); sodium borohydride (15 mg) was added, followed by stirring at room temperature for 15 minutes. After 2-(bromomethyl)benzoic acid methoxymethyl ester as obtained in Reference Example 9 (19 mg) was added, the reaction mixture was stirred at room temperature for 2 hours. After ethyl acetate (30 ml) was added, the reaction mixture was washed with 0.02M hydrochloric acid (2×10 ml) and brine (2×10 ml), after which the organic layer was dried over anhydrous sodium sulfate and concentrated under reduced pressure. The residue obtained was subjected to preparative high performance liquid chromatography [column; D-ODS-5 YMC, mobile phase; 70% (v/v) aqueous acetonitrile (containing 0.05% TFA), flow rate; 10 ml/min] to obtain 150–210 ml fractions, which were collected and concentrated under reduced pressure to remove the acetonitrile, after which the concentrate was extracted with ethyl acetate (30 ml). The organic layer was washed with water (2×10 ml), after which it was dried over anhydrous sodium sulfate and concentrated under reduced pressure to yield compound 85 (12 mg) as a yellow powder.

$^1$H NMR, Pyridine-$d_5$+$D_2O$, δ ppm; 8.31 (1H, dd, J=7.0, 2.0 Hz), 7.42 (1H, dd, J=7.0, 2.0 Hz), 7.37 (1H, dt, J=2.0, 7.0 Hz), 7.35 (1H, s), 7.32 (1H, dt, J=2.0, 7.0 Hz), 5.19 (1H, d, J=12.5 Hz), 5.09 (1H, d, J=12.5 Hz), 4.00 (3H, s), 2.50 (3H, s)

Example 75

Compound 59 (10 mg) was dissolved in pyridine (1.0 ml); sodium borohydride (4.7 mg) was added, followed by stirring at room temperature for 30 minutes, after which 2-picolyl chloride hydrochloride (10.2 mg, produced by Tokyo Kasei) was added, followed by further stirring for 30 minutes. After the reaction mixture was concentrated under reduced pressure, the residue was suspended in ethyl acetate (20 ml); the suspension was washed with 0.1M hydrochloric acid (10 ml) and water (3×10 ml). Next, the organic layer was dried over anhydrous sodium sulfate, after which it was concentrated under reduced pressure. The residue obtained was subjected to preparative high performance liquid chromatography [column; YMC-Pack ODS SH-343-5, mobile phase; 55% (v/v) aqueous acetonitrile (containing 0.05% TFA), flow rate; 10 ml/min] to obtain 10 fractions. Fractions 16 and 17 were combined and concentrated under reduced pressure; the suspension obtained (8 ml) was extracted with ethyl acetate (20 ml). The organic layer was washed with water (2×10 ml), then dried over anhydrous sodium sulfate, after which it was concentrated under reduced-pressure to yield compound 86 (6.5 mg) as a light-yellow powder.

$^1$H NMR, DMSO-$d_6$, δ ppm; 13.00 (1H, s), 8.46 (1H, br d, J=4.4 Hz), 7.77 (1H, dt, J=1.6, 7.6 Hz), 7.29 (2H, m), 7.07 (1H, s), 4.23 (1H, d, J=13.3 Hz), 4.17 (1H, d, J=13.3 Hz), 3.76 (3H, s), 2.58 (3H, s)

Example 76

Compound 1 (20 mg) was suspended in dichloromethane (2.0 ml); WSC (17 mg), 4-dimethylaminopyridine (12 mg) and benzenesulfonamide (produced by Wako Pure Chemical Industries) (16 mg) were added; followed by stirring at room temperature for 15 hours. The reaction mixture was concentrated under reduced pressure; the residue obtained was suspended in ethyl acetate (30 ml) and washed with 0.02M hydrochloric acid (10 ml), water (2×10 ml) and brine (5 ml). The organic layer was dried over anhydrous sodium sulfate, after which it was concentrated under reduced pressure; the residue obtained was subjected to preparative high performance liquid chromatography [column; YMC-Pack ODS SR-343-5, mobile phase; 70% (v/v) aqueous acetonitrile (containing 0.05% TFA), flow rate; 10 ml/min] to obtain 10 ml fractions. Fractions 22 through 25 were combined and concentrated under reduced pressure to remove the acetonitrile, after which the concentrate was extracted with ethyl acetate (15 ml). The organic layer was washed with water (3×5 ml) and brine (5 ml), then dried over anhydrous sodium sulfate, after which it was concentrated under reduced pressure to yield compound 87 (15 mg) as a light-yellow powder.

$^1$NMR, DMSO-$d_6$, δ ppm; 12.99 (1H, s), 12.30 (l, br), 7.88 (2H, m), 7.70–7.52 (3H, m), 7.03 (1H, s), 3.86 (3H, s), 3.68–3.51 (2H, m), 2.58 (3H, s)

Example 77

Compound 1 (20 mg) was suspended in dichloromethane (2.0 ml); WSC (18 mg), 4-dimethylaminopyridine (13 mg) and methanesulfonamide (produced by Wako Pure Chemical Industries) (43 mg) were added; followed by refluxing for 2 hours. The reaction mixture was dissolved in ethyl acetate (30 ml) and washed with 0.02M hydrochloric acid (10 ml), water (2×10 ml) and brine (5 ml). The organic layer was dried over anhydrous sodium sulfate, after which it was concentrated under reduced pressure; the residue obtained was subjected to preparative high performance liquid chromatography [column; YMC-Pack ODS SH-343-5, mobile phase; 70% (v/v) aqueous acetonitrile (containing 0.05% TFA), flow rate; 10 ml/min] to obtain 10 ml fractions. Fraction 16 was concentrated under reduced pressure to remove the acetonitrile, after which the concentrate was extracted with ethyl acetate (15 ml). The organic layer was washed with water (3×5 ml) and brine (5 ml), then dried over anhydrous sodium sulfate, after which it was concentrated under reduced pressure to yield compound 88 (6.6 mg) as a light-yellow powder.

$^1$H NMR, DMSO-$d_6$, δ ppm; 12.99 (1H, s), 7.07 (1H, s), 3.92 (3H, s), 3.64 (1H, d, J=14.4 Hz), 3.58 (1H, d, J=14.4 Hz), 3.19 (3H, S), 2.58 (3H, s)

Example 78

Compound 1 (15 mg) was suspended in dichloromethane (2.0 ml); WSC (9.2 mg), 4-dimethylaminopyridine (6.0 mg) and p-toluenesulfonamide (8.2 mg, produced by Wako Pure Chemical Industries) were added; followed by stirring at room temperature for 2.5 hours and at 40° C. for 2 hours. To this suspension, p-toluenesulfonamide (4.1 mg) was added, followed by stirring at 40° C. for 2 hours. After ethyl acetate (30 ml) was added, the reaction mixture was washed with 0.01M hydrochloric acid and water (each 2×10 ml), after which the organic layer was dried over anhydrous sodium sulfate and concentrated under reduced pressure. The residue obtained was subjected to preparative high performance liquid chromatography [column; D-ODS-5 YMC, mobile phase; 72% (v/v) aqueous acetonitrile (containing 0.05% TFA), flow rate; 10 ml/min] to obtain 150–200 ml fractions, which were collected and concentrated under reduced pressure to remove the acetonitrile, after which the concentrate was extracted with ethyl acetate (30 ml). The organic layer was washed with water (3×10 ml), after which it was dried over anhydrous sodium sulfate and concentrated under reduced pressure to yield compound 89 (5.8 mg) as a yellow powder.

$^1$H NMR, Pyridine-$d_5$, δ ppm; 8.30 (2H, d, J=8.2 Hz), 7.13 (2H, d, J=8.2 Hz), 7.11 (1H, s), 4.20 (1H, d, J=14.6 Hz), 4.13 (3H, s), 4.03 (1H, d, J=14.6 Hz), 2.48 (3H, s), 2.10 (3H, s)

Example 79

Compound 1 (15 mg) was suspended in dichloromethane (3.0 ml); WSC (14 mg), 4-dimethylaminopyridine (9.2 mg) and naphthalene-2-sulfonamide (17 mg, produced by Lancaster Synthesis, Ltd.) were added; followed by stirring at 40° C. for 15 hours. After ethyl acetate (30 ml) was added, the reaction mixture was washed with 0.01M hydrochloric acid and brine (each 2×10 ml), after which the organic layer was dried over anhydrous sodium sulfate and concentrated under reduced pressure. The residue obtained was subjected to preparative high performance liquid chromatography [column; D-ODS-5 YMC, mobile phase; 70% (v/v) aqueous acetonitrile (containing 0.05% TFA), flow rate; 10 ml/min] to obtain 230–300 ml fractions, which were collected and concentrated under reduced pressure to remove the acetonitrile, after which the concentrate was extracted with ethyl acetate (30 ml). The organic layer was washed with water (3×10 ml), after which it was dried over anhydrous sodium sulfate and concentrated under reduced pressure to yield compound 90 (16 mg) as a yellow powder.

$^1$H NMR, CDCl$_3$, δ ppm; 12.72 (1H, s), 8.54 (1H, s), 7.92 (1H, dd, J=7.0, 2.1 Hz), 7.80 (3H, m), 7.55 (2H, m), 6.59 (1H, s), 4.05 (3H, S), 3.75 (1H, d, J=15.8 Hz), 3.57 (1H, d, J=15.8 Hz), 2.64 (3H, s)

Example 80

Compound 1 (15 mg) was suspended in dichloromethane (3.0 ml); WSC (14 mg), 4-dimethylaminopyridine (9.2 mg) and 4-chlorobenzenesulfonamide (16 mg, produced by Aldrich Chemical Company, Inc.) were added; followed by stirring at 40° C. for 15 hours. After ethyl acetate (30 ml) was added, the reaction mixture was washed with 0.01M hydrochloric acid and brine (each 2×10 ml), after which the organic layer was dried over anhydrous sodium sulfate and concentrated under reduced pressure. The residue obtained was subjected to preparative high performance liquid chromatography [column; Pack D-ODS-5 YMC, mobile phase; 70% (v/v) aqueous acetonitrile (containing 0.05% TFA), flow rate; 10 ml/min] to obtain 230–300 ml fractions, which were collected and concentrated under reduced pressure to remove the acetonitrile, after which the concentrate was extracted with ethyl acetate (30 ml). The organic layer was washed with water (3×10 ml), after which it was dried over anhydrous sodium sulfate and concentrated under reduced pressure to yield compound 91 (15 mg) as a yellow powder.

$^1$H NMR, Pyridine-d$_5$, δ ppm; 8.35 (2H, d, J=8.6 Hz), 7.38 (2H, d, J=8.6 Hz), 7.13 (1H, s), 4.21 (1H, d, J=14.9 Hz), 4.11 (3H, s), 4.07 (1H, d, J=14.9 Hz), 2.48 (3H, s)

Example 81

Compound 1 (15 mg) was suspended in dichloromethane (3.0 ml); WSC (14 mg), 4-dimethylaminopyridine (9.2 mg) and 4-nitrobenzenesulfonamide (17 mg, produced by Aldrich Chemical Company, Inc.) were added; followed by stirring at room temperature for 4 hours. After ethyl acetate (30 ml) was added, the reaction mixture was washed with 0.02M hydrochloric acid and brine (each 2×10 ml), after which the organic layer was dried over anhydrous sodium sulfate and concentrated under reduced pressure. The residue obtained was subjected to preparative high performance liquid chromatography [column; Pack D-ODS-5 YMC, mobile phase; 65% (v/v) aqueous acetonitrile (containing 0.05% TFA), flow rate; 10 ml/min] to obtain 230–290 ml fractions, which were collected and concentrated under reduced pressure to remove the acetonitrile, after which the concentrate was extracted with ethyl acetate (30 ml). The organic layer was washed with water (3×10 ml), after which it was dried over anhydrous sodium sulfate and concentrated under reduced pressure to yield compound 92 (17 mg) as a yellow powder.

$^1$H NMR, Pyridine-d$_5$, δ ppm; 8.59 (2H, d, J=8.8 Hz), 8.20 (2H, d, J=8.8 Hz), 7.16 (1H, s), 4.15 (1H, d, J=15.7 Hz), 4.09 (3H, s), 4.07 (1H, d, J=15.7 Hz), 2.48 (3H, s)

Example 82

Compound 1 (15 mg) was suspended in dichloromethane (3.0 ml); WSC (14 mg), 4-dimethylaminopyridine (9.2 mg) and trifluoromethanesulfonamide (13 mg, produced by Tokyo Kasei) were added; followed by stirring at room temperature for 30 minutes. After ethyl acetate (30 ml) was added, the reaction mixture was washed with 0.01M hydrochloric acid and brine (each 2×10 ml), after which the organic layer was dried over anhydrous sodium sulfate and concentrated under reduced pressure. The residue obtained was subjected to preparative high performance liquid chromatography [column; Pack D-ODS-5 YMC, mobile phase; 70% (v/v) aqueous acetonitrile (containing 0.05% TFA), flow rate; 10 ml/min] to obtain 100–180 ml fractions, which were collected and concentrated under reduced pressure to remove the acetonitrile, after which the concentrate was extracted with ethyl acetate (30 ml). The organic layer was washed with water (3×10 ml), after which it was dried over anhydrous sodium sulfate and concentrated under reduced pressure to yield compound 93 (8.9 mg) as a yellow powder.

$^1$H NMR, Pyridine-d$_5$, δ ppm; 7.16 (1H, s), 4.26 (1H, d, J=14.5 Hz), 4.03 (1H, d, J=14.5 Hz), 4.01 (3H, s), 2.48 (3H, s)

Example 83

Compound 1 (15 mg) was dissolved in DMF (1.5 ml); WSC (9.4 mg) was added, followed by stirring at room temperature for 1 hour, after which hydroxylammonium sulfate (4.0 mg, produced by Wako Pure Chemical Industries) was added, followed by stirring at room temperature for 16 hours. The reaction mixture was diluted with ethyl acetate (10 ml) and washed with 0.1M hydrochloric acid (5 ml) and water (2×5 ml). Next, the organic layer was dried over anhydrous sodium sulfate, after which it was concentrated under reduced pressure. The residue obtained was subjected to preparative high performance liquid chromatography [column; Pack ODS SH-343-5YMC, mobile phase; 60% (v/v) aqueous acetonitrile (containing 0.05% TFA), flow rate; 10 ml/min] to obtain 10 ml fractions. Fractions 20 through 24 were combined and concentrated under reduced pressure to yield compound 94 (12 mg) as a light-yellow powder.

$^1$H NMR, DMSO-d$_6$, δ ppm; 13.01 (1H, s), 12.49 (1H, br), 10.65 (1H, s), 9.00 (1H, br), 7.09 (1H, s), 3.91 (3H, s), 3.44 (2H, s), 2.59 (3H, s)

Example 84

Compound 1 (15 mg) was dissolved in DMF (1.5 ml); WSC (9.4 mg) was added, followed by stirring at room temperature for 1 hour, after which O-methylhydroxylammonium chloride (4.1 mg, produced by Wako Pure Chemical Industries) was added, followed by stirring at room temperature for 16 hours. The reaction mixture was diluted with ethyl acetate (10 ml) and washed with 0.1M hydrochloric acid (5 ml) and water (2×5 ml). Next, the organic layer was dried over anhydrous sodium sulfate, after which it was concentrated under reduced pressure. The residue obtained was subjected to preparative high performance liquid chromatography [column; YMC-Pack ODS SH-343-5, mobile phase; 65% (v/v) aqueous acetonitrile (containing 0.05% TFA), flow rate; 10 ml/min] to obtain 10 ml fractions. Fractions 22 through 25 were combined and concentrated under reduced pressure to yield compound 95 (14 mg) as a light-yellow powder.

$^1$H NMR, DMSO-d$_6$, δ ppm; 13.03 (1H, s), 12.40 (1H, br), 11.16 (1H, br), 7.06 (1H, s), 3.90 (3H, s), 3.55 (3H, s), 3.37 (2H, s), 2.58 (3H, s)

Example 85

Compound 5 (50 mg) was suspended in acetic acid (9.5 ml); 30% aqueous hydrogen peroxide (0.5 ml) was added, followed by stirring at 50° C. for 45 minutes. The reaction mixture was concentrated; the residue obtained was purified by preparative high performance liquid chromatography to yield compound 96 (52 mg) as a light-yellow powder.

$^1$H NMR, DMSO-d$_6$, 60° C., δ ppm; 12.96 (1H, br s), 7.01 (1H, s), 4.47–4.36 (1H, m), 3.85 (3H, s), 3.70–3.07 (2H, m), 2.58 (3H, s)

SI-MS spectrum (M+Na)$^+$: m/z 527

Example 86

Compound 5 (50 mg) was suspended in formic acid (4.75 ml); 30% aqueous hydrogen peroxide (0.25 ml) was added, followed by stirring at 60° C. for 2 hours. The reaction mixture was concentrated; the residue obtained was purified by preparative high performance liquid chromatography to yield compound 97 (44 mg) as a light-yellow powder.

$^1$H NMR, DMSO-d$_6$, 60° C., δ ppm; 12.91 (1H, br s), 7.09 (1H, s), 4.48–4.41 (1H, m), 3.89 (3H, s), 3.88–3.68 (2H, m), 2.58 (3H, s)

SI-MS spectrum (M+Na)$^+$: m/z 543

Example 87

Compound 5 (100 mg) was dissolved in DMF (10 ml); potassium carbonate (564 mg) and methyl iodide (254 μl) were added, followed by stirring at room temperature for 7 hours. The reaction mixture was purified in the same manner as in Example 38 to yield compound 98 (88 mg) as a white powder.

$^1$H NMR, CDCl$_3$, 50° C., δ ppm; 6.99 (1H, s), 4.30 (1H, br), 4.09 (3H, s), 4.07 (3H, s), 3.95 (3H, S), 3.76 (1H, br), 3.71 (3H, s), 3.30 (1H, dd, J=14.0, 3.5 Hz), 3.12 (1H, br), 2.65 (3H, S)

SI-MS spectrum (M+H)$^+$: m/z 531

Example 88

Compound 98 (17 mg) was dissolved in formic acid (1.5 ml); 30% aqueous hydrogen peroxide (0.075 ml) was added, followed by stirring at room temperature for 3 hours. The reaction mixture was concentrated; the residue obtained was purified by silica gel chromatography to yield compound 99 (17 mg) as a white powder.

$^1$H NMR, DMSO-d$_6$, δ ppm; 7.54 (1H, s), 5.90 (1H, m), 4.46 (1H, m), 4.13 (3H, s), 3.88 (3H, s), 3.83 (3H, s), 3.77 (2H, m), 3.63 (3H, s), 2.62 (3H, s)

SI-MS spectrum (M+H)$^+$: m/z 563

Example 89

Compound 5 (100 mg) was dissolved in ethanol (10 ml); concentrated sulfuric acid (40 μl) was added, followed by stirring at room temperature for 5 hours. After the reaction mixture was concentrated, the residue obtained was dissolved in ethyl acetate (30 ml) and washed with water (2×20 ml). The organic layer was concentrated, after which it was purified by preparative high performance liquid chromatography to yield compound 100 (98 mg) as a light-yellow powder.

$^1$H NMR, DMSO-d$_6$, δ ppm; 13.03 (1H, s), 7.05 (1H, s), 4.20–4.03 (3H, m), 3.91 (3H, s), 3.19–2.93 (2H, m), 2.56 (3H, s), 1.18 (3H, m)

SI-MS spectrum (M+H)$^+$: m/z 517

Example 90

Compound 98 (20 mg) was dissolved in pyridine (1.0 ml); acetic anhydride (0.1 ml) was added, followed by stirring at room temperature for 2 hours. After the reaction mixture was concentrated, the residue obtained was purified by preparative high performance liquid chromatography to yield compound 101 (16 mg) as a white powder.

$^1$H NMR, DMSO-d$_6$, δ ppm; 7.37 (1H, s), 4.87 (1H, m), 4.08 (3H, s), 3.88 (3H, s), 3.83 (3H, s), 3.64 (3H, br s), 3.30–3.10 (2H, m), 2.62 (3H, s), 1.96 (1.5H, br s), 1.94 (1.5H, br s)

SI-MS spectrum (M+H)$^+$: m/z 573

Example 91

Compound 100 (20 mg) was dissolved in DMF (2.0 ml); sodium hydrogen carbonate (33 mg) and chloromethylmethyl ether (8.8 μl) were added, followed by stirring at room temperature for 30 minutes. After ethyl acetate (20 ml) was added, the reaction mixture was washed with 0.1M hydrochloric acid and water, after which the organic layer was concentrated. The residue obtained was purified by preparative high performance liquid chromatography to yield compound 102 (19 mg) as a light-yellow powder.

$^1$H NMR, DMSO-d$_6$, δ ppm; 12.88 (1H, s), 7.43 (1H, s), 5.78 (1H, m), 5.59 (2H, s), 4.22–4.02 (3H, m), 3.92 (3H, s), 3.50 (3H, s), 3.22–2.95 (2H, m), 2.60 (3H, s), 1.16 (3H, t, J=7.2 Hz)

SI-MS spectrum (M+H)$^+$: m/z 561

Example 92

Compound 5 (30 mg) was dissolved in DMF (3.0 ml); sodium hydrogen carbonate (52 mg) and chloromethylmethyl ether (14 μl) were added, followed by stirring at room temperature for 1 hour. The reaction mixture was purified in the same manner as in Example 91 to yield compound 10$^3$ (30 mg) as a light-yellow powder.

$^1$H NMR, DMSO-d$_6$, δ ppm; 12.89 (1H, s), 7.44 (1H, s), 5.88 (1H, m), 5.59 (2H, s), 5.27–5.15 (2H, m), 4.28–4.18 (1H, m), 3.93 (3H, s), 3.50 (3H, s), 3.35 (3H, s), 3.25–2.98 (2H, m), 2.60 (3H, s)

SI-MS spectrum (M+H)$^+$: m/z 577

Example 93

Compound 1 (50 mg) was suspended in acetic acid (5.0 ml); sodium nitrate (produced by Wako Pure Chemical Industries) (11 mg) was added, followed by stirring at 90° C. for 2 hours. The reaction mixture was concentrated under reduced pressure; the residue obtained was suspended in ethyl acetate (50 ml) and washed with brine (3×20 ml). The organic layer was dried over anhydrous sodium sulfate, after which it was concentrated under reduced pressure; the residue obtained was purified by preparative high performance liquid chromatography (column; Pack D-ODS-5 YMC, mobile phase; 58% (v/v) aqueous acetonitrile (containing 0.05% TFA), flow rate; 10 ml/min] to yield a yellow powder. This powder was further purified by silica gel chromatography (eluted with chloroform/methanol/formic acid) to yield compound 104 (6.3 mg) as a yellow powder.

$^1$H NMR, CD$_3$OD, δ ppm; 3.99 (3H, s), 2.63 (3H, s)

FAB-MS spectrum (M−H)$^-$: m/z 492

Example 94

Compound 103 (15 mg) was dissolved in pyridine (1.0 ml); acetic anhydride (0.2 ml) was added, followed by stirring at room temperature for 1 hour. The reaction mixture was concentrated under reduced pressure to yield a diacetate (16 mg) as a white powder. This powder was dissolved in TFA (1.0 ml) and kept standing at room temperature for 30 minutes. The reaction mixture was concentrated under reduced pressure; the residue was purified by preparative high performance liquid chromatography to yield compound 105 (14 mg) as a light-yellow powder.

$^1$H NMR, DMSO-d$_6$, δ ppm; 13.05 (1H, s), 12.85 (1H, br), 7.06 (0.5H, s), 7.05 (0.5H, s), 4.75 (1H, m), 3.88 (1.5H, s), 3.87 (1.5H, s), 3.40–3.10 (2H, m), 2.58 (3H, s), 1.95 (1.5H, s), 1.91 (1.5H, s)

SI-MS spectrum (M+H)$^+$: m/z 531

Example 95

Using compound 59 (100 mg), pyridine (10 ml), sodium borohydride (47 mg) and methyl iodide (39 µl), the same procedure as in Example 55 was followed to yield compound 106 (93 mg) as a light-yellow powder.

$^1$H NMR, DMSO-d$_6$, δ ppm; 13.04 (1H, s), 12.29 (1H, br), 7.06 (1H, s), 3.92 (3H, s), 2.57 (3H, s), 2.32 (3H, s)

SI-MS spectrum (M+H)$^+$: m/z 415

Example 96

Compound 106 (12 mg) was suspended in acetic acid (1.2 ml); 30% aqueous hydrogen peroxide (0.06 ml) was added, followed by stirring at room temperature for 4 hours. The reaction mixture was concentrated under reduced pressure to yield compound 107 (12 mg) as a light-yellow powder.

$^1$H NMR, DMSO-d$_6$, δ ppm; 13.01 (1H, s), 7.02 (1H, s), 3.85 (3H, s), 2.94 (3H, s), 2.58 (3H, s)

SI-MS spectrum (M+H)$^+$: m/z 431

Example 97

Compound 106 (20 mg) was suspended in formic acid (2.0 ml); 30% aqueous hydrogen peroxide (0.1 ml) was added, followed by stirring at 60° C. for 3 hours. The reaction mixture was concentrated under reduced pressure; the residue obtained was purified by preparative high performance liquid chromatography to yield compound 108 (19 mg) as a light-yellow powder.

$^1$H NMR, DMSO-d$_6$, δ ppm; 12.99 (1H, s), 7.07 (1H, s), 3.87 (3H, s), 3.33 (3H, s), 2.58 (3H, s)

SI-MS spectrum (M+H)$^+$: m/z 447

Example 98

Compound 106 (20 mg) was dissolved in DMF (2.0 ml); potassium carbonate (67 mg) and methyl iodide (30 µl) were added, followed by stirring at room temperature for 8 hours. After ethyl acetate (20 ml) was added, the reaction mixture was washed with water; the organic layer was concentrated under reduced pressure.

Next, the residue obtained was suspended in formic acid (2.0 ml); 30% aqueous hydrogen peroxide (0.1 ml) was added, followed by stirring at room temperature for 2 hours. The reaction mixture was concentrated under reduced pressure; the residue was purified by preparative high performance liquid chromatography to yield compound 109 (21 mg) as a white powder.

$^1$H NMR, CDCl$_3$, δ ppm; 7.14 (1H, s), 4.15 (3H, s), 4.09 (3H, s), 3.94 (3H, s), 3.27 (3H, s), 2.66 (3H, s)

SI-MS spectrum (M+H)$^+$: m/z 475

Example 99

Compound 1 (70 mg) was suspended in ethanol (7.0 ml); concentrated sulfuric acid (70 µl) was added, followed by stirring at 80° C. for 4 hours. After the reaction mixture was concentrated, the residue obtained was dissolved in chloroform (20 ml) and washed with water (2×10 ml). The organic layer was concentrated, after which it was purified by preparative high performance liquid chromatography to yield compound 110 (56 mg) as a light-yellow powder.

$^1$H NMR, DMSO-d$_6$, δ ppm; 13.01 (1H, s), 7.06 (1H, s), 3.98 (2H, q, J=7.1 Hz), 3.90 (3H, s), 3.63 (1H, d, J=13.8 Hz), 3.56 (1H, d, J=13.8 Hz), 2.58 (3H, s), 1.06 (3H, t, J=7.1 Hz)

SI-MS spectrum (M+H)$^+$: m/z 487

Example 100

Compound 1 (100 mg) was dissolved in DMF (10 ml); potassium carbonate (300 mg) and chloromethyl pivalate (313 µl, produced by Wako Pure Chemical Industries) were added, followed by stirring at room temperature for 3 hours. The reaction mixture was treated in the same manner as in Example 91 to yield compound 111 (78 mg) as a light-yellow powder.

$^1$H NMR, CDCl$_3$, δ ppm; 12.85 (1H, s), 8.72 (1H, br), 7.18 (1H, s), 5.79 (1H, d, J=5.4 Hz), 5.76 (1H, d, J=5.4 Hz), 4.07 (3H, s), 3.76 (1H, d, J=17.4 Hz), 3.62 (1H, d, J=17.4 Hz), 2.64 (3H, s), 1.19 (9H, s)

SI-MS spectrum (M+H)$^+$: m/z 573

Example 101

Compound 59 (100 mg) was suspended in chloroform (10 ml); dithioerythritol (39 mg, produced by Wako Pure Chemical Industries) and triethylamine (35 µl) were added, followed by stirring at room temperature for 30 minutes. After ethyl bromopyruvate (125 µl, produced by Wako Pure Chemical Industries) was added, the reaction mixture was further stirred at room temperature for 30 minutes. After the reaction mixture was washed with 0.1M hydrochloric acid and water, the organic layer obtained was concentrated and purified by preparative high performance liquid chromatography to yield compound 112 (111 mg) as a light-yellow powder.

$^1$H NMR, CDCl$_3$, δ ppm; 12.84 (0.7H, s), 12.83 (0.3H, s), 8.50 (0.3H, br s), 7.18 (1H, s), 4.82 (0.7H, br s), 4.41 (1.4H, q, J=7.2 Hz), 4.34 (0.6H, q, J=7.2 Hz), 4.27 (0.3H, d, J=18.0 Hz), 4.17 (0.3H, d, J=18.0 Hz), 4.08 (0.9H, s), 4.07 (2.1H, s), 3.44 (0.7H, d, J=13.5 Hz), 3.13 (0.7H, d, J=13.5 Hz), 2.64 (3H, s), 1.40 (2.1H, t, J=7.2 Hz), 1.36 (0.9H, t, J=7.2 Hz)

SI-MS spectrum (M+H)$^+$: m/z 515

Example 102

Compound 112 (30 mg) was suspended in methanol (5.0 ml); ammonium acetate (450 mg) and acetic acid (300 µl) were added, followed by stirring at room temperature for 2 hours, after which sodium cyanoborohydride (5.5 mg, produced by Aldrich Chemical Company, Inc.) was added, followed by stirring for 2 hours. The reaction mixture was concentrated under reduced pressure; the residue was suspended in ethyl acetate (30 ml) and washed with water (3×20 ml). The organic layer was concentrated under reduced pressure; the residue obtained was purified by preparative high performance liquid chromatography to yield compound 113 (23 mg) as a light-yellow powder.

$^1$H NMR, CDCl$_3$, δ ppm; 13.00 (1H, br), 7.03 (1H, s), 4.22 (2H, q, J=7.1 Hz), 4.08 (1.2H, s), 4.07 (1.8H, s), 3.58 (1H, m), 3.34 (1H, m), 2.90 (1H, m), 2.63 (3H, s), 1.29 (1.2H, t, J=7.1 Hz), 1.28(1.8H, t, J=7.1 Hz)

SI-MS spectrum (M+H)$^+$: m/z 516

Example 103

Compound 113 (15 mg) was suspended in ethanol (3.0 ml); 0.2M aqueous sodium hydroxide (0.87 ml) was added, followed by stirring at room temperature for 3 hours. After 1.0M hydrochloric acid (117 µl) was added, the reaction mixture was concentrated under reduced pressure, after which the residue was subjected to preparative high performance liquid chromatography. The fraction eluted was concentrated under reduced pressure to remove the acetonitrile, after which the concentrate was adjusted to pH 5.0 and desalinized by column chromatography with Diaion HP-20 (10 ml) to yield compound 114 (12 mg) as a light-yellow powder.

$^1$H NMR, DMSO-d$_6$, δ ppm; 13.94 (1H, br), 6.34 (0.5H, s), 6.30 (0.5H, s), 3.87 (1.5H, s), 3.86 (1.5H, s), 2.94 (2H, br s), 2.54 (3H, s)

SI-MS spectrum (M+H)$^+$: m/z 488

Example 104

Compound 1 (30 mg) was suspended in dichloromethane (4.0 ml); WSC (28 mg), 4-dimethylaminopyridine (18 mg) and 4-methoxybenzenesulfonamide (produced by Lancaster Synthesis, Ltd.) (16 mg) were added, followed by stirring at room temperature for 13 hours. The reaction mixture was purified in the same manner as in Example 76 to yield compound 115 (26 mg) as a yellow powder.

$^1$H NMR, CDCl$_3$, δ ppm; 12.74 (1H, s), 7.89 (2H, d, J=8.9 Hz), 6.95 (1H, s), 6.90 (2H, d, J=8.9 Hz), 4.06 (3H, s), 3.84 (3H, s), 3.72 (1H, d, J=16.4 Hz), 3.56 (1H, d, J=16.4 Hz), 2.61 (3H, s)

SI-MS spectrum (M+H)$^+$: m/z 628

Example 105

Palladium (II) acetate (produced by Wako Pure Chemical Industries) (6.4 mg) and tris(2-methylphenyl)phosphine (produced by Tokyo Kasei) (17.2 mg) were dissolved in 1,2-dimethoxyethane (produced by Wako Pure Chemical Industries) (1.0 ml). A 0.1 ml portion of this solution was added to a solution of compound 40 (30 mg) in 1,2-dimethoxyethane (2.7 ml), followed by stirring at room temperature under an argon atmosphere for 15 minutes. To this solution, a 1.0M aqueous solution of sodium hydroxide (0.26 ml) and phenylboric acid (produced by Aldrich Chemical Company, Inc.) (10 mg) were added, followed by refluxing under an argon atmosphere for 3 hours. The reaction mixture was concentrated under reduced pressure; the residue obtained was suspended in ethyl acetate (30 ml) and washed with 0.05M hydrochloric acid (10 ml), water (2×10 ml) and brine (5 ml). The organic layer was dried over anhydrous sodium sulfate, after which it was concentrated under reduced pressure; the residue obtained was purified by preparative high performance liquid chromatography to yield compound 116 (13 mg) as a light-yellow powder.

$^1$H NMR, DMSO-d$_6$, δ ppm; 12.92 (1H, s), 7.56–7.40 (5H, m), 3.95 (3H, s), 3.61 (2H, s), 2.49 (3H, s)

SI-MS spectrum (M+H)$^+$: m/z 535

Examples 106 through 111

Compounds 117 through 121 and compound 124 were obtained by coupling reaction of compound 40 and phenylboric acid derivatives in the same manner as in Example 105.

TABLE 13

| Example Number | Compound Number | Starting Material (Compound 40) | Yield | SI-MS Spectrum (M + H)$^+$: m/z |
|---|---|---|---|---|
| 106 | 117 | 30 mg | 16 mg | 549 |
| 107 | 118 | 30 mg | 14 mg | 579 |
| 108 | 119 | 30 mg | 17 mg | 585 |
| 109 | 120 | 30 mg | 16 mg | 569 |

TABLE 13-continued

| Example Number | Compound Number | Starting Material (Compound 40) | Yield | SI-MS Spectrum (M + H)$^+$: m/z |
|---|---|---|---|---|
| 110 | 121 | 50 mg | 21 mg | 565 |
| 111 | 124 | 50 mg | 16 mg | 550 |

$^1$H NMR, DMSO-d$_6$, δ ppm;

Compound 117
12.93 (1H, s), 7.42 (2H, d, J=8.1 Hz), 7.31 (2H, d, J=8.1 Hz), 3.95 (3H, s), 3.61 (2H, s), 2.50 (3H, s), 2.41 (3H, s)

Compound 118
12.89 (1H, s), 8.07 (2H, d, J=8.3 Hz), 7.66 (2H, d, J=8.3 Hz), 3.96 (3H, s), 3.61 (2H, s), 2.49 (3H, s)

Compound 119
12.93 (1H, s), 8.12 (1H, br s), 8.03 (1H, d, J=8.5 Hz), 7.98 (2H, m), 7.66 (1H, dd, J=8.5, 1.6 Hz), 7.58 (2H, m), 3.96 (3H, s), 3.64 (2H, s), 2.46 (3H, s)

Compound 120
12.90 (1H, s), 7.57 (4H, m), 3.95 (3H, s), 3.60 (2H, s), 2.50 (3H, s)

Compound 121
12.92 (1H, s), 7.46 (2H, d, J=8.5 Hz), 7.06 (2H, d, J=8.5 Hz), 3.94 (3H, s), 3.84 (3H, s), 3.61 (2H, s), 2.50 (3H, s)

Compound 124
13.20 (1H, br), 7.28 (1H, m), 6.95 (2H,-m), 6.87 (1H, m), 3.92 (3H, s), 3.52 (2H, s), 2.50 (3H, s)

Example 112

Compound 96 (102 mg) was suspended in 1,4-dioxane (produced by Wako Pure Chemical Industries) (10 ml); tetrabutylammonium periodate (produced by Aldrich Chemical Company, Inc.) (96 mg) was added, followed by refluxing for 3 hours. After a 10% aqueous solution of sodium thiosulfate (2 ml) was added, the reaction mixture was concentrated and extracted with ethyl acetate (100 ml). The organic layer was washed with water (3×25 ml), after which it was dried over anhydrous sodium sulfate and concentrated under reduced pressure. The residue obtained was subjected to preparative high performance liquid chromatography [column; YMC-Pack ODS SH-343-5, mobile phase; 55% (v/v) aqueous acetonitrile (containing 0.05% TFA), flow rate; 10 ml/min] to obtain 10 ml fractions. Fractions 19 through 24 were combined and concentrated under reduced pressure to remove the acetonitrile, after which the concentrate was extracted with ethyl acetate (50 ml). The organic layer was washed with water (2×20 ml) and brine (10 ml), after which it was dried over anhydrous sodium sulfate and concentrated under reduced pressure. After dichloromethane (50 ml) was added, the residue obtained was extracted with a 1.0–0.4% aqueous solution of sodium iodide (3×50 ml) (produced by Wako Pure Chemical Industries). The water layer was washed with dichloromethane (3×50 ml) and ethyl acetate (50 ml). The water layer obtained was concentrated and corrected to pH 5, after which it was subjected to column chromatography with Diaion HP-20 (100–200 mesh, 20 ml) and washed with water (80 ml) and 50% aqueous methanol (80 ml), after which it was eluted with 50% aqueous methanol (20 ml) and 80% aqueous methanol (40 ml). The eluate was concentrated, after which it was freeze-dried to yield compound 122 (18 mg) as a light-yellow powder.

$^1$H NMR, DMSO-d$_6$, δ ppm; 13.12 (1H, s), 12.19 (1H, br s), 7.13 (1H, s), 3.81 (3H, s), 2.57 (3H, s)

SI-MS spectrum (M+Na)$^+$: m/z 493

Example 113

Compound 59 (30 mg) was suspended in DMF (3.0 ml); sodium borohydride (produced by Wako Pure Chemical Industries) (9 mg) was added, followed by stirring at room temperature for 30 minutes. To this suspension, 3-bromo-2-(bromomethyl)propionic acid (produced by Aldrich Chemical Company, Inc.) (39 mg) was added, followed by stirring at room temperature for 1 hour. After ethyl acetate (50 ml) was added, the reaction mixture was washed with 0.05 M hydrochloric acid (15 ml), water (2×15 ml) and brine (10 ml). The organic layer was dried over anhydrous sodium sulfate, after which it was concentrated under reduced pressure; the residue obtained was purified by preparative high performance liquid chromatography to yield compound 123 (27 mg) as a light-yellow powder.

$^1$H NMR, DMSO-$d_6$, δ ppm, 13.01 (1H, s), 7.06 (1H, s), 5.87 (1H, s), 5.26 (1H, s), 3.83 (3H, s), 3.73 (1H, d, J=13.2 Hz), 3.64 (1H, d, J=13.2 Hz), 2.55 (3H, s)

SI-MS spectrum (M+H)$^+$: m/z 485

Example 114

Compound 111 (12 mg) was suspended in acetic acid (2.4 ml); 30% aqueous hydrogen peroxide (0.12 ml) was added, followed by stirring at 50° C. for 40 minutes. The reaction mixture was concentrated under reduced pressure; the residue obtained was purified by preparative high performance liquid chromatography to yield compound 133 (12 mg) as a light-yellow powder.

$^1$H NMR, CDCl$_3$, δ ppm; 12.64 (1H, s), 11.53 (1H, br), 7.13 (1H, s), 5.88 (1H, d, J=5.5 Hz), 5.84 (1H, d, J=5.5 Hz), 4.30 (1H, d, J=14.2 Hz), 4.19 (1H, d, J=14.2 Hz), 4.04 (3H, s), 2.66 (3H, s), 1.22 (9H, s)

SI-MS spectrum (M+H)$^+$: m/z 589

Example 115

Compound 40 (40 mg) was suspended in acetic acid (5.0 ml); sodium nitrite (produced by Wako Pure Chemical Industries) (9.4 mg) was added; followed by stirring at 40° C. for 1.5 hours. The reaction mixture was concentrated under reduced pressure; the residue obtained was dissolved in ethyl acetate (30 ml) and washed with brine (2×10 ml). The organic layer was dried over anhydrous sodium sulfate, after which it was concentrated under reduced pressure; the residue obtained was purified by preparative high performance liquid chromatography to yield a yellow powder. This powder was further purified by silica gel chromatography (eluted with chloroform/methanol/formic acid) to yield compound 132 (21 mg) as a yellow powder.

$^1$H NMR, DMSO-$d_6$, δ ppm; 13.59 (1H, s), 3.85 (3H, s), 3.59 (1H, d, J=14.7 Hz), 3.51 (1H, d, J=14.7 Hz), 2.54 (3H, s)

SI-MS spectrum (M+H)$^+$: m/z 504

Example 116

Compound 1 (30 mg) and cyclohexyl 1-iodoethyl carbonate (200 mg) as prepared by the method described in the literature [The Journal of Antibiotics, Vol. 40, p. 87 (1987)] were suspended in dichloromethane (3.0 ml); triethylamine (20 μl) was added under ice cooling conditions, followed by refluxing for 1 hour. The reaction mixture was concentrated under reduced pressure; the residue obtained was dissolved in ethyl acetate (30 ml) and washed with 0.05M hydrochloric acid (10 ml), 5% aqueous sodium thiosulfate (10 ml), water (2×10 ml) and brine (5 ml). The organic layer was dried over anhydrous sodium sulfate, after which it was concentrated under reduced pressure; the residue obtained was purified by preparative high performance liquid chromatography to yield compound 134 (27 mg) as a light-yellow powder.

$^1$H NMR, CDCl$_3$, δ ppm; 12.86 (1H, s), 8.79 (1H, br), 7.17 (1H, s), 6.74 (1H, q, J=5.4 Hz), 4.62 (1H, m), 4.07 (3H, m), 3.72 (1H, m), 3.58 (1H, m), 2.64 (3H, s), 2.01–1.16 (10H, m), 1.51 (3H,m)

SI-MS spectrum (M+H)$^+$: m/z 629

Example 117

Compound 132 (10 mg) was suspended in acetic acid (1.9 ml); 30% aqueous hydrogen peroxide (0.1 ml) was added, followed by stirring at 50° C. for 2 hours. The reaction mixture was concentrated; the residue obtained was purified by silica gel chromatography (eluted with chloroform/methanol/formic acid) to yield compound 135 (7.6 mg) as a yellow powder.

$^1$H NMR, CD$_3$OD, 50° C., δ ppm; 4.25 (1H, d, J=14.6 Hz), 4.11 (1H, d, J=14.6 Hz), 3.92 (3H, br s), 2.60 (3H, s)

SI-MS spectrum (M+H)$^+$: m/z 520

Example 118

Compound 72 (75 mg) was oxidized in the same manner as in Example 114 to yield compound 136 (35 mg) as a yellow powder.

$^1$H NMR, DMSO-$d_6$, 50° C., δ ppm; 12.29 (1H, S), 6.97 (1H, s), 4.89 (1H, d, J=13.7 Hz), 4.79 (1H, d, J=13.7 Hz), 3.73 (3H, s), 2.59 (3H, s)

SI-MS spectrum (M+H)$^+$: m/z 499

Example 119

Compound 88 (75 mg) was oxidized in the same manner as in Example 114 to yield compound 137 (54 mg) as a yellow powder.

$^1$H NMR, DMSO-$d_6$, 50° C., δ ppm; 12.95 (1H, s), 7.03 (1H, s), 4.28 (1H, d, J=14.2 Hz), 4.17 (1H, d, J=14.2 Hz), 3.86 (3H, s), 3.25 (3H, s), 2.59 (3H, s)

SI-MS spectrum (M+H)$^+$: m/z 552

Example 120

Compound 134 (70 mg) was oxidized in the same manner as in Example 114 to yield compound 138 (71 mg) as a light-yellow powder.

$^1$H NMR, CDCl$_3$, δ ppm; 12.64 (1H, s), 7.11 (1H, m), 6.85 (1H, q, J=5.4 Hz), 4.65 (1H, m), 4.30 (1H, m), 4.15 (1H, m), 4.04 (3H, m), 2.65 (3H, s), 2.02–1.16 (10H, m), 1.58 (3H, m)

SI-MS spectrum (M+H)$^+$: m/z 645

Example 121

Compound 40 (30 mg) was dissolved in DMF (3 ml); palladium (II) acetate (0.6 mg) and tris(2-methylphenyl) phosphine (1.9 mg) were added, followed by stirring at room temperature under an argon atmosphere for 15 minutes. To this solution, potassium phosphate tribasic n-hydrate (produced by Wako Pure Chemical Industries) (57 mg) and 2-thiophene boronic acid trimethylene glycol ester as obtained in Reference Example 10 (18 mg) were added, the reaction mixture was stirred at 100° C. under an argon atmosphere for 5 hours. The reaction mixture was suspended in ethyl acetate (30 ml) and washed with 0.1M hydrochloric acid (2×10 ml), water (3×10 ml) and brine (5 ml). The organic layer was dried over anhydrous sodium sulfate and concentrated under reduced pressure. The residue obtained was purified by preparative high performance liquid chromatography to yield compound 126 (9.6 mg) as a light-yellow powder.

$^1$H NMR, DMSO-d$_6$, δ ppm; 13.00 (1H, s), 7.76 (1H, d, J=5.1 Hz), 7.73 (1H, d, J=3.7 Hz), 7.24 (1H, dd, J=5.1, 3.7 Hz), 3.94 (3H, s), 3.60 (2H, s), 2.53 (3H, s)

FAB-MS spectrum (M+H)$^+$: m/z 541

Example 122

Establishment of CHO cells expressing costimulatory molecule a) Expression of B7-1 in CHO cells Using petri dishes 10 cm in diameter, 1×10$^5$ Chinese hamster ovary (CHO) cells were cultured in an αMEM medium containing 10% fetal bovine serum for 24 hours. To these cells, the B7-1 cDNA expression plasmid pME-B7-1 as obtained in Reference Example 1 (10 μg) and the neomycin resistance expression plasmid pME-neo (1 μg) were introduced by the calcium phosphate method. Forty-eight hours later, GENETICIN (G418 sulfate, GIBCO) was added to a final concentration of 0.5 mg/ml, and cells that acquired neomycin resistance were selected. For these selected cells, B7-1 expression was examined by flow cytometry (EPICS ELITE, COULTER), and cells showing high expression of B7-1 were obtained. These cells were cloned by the limiting dilution method to obtain B7-1-CHO-22, a cell line that stably expresses high amount of B7-1.

b) Expression of CD28 in CHO cells

Using petri dishes 10 cm in diameter, 1×10$^5$ dihydrofolate reductase deficient (DHFR$^-$) CHO cells were cultured in an αMEM medium containing 10% fetal bovine serum for 24 hours. To these cells, the CD28cDNA expression plasmid pAKKO-CD28as obtained in Reference Example 1 (10 μg) was introduced by the calcium phosphate method. Forty-eight hours later, the medium was replaced with an αMEM medium (no nucleic acid contained) containing 10% dialyzed fetal bovine serum, and cells incorporating the plasmid in their chromosome were selected. For these selected cells, CD28 expression was examined by flow cytometry (EPICS ELITE, COULTER), and cells showing high expression of CD28were obtained. These cells were cloned by the limiting dilution method to obtain CD28-CHO-11, a cell line that stably expresses high amount of CD28.

c) Establishment of CHO cells that produce soluble B7-1-Ig

Using petri dishes 10 cm in diameter, 1×10$^5$ dihydrofolate reductase deficient (DHFR$^{31}$) CHO cells were cultured in an αMEM medium containing 10% fetal bovine serum for 24 hours. To these cells, 10 μg of the expression plasmid encoding soluble B7-1-Ig as obtained in Reference Example 22 was introduced by the calcium phosphate method. Forty-eight hours later, the medium was replaced with an αMEM medium (no nucleic acid contained) containing 10% dialyzed fetal bovine serum, and cells incorporating the plasmid into their chromosome were selected. For these selected cells, the amount of soluble B7-1-Ig produced in the culture supernatant was measured by EIA, and cells showing high productivity were obtained. These cells were cloned by the limiting dilution method to obtain sB7-1-Ig-CHO-20, a cell line that stably produces soluble B7-1-Ig.

d) Preparation of soluble B7-1-Ig

Using petri dishes 15 cm in diameter, the soluble B7-1-Ig-producing CHO cells obtained in term c) above (sB7-1-Ig-CHO-20) were cultured in an αMEM medium containing 10% fetal bovine serum to yield 5 l of culture supernatant. This culture supernatant was crudely purified using a protein G column (Chromatop Superprotein G, 20 cm I.D.×10 cm, NGK Insulators, Ltd.) and further purified by gel filtration chromatography (TSKgel G3000SW, 21.5 cm I.D.×600 cm, Tosoh) to yield 20 mg of a purified standard preparation.

Test Example 1

Binding inhibition test using soluble B7-1-Ig

The CHO cells that expressed CD28obtained in Example 122 were suspended in an αMEM medium (no nucleic acid contained) containing 10% dialyzed fetal bovine serum, seeded into 96-well microplates (flat bottom) to 3×10$^4$ cells/well, and cultured in the presence of 5% CO$_2$ at 37° C. for 48 hours. The culture supernatant was removed by aspiration from each plate to which cells adhered, followed by the addition of phosphate buffer saline (PBS) containing 0.5% paraformaldehyde to fix the cells. After this plate was washed twice with PBS containing 10% Block Ace (Snow Brand Milk Products), 10 μg/ml soluble B7-1-Ig and a sample were added to each well. Binding reaction was carried out by keeping the plate standing at room temperature for 30 minutes. After the reaction, the plate was washed twice with PBS containing 10% Block Ace (Snow Brand Milk Products), followed by the addition of peroxidase-labeled anti-human IgG (Cappel) and 2 hours of reaction. The plate was further washed twice with PBS containing 10% Block Ace (Snow Brand Milk Products), after which 100 μl of a 0.1M citrate buffer containing 6.5 mg/ml ortho-phenylenediamine dihydrochloride (Wako Pure Chemical Industries) and 0.06% hydrogen peroxide was added to each well. Twenty minutes later, the coloring reaction was stopped with 2N sulfuric acid, and the absorbance at 492 nm was determined using a plate reader (BIO-RAD Model 1450). The IC$_{50}$ values (concentration for 50% inhibition of binding) of some compounds are shown in Table 14.

TABLE 14

| Comp. No. | IC$_{50}$ (μg/ml) |
| --- | --- |
| 1 | 0.14 |
| 17 | <0.1 |
| 27 | <0.1 |
| 40 | 0.10 |
| 54 | <0.1 |
| 132 | 0.12 |

Test Example 2

Inhibition test for interleukin 2 (IL-2) production by human peripheral blood T cells Blood was collected from a healthy normal human, overlaid on lymphocyte separation medium (LSM, Organon Teknica Co.), and centrifuged at room temperature at 2,000 rpm for 20 minutes to obtain human peripheral blood mononuclear cells. These mononuclear cells were applied to a nylon wool column (Wako Pure Chemical Industries) and incubated at 37° C. for 40 minutes, after which non-adsorbed cells were collected to enrich T cells. To 96-well microplates (flat bottom) coated with anti-CD3 antibody (OKT3, Ortho Diagnostic Systems), these T cells were seeded at a density of 5×10$^4$ cells/well, followed by the addition of the CHO cells expressing B7-1 obtained in Example 122 to 1×10$^4$ cells/well, and cultured the cells in RPMI-1640 medium containing 10% fetal bovine serum in the presence of 5% CO$_2$ 37° C. for 48 hours. The IL-2 produced in the culture supernatant was quantified using the HUMAN INTERLEUKIN-2 EIA KIT (Cayman Chemical Co.). The IC$_{50}$ value (concentration for 50% suppression of interleukin-2 production) of TAN-2421 Al was found to be 10 μg/ml.

Preparation Example 1

Using TAN-2421 Al (Compound No. 1), all components of the formulation shown below were mixed and filled in gelatin capsules to produce capsular preparations each containing 30 mg of TAN-2421 Al.

| | |
|---|---|
| TAN-2421 A1 | 30 mg |
| Lactose | 100 mg |
| Corn starch | 40 mg |
| Magnesium stearate | 10 mg |
| Total | 180 mg |

Formulation Example 2

TAN-2421A1and magnesium stearate were granulated with an aqueous solution of soluble starch. The granules were dried, which was mixed with lactose and corn starch. The mixture was subjected to compression molding to prepare tablets shown by the following prescription.

| | |
|---|---|
| TAN-2421 A1 | 30 mg |
| Lactose | 65 mg |
| Corn starch | 30 mg |
| Soluble starch | 35 mg |
| Magnesium stearate | 20 mg |
| Total | 180 mg |

Formulation Example 3

TAN-2421A1was dissolved in a physiological saline solution containing 30% (W/V) polyethylene glycol 400 to prepare a 0.005% solution of TAN-2421A1. The solution was subjected to filtration under sterilization, and 30 ml each of which was then distributed into one vial to prepare intravenous injection containing 15 mg of TAN-2421A1per vial.

Formulation Example 4

TAN-2421A1 (40 mg) and mannitol (50 g) were dissolved in sterilized distilled water (1 liter) containing polyethylene glycol 400 (30% w/w). The solution was subjected to filtration under sterilization, and 1 ml each of which was then distributed in one ampoule to prepare intravenous injection containing 40 μg of TAN-2421A1 per ampoul.

Toxicity test

When TAN-2421 A1 was intraperitoneally administered to mice at 400 mg/kg, no animals died.

What is claimed is:
1. A compound having the structure:

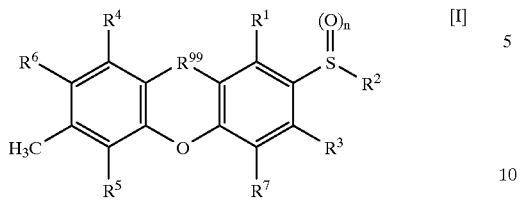

wherein
R$^1$ is a carboxyl group, an esterified carboxyl group, or an amidated carboxyl group;
R$^2$ is a hydrogen atom, a hydroxyl group, a hydrocarbon group, or a substituted hydrocarbon group;
R$^3$ and R$^4$ are the same or different and are a hydroxyl group or a hydroxyl group which is substituted by an acyl group, a C$_{1-10}$ alkyl group or a substituted C$_{1-10}$ alkyl group;
R$^5$ and R$^6$ are the same or different and are a hydrogen atom or a halogen atom;
R$^7$ is a hydrogen atom, a nitro group, a halogen atom, a hydrocarbon group, a substituted hydrocarbon group, a heterocyclic group, a substituted heterocyclic group, an acyl group, or a substituted acyl group;
n is an integer of is 0 to 2;
R$^{99}$ is a carbonyl or —CH$_2$—; and
when n is 0, R$^2$ may be a group represented by the structure:

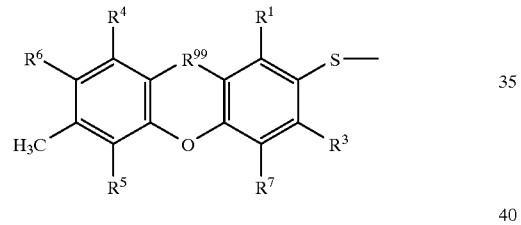

wherein the symbols have the same meanings as defined above, or a salt thereof.

2. The compound according to claim 1, wherein R$^7$ is a hydrogen atom or a halogen atom.

3. The compound according to claim 1, wherein R$^2$ is —CH$_2$(CHOH)$_m$—R$^{2'}$, wherein m is 0 or 1, and R$^{2'}$ is a carboxyl group, an esterified carboxyl group, an amidated carboxyl group, a hydroxylmethyl group, or a substituted hydroxylmethyl group; R$^7$ is a hydrogen atom; and R$^{99}$ is a carbonyl.

4. The compound according to claim 1, wherein
R$^2$ is:
 (i) a hydrogen atom,
 (ii) a hydroxyl group, or
 (iii) a C$_{1-19}$ hydrocarbon group or a C$_{1-19}$ hydrocarbon group which is substituted by a substituent selected from the group consisting of (a) C$_{1-8}$ alkoxycarbonylcarbonyl, (b) carboxyl, esterified carboxyl or amidated carboxyl, (c) hydroxyl or hydroxyl which is acylated, (d) amino, or amino which is substituted by C$_{1-10}$ alkyl, C$_{1-6}$ alkanoyl, C$_{1-6}$ alkylsulfonyl or C$_{6-14}$ arylsulfonyl, (e) C$_{1-6}$ alkoxy, (f) cyano, (g) sulfo, (h) a 5- or 6-membered heterocyclic group or a 5- or 6-membered heterocyclic group which is substituted by C$_{1-6}$ alkyl, C$_{1-6}$ alkoxy, nitro, cyano, amino, halogen, hydroxyl or oxo, (i) nitro, (j) halogen and (k) oxo;

R$^3$ and R$^4$ are the same or different and are a hydroxyl group or a hydroxyl group which is substituted by (a) an acyl group or (b) a C$_{1-10}$ alkyl group or a substituted C$_{1-10}$ alkyl group;
R$^7$ is:
 (i) a hydrogen atom,
 (ii) a nitro group,
 (iii) a halogen atom,
 (iv) a C$_{1-19}$ hydrocarbon group or a C$_{1-19}$ hydrocarbon group which is substituted by a substituent selected from the group consisting of (a) carboxyl, esterified carboxyl or amidated carboxyl, (b) hydroxyl or hydroxyl which is acylated, (c) amino or amino which is substituted by C$_{1-10}$ alkyl, C1-6 alkanoyl, C1-6 alkylsulfonyl or C$_{6-14}$ arylsulfonyl, (d) C1-6 alkoxy, (e) cyano, (f) sulfo, (g) a 5- or 6-membered heterocyclic group or a 5- or 6-membered heterocyclic group which is substituted by C$_{1-6}$ alkyl, C$_{1-6}$ alkoxy, nitro, cyano, amino, halogen, hydroxyl or oxo, (h) nitro, (i) halogen and (j) oxo,
 (v) a 5- or 6-membered heterocyclic group, or a 5- or 6-membered heterocyclic group which is substituted by a substituent selected from the group consisting of (a) C$_{1-6}$ alkyl, (b) carboxyl, esterified carboxyl or amidated carboxyl, (c) hydroxyl or hydroxyl which is acylated, (d) amino or amino which is substituted by C$_{1-10}$ alkyl, C$_{1-6}$ alkanoyl, C1-6 alkylsulfonyl or C$_{6-14}$ arylsulfonyl, (e) C$_{1-6}$ alkoxy, (f) cyano, (g) sulfo, (h) nitro, (i) halogen and (j) oxo, or
 (vi) an acyl group or an acyl substituent which is substituted by a substituent selected from the group consisting of (a) C$_{1-6}$ alkyl, (b) carboxyl, esterified carboxyl, or amidated carboxyl, (c) hydroxyl or hydroxyl which is acylated, (d) amino or amino which is substituted by C$_{1-10}$ alkyl, C$_{1-6}$ alkanoyl, C$_{1-6}$ alkylsulfonyl or C$_{6-14}$ arylsulfonyl, (e) C$_{1-6}$ alkoxy, (f) cyano, (g) sulfo, (h) a 5- or 6-membered heterocyclic group or a 5- or 6-membered heterocyclic group which is substituted by C$_{1-6}$ alkyl, C$_{1-6}$ alkoxy, nitro, cyano, amino, halogen, hydroxyl or oxo, (i) nitro, (j) halogen and (k) oxo.

5. The compound according to claim 1, wherein
R$^1$ is a carboxyl group or an esterified carboxyl group;
R$^2$ is:
 (i) a hydrogen atom,
 (ii) a hydroxyl group,
 (iii) a C$_{1-10}$ alkyl group or a C$_{1-10}$ alkyl group which is substituted by a substituent selected from the group consisting of (a) C$_{1-8}$ alkoxycarbonylcarbonyl, (b) carboxyl, esterified carboxyl or amidated carboxyl, (c) hydroxyl or acylated hydroxyl, (d) amino or amino which is substituted by C$_{1-4}$ alkylsulfonyl or C$_{6-14}$ arylsulfonyl, (e) C$_{1-6}$ alkoxy, (f) cyano, (g) sulfo and (h) a 5- or 6-membered heterocyclic group or a 5- or 6-membered heterocyclic group which is substituted by hydroxyl or oxo,
 (iv) a C$_{2-8}$ alkenyl group or a C$_{2-8}$ alkenyl group which is substituted by carboxyl, or
 (v) a C$_{7-19}$ aralkyl group or a C$_{7-19}$ aralkyl group which is substituted by a substituent selected from the group consisting of (a) cyano, (b) carboxyl, esterified carboxyl or amidated carboxyl, (c) hydroxyl, (d) nitro, (e) halogen and (f) a 5- or 6-membered nitrogen-containing heterocyclic group;
R$^3$ and R$^4$ are (i) a hydroxyl group or a hydroxyl group which is substituted by C$_{1-7}$ acyl or (ii) a C$_{1-10}$ alkoxy group or a C$_{1-10}$ alkoxy group which is substituted by C$_{1-6}$ alkoxy;

R⁷ is:
(i) a hydrogen atom,
(ii) a nitro group,
(iii) a halogen atom,
(iv) a $C_{1-10}$ alkyl group,
(v) a $C_{6-14}$ aryl group or a $C_{6-14}$ aryl group substituted by a substituent selected from the group consisting of (a) $C_{1-6}$ alkyl, (b) carboxyl, (c) $C_{1-6}$ alkoxy, (d) amino, (e) nitro and (f) halogen,
(vi) $C_{1-6}$ alkanoyl group, or
(vii) a 5- or 6-membered heterocyclic group containing from 1 to 4 hetero atoms independently selected from the group consisting of nitrogen, oxygen and sulfur.

6. The compound according to claim 1, wherein $R^1$ is —COOR²⁸, wherein $R^{28}$ is a hydrogen atom, a $C_{1-8}$ alkyl group or $C_{1-8}$ alkyl group substituted with a $C_{1-6}$ alkoxy, $R^2$ is:
(i) a hydrogen atom,
(ii) a hydroxyl group,
(iii) a —CH₂(CHOR^b)_{m1}COOR²⁹, wherein m1 is 0 or 1, $R^b$ is a hydrogen atom or a $C_{1-6}$ alkanoyl group, and $R^{29}$ is a hydrogen atom, a $C_{1-8}$ alkyl group or a $C_{1-8}$ alkyl group which is substituted by $C_{1-6}$ alkoxy, $C_{1-6}$ alkanoyloxy or $C_{4-7}$ cycloalkylcarbonyloxy,
(iv) a —CH₂(CHOH)_{m2}CONR³⁰R³¹, wherein m2 is 0 or 1, $R^{30}$ and $R^{31}$ are the same or different and are a hydrogen atom, a $C_{1-8}$ alkyl group, or a $C_{1-8}$ alkyl group which is substituted by carboxyl, $C_{1-6}$ alkoxy or $C_{2-5}$ alkoxycarbonyl,
(v) a —CH_{m2}(CHOH)₃CONHS(=O)₂R³², wherein m3 is 0 or 1, and $R^{32}$ is a $C_{1-4}$ alkyl group, $C_{1-4}$ alkyl group which is substituted by 1 to 3 halogen atoms, a $C_{6-14}$ aryl group, or a $C_{6-14}$ aryl group which is substituted by $C_{1-6}$ alkyl, nitro, $C_{1-6}$ alkoxy or halogen,
(vi) a —CH₂(CHOH)_{m4}CONHOR³³, wherein m4 is 0 or 1, and $R^{33}$ is a hydrogen atom or a $C_{1-4}$ alkyl group,
(vii) a —CH₂(CHOH)_{m5}R³⁴, wherein m5 is 0 or 1, and $R^{34}$ is a 3- to 8-membered heterocyclic ring containing from 1 to 4 hetero atoms independently selected from the group consisting of nitrogen, oxygen and sulfur, wherein any of the carbon atoms can be substituted by hydroxyl or oxo,
(viii) a —CH₂(CHOH)_{m6}—CH₂OR³⁵, wherein m6 is 0 or 1, and $R^{35}$ is a hydrogen atom, a $C_{1-8}$ alkyl group or a $C_{1-8}$ alkanoyl group,
(ix) a —CH₂(CHOH)_{m7}—COCOOR³⁶, wherein m7 is 0 or 1, and $R^{36}$ is a hydrogen atom or a $C_{1-8}$ alkyl group,
(x) a $C_{2-8}$ alkyl or a $C_{2-8}$ alkyl group which is substituted by carboxyl, or
(xi) a $C_{7-9}$ aralkyl group or a $C_{7-19}$ aralkyl group which is substituted by carboxyl, cyano, halogen, nitro, hydroxyl, carbamoyl, $C_{2-5}$ alkoxycarbonyl or a k3- to 8-membered heterocyclic ring containing from 1 to 4 hetero atoms independently selected from the group consisting of nitrogen, oxygen and sulfur;
$R^3$ is —OR³⁷, wherein $R^{37}$ is a hydrogen atom, a $C_{1-8}$ alkyl group, a $C_{1-8}$ alkyl group which is substituted by $C_{1-6}$ alkoxy, or a $C_{1-6}$ alkanoyl group;
$R^4$ is:
(i) a —OR³⁸, wherein $R^{38}$ is (a) a hydrogen atom, (b) a $C_{1-8}$ alkyl group or a $C_{1-8}$ alkyl group which is substituted by $C_{1-6}$ alkoxy, (c) a $C_{1-6}$ alkanoyl group or (d) a $C_{7-11}$ aroyl group, or (ii) a —OCOOR³⁹, wherein $R^{39}$ is a $C_{1-6}$ alkyl group or a $C_{6-14}$ aryl group; and
$R^7$ is:
(i) a hydrogen atom,
(ii) a nitro group,
(iii) a halogen atom,
(iv) a $C_{1-8}$ alkyl group,
(v) a $C_{6-14}$ aryl group or a $C_{6-14}$ aryl group which is substituted by halogen, carboxyl, $C_{1-6}$ alkyl, $C_{1-6}$ alkoxy, amino or nitro,
(vi) a $C_{1-6}$ alkanoyl group, or
(vii) a 3- to 8- membered heterocyclic ring containing from 1 to 4 hetero atoms independently selected from the group consisting of nitrogen, oxygen and sulfur.

7. The compound according to claim 1, wherein $R^2$ is —CH₂COOR⁴⁰, wherein $R^{40}$ is a hydrogen atom, a $C_{1-4}$ alkyl or a $C_{1-4}$ alkyl group which is substituted by $C_{1-6}$ alkoxy, $C_{1-6}$ alkanoyloxy or $C_{4-7}$ cycloalkylcarbonyloxy; $R^3$ and $R^4$ are hydroxyl groups; $R^5$ and $R^6$ are chlorine atoms; and $R^7$ is hydrogen, bromine, iodine or a nitro group.

8. The compound according to claim 1, wherein n is 0 or 1.

9. The compound according to claim 1, wherein $R^{99}$ is a carbonyl.

10. The compound according to claim 1, having the structural formula

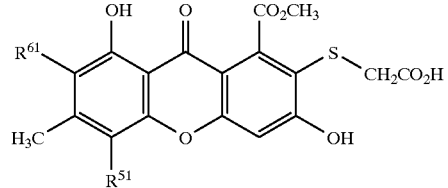

wherein $R^{51}$ is a hydrogen atom or a chlorine atom, and $R^{61}$ is a hydrogen atom or a chlorine atom.

11. The compound according to claim 1, having the structural formula

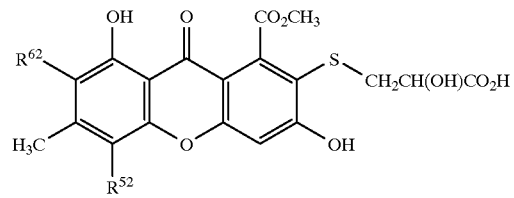

wherein $R^{52}$ is a hydrogen atom or a chlorine atom and $R^{62}$ is a hydrogen atom or a chlorine atom.

12. The compound according to claim 1, wherein the compound is methyl 2-(carboxymethylsulfinyl)-5,7-dichloro-3,8-dihydroxy-6-methyl-9-oxo-9H-xanthene-1-carboxylate, methyl 2-(carboxymethylsulfinyl)-5,7-dichloro-3,8-dihydroxy-4-iodo-6-methyl-9-oxo-9H-xanthene-1-carboxylate, methyl 5,7-dichloro-3,8-dihydroxy-6-methyl-9-oxo-2-(pivaloyloxymethoxycarbonylmethylthio)-9H-xanthene-1-carboxylate, methyl 5,7-dichloro-3,8-dihydroxy-6-methyl-9-oxo-2-(pivaloyloxymethoxycarbonylmethylsulfinyl)-9H-xanthene-1-carboxylate or methyl 5,7-dichloro-2-[1-(cyclohexyloxycarbonyloxy)ethoxycarbonylmethylthio]-3,8-dihydroxy-6-methyl-9-oxo-9H-xanthene-1-carboxylate.

13. A pharmaceutical composition comprising the compound according to claim 1, or a salt thereof, and a pharmaceutically acceptable carrier, excipient or diluent thereof.

14. The pharmaceutical composition according to claim 13, which is a graft rejection inhibitor, or a therapeutic treatment for allergy, rheumatoid arthritis, autoimmune disease, nephritis or diabetes mellitus.

15. A composition for inhibiting a signal transduction by T-cells, comprising the compound according to claim 1, or a salt thereof, and a pharmaceutically acceptable carrier, excipient or diluent thereof.

16. A method for producing the compound according to claim 1 having the structure:

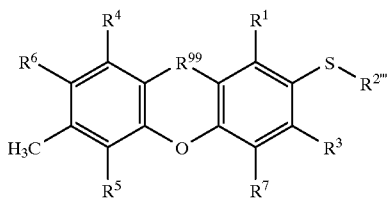

wherein $R^{2'''}$ is a hydrogen atom, a hydrocarbon group or a substituted hydrocarbon group; $R^1$ is a carboxyl group, an esterified carboxyl group, or an amidated carboxyl group; $R^3$ and $R^4$ are the same or different and are a hydroxyl group or a substituted hydroxyl group; $R^5$ and $R^6$ are the same or different and are a hydrogen atom or a halogen atom; $R^7$ is a hydrogen atom, a nitro group, a halogen atom, a hydrocarbon group, a substituted hydrocarbon group, a heterocyclic group, a substituted heterocyclic group, an acyl group or a substituted acyl group; and $R^{99}$ is a carbonyl or —$CH_2$—, or a salt thereof, comprising reducing the compound having the structure:

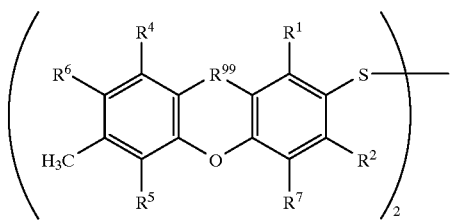

wherein each of the symbols has the same meaning as defined above, or a salt thereof; and collecting said compound I', or a salt thereof, and optionally, reacting said compound I' with a hydrocarbon or a substituted hydrocarbon when $R^2$ is a hydrocarbon group or a substituted hydrocarbon group.

17. A method for producing the compound according to claim 10, or a salt thereof, comprising culturing the microorganism, *Aspergillus terreus* FL-67283; producing said compound in said culture; and collecting said compound from said culture.

18. A method for producing the compound according to claim 11, or a salt thereof, comprising culturing the microorganism, *Aspergillus terreus* FL-67283; producing said compound in said culture; and collecting said compound from said culture.

19. A method for inhibiting signal transduction of T-cell in a mammal, which comprises administering an effective amount of the compound according to claim 1, or a salt thereof, to the mammal.

20. A method of treating or inhibiting graft rejection, allergy, rheumatoid arthritis autoimmune disease, nephritis or diabetes mellitus in a mammal, which comprises administering an effective amount of the compound according to claim 1, or a salt thereof, to the mammal.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 660 bases
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO:1:

```
ATGCTCAGGC TGCTCTTGGC TCTCAACTTA TTCCCTTCAA TTCAAGTAAC AGGAAACAAG      60

ATTTTGGTGA AGCAGTCGCC CATGCTTGTA GCGTACGACA ATGCGGTCAA CCTTAGCTGC     120

AAGTATTCCT ACAATCTCTT CTCAAGGGAG TTCCGGGCAT CCCTTCACAA AGGACTGGAT     180

AGTGCTGTGG AAGTCTGTGT TGTATATGGG AATTACTCCC AGCAGCTTCA GGTTTACTCA     240

AAAACGGGGT TCAACTGTGA TGGGAAATTG GGCAATGAAT CAGTGACATT CTACCTCCAG     300

AATTTGTATG TTAACCAAAC AGATATTTAC TTCTGCAAAA TTGAAGTTAT GTATCCTCCT     360

CCTTACCTAG ACAATGAGAA GAGCAATGGA ACCATTATCC ATGTGAAAGG GAAACACCTT     420

TGTCCAAGTC CCTATTTCC CGGACCTTCT AAGCCCTTTT GGGTGCTGGT GGTGGTTGGT     480

GGAGTCCTGG CTTGCTATAG CTTGCTAGTA ACAGTGGCCT TTATTATTTT CTGGGTGAGG     540

AGTAAGAGGA GCAGGCTCCT GCACAGTGAC TACATGAACA TGACTCCCCG CCGCCCCGGG     600

CCCACCCGCA AGCATTACCA GCCCTATGCC CCACCACGCG ACTTCGCAGC CTATCGCTCC     660
```

(2) INFORMATION FOR SEQ ID NO:2:

(i) SEQUENCE CHARACTERISTICS:
        (A) LENGTH:  867 bases
        (B) TYPE:  nucleic acid
        (C) STRANDEDNESS:  double
        (D) TOPOLOGY:  linear (ii) MOLECULE TYPE:  cDNA (xi) SEQUENCE DESCRIPTION: SEQ ID NO:2:

```
ATGGGCCACA CACGGAGGCA GGGAACATCA CCATCCAAGT GTCCATACCT CAATTTCTTT      60
CAGCTCTTGG TGCTGGCTGG TCTTTCTCAC TTCTGTTCAG GTGTTATCCA CGTGACCAAG     120
GAAGTCAAAG AAGTGGCAAC GCTGTCCTGT GGTCACAATG TTTCTGTTGA AGAGCTGGCA     180
CAAACTCGCA TCTACTGGCA AAAGGAGAAG AAAATGGTGC TGACTATGAT GTCTGGGGAC     240
ATGAATATAT GGCCCGAGTA CAAGAACCGG ACCATCTTTG ATATCACTAA TAACCTCTCC     300
ATTGTGATCC TGGCTCTGCG CCCATCTGAC GAGGGCACAT ACGAGTGTGT TGTTCTGAAG     360
TATGAAAAAG ACGCTTTCAA GCGGGAACAC CTGGCTGAAG TGACGTTATC AGTCAAAGCT     420
GACTTCCCTA CACCTAGTAT ATCTGACTTT GAAATTCCAA CTTCTAATAT TAGAAGGATA     480
ATTTGCTCAA CCTCTGGAGG TTTTCCAGAG CCTCACCTCT CCTGGTTGGA AAATGGAGAA     540
GAATTAAATG CCATCAACAC AACAGTTTCC CAAGATCCTG AAACTGAGCT CTATGCTGTT     600
AGCAGCAAAC TGGATTTCAA TATGACAACC AACCACAGCT TCATGTGTCT CATCAAGTAT     660
GGACATTTAA GAGTGAATCA GACCTTCAAC TGGAATACAA CCAAGCAAGA GCATTTTCCT     720
GATAACCTGC TCCCATCCTG GCCATTACC  TTAATCTCAG TAAATGGAAT TTTTGTGATA     780
TGCTGCCTGA CCTACTGCTT TGCCCCAAGA TGCAGAGAGA GAAGGAGGAA TGAGAGATTG     840
AGAAGGGAAA GTGTACGCCC TGTATAA                                        867
```

(2) INFORMATION FOR SEQ ID NO:3:

(i) SEQUENCE CHARACTERISTICS:
        (A) LENGTH:  1428 bases
        (B) TYPE:  nucleic acid
        (C) STRANDEDNESS:  double
        (D) TOPOLOGY:  linear (ii) MOLECULE TYPE:  cDNA (xi) SEQUENCE DESCRIPTION: SEQ ID NO:3:

```
ATGGGCCACA CACGGAGGCA GGGAACATCA CCATCCAAGT GTCCATACCT CAATTTCTTT      60
CAGCTCTTGG TGCTGGCTGG TCTTTCTCAC TTCTGTTCAG GTGTTATCCA CGTGACCAAG     120
GAAGTCAAAG AAGTGGCAAC GCTGTCCTGT GGTCACAATG TTTCTGTTGA AGAGCTGGCA     180
CAAACTCGCA TCTACTGGCA AAAGGAGAAG AAAATGGTGC TGACTATGAT GTCTGGGGAC     240
ATGAATATAT GGCCCGAGTA CAAGAACCGG ACCATCTTTG ATATCACTAA TAACCTCTCC     300
ATTGTGATCC TGGCTCTGCG CCCATCTGAC GAGGGCACAT ACGAGTGTGT TGTTCTGAAG     360
TATGAAAAAG ACGCTTTCAA GCGGGAACAC CTGGCTGAAG TGACGTTATC AGTCAAAGCT     420
GACTTCCCTA CACCTAGTAT ATCTGACTTT GAAATTCCAA CTTCTAATAT TAGAAGGATA     480
ATTTGCTCAA CCTCTGGAGG TTTTCCAGAG CCTCACCTCT CCTGGTTGGA AAATGGAGAA     540
GAATTAAATG CCATCAACAC AACAGTTTCC CAAGATCCTG AAACTGAGCT CTATGCTGTT     600
AGCAGCAAAC TGGATTTCAA TATGACAACC AACCACAGCT TCATGTGTCT CATCAAGTAT     660
GGACATTTAA GAGTGAATCA GACCTTCAAC TGGAATACAA CCAAGCAAGA GCATTTTCCT     720
```

```
GATCATCAGG AGCCCAAATC TTCTGACAAA ACTCACACGT CTCCACCGTC CCCGGCGCCT      780

GAACTCCTGG GGGGACCGTC AGTCTTCCTC TTCCCCCCAA AACCCAAGGA CACCCTCATG      840

ATCTCCCGGA CCCCTGAGGT CACATGCGTG GTGGTGGACG TGAGCCACGA AGACCCTGAG      900

GTCAAGTTCA ACTGGTACGT GGACGGCGTG GAGGTGCATA ATGCCAAGAC AAAGCCGCGG      960

GAGGAGCAGT ACAACAGCAC GTACCGTGTG GTCAGCGTCC TCACCGTCCT GCACCAGGAC     1020

TGGCTGAATG GCAAGGAGTA CAAGTGCAAG GTCTCCAACA AAGCCCTCCC AGCCCCCATC     1080

GAGAAAACCA TCTCCAAAGC CAAAGGGCAG CCCCGAGAAC CACAGGTGTA CACCCTGCCC     1140

CCATCCCGGG AGGAGATGAC CAAGAACCAG GTCAGCCTGA CCTGCCTGGT CAAAGGCTTC     1200

TATCCCAGCG ACATCGCCGT GGAGTGGGAG AGCAATGGGC AGCCGGAGAA CAACTACAAG     1260

ACCACGCCTC CCGTGCTGGA CTCCGACGGC TCCTTCTTCC TCTATAGCAA GCTCACCGTG     1320

GACAAGAGCA GGTGGCAGCA GGGGAACGTC TTCTCATGCT CCGTGATGCA TGAGGCTCTG     1380

CACAACCACT ACACGCAGAA GAGCCTCTCC CTGTCCCCGG GTAAATGA                  1428

(2) INFORMATION FOR SEQ ID NO:4:

(i) SEQUENCE CHARACTERISTICS:
        (A) LENGTH:  33 bases
        (B) TYPE:  nucleic acid
        (C) STRANDEDNESS:  single
        (D) TOPOLOGY:  linear (ii) MOLECULE TYPE:  Other nucleic acid, Synthetic DNA (xi) SEQUENCE DESCRIPTION: SEQ ID NO:4:

TGGATCCATG GGCCACACAC GGAGGCAGGG AAC                                    33

(2) INFORMATION FOR SEQ ID NO:5:

(i) SEQUENCE CHARACTERISTICS:
        (A) LENGTH:  35 bases
        (B) TYPE:  nucleic acid
        (C) STRANDEDNESS:  single
        (D) TOPOLOGY:  linear (ii) MOLECULE TYPE:  Other nucleic acid, Synthetic DNA (xi) SEQUENCE DESCRIPTION: SEQ ID NO:5:

TGGATCCTTA TACAGGGCGT ACACTTTCCC TTCTC                                  35

(2) INFORMATION FOR SEQ ID NO:6:

(i) SEQUENCE CHARACTERISTICS:
        (A) LENGTH:  35 bases
        (B) TYPE:  nucleic acid
        (C) STRANDEDNESS:  single
        (D) TOPOLOGY:  linear (ii) MOLECULE TYPE:  Other nucleic acid, Synthetic DNA (xi) SEQUENCE DESCRIPTION: SEQ ID NO:6:

TCTCGAGGTC GACATGCTCA GGCTGCTCTT GGCTC                                  35

(2) INFORMATION FOR SEQ ID NO:7:

(i) SEQUENCE CHARACTERISTICS:
        (A) LENGTH:  29 bases
        (B) TYPE:  nucleic acid
        (C) STRANDEDNESS:  single
        (D) TOPOLOGY:  linear
```

(ii) MOLECULE TYPE:  Other nucleic acid, Synthetic DNA (xi) SEQUENCE DESCRIPTION: SEQ ID NO:7:

AACTAGTTCA GGAGCGATAG GCTGCGAAG                                            29

(2) INFORMATION FOR SEQ ID NO:8:

(i) SEQUENCE CHARACTERISTICS:
        (A) LENGTH:  22 bases
        (B) TYPE:  nucleic acid
        (C) STRANDEDNESS:  single
        (D) TOPOLOGY:  linear (ii) MOLECULE TYPE:  Other nucleic acid, Synthetic DNA (xi) SEQUENCE DESCRIPTION: SEQ ID NO:8:

CTTTGATATC ACTAATAACC TC                                                   22

(2) INFORMATION FOR SEQ ID NO:9:

(i) SEQUENCE CHARACTERISTICS:
        (A) LENGTH:  30 bases
        (B) TYPE:  nucleic acid
        (C) STRANDEDNESS:  single
        (D) TOPOLOGY:  linear (ii) MOLECULE TYPE:  Other nucleic acid, Synthetic DNA (xi) SEQUENCE DESCRIPTION: SEQ ID NO:9:

GGTGATCAGG AAAATGCTCT TGCTTGGTTG                                           30

(2) INFORMATION FOR SEQ ID NO:10:

(i) SEQUENCE CHARACTERISTICS:
        (A) LENGTH:  69 bases
        (B) TYPE:  nucleic acid
        (C) STRANDEDNESS:  single
        (D) TOPOLOGY:  linear (ii) MOLECULE TYPE:  Other nucleic acid, Synthetic DNA (xi) SEQUENCE DESCRIPTION: SEQ ID NO:10:

GGTGATCAGG AGCCCAAATC TTCTGACAAA ACTCACACGT CTCCACCGTC CCCGGCGCCT          60

GAACTCCTG                                                                  69

(2) INFORMATION FOR SEQ ID NO:11:

(i) SEQUENCE CHARACTERISTICS:
        (A) LENGTH:  36 bases
        (B) TYPE:  nucleic acid
        (C) STRANDEDNESS:  single
        (D) TOPOLOGY:  linear (ii) MOLECULE TYPE:  Other nucleic acid, Synthetic DNA (xi) SEQUENCE DESCRIPTION: SEQ ID NO:11:

CCCTGCAGTC TAGATCATTT ACCCGGGGAC AGGGAG                                    36